US012624362B2

(12) United States Patent
Sinclair et al.

(10) Patent No.: US 12,624,362 B2
(45) Date of Patent: May 12, 2026

(54) MUTANT REVERSE TETRACYCLINE TRANSACTIVATORS FOR EXPRESSION OF GENES

(71) Applicant: President and Fellows of Harvard College, Cambridge, MA (US)

(72) Inventors: David A. Sinclair, Cambridge, MA (US); Yuancheng Lu, Cambridge, MA (US); Noah Justin Davidsohn, La Jolla, CA (US)

(73) Assignee: PRESIDENT AND FELLOWS OF HARVARD COLLEGE

( * ) Notice: Subject to any disclaimer, the term of this patent is extended or adjusted under 35 U.S.C. 154(b) by 1409 days.

(21) Appl. No.: 17/280,294

(22) PCT Filed: Sep. 27, 2019

(86) PCT No.: PCT/US2019/053492
§ 371 (c)(1),
(2) Date: Mar. 26, 2021

(87) PCT Pub. No.: WO2020/069339
PCT Pub. Date: Apr. 2, 2020

(65) Prior Publication Data
US 2021/0403923 A1    Dec. 30, 2021

Related U.S. Application Data

(60) Provisional application No. 62/738,894, filed on Sep. 28, 2018.

(51) Int. Cl.
| *C12N 15/63* | (2006.01) |
| *A61K 48/00* | (2006.01) |
| *C12N 15/86* | (2006.01) |

(52) U.S. Cl.
CPC ........ *C12N 15/635* (2013.01); *A61K 48/0058* (2013.01); *C12N 15/86* (2013.01); *C12N 2750/14143* (2013.01); *C12N 2750/14171* (2013.01); *C12N 2830/003* (2013.01)

(58) Field of Classification Search
CPC ................. C12N 15/635; C12N 15/86; C12N 2750/14143; C12N 2750/14171; C12N 2830/003; A61K 48/0058
See application file for complete search history.

(56) References Cited

U.S. PATENT DOCUMENTS

| 5,399,363 | A | 3/1995 | Liversidge et al. |
| 5,543,158 | A | 8/1996 | Gref et al. |
| 5,552,157 | A | 9/1996 | Yagi et al. |
| 5,565,213 | A | 10/1996 | Nakamori et al. |
| 5,567,434 | A | 10/1996 | Szoka, Jr. |
| 5,589,362 | A | 12/1996 | Bujard et al. |
| 5,641,515 | A | 6/1997 | Ramtoola |
| 5,650,298 | A | 7/1997 | Bujard et al. |
| 5,738,868 | A | 4/1998 | Shinkarenko |
| 5,741,516 | A | 4/1998 | Webb et al. |
| 5,795,587 | A | 8/1998 | Gao et al. |
| 5,928,941 | A | 7/1999 | Lee et al. |
| 6,750,015 | B2 | 6/2004 | Horwitz et al. |
| 7,541,446 | B2 | 6/2009 | Hillen et al. |
| 8,080,647 | B2 * | 12/2011 | Gordon-Kamm ........................... C12N 15/8238 800/312 |
| 8,158,415 | B2 | 4/2012 | Jo et al. |
| 8,326,547 | B2 | 12/2012 | Liu et al. |
| 8,383,364 | B2 | 2/2013 | Berkhout et al. |
| 8,609,373 | B2 | 12/2013 | Liu et al. |
| 8,716,465 | B2 | 5/2014 | Rossi et al. |
| 8,748,179 | B2 | 6/2014 | Egusa et al. |
| 8,883,506 | B2 | 11/2014 | Rossi et al. |
| 8,932,856 | B2 | 1/2015 | Jaenisch et al. |
| 8,940,536 | B2 | 1/2015 | Jaenisch et al. |

(Continued)

FOREIGN PATENT DOCUMENTS

| AU | 746850 B2 | 5/2002 |
| CN | 101302553 A | 11/2008 |

(Continued)

OTHER PUBLICATIONS

Roney IJ, Rudner AD, Couture JF, Karn M. Improvement of the reverse tetracycline transactivator by single amino acid substitutions that reduce leaky target gene expression to undetectable levels. Sci Rep. 2016;6:27697. Published Jun. 21, 2016. doi: 10.1038/srep27697 (Year: 2016).*

Matsui, R., Tanabe, Y., & Watanabe, D. (2012). Avian adeno-associated virus vector efficiently transduces neurons in the embryonic and post-embryonic chicken brain. PLoS One, 7(11), e48730. (Year: 2012).*

Choi, Jun-Hyeok, et al. "Optimization of AAV expression cassettes to improve packaging capacity and transgene expression in neurons." Molecular brain 7 (2014): 1-10. (Year: 2014).*

Fan, Xiujun, et al. "Transient, inducible, placenta-specific gene expression in mice." Endocrinology 153.11 (2012): 5637-5644. (Year : 2012).*

(Continued)

*Primary Examiner* — Jennifer Dunston
*Assistant Examiner* — Christina Tran
(74) *Attorney, Agent, or Firm* — NIXON PEABODY LLP; David S. Resnick; Nicole D. Kling

(57) ABSTRACT

Provided herein are mutant reverse tetracycline transactivator (rtTA) proteins and engineered nucleic acids that encode a mutant rtTA that are useful in regulating gene expression, inducing cellular reprogramming, tissue repair, tissue regeneration, organ regeneration, reversing aging, treating a disease, or any combination thereof. Also provided herein are recombinant viruses comprising the engineered nucleic acids and methods of regulating cellular reprogramming, tissue repair, tissue regeneration, or any combination thereof by administering an engineered nucleic acid or recombinant virus comprising the same in a cell, tissue or subject comprising administering a mutant rtTA and an inducible nucleic acid encoding a transgene.

27 Claims, 31 Drawing Sheets
Specification includes a Sequence Listing.

(56) References Cited

U.S. PATENT DOCUMENTS

| | | | |
|---|---|---|---|
| 8,957,037 | B2 | 2/2015 | Collard et al. |
| 9,127,283 | B2 | 9/2015 | Bisgrove et al. |
| 9,175,268 | B2 | 11/2015 | Mack |
| 9,175,311 | B2 | 11/2015 | Townes et al. |
| 9,228,204 | B2 | 1/2016 | Pulst et al. |
| 9,497,943 | B2 | 11/2016 | Jaenisch et al. |
| 9,580,689 | B2 | 2/2017 | Kikyo et al. |
| 9,644,164 | B2 | 5/2017 | Gieselman et al. |
| 9,695,445 | B2 | 7/2017 | Fusaki et al. |
| 9,850,499 | B2 | 12/2017 | Baylink et al. |
| 9,862,930 | B2 | 1/2018 | Dowdy et al. |
| 9,920,333 | B2 | 3/2018 | Pulst et al. |
| 11,058,729 | B2 | 7/2021 | Tomarev et al. |
| 11,525,119 | B2 | 12/2022 | Vo et al. |
| RE49,583 | E | 7/2023 | Berkhout et al. |
| 11,692,029 | B2 | 7/2023 | Min et al. |
| 12,274,733 | B2 | 4/2025 | Sinclair et al. |
| 12,409,207 | B2 | 9/2025 | Sinclair et al. |
| 12,414,982 | B2 | 9/2025 | Sinclair et al. |
| 2002/0165180 | A1 | 11/2002 | Weaver |
| 2003/0065157 | A1 | 4/2003 | Lasek |
| 2003/0138772 | A1 | 7/2003 | Gao et al. |
| 2003/0138799 | A1 | 7/2003 | Ruppert et al. |
| 2003/0165921 | A1 | 9/2003 | Tang et al. |
| 2003/0186281 | A1 | 10/2003 | Hillen |
| 2004/0038249 | A1 | 2/2004 | Darteil et al. |
| 2004/0219579 | A1 | 11/2004 | Aziz et al. |
| 2004/0235073 | A1 | 11/2004 | Ruppert et al. |
| 2005/0064454 | A1 | 3/2005 | Young et al. |
| 2005/0208496 | A1 | 9/2005 | Ohtani et al. |
| 2006/0263774 | A1 | 11/2006 | Clark et al. |
| 2007/0042392 | A1 | 2/2007 | Tang et al. |
| 2007/0048301 | A1 | 3/2007 | Bodary-Winter et al. |
| 2007/0060743 | A1 | 3/2007 | Tang et al. |
| 2007/0072175 | A1 | 3/2007 | Cooper et al. |
| 2007/0161031 | A1 | 7/2007 | Trinklein et al. |
| 2008/0050379 | A1 | 2/2008 | Young et al. |
| 2008/0050393 | A1 | 2/2008 | Tang et al. |
| 2008/0233648 | A1 | 9/2008 | Sugaya et al. |
| 2010/0040649 | A1 | 2/2010 | Berkhout et al. |
| 2010/0048678 | A1 | 2/2010 | Smit et al. |
| 2010/0074864 | A1 | 3/2010 | Achiron et al. |
| 2010/0099144 | A1 | 4/2010 | Jo et al. |
| 2010/0150889 | A1 | 6/2010 | Townes et al. |
| 2010/0190250 | A1 | 7/2010 | Hu et al. |
| 2010/0273220 | A1 | 10/2010 | Yanik et al. |
| 2010/0285589 | A1 | 11/2010 | Lowry et al. |
| 2011/0002940 | A1 | 1/2011 | Piek et al. |
| 2011/0061118 | A1 | 3/2011 | Ralf et al. |
| 2011/0081708 | A1 | 4/2011 | Liu et al. |
| 2011/0190729 | A1 | 8/2011 | Kirkland et al. |
| 2011/0190730 | A1 | 8/2011 | Kirkland et al. |
| 2011/0258713 | A1 | 10/2011 | Zhu et al. |
| 2012/0064048 | A1 | 3/2012 | Collard et al. |
| 2012/0095188 | A1 | 4/2012 | Jo et al. |
| 2012/0128655 | A1 | 5/2012 | Kim et al. |
| 2012/0129254 | A1 | 5/2012 | Bisgrove et al. |
| 2012/0196328 | A1 | 8/2012 | Liu et al. |
| 2012/0208278 | A1 | 8/2012 | Yanik et al. |
| 2012/0225076 | A1 | 9/2012 | Peeper et al. |
| 2012/0322864 | A1 | 12/2012 | Rossi et al. |
| 2012/0322865 | A1 | 12/2012 | Rossi et al. |
| 2013/0017596 | A1 | 1/2013 | Townes et al. |
| 2013/0059752 | A1 | 3/2013 | Bodary-Winter et al. |
| 2013/0065791 | A1 | 3/2013 | Rosenthal et al. |
| 2013/0130387 | A1 | 5/2013 | Itskovitz-Eldor et al. |
| 2014/0107190 | A1 | 4/2014 | Molina et al. |
| 2014/0128277 | A1 | 5/2014 | Moller et al. |
| 2014/0170752 | A1 | 6/2014 | Pulst et al. |
| 2014/0323411 | A1 | 10/2014 | Kostarelos |
| 2015/0087594 | A1 | 3/2015 | Edenhoffer et al. |
| 2015/0133531 | A1 | 5/2015 | Wiegand |
| 2015/0159143 | A1 | 6/2015 | Dowdy et al. |
| 2015/0225728 | A1* | 8/2015 | De Lange ............. C12N 15/65 435/189 |

| | | | |
|---|---|---|---|
| 2015/0267174 | A1 | 9/2015 | Hayashi et al. |
| 2015/0299701 | A1 | 10/2015 | Collard et al. |
| 2016/0032393 | A1 | 2/2016 | Achiron et al. |
| 2016/0076000 | A1 | 3/2016 | Townes et al. |
| 2016/0102127 | A1 | 4/2016 | Thepen et al. |
| 2016/0143951 | A1 | 5/2016 | Lawrence et al. |
| 2017/0073643 | A1 | 3/2017 | Valamehr et al. |
| 2018/0155789 | A1 | 6/2018 | Maeder et al. |
| 2018/0161358 | A1* | 6/2018 | Arber ..................... C12N 15/86 |
| 2018/0195047 | A1 | 7/2018 | Jo |
| 2018/0216079 | A1 | 8/2018 | Dowdy et al. |
| 2018/0299430 | A1 | 10/2018 | Kuo et al. |
| 2018/0305689 | A1 | 10/2018 | Sætrom et al. |
| 2019/0055518 | A1 | 2/2019 | Young-Ae |
| 2019/0292250 | A1* | 9/2019 | Hinderer ............... C07K 16/22 |
| 2021/0324414 | A1 | 10/2021 | Weiss et al. |
| 2023/0048010 | A1 | 2/2023 | Sinclair et al. |
| 2023/0338468 | A1 | 10/2023 | Sinclair et al. |
| 2024/0261370 | A1 | 8/2024 | Sinclair et al. |
| 2024/0316148 | A1 | 9/2024 | Sinclair et al. |
| 2025/0325628 | A1 | 10/2025 | Sinclair et al. |

FOREIGN PATENT DOCUMENTS

| | | |
|---|---|---|
| CN | 104837862 A | 8/2015 |
| DE | 19851415 A1 | 5/2000 |
| EP | 1071776 A2 | 1/2001 |
| EP | 1358349 A2 | 11/2003 |
| EP | 1394274 A2 | 3/2004 |
| EP | 1572987 A2 | 9/2005 |
| EP | 1578367 A2 | 9/2005 |
| EP | 1578996 A2 | 9/2005 |
| EP | 1888627 A2 | 2/2008 |
| EP | 2103685 A1 | 3/2008 |
| EP | 2096169 B1 | 10/2008 |
| EP | 2021499 A2 | 2/2009 |
| EP | 2126135 A2 | 12/2009 |
| EP | 2132225 A1 | 12/2009 |
| EP | 2435557 A1 | 5/2010 |
| EP | 2191018 A2 | 6/2010 |
| EP | 2191840 A1 | 6/2010 |
| EP | 2612911 B1 | 8/2011 |
| EP | 2388336 A1 | 11/2011 |
| EP | 2407488 A2 | 1/2012 |
| EP | 2421563 A1 | 2/2012 |
| EP | 2432881 A2 | 3/2012 |
| EP | 2478101 A1 | 7/2012 |
| EP | 2572000 A2 | 3/2013 |
| EP | 2638163 A1 | 9/2013 |
| EP | 2655621 A1 | 10/2013 |
| EP | 2675903 A1 | 12/2013 |
| EP | 2852671 A2 | 4/2015 |
| EP | 2931914 A1 | 10/2015 |
| EP | 3060237 A1 | 8/2016 |
| EP | 3452101 A2 | 5/2017 |
| EP | 3194623 A1 | 7/2017 |
| EP | 2643459 B1 | 9/2017 |
| EP | 3334755 A1 | 6/2018 |
| EP | 3385373 A1 | 10/2018 |
| WO | WO 9954460 A2 | 10/1999 |
| WO | WO 2000/069450 A1 | 11/2000 |
| WO | WO 2001/094629 A2 | 12/2001 |
| WO | WO 2004/073657 A2 | 9/2004 |
| WO | WO 2005/052164 A1 | 6/2005 |
| WO | WO 2006/123930 A2 | 11/2006 |
| WO | WO 2007/058527 A2 | 5/2007 |
| WO | WO 2007/078599 A2 | 7/2007 |
| WO | WO 2008/051854 A2 | 5/2008 |
| WO | WO 2008/081435 A2 | 7/2008 |
| WO | WO 2009/028945 A2 | 3/2009 |
| WO | WO 2009/061442 A1 | 5/2009 |
| WO | WO 2010/030003 A1 | 9/2009 |
| WO | WO 2010/104357 A2 | 9/2010 |
| WO | WO 2010/123501 A1 | 10/2010 |
| WO | WO 2010/135329 A2 | 11/2010 |
| WO | WO 2010/138263 A2 | 12/2010 |
| WO | WO 2011/017910 A1 | 2/2011 |
| WO | WO 2011/034421 A1 | 3/2011 |
| WO | WO 2011/145615 A1 | 5/2011 |

(56) References Cited

FOREIGN PATENT DOCUMENTS

| WO | WO 2011/144718 A2 | 11/2011 |
| WO | WO 2012/014207 A2 | 2/2012 |
| WO | WO 2012/065143 A1 | 5/2012 |
| WO | WO 2012/071549 A2 | 5/2012 |
| WO | WO 2012/087983 A1 | 6/2012 |
| WO | WO 2012/120026 A1 | 9/2012 |
| WO | WO 2012/136841 A1 | 10/2012 |
| WO | WO 2013/177133 A2 | 11/2013 |
| WO | WO 2014/053082 A1 | 4/2014 |
| WO | WO 2014/152607 A2 | 9/2014 |
| WO | WO 2015/077498 A1 | 11/2014 |
| WO | WO 2014/191391 A1 | 12/2014 |
| WO | WO 2016/171448 A1 | 4/2016 |
| WO | WO 2016/170348 A2 | 10/2016 |
| WO | WO 2017/026776 A1 | 2/2017 |
| WO | WO 2017/173354 A2 | 10/2017 |
| WO | WO 2017/180587 A2 | 10/2017 |
| WO | WO 2018/041959 A1 | 3/2018 |
| WO | WO 2019/053012 A1 | 9/2018 |
| WO | WO 2018/204764 A1 | 11/2018 |
| WO | WO-2019023680 A1 * | 1/2019 | ............ C07K 14/32 |
| WO | WO 2019/094778 A1 | 5/2019 |
| WO | WO-2019099552 A1 * | 5/2019 |
| WO | WO 2020/012164 A1 | 1/2020 |
| WO | WO 2020/069339 A1 | 4/2020 |
| WO | WO 2020/069373 A1 | 4/2020 |
| WO | WO 2021/183825 A1 | 9/2021 |
| WO | WO 2021/183946 A1 | 9/2021 |
| WO | WO 2022/232327 A2 | 11/2022 |
| WO | WO 2023/004367 A2 | 1/2023 |
| WO | WO 2023/196851 A1 | 10/2023 |

OTHER PUBLICATIONS

Kim, C. H., Oh, Y., & Lee, T. H. (1997). Codon optimization for high-level expression of human erythropoietin (EPO) in mammalian cells. Gene, 199(1-2), 293-301. (Year: 1997).*

International Search Report and Written Opinion for Application No. PCT/US2019/053545, mailed Dec. 19, 2019.

International Preliminary Report on Patentability for Application No. PCT/US2019/053545, mailed Apr. 8, 2021.

International Search Report and Written Opinion for Application No. PCT/US2019/053492, mailed Feb. 2, 2020.

International Preliminary Report on Patentability for Application No. PCT/US2019/053492, mailed Apr. 8, 2021.

No Author Listed, Tet-On® 3G Inducible Expression System. Clontech Laboratories, Inc. 8 pages.

Agha-Mohammadi et al., Second-generation tetracycline-regulatable promoter: repositioned tet operator elements optimize transactivator synergy while shorter minimal promoter offers tight basal leakiness. J Gene Med. Jul. 2004;6(7):817-28. doi: 10.1002/jgm.566.

Aida et al., Cloning-free CRISPR/Cas system facilitates functional cassette knock-in in mice. Genome Biol. Apr. 29, 2015;16(1):87. doi: 10.1186/s13059-015-0653-x.

Alaei et al., An improved reprogrammable mouse model harbouring the reverse tetracycline-controlled transcriptional transactivator 3. Stem Cell Res. Jul. 2016;17(1):49-53. doi: 10.1016/j.scr.2016.05.008. Epub May 25, 2016.

Azte et al., Selecting the optimal Tet-On system for doxycycline-inducible gene expression in transiently transfected and stably transduced mammalian cells. Biotechnol J. Jan. 2016;11(1):71-9. doi: 10.1002/biot.201500236. Epub Sep. 24, 2015.

Bar-Nur et al., Small molecules facilitate rapid and synchronous iPSC generation. Nat Methods. Nov. 2014;11(11):1170-6. doi: 10.1038/nmeth.3142. Epub Sep. 24, 2014.

Baron et al., Tet repressor-based system for regulated gene expression in eukaryotic cells: principles and advances. Methods Enzymol. 2000;327:401-21. doi: 10.1016/s0076-6879(00)27292-3.

Bussian et al., Clearance of senescent glial cells prevents tau-dependent pathology and cognitive decline. Nature. Oct. 2018;562(7728):578-582. doi: 10.1038/s41586-018-0543-y. Epub Sep. 19, 2018.

Carey et al., Reprogramming of murine and human somatic cells using a single polycistronic vector. Proc Natl Acad Sci U S A. Jan. 6, 2009;106(1):157-62. doi: 10.1073/pnas.0811426106. Epub Dec. 24, 2008.

Cho et al., Generation of transgenic mice. Curr Protoc Cell Biol. Mar. 2009;Chapter 19:Unit 19.11. doi: 10.1002/0471143030.cb1911s42.

Danke et al., Adjusting transgene expression levels in lymphocytes with a set of inducible promoters. J Gene Med. Jun. 2010;12(6):501-15. doi: 10.1002/jgm.1461.

Das et al., Selecting the optimal Tet-On system for doxycycline-inducible gene expression in transiently transfected and stably transduced mammalian cells. Biotechnol J. Jan. 2016;11(1):71-9. doi: 10.1002/biot.201500236. Epub Sep. 24, 2015.

Doench et al., Optimized sgRNA design to maximize activity and minimize off-target effects of CRISPR-Cas9. Nat Biotechnol. Feb. 2016;34(2):184-191. doi: 10.1038/nbt.3437. Epub Jan. 18, 2016.

Dong et al., Poly(glycoamidoamine) Brushes Formulated Nanomaterials for Systemic siRNA and mRNA Delivery in Vivo. Nano Lett. Feb. 10, 2016;16(2):842-8. doi: 10.1021/acs.nanolett.5b02428. Epub Jan. 13, 2016.

Gossen et al., Transcriptional activation by tetracyclines in mammalian cells. Science. Jun. 23, 1995;268(5218):1766-9. doi: 10.1126/science.7792603.

Hsu et al., Development and applications of CRISPR-Cas9 for genome engineering. Cell. Jun. 5, 2014;157(6):1262-1278. doi: 10.1016/j.cell.2014.05.010.

Jiang et al., Tetracycline-regulated gene expression mediated by a novel chimeric repressor that recruits histone deacetylases in mammalian cells. J Biol Chem. Nov. 30, 2001;276(48):45168-74.

Lozano-Torres et al., An OFF-ON Two-Photon Fluorescent Probe for Tracking Cell Senescence in Vivo. J Am Chem Soc. Jul. 5, 2017;139(26):8808-8811. doi: 10.1021/jacs.7b04985. Epub Jun. 23, 2017.

Manukyan et al., Epigenome rejuvenation: HP1β mobility as a measure of pluripotent and senescent chromatin ground states. Sci Rep. Apr. 25, 2014;4:4789. doi: 10.1038/srep04789.

Moreira et al., Assessing Executive Dysfunction in Neurodegenerative Disorders: A Critical Review of Brief Neuropsychological Tools. Front Aging Neurosci. Nov. 9, 2017;9:369. doi: 10.3389/fnagi.2017.00369. eCollection 2017.

Nehlin et al., The Werner syndrome. A model for the study of human aging. Ann N Y Acad Sci. Jun. 2000;908:167-79. doi: 10.1111/j.1749-6632.2000.tb06645.x.

Ocampo et al., In Vivo Amelioration of Age-Associated Hallmarks by Partial Reprogramming. Cell. Dec. 15, 2016;167(7):1719-1733.e12. doi: 10.1016/j.cell.2016.11.052.

O'Connor et al., Genetic medicines: treatment strategies for hereditary disorders. Nat Rev Genet. Apr. 2006;7(4):261-76. doi: 10.1038/nrg1829.

Ramamoorth et al., Non viral vectors in gene therapy—an overview. J Clin Diagn Res. Jan. 2015;9(1):GE01-6. doi: 10.7860/JCDR/2015/10443.5394. Epub Jan. 1, 2015.

Roney et al., Improvement of the reverse tetracycline transactivator by single amino acid substitutions that reduce leaky target gene expression to undetectable levels. Sci Rep. Jun. 21, 2016;6:27697. doi: 10.1038/srep27697.

Sander et al., CRISPR-Cas systems for editing, regulating and targeting genomes. Nat Biotechnol. Apr. 2014;32(4):347-55. doi: 10.1038/nbt.2842. Epub Mar. 2, 2014.

Sarin et al., Inhibition of acquired immunodeficiency syndrome virus by oligodeoxynucleoside methylphosphonates. Proc Natl Acad Sci USA. Oct. 1988;85(20):7448-51. Doi 10.1073/pnas.85.20.7448.

Senis et al, AAV vector-mediated in vivo reprogramming into pluripotency. Nat Commun. Jul. 9, 2018;9(1):2651. doi: 10.1038/s41467-018-05059-x.

Smalley, First AAV gene therapy poised for landmark approval. Nat Biotechnol. Nov. 9, 2017;35(11):998-999. doi: 10.1038/nbt1117-998.

Tammam et al., Nuclear delivery of recombinant OCT4 by chitosan nanoparticles for transgene-free generation of protein-induced pluripotent stem cells. Oncotarget. Jun. 21, 2016;7(25):37728-37739. doi: 10.18632/oncotarget.9276.

(56)                   References Cited

OTHER PUBLICATIONS

Tyner et al., p53 mutant mice that display early ageing-associated phenotypes. Nature. Jan. 3, 2002;415(6867):45-53. doi: 10.1038/415045a.

Wang et al., Spatiotemporal control of gene expression by a light-switchable transgene system. Nat Methods. Feb. 12, 2012;9(3):266-9. doi: 10.1038/nmeth.1892.

Wright et al., Identification of factors that contribute to recombinant AAV2 particle aggregation and methods to prevent its occurrence during vector purification and formulation. Mol Ther. Jul. 2005;12(1):171-8. doi: 10.1016/j.ymthe.2005.02.021.

Yilmazer et al., In vivo cell reprogramming towards pluripotency by virus-free overexpression of defined factors. PLoS One. 2013;8(1):e54754. doi: 10.1371/journal.pone.0054754. Epub Jan. 23, 2013.

Zahid et al., Protein transduction domains: applications for molecular medicine. Curr Gene Ther. Oct. 2012;12(5):374-80. doi: 10.2174/156652312802762527.

Zhao et al., A coumermycin/novobiocin-regulated gene expression system. Hum Gene Ther. Nov. 20, 2003;14(17):1619-29. doi: 10.1089/104303403322542266.

Zhou et al., Generation of induced pluripotent stem cells using recombinant proteins. Cell Stem Cell. May 8, 2009;4(5):381-4. doi: 10.1016/j.stem.2009.04.005. Epub Apr. 23, 2009.

Zhou et al., Optimization of the Tet-On system for regulated gene expression through viral evolution. Gene Ther. Oct. 2006;13(19):1382-90. doi: 10.1038/sj.gt.3302780. Epub May 25, 2006.

International Search Report and Written Opinion for Application No. PCT/US2023/065374, mailed Jun. 6, 2023.

Chtarto et al., A regulatable AAV vector mediating GDNF biological effects at clinically-approved sub-antimicrobial doxycycline doses. Mol Ther Methods Clin Dev. Mar. 30, 2016:5:16027. doi: 10.1038/mtm.2016.27. eCollection 2016.

Das et al., Tet-On Systems for Doxycycline-inducible Gene Expression. Curr Gene Ther. 2016;16(3):156-67. doi: 10.2174/1566523216666160524144041.

Gill et al., Multi-omic rejuvenation of human cells by maturation phase transient reprogramming. Elife. Apr. 8, 2022:11:e71624. doi: 10.7554/eLife.71624.

Gossen et al., Tight control of gene expression in mammalian cells by tetracycline-responsive promoters. Proc Natl Acad Sci U S A. Jun. 15, 1992;89(12):5547-51. doi: 10.1073/pnas.89.12.5547.

Heinz et al., Retroviral and transposon-based tet-regulated all-in-one vectors with reduced background expression and improved dynamic range. Hum Gene Ther. Feb. 2011;22(2):166-76. doi: 10.1089/hum.2010.099. Epub Dec. 19, 2010.

Hishida et al., In vivo partial cellular reprogramming enhances liver plasticity and regeneration. Cell Rep. Apr. 26, 2022;39(4):110730. doi: 10.1016/j.celrep.2022.110730.

Hosoda et al., Development of a tightly-regulated tetracycline-dependent transcriptional activator and repressor co-expression system for the strong induction of transgene expression. Cytotechnology. May 2011;63(3):211-6. doi: 10.1007/s10616-011-9335-z. Epub Feb. 20, 2011.

Karg et al., Sustained vision recovery by OSK gene therapy in a mouse model of glaucoma. Cell Reprogram. Dec. 2023;25(6):288-299. doi: 10.1089/cell.2023.0074. Epub Dec. 7, 2023.

Loew et al., Improved Tet-responsive promoters with minimized background expression. BMC Biotechnol. Nov. 24, 2010:10:81. doi: 10.1186/1472-6750-10-81.

Lu et al., Reprogramming to recover youthful epigenetic information and restore vision. Nature. Dec. 2020;588(7836):124-129. doi: 10.1038/s41586-020-2975-4. Epub Dec. 2, 2020. with Supplementary Information. 35 pages.

Michalon et al., Inducible and neuron-specific gene expression in the adult mouse brain with the rtTA2S-M2 system. Genesis. Dec. 2005;43(4):205-12. doi: 10.1002/gene.20175.

No Author Listed, Tet-On® 3G Inducible Expression Systems User Manual. Clonetech Laboratories, Inc. 2014. 24 pages. Published online at takarabio.com.

No Author Listed, Tet-One technology overview. Takara Bio USA, Inc. Accessed at: https://www.takarabio.com/learning-centers/gene-function/inducible-systems/tet-inducible-systems/tet-one-technology-overview. Last accessed: May 15, 2024. 3 pages.

Pico et al., Comparative analysis of mouse strains for in vivo reprogramming. bioRxiv. Mar. 8, 2024. 32 pages. https://doi.org/10.1101/2024.03.08.584074.

Randolph et al., An all-in-one, Tet-On 3G inducible PiggyBac system for human pluripotent stem cells and derivatives. Sci Rep. May 8, 2017;7(1):1549. doi: 10.1038/s41598-017-01684-6.

Sheng et al., Generation and characterization of a Tet-On (rtTA-M2) transgenic rat. BMC Dev Biol. Feb. 16, 2010:10:17. doi: 10.1186/1471-213X-10-17.

Takahashi et al., Induction of pluripotent stem cells from adult human fibroblasts by defined factors. Cell. Nov. 30, 2007;131(5):861-72. doi: 10.1016/j.cell.2007.11.019.

Takahashi et al., Induction of pluripotent stem cells from mouse embryonic and adult fibroblast cultures by defined factors. Cell. Aug. 25, 2006;126(4):663-76. doi: 10.1016/j.cell.2006.07.024. Epub Aug. 10, 2006.

Zhang et al., Reducing Background Expression of Target Gene with tTS/rtTA System in Cell Model. Journal of Sun Yat-Sen University (Medical Sciences). Jul. 30, 2006; 27(4): 361-364.

Zhu et al., Silencing and un-silencing of tetracycline-controlled genes in neurons. PLoS One. Jun. 20, 2007;2(6):e533. doi: 10.1371/journal.pone.0000533.

Lamartina et al., Construction of an rtTA2(s)-m2/tts(kid)-based transcription regulatory switch that displays No. basal activity, good inducibility, and high responsiveness to doxycycline in mice and non-human primates. Mol Ther. Feb. 2003;7(2):271-80. doi: 10.1016/s1525-0016(02)00051-5.

Uchida et al., Tight regulation of transgene expression by tetracycline-dependent activator and repressor in brain. Genes Brain Behav. Feb. 2006;5(1):96-106. doi: 10.1111/j.1601-183X.2005.00139.x.

Urlinger et al., Exploring the sequence space for tetracycline-dependent transcriptional activators: novel mutations yield expanded range and sensitivity. Proc Natl Acad Sci U S A. Jul. 5, 2000;97(14):7963-8. doi: 10.1073/pnas.130192197.

Yao et al., Systemic and localized reversible regulation of transgene expression by tetracycline with tetR-mediated transcription repression switch. J Surg Res. Apr. 2007;138(2):267-74. doi: 10.1016/j.jss.2006.05.007. Epub Jan. 24, 2007.

U.S. Appl. No. 18/854,506, filed Oct. 4, 2024, Sinclair et al.

International Preliminary Report on Patentability for Application No. PCT/US2023/065374, mailed Oct. 17, 2024.

[No Author Listed], *Homo sapiens* tet methylcytosine dioxygenase 3 (TET3), transcript variant 2, mRNA. NCBI Ref Seq No. NM_001366022.1. Sep. 20, 2018. Accessible at https://www.ncbi.nlm.nih.gov/nuccore/1478050930?sat=47&satkey=7913.

[No Author Listed], Optic Nerve Crush. EYECRO. 2024. Accessed at: https://eyecro.com/models/optic-nerve-crush/. [last accessed: Sep. 18, 2024].

Bareyre et al., In vivo imaging reveals a phase-specific role of STAT3 during central and peripheral nervous system axon regeneration. Proc Natl Acad Sci USA. Apr. 12, 2011;108(15):6282-7. doi: 10.1073/pnas.1015239108. Epub Mar. 29, 2011.

Bekris et al., The Genetics of Parkinson's Disease. J Geriatr Psychiatry Neurol. Dec. 2010;23(4):228-42. doi: 10.1177/0891988710383572. Epub Oct. 11, 2010.

Brennan et al., Ocular Salvage and Vision Preservation Using a Topotecan-Based Regimen for Advanced Intraocular Retinoblastoma. J Clin Oncol. Jan. 2017;35(1):72-77. doi: 10.1200/JCO.2016.69.2996. Epub Oct. 31, 2016.

Cameron et al., Optic Nerve Crush in Mice to Study Retinal Ganglion Cell Survival and Regeneration. Bio Protoc. Mar. 20, 2020;10(6):e3559. doi: 10.21769/BioProtoc.3559.

Chan et al., Engineered AAVs for efficient noninvasive gene delivery to the central and peripheral nervous systems. Nat Neurosci. Author manuscript; available in PMC: Dec. 26, 2017. Published in final edited form as: Nat Neurosci. Jun. 26, 2017;20(8):1172-1179. doi: 10.1038/nn.4593.

(56)        References Cited

OTHER PUBLICATIONS

Chtarto et al., Tetracycline-inducible transgene expression mediated by a single AAV vector. Gene Ther. Jan. 2003;10(1):84-94. doi: 10.1038/sj.gt.3301838.

Ellis et al., A survey of ex vivo/in vitro transduction efficiency of mammalian primary cells and cell lines with Nine natural adeno-associated virus (AAV1-9) and one engineered adeno-associated virus serotype. Virol J. Mar. 6, 2013;10:74. doi: 10.1186/1743-422X-10-74.

Fan et al., Transient, Inducible, Placenta-Specific Gene Expression in Mice. Endocrinology. Nov. 2012;153(11):5637-44. doi: 10.1210/en.2012-1556. Epub Sep. 25, 2012.

Fardi et al., Epigenetic mechanisms as a new approach in cancer treatment: An updated review. Genes Dis. Jun. 18, 2018;5(4):304-311. doi: 10.1016/j.gendis.2018.06.003. eCollection Dec. 2018.

Gjoneska et al., Conserved epigenomic signals in mice and humans reveal immune basis of Alzheimer's disease. Nature. Feb. 19, 2015;518(7539):365-9. doi: 10.1038/nature14252.

Goertsen et al., AAV capsid variants with brain-wide transgene expression and decreased liver targeting after intravenous delivery in mouse and marmoset. Nat Neurosci. Jan. 2022;25(1):106-115. doi: 10.1038/s41593-021-00969-4. Epub Dec. 9, 2021.

Hager et al., An internal polyadenylation signal substantially increases expression levels of lentivirus-delivered transgenes but has the potential to reduce viral titer in a promoter-dependent manner. Hum Gene Ther. Aug. 2008;19(8):840-50. doi: 10.1089/hum.2007.165.

Khalilpour et al., Ischemic optic neuropathy as a model of neurodegenerative disorder: A review of pathogenic mechanism of axonal degeneration and the role of neuroprotection. J Neurol Sci. Apr. 15, 2017;375:430-441. doi: 10.1016/j.jns.2016.12.044. Epub Dec. 26, 2016.

Krolak et al., A High-Efficiency AAV for Endothelial Cell Transduction Throughout the Central Nervous System. Nat Cardiovasc Res. Author manuscript; available in PMC: Oct. 13, 2022. Published in final edited form as: Nat Cardiovasc Res. Apr. 13, 2022;1(4):389-400. doi: 10.1038/s44161-022-00046-4.

Lambert et al., Towards a Microbead Occlusion Model of Glaucoma for a Non-Human Primate. Sci Rep. Aug. 9, 2019;9(1):11572. doi: 10.1038/s41598-019-48054-y.

Li et al., Epigenetics and Common Ophthalmic Diseases. Yale J Biol Med. Dec. 23, 2016;89(4):597-600. eCollection Dec. 2016.

Li et al., Production of Lentiviral Vectors for Transducing Cells from the Central Nervous System. J Vis Exp. May 24, 2012;(63):e4031. doi: 10.3791/4031.

Mahmoudi et al., Old fibroblasts secrete inflammatory cytokines that drive variability in reprogramming efficiency and may affect wound healing between old individuals. Biorxiv. Oct. 19, 2018. doi: https://doi.org/10.1101/448431.

Mathiesen et al., CNS Transduction Benefits of AAV-PHP.eB over AAV9 Are Dependent on Administration Route and Mouse Strain. Mol Ther Methods Clin Dev. Oct. 20, 2020:19:447-458. doi: 10.1016/j.omtm.2020.10.011. eCollection Dec. 11, 2020.

Mertens et al., Directly Reprogrammed Human Neurons Retain Aging-Associated Transcriptomic Signatures and Reveal Age-Related Nucleocytoplasmic Defects. Cell Stem Cell. Dec. 3, 2015;17(6):705-718. doi: 10.1016/j.stem.2015.09.001. Epub Oct. 8, 2015.

Nakagawa et al., Generation of induced pluripotent stem cells without Myc from mouse and human fibroblasts. Nat Biotechnol. Jan. 2008;26(1):101-6. doi: 10.1038/nbt1374. Epub Nov. 30, 2007.

Olova et al., Partial reprogramming induces a steady decline in epigenetic age before loss of somatic identity. Aging Cell. Feb. 2019;18(1):e12877. doi: 10.1111/acel.12877. Epub Nov. 18, 2018.

Reichmuth et al., mRNA vaccine delivery using lipid nanoparticles. Ther Deliv. 2016;7(5):319-34. doi: 10.4155/tde-2016-0006.

Shannon, A Mathematical Theory of Communication. The Bell System Technical Journal. 1948; 1: 379-423. https://doi.org/10.1002/j.1538-7305.1948.tb01338.x.

Wang et al., 2A self-cleaving peptide-based multi-gene expression system in the silkworm Bombyx mori. Sci Rep. Nov. 5, 2015:5:16273. doi: 10.1038/srep16273.

Abad et al., Reprogramming in vivo produces teratomas and iPS cells with totipotency features. Nature. Oct. 17, 2013;502(7471):340-5. doi: 10.1038/nature12586. Epub Sep. 11, 2013.

Hansson et al., Highly coordinated proteome dynamics during reprogramming of somatic cells to pluripotency. Cell Rep. Dec. 27, 2012;2(6):1579-92. doi: 10.1016/j.celrep.2012.10.014.

Karg et al., Partial epigenetic reprogramming of RPE cells reverses age and rejuvenates mitochondrial metabolism. Investigative Ophthalmology & Visual Science. Jun. 2023; 64(8): 2966. ARVO Annual Meeting Abstract.

Ksander et al., Epigenetic reprogramming-A novel gene therapy that restores vision loss in a nonhuman primate model of NAION. Investigative Ophthalmology & Visual Science. Jun. 2023; 64(8): 474. ARVO Annual Meeting Abstract.

Kurian et al., Conversion of human fibroblasts to angioblast-like progenitor cells. Nat Methods. Jan. 2013;10(1):77-83. doi: 10.1038/nmeth.2255. Epub Dec. 2, 2012.

Ohnishi et al., Premature termination of reprogramming in vivo leads to cancer development through altered epigenetic regulation. Cell. Feb. 13, 2014;156(4):663-77. doi: 10.1016/j.cell.2014.01.005.

Polo et al., A molecular roadmap of reprogramming somatic cells into iPS cells. Cell. Dec. 21, 2012;151(7):1617-32. doi: 10.1016/j.cell.2012.11.039.

Roux et al., Diverse partial reprogramming strategies restore youthful gene expression and transiently suppress cell identity. Cell Syst. Jul. 20, 2022;13(7):574-587.e11. doi: 10.1016/j.cels.2022.05.002. Epub Jun. 10, 2022.

Roux et al., Partial reprogramming restores youthful gene expression through transient suppression of cell identity. bioRxiv. May 23, 2021. DOI: 10.1101/2021.05.21.444556.

Sahu et al., Targeted partial reprogramming of age-associated cell states improves markers of health in mouse models of aging. Sci Transl Med. Sep. 11, 2024;16(764):eadg1777. doi: 10.1126/scitranslmed.adg1777. Epub Sep. 11, 2024.

Soldner et al., Parkinson's disease patient-derived induced pluripotent stem cells free of viral reprogramming factors. Cell. Mar. 6, 2009;136(5):964-77. doi: 10.1016/j.cell.2009.02.013.

Sun et al., Tetracycline-inducible expression systems: new strategies and practices in the transgenic mouse modeling. Acta Biochim Biophys Sin (Shanghai). Apr. 2007;39(4):235-46. doi: 10.1111/j.1745-7270.2007.00258.x.

Thier et al., Direct conversion of fibroblasts into stably expandable neural stem cells. Cell Stem Cell. Apr. 6, 2012;10(4):473-9. doi: 10.1016/j.stem.2012.03.003. Epub Mar. 22, 2012.

Vivien et al., Non-viral expression of mouse Oct4, Sox2, and Klf4 transcription factors efficiently reprograms tadpole muscle fibers in vivo. J Biol Chem. Mar. 2, 2012;287(10):7427-35. doi: 10.1074/jbc.M111.324368. Epub Jan. 9, 2012.

U.S. Appl. No. 18/318,566, filed May 16, 2023, Sinclair et al.

U.S. Appl. No. 18/583,191, filed Feb. 21, 2024, Sinclair et al.

U.S. Appl. No. 18/583,147, filed Feb. 21, 2024, Sinclair et al.

* cited by examiner

RYBxO8mRbwMFOFCf7oNIW1BYMn0.1517864547939.2 h4/WfaYUZUO1YMa++1ncGxqKVrM.1432319569769.0

BsrDI (371)

AlwNI (910)

1000

AflIII - PciI (1319)

EcoRI (1893)

SacII (1936)

AfeI (1961)

2000

BbsI (2487)

EcoO109I - KflI - PpuMI (2619)

ZraI (2748)

AatII (2750)

AarI (2796)

AvrII (2842)

AflIII (2942)

EagI - NotI (3120)

XcmI (3145)

PflMI (3238)

BstXI (3422)

PaeR7I - XhoI (3476)

Extracted region from rtTA4

PasI (3562)

HincII - HpaI (4259)

MfeI (4268)

BsmI (4273)

BamHI (4329)

BsaBI* (4347)

4000

NgoMIV (4839)

NaeI (4841)

5000

XmnI (5488)

TatI (5605)

ScaI (5607)

pBR322_origin

CGG

ITR hubC_promoter

3000 pAAV-UBC-rtTA4-WPRE3-SV40pA 5657 bp

5'  TTATGCAGTGCTGCCATAACCATGAGTGATAACACTGCGGCCAACTTACTTCTGACAACGATCGGAGGACCGAAGGAGCTAACCG

···  +++++++++++++++++++++++++++++++++++++++++++++++++++++++++++++++++++++++++++++++++++++++  85

3'  AATACGTCACGACGGTATTGGTACTCACTATTGTGACGCCGGTTGAATGAAGACTGTTGCTAGCCTCCTGGCTTCCTCGATTGGC

CTTTTTTGCACAACATGGGGGATCATGTAACTCGCCTTGATCGTTGGGAACCGGAGCTGAATGAAGCCATACCAAACGACGAGCG

+++++++++++++++++++++++++++++++++++++++++++++++++++++++++++++++++++++++++++++++++++++++  170

GAAAAAACGTGTTGTACCCCCTAGTACATTGAGCGGAACTAGCAACCCTTGGCCTCGACTTACTTCGGTATGGTTTGCTGCTCGC

TGACACCACGATGCCTGTAGTAATGGTAACAACGTTGCGCAAACTATTAACTGGCGAACTACTTACTCTAGCTTCCCGGCAACAA

+++++++++++++++++++++++++++++++++++++++++++++++++++++++++++++++++++++++++++++++++++++++  255

ACTGTGGTGCTACGGACATCATTACCATTGTTGCAACGCGTTTGATAATTGACCGCTTGATGAATGAGATCGAAGGGCCGTTGTT

TTAATAGACTGGATGGAGGCGGATAAAGTTGCAGGACCACTTCTGCGCTCGGCCCCTTCCGGCTGGCTGGTTTATTGCTGATAAAT

+++++++++++++++++++++++++++++++++++++++++++++++++++++++++++++++++++++++++++++++++++++++  340

AATTATCTGACCTACCTCCGCCTATTTCAACGTCCTGGTGAAGACGCGAGCCGGGAAGGCCGACCGACCAAATAACGACTATTTA

BsrDI

CTGGAGCCGGTGAGCGTGGGTCTCGCGGTATCATTGCAGCACTGGGGCCAGATGGTAAGCCCTCCCGTATCGTAGTTATCTACAC

+++++++++++++++++++++++++++++++++++++++++++++++++++++++++++++++++++++++++++++++++++++++  425

GACCTCGGCCACTCGCACCCAGAGCGCCATAGTAACGTCGTGACCCCGGTCTACCATTCGGGAGGGCATAGCATCAATAGATGTG

GACGGGGAGTCAGGCAACTATGGATGAACGAAATAGACAGATCGCTGAGATAGGTGCCTCACTGATTAAGCATTGGTAACTGTCA

+++++++++++++++++++++++++++++++++++++++++++++++++++++++++++++++++++++++++++++++++++++++  510

CTGCCCCTCAGTCCGTTGATACCTACTTGCTTTATCTGTCTAGCGACTCTATCCACGGAGTGACTAATTCGTAACCATTGACAGT

GACCAAGTTTACTCATATATACTTTAGATTGATTTAAAACTTCATTTTTAATTTAAAAGGATCTAGGTGAAGATCCTTTTTGATA

+++++++++++++++++++++++++++++++++++++++++++++++++++++++++++++++++++++++++++++++++++++++  595

CTGGTTCAAATGAGTATATATGAAATCTAACTAAATTTTGAAGTAAAAATTAAATTTTCCTAGATCCACTTCTAGGAAAAACTAT

ATCTCATGACCAAAATCCCTTAACGTGAGTTTTCGTTCCACTGAGCGTCAGACCCCGTAGAAAAGATCAAAGGATCTTCTTGAGA

+++++++++++++++++++++++++++++++++++++++++++++++++++++++++++++++++++++++++++++++++++++++  680

TAGAGTACTGGTTTTAGGGAATTGCACTCAAAAGCAAGGTGACTCGCAGTCTGGGGCATCTTTTTCTAGTTTCCTAGAAGAACTCT pBR322_origin  >

FIG. 2A

| Feature | Location | Size | | | Type |
|---|---|---|---|---|---|
| pBR322_origin | 659 .. 1278 | 620 bp | | → | rep_origin |
| /direction    = RIGHT | | | | | |
| CGG | 1308 .. 1310 | 3 bp | | ⊢⊣ | misc_feature |
| ITR | 1692 .. 1832 | 141 bp | | → | repeat_region |
| RYBxO8mRbwMFOFCf7oNIW1BY... | 1894 .. 3065 | 1172 bp | | → | misc_feature |
| h4/WfaYUZUO1YMa++1ncGxqKV... | 1900 .. 1900 | 1 bp | | → | misc_feature |
| hUbC_promoter | 1901 .. 3115 | 1215 bp | | → | promoter |
| forward | 1901 .. 1915 | 15 bp | | → | primer_bind |
| seq-primer | 2980 .. 2999 | 20 bp | | → | primer_bind |
| RYBxO8mRbwMFOFCf7oNIW1BY... | 3066 .. 3120 | 55 bp | | → | misc_feature |
| reverse | 3091 .. 3115 | 25 bp | | → | primer_bind |
| Extracted region from rtTA4 | 3121 .. 3887 | 767 bp | | → | misc_feature |
| rtTA4 | 3140 .. 3886 | 747 bp | | → | gene |
| RYBxO8mRbwMFOFCf7oNIW1BY... | 3886 .. 7550 | 3663 bp | | → | misc_feature |
| Extracted region from PlateA-Sam... | 3892 .. 3896 | 5 bp | | → | misc_feature |
| WPRE3 | 3898 .. 4145 | 248 bp | | → | polyA_signal |
| Fwd-qPCR-2 | 3982 .. 4007 | 26 bp | | → | primer_bind |
| Probe | 4010 .. 4038 | 29 bp | | → | misc_feature |
| Rev-qPCR-2 | 4051 .. 4070 | 20 bp | | → | primer_bind |
| SV40 Late poly A | 4192 .. 4325 | 134 bp | | → | polyA_signal |
| Reverse | 4300 .. 4327 | 28 bp | | ← | misc_feature |
| ITR 3' | 4408 .. 4547 | 140 bp | | → | misc_feature |
| f1_origin | 4731 .. 5037 | 307 bp | | → | rep_origin |
| /direction    = RIGHT | | | | | |
| AmpR | 5301 .. 6161 | 861 bp | | → | misc_feature |

FIG. 3

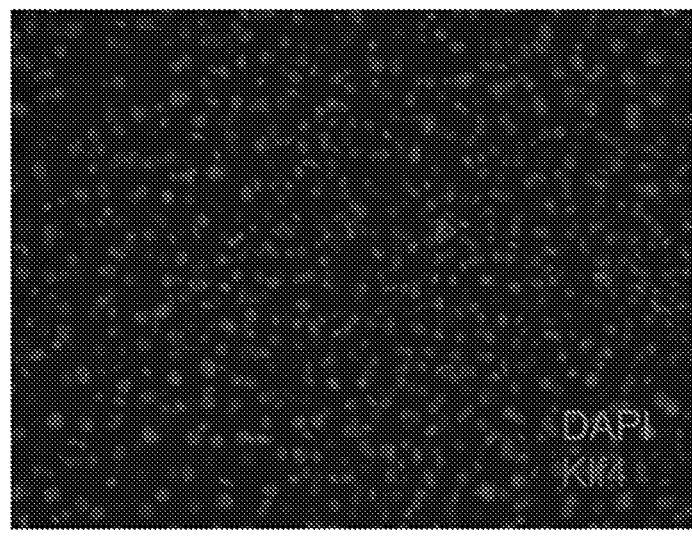
rtTA4 TRE-OSK no DOX
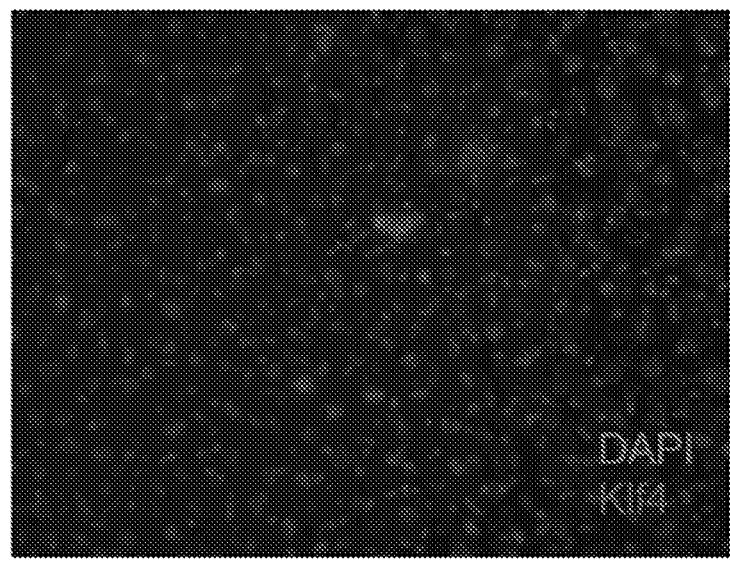
rtTA4 TRE-OSK with DOX
FIG. 8A

MUTANT REVERSE TETRACYCLINE TRANSACTIVATORS FOR EXPRESSION OF GENES

RELATED APPLICATIONS

This application is a national stage filing under 35 U.S.C. § 371 of international PCT application number PCT/US2019/053492, filed Sep. 27, 2019, which claims the benefit under 35 U.S.C. § 119 (e) of U.S. provisional application No. 62/738,894, filed Sep. 28, 2018, each of which is incorporated by reference herein in its entirety.

REFERENCE TO AN ELECTRONIC SEQUENCE LISTING

The contents of the electronic sequence listing (H082470300US01-SUBSEQ-FL.txt; Size: 101,807 bytes; and Date of Creation: Apr. 19, 2024) is herein incorporated by reference in its entirety.

BACKGROUND OF THE INVENTION

Inducible gene expression holds great promise for gene therapy and other biomedical applications. On-demand and tightly regulated gene expression can obviate toxicity associated with prolonged expression or toxicity associated with super physiological expression of exogenous genes.

As an example, tetracycline-on (Tet-On) systems often use a reverse tetracycline transactivator (rtTA) to induce gene expression. Reverse tetracycline transactivators (rt-TAs) comprise a mutant tetracycline repressor DNA binding protein (TetR) and a transactivation domain (e.g., Gossen et al., Science. 1995 Jun. 23;268 (5218): 1766-9). These trans-activators can be activated in the presence of a tetracycline (e.g., doxycycline) and subsequently bind to promoters comprising a tetracycline-responsive element (TRE) to induce gene expression (Gossen et al., Science. 1995 Jun. 23: 268 (5218): 1766-9); Baron et al., Methods Enzymol. 2000; 327:401-21. A TRE comprises at least one Tet operator (Tet-O) sequence (e.g., multiple repeats of Tet-O sequences) and may be located upstream of a minimal promoter (e.g., minimal promoter sequence derived from the human cytomegalovirus (hCMV) immediate-early promoter).

The tendency of Tet-On systems to turn on gene expression (be "leaky") even in the absence of a tetracycline, however, has hindered their use. Therefore, improved Tet-On systems with little to no leakiness and high tetracycline sensitivity are needed.

SUMMARY OF THE INVENTION

The present disclosure stems from the unexpected discovery that four mutations in the residues corresponding to positions G72, G12, F67, and R171 in rtTA3 (SEQ ID NO: 11) significantly improve the sensitivity and lower the leakiness of Tet-On systems in vivo. Provided herein, in some embodiments, are mutant rtTAs (e.g., rtTA4), engineered nucleic acids (e.g., expression vectors, including viral and non-viral vectors) encoding the same, recombinant viruses (e.g., lentivirus, adenovirus, alphavirus, vaccinia virus, retrovirus, herpes virus, or AAV) comprising the engineered nucleic acids (e.g., expression vectors), pharmaceutical compositions, and kits thereof. In some embodiments, the engineered nucleic acids encoding a mutant rtTA4 further encodes a transgene (e.g., a protein-encoding sequence, a gene-targeting nucleic acid, and/or a therapeutic sequence) operably linked to a tetracycline-responsive element (TRE) promoter. In some embodiments, the pharmaceutical compositions and kits further comprise a second vector (e.g., multiple second vectors) or a second recombinant virus (e.g., multiple second recombinant viruses) (e.g., lentivirus, adenovirus, alphavirus, vaccinia virus, retrovirus, herpes virus, or AAV) that comprises a tetracycline-responsive element (TRE) promoter operably linked to a transgene. In some embodiments, the pharmaceutical compositions and kits further comprise multiple vectors or multiple recombinant viruses (e.g., lentiviruses, vaccinia viruses, alphaviruses, adenoviruses, retroviruses, herpes viruses, or adeno-associated viruses (AAV)) that comprise a tetracycline-responsive element (TRE) promoter operably linked to a transgene. Methods of promoting gene expression comprising administering (1) any of the engineered nucleic acids (e.g., expression vectors) described herein that encode a mutant rtTA (e.g., rtTA4) and (2) tetracycline to a cell, tissue, or subject in need thereof are also provided herein. In certain embodiments, the methods further comprise administering (3) a second nucleic acid (e.g., an engineered nucleic acid, including an expression vector) comprising a TRE promoter operably linked to a transgene. In certain embodiments, multiple second engineered nucleic acids (e.g., expression vectors) are administered.

The mutant rtTAs (e.g., rtTA4s), engineered nucleic acids (e.g., expression vectors), recombinant viruses, pharmaceutical compositions, kits, and methods described herein are useful in regulating gene expression in vivo. Without being bound by a particular theory, the reduction in leakiness improves the toxicity profile of the rtTA4 Tet-On system compared to rtTA3 Tet-On system and allows for transient expression of transgenes.

Aspects of the present disclosure provide mutant rtTAs (e.g., rtTA4). A mutant rtTA of the present disclosure comprises four mutations corresponding to positions G72, G12, F67, and R171 of rtTA3 (SEQ ID NO: 11), and such a mutant rtTA comprising four mutations at these positions is referred to as rtTA4. In certain embodiments, a mutant rtTA further comprises at least one (e.g., at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 80, 90, 100, 110, 120, 130, 140, 150, 160, 170, 180, 190, 200, 210, 220, 230, or 240) mutation in a residue corresponding to a position in rtTA3 (SEQ ID NO: 11) that is not G72, G12, F67, or R171. In certain embodiments, the mutation in a residue corresponding to a position in rtTA3 (SEQ ID NO: 11) that is not positions G72, G12, F67, or R171 is a point mutation, truncation mutation, deletion, or insertion.

In certain embodiments, the G72 mutation is G72V, G72I, G72L, or G72P; the G12 mutation is G12S or G12T; the F67 mutation is F67S or F67T; and the R171 mutation is R171K or R171H.

In certain embodiments, the four mutations are G72V or G72P, G12S, F67S, and R171K. An amino acid sequence encoding mutant rtTA (e.g., rtTA4) may comprise a sequence that is at least 70% (e.g., at least 75%, 80%, 85%, 90%, 95%, 98%, 99%, or 100%) identical to SEQ ID NO: 13 and comprises a mutation in a residue corresponding to the following positions in rtTA3 (SEQ ID NO: 11): G72, G12, F67, and R171. A nucleic acid encoding mutant rtTA (e.g., rtTA4) may be codon optimized and may comprise a sequence that is at least 70% (e.g., at least 75%, 80%, 85%, 90%, 95%, 98%, 99%, or 100%) identical to SEQ ID NO: 12.

In another aspect of the present disclosure, a nucleic acid (e.g., an engineered nucleic acid, including an expression vector) (e.g., viral expression vector, including lentiviral, retroviral, adenoviral, herpes virus, or adeno-associated virus (AAV)) comprises a nucleic acid sequence encoding a mutant rtTA (e.g., rtTA4) operably linked to a promoter (e.g., constitutive or tissue-specific promoter). In certain embodiments, a nucleic acid (e.g., an engineered nucleic acid, including an expression vector) encoding a mutant rtTA (e.g., rtTA4) comprises a sequence that is at least 70% (e.g., at least 75%, 80%, 85%, 90%, 95%, 98%, 99%, or 100%) identical to SEQ ID NO: 17. In certain embodiments, a nucleic acid (e.g., an engineered nucleic acid, including an expression vector) encoding a mutant rtTA (e.g., rtTA4) consists of SEQ ID NO: 17. In certain embodiments, a nucleic acid (e.g., an engineered nucleic acid, including an expression vector) encoding a mutant rtTA (e.g., rtTA4) comprises a sequence that is at least 70% (e.g., at least 75%, 80%, 85%, 90%, 95%, 98%, 99%, or 100%) identical to a desmin-rtTA4 vector (SEQ ID NO: 30). In certain embodiments, a nucleic acid (e.g., an engineered nucleic acid, including an expression vector) encoding a mutant rtTA (e.g., rtTA4) consists of SEQ ID NO: 30.

The promoter operably linked to the nucleic acid encoding a mutant rtTA (e.g., rtTA4) may be a constitutive promoter (e.g., CP1, CMV, EF1a, SV40, PGK1, Ubc, human beta actin, CAG, Ac5, polyhedrin, TEF1, GDS, CaM3 5S, Ubi, H1, or U6 promoter). To allow for tissue-specific expression of artTA, the promoter may be tissue-specific (e.g., an eye-specific promoter, a bone-specific promoter, a lung-specific promoter, a breast-specific promoter, a pancreas-specific promoter, a muscle-specific promoter, a liver-specific promoter, a skin-specific promoter, a heart-specific promoter, a brain-specific promoter, a nerve tissue-specific promoter, a kidney-specific promoter, a testes-specific promoter, an ovary-specific promoter, or an intestine-specific promoter).

In certain embodiments, the nucleic acid (e.g., an engineered nucleic acid, including an expression vector) encoding a mutant rtTA (e.g., rtTA4) further encodes a tetracycline repressor (e.g., tetR, tetRKRAB, TRSID), which can prevent rtTA binding to a TRE promoter in the absence of a tetracycline. In certain embodiments, the nucleic acid sequence encoding a mutant rtTA (e.g., rtTA4) and the nucleic acid sequence encoding a tetracycline repressor (e.g., tetRKRAB) is operably linked to the same promoter. In certain embodiments, a separator sequence (e.g., an internal ribosome entry site (IRES) or 2A peptide) is present in a nucleic acid (e.g., an engineered nucleic acid, including an expression vector) and separates at least two nucleic acid sequences, which may be helpful in producing two separate amino acid sequences from one expression vector.

In certain embodiments, a nucleic acid (e.g., an engineered nucleic acid, including an expression vector) encoding mutant rtTA (e.g., rtTA4) further comprises a Woodchuck Hepatitis Virus (WHP) Posttranscriptional Regulatory Element (WPRE), which may be useful in enhancing transgene expression (e.g., from a viral vector). In certain embodiments, a WPRE sequence is at least 70% (e.g., at least 75%, at least 80%, at least 85%, at least 90%, at least 95%, at least 98%, at least 99%, or at least 100%) identical to SEQ ID NO: 21.

In certain embodiments, the nucleic acid (e.g., an engineered nucleic acid, including an expression vector) encoding a mutant rtTA (e.g., rtTA4) is a viral vector (e.g., lentivirus vector, adenovirus vector, vaccinia viruses, alphviruses, adeno-associated virus vector, adeno-associated virus (AAV) vector, or retrovirus vector). In certain embodiments, an AAV vector is an AAV1, AAV2, AAV3, AAV4, AAV5, AAV6, AAV7, AAV8, AAV9, or AAV10 vector. A viral vector (e.g., AAV vector) may further comprise inverted terminal repeat sequences (ITRs). In certain embodiments, an ITR comprises a sequence that is at least 70% identical to (e.g., at least 75%, at least 80%, at least 85%, at least 90%, at least 95%, at least 98%, at least 99%, or at least 100%) identical to SEQ ID NO: 22.

Another aspect of the present disclosure provides recombinant viruses harboring any engineered nucleic acids (e.g., expression vectors) encoding mutant rtTA (e.g., rtTA4).

In yet another aspect of the present disclosure, pharmaceutical compositions comprising any of the mutant rtTAs (e.g., rtTA4) and a pharmaceutically acceptable excipient are provided. The pharmaceutical composition may further comprise a second nucleic acid (e.g., an engineered nucleic acid, including an expression vector) encoding a transgene. The second nucleic acid (e.g., an engineered nucleic acid, including an expression vector) comprises a tetracycline-responsive element (TRE) promoter (e.g., a TRE3G sequence that is at least 70%, least 75%, at least 80%, at least 85%, at least 90%, at least 95%, at least 98%, at least 99%, or at least 100% identical to SEQ ID NO: 7) operably linked to the transgene. In some embodiments, the TRE promoter is a TRE2 or P tight promoter. In some embodiments, a TRE promoter is a TRE2 promoter and comprises a sequence that is at least 70%, least 75%, at least 80%, at least 85%, at least 90%, at least 95%, at least 98%, at least 99%, or at least 100% identical to SEQ ID NO: 23. In some embodiments, a TRE promoter is a P tight promoter and comprises a sequence that is at least 70%, least 75%, at least 80%, at least 85%, at least 90%, at least 95%, at least 98%, at least 99%, or at least 100% identical to SEQ ID NO: 24.

In certain embodiments, a transgene is any protein-encoding gene. In certain embodiments, a transgene is a gene-targeting nucleic acid. In certain embodiments, a transgene is a therapeutic sequence. In certain embodiments, a therapeutic sequence may be useful in treating acute injuries, neurodegenerative disease, chronic diseases, proliferative diseases, cardiovascular diseases, genetic diseases, inflammatory diseases, autoimmune diseases, neurological diseases, hematological diseases, painful conditions, psychiatric disorders, metabolic disorders, cancers, aging, age-related diseases, and diseases affecting any tissue in a subject.

In certain embodiments, the inducible nucleic acid (e.g., an engineered nucleic acid, including an expression vector) (e.g., viral vector) encodes OCT4, SOX2, and KLF4. See, e.g., the U.S. Provisional Application entitled CELLULAR REPROGRAMMING TO REVERSE AGING AND PROMOTE ORGAN AND TISSUE REGENERATION under U.S. Ser. No. 62/738,922, which was filed on Sep. 28, 2018, U.S. Ser. No. 62/792,283, entitled CELLULAR REPROGRAMMING TO REVERSE AGING AND PROMOTE ORGAN AND TISSUE REGENERATION, filed Jan. 14, 2019, U.S. Ser. No. 62/865,877, entitled CELLULAR REPROGRAMMING TO REVERSE AGING AND PROMOTE ORGAN AND TISSUE REGENERATION filed Jun. 24, 2019, and U.S. Ser. No. 62/880,488, entitled CELLULAR REPROGRAMMING TO REVERSE AGING AND PROMOTE ORGAN AND TISSUE REGENERATION, filed Jul. 30, 2019, and the PCT Application entitled CELLULAR REPROGRAMMING TO REVERSE AGING AND PROMOTE ORGAN AND TISSUE REGENERATION under PCT/US2019/053545, which was filed on the same day as the instant application, each of which is incorporated by reference herein in its entirety In certain embodiments, the nucleic acid (e.g., an engineered nucleic acid, including an expression vector) encoding a mutant rtTA (e.g., rtTA4) and the nucleic acid (e.g., an engineered nucleic acid, including an expression vector) encoding a transgene operably linked to a TRE promoter are both viral vectors and are in viruses (e.g., lentivirus, adenovirus, alphavirus, vaccinia virus, retrovirus, herpes virus, or AAV). In certain embodiments, a pharmaceutical composition comprises both viral vectors and/or both viruses.

In yet another aspect of the present disclosure, cells and/or systems are provided comprising any of the mutant rtTAs (e.g., rtTA4), any of the engineered nucleic acids (e.g., expression vectors) encoding a mutant rtTA and/or a transgene operably linked to a TRE promoter, and/or any of the viruses (e.g., lentivirus, adenovirus, alphavirus, vaccinia virus, retrovirus, herpes virus, or AAV).

In yet another aspect of the present disclosure, kits are provided comprising any of the mutant rtTAs (e.g., rtTA4), any of the engineered nucleic acids (e.g., expression vectors) encoding a mutant rtTA, any of the viruses (e.g., lentivirus, adenovirus, alphavirus, vaccinia virus, retrovirus, herpes virus, or AAV), cells, systems, and/or any of the pharmaceutical compositions described herein.

Another aspect of the present disclosure provides methods for promoting gene expression comprising administering (1) any of the mutant rtTAs (e.g., rtTA4), any of the engineered nucleic acids (e.g., expression vectors) encoding a mutant rtTA (e.g., rtTA4), or a recombinant virus comprising any of the engineered nucleic acids (e.g., expression vectors) encoding a mutant rtTA: (2) any of the engineered nucleic acids (e.g., expression vectors) encoding a transgene operably linked to a TRE promoter; and (3) a tetracycline (e.g., doxycycline) to a cell, tissue, or a subject in need thereof. In certain embodiments, the engineered nucleic acids (e.g., expression vectors) encoding a mutant rtTA or a recombinant virus comprising any of the mutant rtTA expression vectors described herein further encodes a tetracycline repressor (e.g., tetRKRAB). In certain embodiments, a nucleic acid (e.g., an engineered nucleic acid, including an expression vector) encoding a mutant rtTA or a recombinant virus of the present disclosure further comprises a transgene operably linked to a TRE promoter (e.g., TRE3G, a TRE2, or a P tight promoter). The method may further comprise withdrawing (i.e., ceasing the administration of) the tetracycline.

In certain embodiments, the subject is a mammal (e.g., human or non-human). In certain embodiments, the subject has a disease (e.g., an acute injury, a neurodegenerative disease, a chronic disease, a proliferative disease, a cardiovascular disease, a genetic disease, an inflammatory disease, an autoimmune disease, a neurological disease, a hematological disease, a painful condition, a psychiatric disorder, a metabolic disorder, cancer, aging, an age-related disease, and any disease affecting any tissue in a subject). In certain embodiments, the method comprises regulating cellular reprogramming, tissue repair, treating a disease (e.g., an acute injury, a neurodegenerative disease, a chronic disease, a proliferative disease, a cardiovascular disease, a genetic disease, an inflammatory disease, an autoimmune disease, a neurological disease, a hematological disease, a painful condition, a psychiatric disorder, a metabolic disorder, cancer, aging, an age-related disease, and any disease affecting any tissue in a subject), tissue regeneration, organ regeneration, reversing aging, or any combination thereof.

The details of one or more embodiments of the invention are set forth herein. Other features, objects, and advantages of the invention will be apparent from the Detailed Description, Examples, Figures, and Claims.

References cited in this application are incorporated herein by reference.

Definitions

"AAV" or "adeno-associated virus" is a nonenveloped virus that is capable of carrying and delivering nucleic acids (e.g., nucleic acids encoding a transgene, a mutant rtTA4, or any combination thereof) and belongs to the genus Dependoparvovirus. In general, AAV does not integrate into the genome. The tissue-specific targeting capabilities of AAV is often determined by the AAV capsid serotype (see, e.g., Table 1 below for examples of AAV serotypes and their utility in tissue-specific delivery). Non-limiting serotypes of AAV include AAV1, AAV2, AAV3, AAV4, AAV5, AAV6, AAV7, AAV8, AAV9, AAV10, AAV11, and variants thereof. In certain embodiments, the AAV serotype is a variant of AAV9 (e.g., AAV PHP.b).

A "recombinant virus" is a virus (e.g., lentivirus, adenovirus, alphavirus, vaccinia virus, retrovirus, herpes virus, or adeno-associated (AAV)) that has been isolated from its natural environment (e.g., from a host cell, tissue, or a subject) or is artificially produced.

The term "AAV vector," as used herein, is a nucleic acid that comprises AAV inverted terminal repeats (ITRs) flanking an expression cassette (e.g., an expression cassette comprising a nucleic acid encoding a transgene alone or in combination or an expression cassette encoding rtTA or tTA). An AAV vector may further comprise a promoter sequence.

The terms "administer." "administering." or "administration," as used herein refers to introduction of a nucleic acid (e.g., an engineered nucleic acid encoding a transgene and/or encoding a mutant rtTA), a recombinant cell, a recombinant virus (e.g., lentivirus, adenovirus, alphavirus, vaccinia virus, retrovirus, herpes virus, or AAV), a mutant rtTA (e.g., rtTA4), or any combination thereof or a pharmaceutical composition thereof. An engineered nucleic acid, recombinant cell, mutant rtTA4, virus (e.g., lentivirus, adenovirus, alphavirus, vaccinia virus, retrovirus, herpes virus, or AAV), or pharmaceutical compositions thereof may be administered intravenously, intradermally, intraarterially, intralesionally, intratumorally, intracranially, intraarticularly, intraprostaticaly, intrapleurally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, systemically, injection, infusion, continuous infusion, localized perfusion bathing target cells directly, via a catheter, in creams, in lipid compositions (e.g., liposomes), or by other method or any combination of the forgoing as would be known to one of ordinary skill in the art (see, for example, Remington's Pharmaceutical Sciences (1990), incorporated herein by reference). The nucleic acids (e.g., engineered nucleic acids, including expression vectors), recombinant cells, mutant rtTA protein, or recombinant viruses (e.g., lentivirus, adenovirus, alphavirus, vaccinia virus, retrovirus, herpes virus, or AAV) of the present disclosure may be administered to any tissue, cell, organ, or subject.

The term "epigenome" or "epigenetics" refers to the modification and structural changes within a cell that control the expression of nucleic acids (e.g., engineered nucleic acids) or genomic information in a cell. Changes to the epigenome occur during, and drive the processes of embryonic development, disease progression, and aging.

The term "cellular senescence" refers to a cell that has exited the cell cycle, displays epigenetic markers consistent with senescence, or expressing senescence cell markers (e.g. senescence-associated beta-galactosidase, or inflammatory cytokines). Cellular senescence may be partial or complete.

The term "gene expression" refers to the degree to which certain genes or all genes in a cell or tissue are transcribed into RNA. In some instances, the RNA is translated by the cell into a protein. The epigenome dictates gene expression patterns.

The term "cellular reprogramming" refers to the process of altering the epigenome of a cell using reprogramming factors (e.g. reversing or preventing epigenetic changes in cells that are causes of dysfunction, deterioration, cell death, senescence or aging). Cellular reprogramming may be complete reprogramming, such that a differentiated cell (e.g., somatic cell) is reprogrammed to a pluripotent stem cell. Cellular reprogramming may be incomplete, such that a differentiated cell (e.g., somatic cell) retains its cellular identity (e.g., lineage-specific stem cell). Cellular reprogramming may be incomplete, e.g., a stem cell is not created. | such that a cell is rejuvenated, or takes on more youthful attributes (e.g. increased survival, reduced inflammation, or ability to divide). Cellular reprogramming may provide additional cellular functions, or prevent cellular aging (e.g., transdifferentiation, or transition into cellular senescence). Cellular reprogramming may induce temporary or permanent gene expression changes. In some embodiments, incomplete cellular reprogramming is shown by the lack of Nanog expression. In some embodiments, cellular reprogramming prevents senescence from occurring.

The terms "condition," "disease," and "disorder" are used interchangeably. Non-limiting examples of conditions, diseases, and disorders include acute injuries, neurodegenerative disease, chronic diseases, proliferative diseases, cardiovascular diseases, genetic diseases, inflammatory diseases, autoimmune diseases, neurological diseases, hematological diseases, painful conditions, psychiatric disorders, metabolic disorders, cancers, aging, age-related diseases, and diseases affecting any tissue in a subject. For example, age-related conditions include, heart failure, stroke, heart disease, atherosclerosis, neurodegenerative diseases (e.g., Parkinson's disease and Alzheimer's disease), cognitive decline, memory loss, diabetes, osteoporosis, arthritis, muscle loss, hearing loss (partial or total), eye-related conditions (e.g., poor eye sight or retinal disease), glaucoma, and cancer. In certain embodiments, the disease is a retinal disease (e.g., macular degeneration). In some embodiments, an age-related condition is senescence. As a non-limiting example, senescence of glial cells may be a cause of Alzheimer's disease. See e.g., Bussian, et al., Nature. 2018 Sep. 19.

As used herein, an "ocular disease" or "eye disease" is a disease or condition of the eye. Non-limiting examples of conditions that affect the eye include Ectropion, Lagophthalmos, Blepharochalasis, Ptosis, Stye, Xanthelasma, Dermatitis, Demodex, leishmaniasis, loiasis, onchocerciasis, phthiriasis, (herpes simplex), leprosy, molluscum contagiosum, tuberculosis, yaws, zoster, impetigo, Dacryoadenitis, Epiphora, exophthalmos, Conjunctivitis, Scleritis, Keratitis, Corneal ulcer/Corneal abrasion, Snow blindness/Arc eye, Thygeson's superficial punctate keratopathy, Corneal neovascularization, Fuchs' dystrophy, Keratoconus, Keratoconjunctivitis sicca, Iritis, iris, Uveitis, Sympathetic ophthalmia, Cataract, lens, Chorioretinal inflammation, Focal chorioretinal inflammation, chorioretinitis, choroiditis, retinitis, retinochoroiditis, Disseminated chorioretinal inflammation, exudative retinopathy, Posterior cyclitis, Pars planitis, chorioretinal inflammations, Harada's disease, Chorioretinal inflammation, choroid, Chorioretinal scars, Macula scars, posterior pole (postinflammatory) (post-traumatic), Solar retinopathy, Choroidal degeneration, Atrophy, Sclerosis, angioid streaks, choroidal dystrophy, Choroideremia, choroidal, areolar, (peripapillary), Gyrate atrophy, choroid, ornithinaemia, Choroidal haemorrhage, Choroidal haemorrhage, NOS (Not Otherwise Specified), Choroidal detachment, Chorioretinal, Chorioretinal inflammation, infectious and parasitic diseases, Chorioretinitis, syphilitic, toxoplasma, tuberculosis, chorioretinal, Retinal detachment, retina, choroid, distorted vision, Retinoschisis, Hypertensive retinopathy, Diabetic retinopathy, Retinopathy, Retinopathy of prematurity, Age-related macular degeneration, macula, Macular degeneration, Bull's Eye Maculopathy, Epiretinal membrane, Peripheral retinal degeneration, Hereditary retinal dystrophy, Retinitis pigmentosa, Retinal haemorrhage, retinal layers, Central serous retinopathy, Retinal detachment, retinal disorders, Macular edema, macula, Retinal disorder, Diabetic retinopathy, Glaucoma, optic neuropathy, ocular hypertension, open-angle glaucoma, angle-closure glaucoma. Normal Tension glaucoma, open-angle glaucoma, angle-closure glaucoma, Floaters, Leber's hereditary optic neuropathy, Optic disc drusen, Strabismus, Ophthalmoparesis, eye muscles, Progressive external ophthaloplegia, Esotropia, Exotropia, Disorders of refraction, accommodation, Hypermetropia, Myopia, Astigmatism, Anisometropia, Presbyopia, ophthalmoplegia, Amblyopia, Leber's congenital amaurosis, Scotoma, Anopsia, Color blindness, Achromatopsia/Maskun, cone cells, Nyctalopia, Blindness, River blindness, Micropthalmia/coloboma, optic nerve, brain, spinal cord, Red eye, Argyll Robertson pupil, pupils, Keratomycosis, Xerophthalmia, and Aniridia. In some embodiments, the ocular disease is acute or chronic eye injury.

In some embodiments, the ocular disease is a scratched cornea.

In some embodiments, an ocular disease is a corneal disease (e.g., a disease affecting the cornea or corneal cells). In some embodiments, an ocular disease is acanthamoeba keratitis, ectropion, lagoph amblyopia, anisocoria, astigmatism, Bell's Palsy, blepharitis, blurry vision, burning eyes, cataracts, macular degeneration, age-related macular degeneration, diabetic eye disease, glaucoma, dry eye, poor vision (e.g., low vision), astigmatism, blepharitis, cataract, chalazion, conjunctivitis, diabetic retinopathy, dry eye, glaucoma, keratitis, keratonconus, macular degeneration, ocular hypertension, pinquecula, pterygium, retinitis pigmentosa, or ocular cancer (e.g., retinoblastoma, melanoma of the eye, lymphoma of the eye, medulloepithelioma, squamous cell cancer of the conjunctiva). Examples of corneal diseases include, but are not limited to, corneal neovascularization (NV), corneal dystrophy, corneal inflammation, corneal abrasion, and corneal fibrosis. In some embodiments, the ocular disease is Keritaconus. In some embodiments, an ocular disease is macular degeneration. Additional non-limiting examples of eye diseases may be found in the International Statistical Classification of Diseases and Related Health Problems (e.g., VII Diseases of the eye and adnexa).

An ocular disease may affect any part of the eye and/or adnexa. In some embodiments, the ocular disease is a disorder of the eyelid, lacrimal system and/or orbit. In some embodiments, the ocular disease is a disorders of conjunctiva. In some embodiments, the ocular disease is a disorder of sclera, cornea, iris and/or ciliary body. In some embodiments, the ocular disease is a disorder of the lens. In some embodiments, the ocular disease is a disorder of choroid and/or retina. In some embodiments, the ocular disease is glaucoma. In some embodiments, the ocular disease is a disorder of vitreous body and/or globe. In some embodiments, the ocular disease is a disorder of optic nerve and/or visual pathways. In some embodiments, the ocular disease is a disorder of ocular muscles, binocular movement, accommodation and/or refraction. In some embodiments, the ocular disease is ocular muscles, binocular movement, accommodation and refraction. In some embodiments, the ocular disease is a visual disturbance and/or blindness.

The term "genetic disease" refers to a disease caused by one or more abnormalities in the genome of a subject, such as a disease that is present from birth of the subject. Genetic diseases may be heritable and may be passed down from the parents' genes. A genetic disease may also be caused by mutations or changes of the DNAs and/or RNAs of the subject. In such cases, the genetic disease will be heritable if it occurs in the germline. Exemplary genetic diseases include, but are not limited to, Aarskog-Scott syndrome, Aase syndrome, achondroplasia, acrodysostosis, addiction, adreno-leukodystrophy, albinism, ablepharon-macrostomia syndrome, alagille syndrome, alkaptonuria, alpha-1 antitrypsin deficiency, Alport's syndrome, Alzheimer's disease, asthma, autoimmune polyglandular syndrome, androgen insensitivity syndrome, Angelman syndrome, ataxia, ataxia telangiectasia, atherosclerosis, attention deficit hyperactivity disorder (ADHD), autism, baldness, Batten disease, Beckwith-Wiedemann syndrome, Best disease, bipolar disorder, brachydactyl), breast cancer, Burkitt lymphoma, chronic myeloid leukemia, Charcot-Marie-Tooth disease, Crohn's disease, cleft lip, Cockayne syndrome, Coffin Lowry syndrome, colon cancer, congenital adrenal hyperplasia, Cornelia de Lange syndrome, Costello syndrome, Cowden syndrome, craniofrontonasal dysplasia, Crigler-Najjar syndrome, Creutzfeldt-Jakob disease, cystic fibrosis, deafness, depression, diabetes, diastrophic dysplasia, DiGeorge syndrome, Down's syndrome, dyslexia, Duchenne muscular dystrophy, Dubowitz syndrome, ectodermal dysplasia Ellis-van Creveld syndrome, Ehlers-Danlos, epidermolysis bullosa, epilepsy, essential tremor, familial hypercholesterolemia, familial Mediterranean fever, fragile X syndrome, Friedreich's ataxia, Gaucher disease, glaucoma, glucose galactose malabsorption, glutaricaciduria, gyrate atrophy, Goldberg Shprintzen syndrome (velocardiofacial syndrome), Gorlin syndrome, Hailey-Hailey disease, hemihypertrophy, hemochromatosis, hemophilia, hereditary motor and sensory neuropathy (HMSN), hereditary non polyposis colorectal cancer (HNPCC), Huntington's disease, immunodeficiency with hyper-IgM, juvenile onset diabetes, Klinefelter's syndrome, Kabuki syndrome, Leigh's disease, long QT syndrome, lung cancer, malignant melanoma, manic depression, Marfan syndrome, Menkes syndrome, miscarriage, mucopolysaccharide disease, multiple endocrine neoplasia, multiple sclerosis, muscular dystrophy, myotrophic lateral sclerosis, myotonic dystrophy, neurofibromatosis, Niemann-Pick disease, Noonan syndrome, obesity, ovarian cancer, pancreatic cancer, Parkinson's disease, paroxysmal nocturnal hemoglobinuria, Pendred syndrome, peroneal muscular atrophy, phenylketonuria (PKU), polycystic kidney disease, Prader-Willi syndrome, primary biliary cirrhosis, prostate cancer, REAR syndrome, Refsum disease, retinitis pigmentosa, retinoblastoma, Rett syndrome, Sanfilippo syndrome, schizophrenia, severe combined immunodeficiency, sickle cell anemia, spina bifida, spinal muscular atrophy, spinocerebellar atrophy, sudden adult death syndrome, Tangier disease, Tay-Sachs disease, thrombocytopenia absent radius syndrome, Townes-Brocks syndrome, tuberous sclerosis, Turner syndrome, Usher syndrome, von Hippel-Lindau syndrome, Waardenburg syndrome, Weaver syndrome, Werner syndrome, Williams syndrome, Wilson's disease, xeroderma piginentosum, and Zellweger syndrome.

The term "musculoskeletal disease" or "MSD" refers to an injury and/or pain in a subject's joints, ligaments, muscles, nerves, tendons, and structures that support limbs, neck, and back. In certain embodiments, an MSD is a degenerative disease. In certain embodiments, an MSD includes an inflammatory condition. Body parts of a subject that may be associated with MSDs include upper and lower back, neck, shoulders, and extremities (arms, legs, feet, and hands). In certain embodiments, an MSD is a bone disease, such as achondroplasia, acromegaly, bone callus, bone demineralization, bone fracture, bone marrow disease, bone marrow neoplasm, dyskeratosis congenita, leukemia (e.g., hairy cell leukemia, lymphocytic leukemia, myeloid leukemia, Philadelphia chromosome-positive leukemia, plasma cell leukemia, stem cell leukemia), systemic mastocytosis, myelodysplastic syndromes, paroxysmal nocturnal hemoglobinuria, myeloid sarcoma, myeloproliferative disorders, multiple myeloma, polycythemia vera, pearson marrow-pancreas syndrome, bone neoplasm, bone marrow neoplasm, Ewing sarcoma, osteochondroma, osteoclastoma, osteosarcoma, brachydactyly, Camurati-Engelmann syndrome, Craniosynostosis, Crouzon craniofacial dysostosis, dwarfism, achondroplasia, bloom syndrome, Cockayne syndrome, Ellis-van Creveld syndrome, Seckel syndrome, spondyloepiphyseal dysplasia, spondyloepiphyseal dysplasia congenita, Werner syndrome, hyperostosis, osteophyte, Klippel-Trenaunay-Weber syndrome, Marfan syndrome, McCune-Albright syndrome, osteitis, osteoarthritis, osteochondritis, osteochondrodysplasia, Kashin-Beck disease, Leri-Weill dyschondrosteosis, osteochondrosis, osteodystrophy, osteogenesis imperfecta, osteolysis, Gorham-Stout syndrome, osteomalacia, osteomyelitis, osteonecrosis, osteopenia, osteopetrosis, osteoporosis, osteosclerosis, otospondylomegaepiphyseal dysplasia, pachydermoperiostosis, Paget disease of bone, Polydactyly, Meckel syndrome, rickets, Rothmund-Thomson syndrome, Sotos syndrome, spondyloepiphyseal dysplasia, spondyloepiphyseal dysplasia congenita, syndactyly, Apert syndrome, syndactyly type II, or Werner syndrome. In certain embodiments, an MSD is a cartilage disease, such as cartilage neoplasm, osteochondritis, osteochondrodysplasia, Kashin-Beck disease, or Leri-Weill dyschondrosteosis. In certain embodiments, an MSD is hernia, such as intervertebral disk hernia. In certain embodiments, an MSD is a joint disease, such as arthralgia, arthritis (e.g., gout (e.g., Kelley-Seegmiller syndrome, Lesch-Nyhan syndrome), Lyme disease, osteoarthritis, psoriatic arthritis, reactive arthritis, rheumatic fever, rheumatoid arthritis, Felty syndrome, synovitis, Blau syndrome, nail-patella syndrome, spondyloarthropathy, reactive arthritis, Stickler syndrome, synovial membrane disease, synovitis, or Blau syndrome. In certain embodiments, an MSD is Langer-Giedion syndrome. In certain embodiments, an MSD is a muscle disease, such as Barth syndrome, mitochondrial encephalomyopathy, MELAS syndrome, MERRF syndrome, MNGIE syndrome, mitochondrial myopathy, Kearns-Sayre syndrome, myalgia, fibromyalgia, polymyalgia rheumatica, myoma, myositis, dermatomyositis, neuromuscular disease, Kearns-Sayre syndrome, muscular dystrophy, myasthenia, congenital myasthenic syndrome, Lambert-Eaton myasthenic syndrome, myasthenia gravis, myotonia, myotonia congenita, spinal muscular atrophy, tetany, ophthalmoplegia, or rhabdomyolysis. In certain embodiments, an MSD is Proteus syndrome. In certain embodiments, an MSD is a rheumatic diseases, such as arthritis (e.g., gout (e.g., Kelley-Seegmiller syndrome, Lesch-Nyhan lyme disease)), osteoarthritis, psoriatic arthritis, reactive arthritis, rheumatic fever, rheumatoid arthritis, Felty syndrome, synovitis, Blau syndrome, gout (e.g., Kelley-Seegmiller syndrome, Lesch-Nyhan syndrome), polymyalgia rheumatica, rheumatic fever, rheumatic heart disease, or Sjogren syndrome. In certain embodiments, an MSD is Schwartz-Jampel syndrome. In certain embodiments, an MSD is a skeleton disease, such as Leri-Weill dyschondrosteosis, skeleton malformations, Melnick-Needles syndrome, pachydermoperiostosis, Rieger syndrome, spinal column disease, intervertebral disk hernia, scoliosis, spina bifida, spondylitis, ankylosing spondylitis, spondyloarthropathy, reactive arthritis, spondyloepiphyseal dysplasia, spondyloepiphyseal dysplasia congenita, or spondylosis. In some embodiments, the disease is a musculoskeletal disease.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant." depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "premalignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., Stedman's Medical Dictionary, 25th ed.; Hensyl ed.; Williams & Wilkins: Philadelphia, 1990. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma: colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/ lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation. In some embodiments, the inflammatory disease is inflammaging (e.g., inflammation that is a side effect of aging).

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

The term "liver disease" or "hepatic disease" refers to damage to or a disease of the liver. Non-limiting examples of liver disease include intrahepatic cholestasis (e.g., alagille syndrome, biliary liver cirrhosis), fatty liver (e.g., alcoholic fatty liver, Reye's syndrome), hepatic vein thrombosis, hepatolenticular degeneration (i.e., Wilson's disease), hepatomegaly, liver abscess (e.g., amebic liver abscess), liver cirrhosis (e.g., alcoholic, biliary, and experimental liver cirrhosis), alcoholic liver diseases (e.g., fatty liver, hepatitis, cirrhosis), parasitic liver disease (e.g., hepatic echinococcosis, fascioliasis, amebic liver abscess), jaundice (e.g., hemolytic, hepatocellular, cholestatic jaundice), cholestasis, portal hypertension, liver enlargement, ascites, hepatitis (e.g., alcoholic hepatitis, animal hepatitis, chronic hepatitis (e.g., autoimmune, hepatitis B, hepatitis C, hepatitis D, drug induced chronic hepatitis), toxic hepatitis, viral human hepatitis (e.g., hepatitis A, hepatitis B, hepatitis C, hepatitis D, hepatitis E), granulomatous hepatitis, secondary biliary cirrhosis, hepatic encephalopathy, varices, primary biliary cirrhosis, primary sclerosing cholangitis, hepatocellular adenoma, hemangiomas, bile stones, liver failure (e.g., hepatic encephalopathy, acute liver failure), angiomyolipoma, calcified liver metastases, cystic liver metastases, fibrolamellar hepatocarcinoma, hepatic adenoma, hepatoma, hepatic cysts (e.g., Simple cysts, Polycystic liver disease, hepatobiliary cystadenoma, choledochal cyst), mesenchymal tumors (mesenchymal hamartoma, infantile hemangioendothelioma, hemangioma, peliosis hepatis, lipomas, inflammatory pseudotumor), epithelial tumors (e.g., bile duct hamartoma, bile duct adenoma), focal nodular hyperplasia, nodular regenerative hyperplasia, hepatoblastoma, hepatocellular carcinoma, cholangiocarcinoma, cystadenocarcinoma, tumors of blood vessels, angiosarcoma, Karposi's sarcoma, hemangioendothelioma, embryonal sarcoma, fibrosarcoma, leiomyosarcoma, rhabdomyosarcoma, carcinosarcoma, teratoma, carcinoid, squamous carcinoma, primary lymphoma, peliosis hepatis, erythrohepatic porphyria, hepatic porphyria (e.g., acute intermittent porphyria, porphyria cutanea tarda), and Zellweger syndrome.

The term "spleen disease" refers to a disease of the spleen. Example of spleen diseases include, but are not limited to, splenomegaly, spleen cancer, asplenia, spleen trauma, idiopathic purpura. Felty's syndrome, Hodgkin's disease, and immune-mediated destruction of the spleen.

The term "lung disease" or "pulmonary disease" refers to a disease of the lung. Examples of lung diseases include, but are not limited to, bronchiectasis, bronchitis, bronchopulmonary dysplasia, interstitial lung disease, occupational lung disease, emphysema, cystic fibrosis, acute respiratory distress syndrome (ARDS), severe acute respiratory syndrome (SARS), asthma (e.g., intermittent asthma, mild persistent asthma, moderate persistent asthma, severe persistent asthma), chronic bronchitis, chronic obstructive pulmonary disease (COPD), emphysema, interstitial lung disease, sarcoidosis, asbestosis, aspergilloma, aspergillosis, pneumonia (e.g., lobar pneumonia, multilobar pneumonia, bronchial pneumonia, interstitial pneumonia), pulmonary fibrosis, pulmonary tuberculosis, rheumatoid lung disease, pulmonary embolism, and lung cancer (e.g., non-small-cell lung carcinoma (e.g., adenocarcinoma, squamous-cell lung carcinoma, large-cell lung carcinoma), small-cell lung carcinoma).

A "hematological disease" includes a disease which affects a hematopoietic cell or tissue. Hematological diseases include diseases associated with aberrant hematological content and/or function. Examples of hematological diseases include diseases resulting from bone marrow irradiation or chemotherapy treatments for cancer, diseases such as pernicious anemia, hemorrhagic anemia, hemolytic anemia, aplastic anemia, sickle cell anemia, sideroblastic anemia, anemia associated with chronic infections such as malaria, trypanosomiasis, HTV, hepatitis virus or other viruses, myelophthisic anemias caused by marrow deficiencies, renal failure resulting from anemia, anemia, polycythemia, infectious mononucleosis (EVI), acute non-lymphocytic leukemia (ANLL), acute myeloid leukemia (AML), acute promyelocytic leukemia (APL), acute myelomonocytic leukemia (AMMoL), polycythemia vera, lymphoma, acute lymphocytic leukemia (ALL), chronic lymphocytic leukemia, Wilm's tumor, Ewing's sarcoma, retinoblastoma, hemophilia, disorders associated with an increased risk of thrombosis, herpes, thalassemia, antibody-mediated disorders such as transfusion reactions and erythroblastosis, mechanical trauma to red blood cells such as micro-angiopathic hemolytic anemias, thrombotic thrombocytopenia purpura and disseminated intravascular coagulation, infections by parasites such as Plasmodium, chemical injuries from, e.g., lead poisoning, and hypersplenism.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease. Examples of neurological diseases include, but are not limited to, headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological diseases. Further examples of neurological diseases include acquired epileptiform aphasia: acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension: Binswanger's disease; blepharospasm; Bloch Sulzberger syndrome; brachial plexus injury; brain abscess; bbrain injury; brain tumors (including glioblastoma multiforme); spinal tumor; Brown-Sequard syndrome: Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome: Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy: Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly: hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome: Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex: phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy: progressive multifocal leukoencephalopathy: progressive sclerosing poliodystrophy; progressive supranuclear palsy; pseudotumor cerebri: Ramsay-Hunt syndrome (Type I and Type II); Rasmussen's Encephalitis; reflex sympathetic dystrophy syndrome; Refsum disease; repetitive motion disorders: repetitive stress injuries; restless legs syndrome; retrovirus-associated myelopathy: Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea: Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

A "painful condition" includes, but is not limited to, neuropathic pain (e.g., peripheral neuropathic pain), central pain, deafferentiation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawal symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain and the like. One or more of the painful conditions contemplated herein can comprise mixtures of various types of pain provided above and herein (e.g. nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition.

The term "psychiatric disorder" refers to a disease of the mind and includes diseases and disorders listed in the Diagnostic and Statistical Manual of Mental Disorders-Fourth Edition (DSM-IV), published by the American Psychiatric Association, Washington D. C. (1994). Psychiatric disorders include, but are not limited to, anxiety disorders (e.g., acute stress disorder agoraphobia, generalized anxiety disorder, obsessive-compulsive disorder, panic disorder, posttraumatic stress disorder, separation anxiety disorder, social phobia, and specific phobia), childhood disorders, (e.g., attention-deficit/hyperactivity disorder, conduct disorder, and oppositional defiant disorder), eating disorders (e.g., anorexia nervosa and bulimia nervosa), mood disorders (e.g., depression, bipolar disorder, cyclothymic disorder, dysthymic disorder, and major depressive disorder), personality disorders (e.g., antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder), psychotic disorders (e.g., brief psychotic disorder, delusional disorder, schizoaffective disorder, schizophreniform disorder, schizophrenia, and shared psychotic disorder), substance-related disorders (e.g., alcohol dependence, amphetamine dependence, cannabis dependence, cocaine dependence, hallucinogen dependence, inhalant dependence, nicotine dependence, opioid dependence, phencyclidine dependence, and sedative dependence), adjustment disorder, autism, delirium, dementia, multi-infarct dementia, learning and memory disorders (e.g., amnesia and age-related memory loss), and Tourette's disorder.

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., Type I diabetes, Type II diabetes, gestational diabetes), hyperglycemia, hyperinsulinemia, insulin resistance, and obesity.

In some embodiments, a disease is characterized by cellular dysfunction. For example, a disease may be a mitochondrial disease. Non-limiting mitochondrial diseases include Freidrich's ataxia, alphers disease, barth syndrome, beta-oxidation defects, carnitine deficiency, CPT I deficiency, and mitochondrial DNA depletion. Cellular dysfunction may include mitochondria dysfunction, RNA replication dysfunction, DNA replication dysfunction, translation dysfunction, and/or protein folding dysfunction.

In some embodiments, the disease or condition by a wood, bleeding out, injuries (e.g., broken bones, gunshot wound, cut, scarring during surgery (e.g., cesarean).

In some embodiments, the disease is an infectious disease (e.g., a disease caused by a pathogen and/or virus). Non-limiting examples of infectious diseases include tuberculosis, HIV/AIDS, rabies, plague, cholera, dengue fever, measles, malaria, meningitis, whooping cough, lyme disease, influenza, hepatitis C, typhoid fever, and poliomyelitis.

The terms "effective amount" and "therapeutically effective amount," as used herein, refer to the amount or concentration of an inventive compound, that, when administered to a subject, is effective to at least partially treat a condition from which the subject is suffering.

As used herein, a protein that is "functional" or "active" is one that retains its biological activity (e.g., capable of acting as a transcription factor or as an inducing agent). Conversely, a protein that is not functional or is inactive is one that is not capable of performing one or more of its wild-type functions.

A "eukaryotic cell" is a cell that comprises a nucleus that is enclosed by a membrane. Non-limiting examples of eukaryotic cells include animal cells, plant cells fungi or protoctista cells, optionally wherein the animal cell is a mammalian cell.

The term "gene" refers to a nucleic acid fragment that expresses a protein, including regulatory sequences preceding (5' non-coding sequences) and following (3' non-coding sequences) the coding sequence. "Native gene" refers to a gene as found in nature with its own regulatory sequences. "Chimeric gene" or "chimeric construct" refers to any gene or a construct, not a native gene, comprising regulatory and coding sequences that are not found together in nature. Accordingly, a chimeric gene or chimeric construct may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but which is introduced into the host organism by gene transfer. Foreign genes can comprise native genes inserted into a non-native organism, or chimeric genes. A "transgene" is a gene that has been introduced into the genome by a transformation procedure.

"Homolog" or "homologous" refers to sequences (e.g., nucleic acid or amino acid sequences) that share a certain percent identity (e.g., at least 5%, at least 10%, at least 15%, at least 20%, at least 25%, at least 30%, at least 35%, at least 40%, at least 45%, at least 50%, at least 55%, at least 60%, at least 65%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% percent identity). Homologous sequences include, but are not limited to, paralogous or orthologous sequences. Paralogous sequences arise from duplication of a gene within a genome of a species, while orthologous sequences diverge after a speciation event. A functional homolog retains one or more biological activities of a wild-type protein. In certain embodiments, a functional homolog of protein encoded by a transgene retains at least 10%, at least 20%, at least 30%, at least 40%, at least 50%, at least 60%, at least 70%, at least 80%, at least 90%, or at least 100% of the biological activity (e.g., transcription factor activity) of a wild-type counterpart.

"Inverted terminal repeats" or "ITRs" are nucleic acid sequences that are reverse complements of one another. In general, in an AAV vector, ITRs are found on either side of a cassette (e.g., an expression cassette comprising a nucleic acid encoding a transgene, a mutant rtTA, or any combination thereof). AAV ITRs include ITRs from AAV1, AAV2, AAV3, AAV4, AAV5, AAV6, AAV7, AAV8, AAV9, AAV10, AAV11, and AAV variants thereof.

The terms "nucleic acid." "polynucleotide", "nucleotide sequence", "nucleic acid molecule", "nucleic acid sequence", and "oligonucleotide" refer to a series of nucleotide bases (also called "nucleotides") in DNA and RNA, and mean any chain of two or more nucleotides. The terms "nucleic acid" or "nucleic acid sequence", "nucleic acid molecule", "nucleic acid fragment" or "polynucleotide" may be used interchangeably with "gene", "mRNA encoded by a gene" and "cDNA".

The nucleic acids can be chimeric mixtures or derivatives or modified versions thereof, single-stranded or double-stranded. The oligonucleotide can be modified at the base moiety, sugar moiety, or phosphate backbone, for example, to improve stability of the molecule, its hybridization parameters, etc. A nucleotide sequence typically carries genetic information, including the information used by cellular machinery to make proteins and enzymes. These terms include double- or single-stranded genomic and cDNA, RNA, any synthetic and genetically manipulated polynucleotide, and both sense and antisense polynucleotides. This includes single-and double-stranded molecules, i.e., DNA-DNA, DNA-RNA and RNA-RNA hybrids, as well as "protein nucleic acids" (PNAs) formed by conjugating bases to an amino acid backbone. This also includes nucleic acids containing carbohydrate or lipids. Exemplary DNAs include single-stranded DNA (ssDNA), double-stranded DNA (dsDNA), plasmid DNA (pDNA), genomic DNA (gDNA), complementary DNA (cDNA), antisense DNA, chloroplast DNA (ctDNA or cpDNA), microsatellite DNA, mitochondrial DNA (mtDNA or mDNA), kinetoplast DNA (kDNA), provirus, lysogen, repetitive DNA, satellite DNA, and viral DNA. Exemplary RNAs include single-stranded RNA (ssRNA), double-stranded RNA (dsRNA), small interfering RNA (siRNA), messenger RNA (mRNA), precursor messenger RNA (pre-mRNA), small hairpin RNA or short hairpin RNA (shRNA), microRNA (miRNA), guide RNA (gRNA), transfer RNA (tRNA), antisense RNA (as-RNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, and viral satellite RNA.

The nucleic acids described herein may be synthesized by standard methods known in the art, e.g., by use of an automated DNA synthesizer (such as those that are commercially available from Biosearch, Applied Biosystems, etc.). As examples, phosphorothioate oligonucleotides may be synthesized by the method of Stein et al., *Nucl. Acids Res.,* 16, 3209, (1988), methylphosphonate oligonucleotides can be prepared by use of controlled pore glass polymer supports (Sarin et al., *Proc. Natl. Acad. Sci. U.S.A.* 85, 7448-7451, (1988)). A number of methods have been developed for delivering antisense DNA or RNA to cells, e.g., antisense molecules can be injected directly into the tissue site, or modified antisense molecules, designed to target the desired cells (antisense linked to peptides or antibodies that specifically bind receptors or antigens expressed on the target cell surface) can be administered systemically. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines. However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells.

Expression of the sequence encoding the antisense RNA can be by any promoter known in the art to act in mammalian, preferably human, cells. Such promoters can be inducible or constitutive. Any type of plasmid, cosmid, yeast artificial chromosome, or viral vector can be used to prepare the recombinant DNA construct that can be introduced directly into the tissue site.

The nucleic acids may be flanked by natural regulatory (expression control) sequences or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications, such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, isotopes (e.g., radioactive isotopes), biotin, and the like.

A "recombinant nucleic acid molecule" or "engineered nucleic acid" is a nucleic acid molecule that has undergone a molecular biological manipulation, i.e., non-naturally occurring nucleic acid molecule or genetically engineered nucleic acid molecule. Furthermore, the terms "recombinant DNA molecule" or "engineered nucleic acid" refer to a nucleic acid sequence which is not naturally occurring, or can be made by the artificial combination of two otherwise separated segments of nucleic acid sequence, i.e., by ligating together pieces of DNA that are not normally continuous. By "recombinantly produced" is meant artificial combination often accomplished by either chemical synthesis means, or by the artificial manipulation of isolated segments of nucleic acids, e.g., by genetic engineering techniques using restriction enzymes, ligases, and similar recombinant techniques as described by, for example, Sambrook et al., *Molecular Cloning,* second edition, Cold Spring Harbor Laboratory, Plainview, N.Y.; (1989), or Ausubel et al., *Current Protocols in Molecular Biology,* Current Protocols (1989), and DNA Cloning: *A Practical Approach,* Volumes I and II (ed. D. N. Glover) IREL Press, Oxford, (1985); each of which is incorporated herein by reference.

Such manipulation may be done to replace a codon with a redundant codon encoding the same or a conservative amino acid, while typically introducing or removing a sequence recognition site. Alternatively, it may be performed to join together nucleic acid segments of desired functions to generate a single genetic entity comprising a desired combination of functions not found in nature. Restriction enzyme recognition sites are often the target of such artificial manipulations, but other site specific targets, e.g., promoters, DNA replication sites, regulation sequences, control sequences, open reading frames, or other useful features may be incorporated by design.

As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, New York, 1989, or *Current Protocols in Molecular Biology*, F. M. Ausubel, et al., eds., John Wiley & Sons, Inc., New York. Conservative substitutions of amino acids include substitutions made amongst amino acids within the following groups: (a) M, I, L, V; (b) F. Y, W; (c) K, R. H; (d) A, G; (e) S. T: (f) Q. N; and (g) E, D.

A "recombinant cell" or an "engineered cell" is a cell comprising a recombinant nucleic acid.

"A residue in sequence X corresponding to position a in sequence Y" refers to the residue at the counterpart position of a in sequence X when sequences X and Y are aligned using an amino acid sequence alignment tools known in the art, for example, Clustal Omega or BLAST®.

The terms "leaky" or "leakiness" when used in reference to an inducible system (e.g., Tet-On system or Tet-Off) refers to expression of a transgene from an inducible promoter in the absence of gene induction. For example, in a Tet-On system, expression of a transgene in the absence of tetracycline (e.g., doxycycline) is considered a "leaky" system. As another example, in a Tet-Off system, expression of a transgene in the presence of tetracycline (e.g., doxycycline) is considered a "leaky" system. The level of "leakiness" of an inducible system may be determined by measuring the level of gene expression (e.g., by western blot, RNA analysis or ELISAs) in the absence of gene induction (e.g., in the absence of a tetracycline in a Tet-On system or in the presence of a tetracycline in a Tet-Off system).

The term "promoter" refers to a control region of a nucleic acid sequence at which initiation and rate of transcription of the remainder of a nucleic acid sequence are controlled. A promoter may also contain sub-regions at which regulatory proteins and molecules may bind, such as RNA polymerase and other transcription factors. Promoters may be constitutive, inducible, activatable, repressible, tissue-specific, or any combination thereof. A promoter drives expression or drives transcription of the nucleic acid sequence that it regulates. Herein, a promoter is considered to be "operably linked" when it is in a correct functional location and orientation in relation to a nucleic acid sequence it regulates to control ("drive") transcriptional initiation of that sequence, expression of that sequence, or a combination thereof.

A promoter may promote ubiquitous expression or tissue-specific expression of an operably linked nucleic acid sequence from any species, including humans. In some embodiments, the promoter is a eukaryotic promoter. Non-limiting examples of eukaryotic promoters include TDH3, PGK1, PKC1, TDH2, PYK1, TPI1, ATI, CMV, EF1a, SV40, PGK1 (human or mouse), Ubc, human beta actin, CAG, TRE, UAS, Ac5, Polyhedrin, CaMKIIa, GAL1, GAL10, TEF1, GDS, ADHI, CaMV35S, Ubi, H1, and U6, as would be known to one of ordinary skill in the art (see, e.g., Addgene website: blog.addgene.org/plasmids-101-the-promoter-region).

Non-limiting examples of ubiquitous promoters include tetracycline-responsive promoters (under the relevant conditions), CMV, EF1 alpha, a SV40 promoter, PGK1, Ubc, CAG, human beta actin gene promoter, and a promoter comprising an upstream activating sequence (UAS). In certain embodiments, the promoter is a mammalian promoter. Non-limiting examples of tissue-specific promoters include brain-specific, liver-specific, muscle-specific, nerve cell-specific, lung-specific, heart-specific, bone-specific, intestine-specific, skin-specific promoters, brain-specific promoters, and eye-specific promoters. As an example, a muscle-specific promoter is a desmin promoter (e.g., a sequence that is at least 70% (e.g., at least 75%, 80%, 85%, 90%, 95%, 98%, 99%, or 100%) identical to SEQ ID NO: 29).

Non-limiting examples of constitutive promoters include CP1, CMV, EF1 alpha, SV40, PGK1, Ubc, human beta actin, beta tubulin, CAG, Ac5, polyhedrin, TEF1, GDS, CaM3 5S, Ubi, H1, and U6 . . . . An Ubc promoter may comprise a sequence at is at least 70% (e.g., at least 75%, 80%, 85%, 90%, 95%, 98%, 99%, or 100%) identical to SEQ ID NO: 18.

An "inducible promoter" is one that is characterized by initiating or enhancing transcriptional activity when in the presence of, influenced by, or contacted by an inducing agent. An inducing agent may be endogenous or a normally exogenous condition, compound, agent, or protein that contacts an engineered nucleic acid in such a way as to be active in inducing transcriptional activity from the inducible promoter. In certain embodiments, an inducing agent is a tetracycline-sensitive protein (e.g., rtTA).

Inducible promoters for use in accordance with the present disclosure include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline responsive promoter systems, which include a tetracycline repressor protein (tetRTetR, e.g., SEQ ID NO: 26 or TetRKRAB, e.g., SEQ ID NO: 27), a tetracycline operator sequence (tetO), and a tetracycline transactivator fusion protein ((TA), and a tetracycline operator sequence (tetO) and a reverse tetracycline transactivator fusion protein (rtTA)), steroid-regulated promoters (e.g., promoters based on the rat glucocorticoid receptor, human estrogen receptor, moth ecdysone receptors, and promoters from the steroid/retinoid/thyroid 25 receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters. A non-limiting example of an inducible system that uses a light-regulated promoter is provided in Wang et al., *Nat. Methods*. 2012 Feb. 12;9 (3): 266-9.

As used herein, a "TRE promoter" is a promoter comprising a tetracycline-responsive element (TRE). As used herein, a TRE comprises at least one (e.g., at least 2, 3, 4, 5, 6, 7, 8, 9, 10, 11, 12, 13, 14, 15, 16, 17, 18, 19, or 20) Tet-O sequences. A non-limiting example of a Tet-O sequence is sequence that is at least 70% (e.g., 75%, 80%, 85%, 90%, 95%, 98%, 99%, or 100%) identical to SEQ ID NO: 19. In some embodiments, a TRE promoter further comprises a minimal promoter located downstream of a tet-O sequence. A minimal promoter is a promoter that comprises the minimal elements of a promoter (e.g., TATA box and transcription initiation site), but is inactive in the absence of an upstream enhancer (e.g., sequences comprising Tet-O). As an example, a minimal promoter may be a minimal CMV promoter that comprises a sequence that is at least 70% (e.g., at least 75%, 80%, 85%, 90%, 95%, 98%, 99%, or 100%) identical to SEQ ID NO: 20. For example, a TRE promoter may be a TRE3G promoter (e.g., a TRE3G promoter that comprises a sequence that is at least 70% (e.g., at least 75%, 80%, 85%, 90%, 95%, 98%, 99%, or 100%) identical to SEQ ID NO: 7. In some embodiments, a TRE promoter is a TRE2 promoter comprising a sequence that is at least 70% (e.g., at least 75%, 80%, 85%, 90%, 95%, 98%, 99%, or 100%) identical to SEQ ID NO: 23. In some embodiments, a TRE promoter is a P tight promoter comprising a sequence that is at least 70% (e.g., at least 75%, 80%, 85%, 90%, 95%, 98%, 99%, or 100%) identical to SEQ ID NO: 24.

A "reverse tetracycline transactivator" ("rtTA"), as used herein, is an inducing agent that binds to a TRE promoter (e.g., a TRE3G, P tight, or TRE2 promoter) in the presence of tetracycline (e.g., doxycycline) and is capable of driving expression of a transgene that is operably linked to the TRE promoter. rtTAs generally comprise a mutant tetracycline repressor DNA binding protein (TetR) and a transactivation-domain (see. e.g., Gossen et al., Science. 1995 Jun. 23;268 (5218): 1766-9. Any suitable transactivation domain may be used. Non-limiting examples include VP64, P65, RTA, and MPH MS2-P65-HSF1. In some embodiments, a rtTA of the present disclosure comprises at least 1, 2, 3, 4, 5. 6, 7, 8, 9. 10, 11, 12, 13, 14, 15, 16, 17, 18, 19, 20, 30, 40, 50, 60, 70, 80, 90, or 100 transactivation domains. The mutant TetR domain is capable of binding to a TRE promoter when bound to tetracycline.

The rtTA may be rtTA3, rtTA4, or variants thereof. As used herein, a rtTA3 amino acid sequence comprises the following amino acids at a position corresponding to the residue in SEQ ID NO: 11: glycine at a residue 72, glycine at residue 12, phenylalanine at residue 67, and arginine at residue 171. In certain embodiments, a nucleic acid encoding rtTA3 comprises a sequence that is at least 70% (e.g., at least 75%, at least 80%, at least 85%, at least 90%, at least 95%, or at least 100%) identical to SEQ ID NO: 10 and/or the nucleic acid sequence encodes a rtTA3 protein that comprises the following amino acids at a position corresponding to the residue in SEQ ID NO: 11: glycine at a residue 72, glycine at residue 12, phenylalanine at residue 67, and arginine at residue 171. ArtTA3 nucleotide sequence may consist of SEQ ID NO: 10. In certain embodiments, an amino acid sequence encoding rtTA3 comprises a sequence that is at least 70% (e.g., at least 75%, at least 80%, at least 85%, at least 90%, at least 95%, at least 98%, at least 99%, or at least 100%) identical to (SEQ ID NO: 11), and comprises the following amino acids corresponding to the indicated positions in SEQ ID NO: 11: glycine at residue 72, glycine at residue 12, phenylalanine at residue 67, and arginine at residue 171. ArtTA3 amino acid sequence may consist of SEQ ID NO: 11.

As used herein, a rtTA4 amino acid sequence comprises mutations at positions corresponding to the following residues in SEQ ID NO: 11: G72; G12; F67; and R171. In certain embodiments, G72; G12; F67; and R171 may be mutated to any residue. In certain embodiments, a nucleic acid encoding rtTA4 comprises a sequence that is at least 70% (e.g., at least 75%, at least 80%, at least 85%, at least 90%, at least 95%, at least 98%, at least 99%, or at least 100%) identical to SEQ ID NO: 12 and encodes a protein with a mutation at the following residues corresponding to the following positions in rtTA3 (SEQ ID NO: 11): G72; G12; F67; and R171. ArtTA4 nucleic acid sequence may consist of SEQ ID NO: 12.

In certain embodiments, an amino acid sequence encoding rtTA4 comprises a sequence that is at least 70% (e.g., at least 75%, at least 80%, at least 85%, at least 90%, at least 95%, at least 98%, at least 99%, or at least 100%) identical to SEQ ID NO: 13 and/or encodes a protein with a mutation at the following residues corresponding to the following positions in rtTA3 (SEQ ID NO: 11): G72; G12; F67; and R171. In certain embodiments, a rtTA4 amino acid sequence comprises the following mutations relative to rtTA3: a valine (V) or proline (P) mutation at a residue corresponding to position G72 in SEQ ID NO: 11, a serine(S) mutation at a residue corresponding to position G12 in SEQ ID NO: 11, a serine(S) mutation at a residue corresponding to position F67 in SEQ ID NO: 11, and an lysine (K) mutation at a residue corresponding to position R171 in SEQ ID NO: 11. ArtTA4 amino acid sequence may consist of SEQ ID NO: 13.

A "multicistronic vector" is a vector that encodes more than one amino acid sequence (e.g., a vector encoding at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100 proteins). A multicistronic vector allows for expression of multiple amino acid sequences from a nucleic acid sequence. Nucleic acid sequences encoding each protein may be connected or separated such that they produce unconnected proteins. For example, internal ribosome entry sites (IRES) or polypeptide cleavage signals may be placed between nucleic acid sequences encoding each transcription factor in a vector. Exemplary polypeptide cleavage signals include 2A peptides (e.g., T2A, P2A, E2A, and F2A). A 2A peptide may comprise a sequence that is at least 70% (e.g., at least at least 75%, 80%, 85%, 90%, 95%, 98%, 99%, or 100%) identical to SEQ ID NO: 9. In some embodiments, a nucleic acid (e.g., an engineered nucleic acid, including an expression vector) of the present disclosure is a multicistronic expression vector.

A "protein," "peptide." or "polypeptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

A "prokaryotic cell" is a cell that lacks a membrane-bound organelle. Non-limiting examples of prokaryotes include archaea and bacteria.

"Reversing aging." as used herein, refers to modifying the physical characteristics associated with aging. All animals typically go through a period of growth and maturation followed by a period of progressive and irreversible physiological decline ending in death. The length of time from birth to death is known as the life span of an organism, and each organism has a characteristic average life span. Aging is a physical manifestation of the changes underlying the passage of time as measured by percent of average life span.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals, such as cattle, pigs, horses, sheep, goats, cats, and/or dogs) and birds (e.g., commercially relevant birds, such as chickens, ducks, geese, and/or turkeys). In certain embodiments, the animal is a mammal. The animal may be a male or female and at any stage of development. A non-human animal may be a transgenic animal.

A "terminator" or "terminator sequence," as used herein, is a nucleic acid sequence that causes transcription to stop. A terminator may be unidirectional or bidirectional. It is comprised of a DNA sequence involved in specific termination of an RNA transcript by an RNA polymerase. A terminator sequence prevents transcriptional activation of downstream nucleic acid sequences by upstream promoters. Thus, in certain embodiments, a terminator that ends the production of an RNA transcript is contemplated.

The most commonly used type of terminator is a forward terminator. When placed downstream of a nucleic acid sequence that is usually transcribed, a forward transcriptional terminator will cause transcription to abort. In some embodiments, bidirectional transcriptional terminators may be used, which usually cause transcription to terminate on both the forward and reverse strand. In some embodiments, reverse transcriptional terminators may be used, which usually terminate transcription on the reverse strand only.

Non-limiting examples of mammalian terminator sequences include bovine growth hormone terminator, and viral termination sequences such as, for example, the SV40 terminator, spy, yejM, secG-leuU, thrl ABC, rrnB TI, his-LGDCBHAFI, metZWV, rrnC, xapR, aspA, and arcA terminator. In certain embodiments, the terminator sequence is SV40 and comprises a sequence that is at least 70% (e.g., at least 75%, 80%, 85%, 90%, 95%, 98%, 99%, or 100%) identical to SEQ ID NO: 8.

A "Tet-Off" system, as used herein, is a type of inducible system that is capable of repressing expression of a particular transgene in the presence of tetracycline (e.g., doxycycline (DOX)). Conversely, a Tet-Off system is capable of inducing expression of a particular transgene in the absence of tetracycline (e.g., doxycycline, DOX). In certain embodiments, a Tet-Off system comprises a tetracycline-responsive promoter operably linked to a transgene (e.g., encoding a protein, a gene-targeting nucleic acid, and/or a therapeutic gene) and a tetracycline-controlled transactivator ((TA). The transgene with the tetracycline-responsive promoter (e.g., TRE3G, a TRE2, or a P tight promoter) and the tetracycline-controlled transactivator may be encoded on the same vector or be encoded on separate vectors.

A "Tet-On" system, as used herein, is a type of inducible system that is capable of inducing expression of a particular transgene in the presence of tetracycline (e.g., doxycycline (DOX)). In certain embodiments, a Tet-On system comprises a tetracycline-responsive promoter operably linked to a transgene (e.g., a therapeutic sequence, a gene-targeting nucleic acid, and/or a nucleic acid encoding a protein) and a reverse tetracycline-controlled transactivator (rtTA).

The expression cassette encoding a tetracycline-responsive promoter (e.g., a promoter comprising a TRE, including TRE3G, P tight, and TRE2) and a reverse tetracycline-controlled transactivator may be encoded on the same vector or be encoded on separate vectors.

The term "tetracycline repressor" or "TetR" refers to a protein that is capable of binding to a Tet-O sequence (e.g., a Tet-O sequence in a TRE) in the absence of tetracycline (e.g., doxycycline) and prevents binding of rtTA (e.g., rtTA3, rtTA4, or variants thereof) in the absence of tetracycline (e.g., doxycycline). TetRs prevent gene expression from promoters comprising a TRE in the absence of tetracycline (e.g., doxycycline). In the presence of tetracycline, TetRs cannot bind promoters comprising a TRE, and TetR cannot prevent transcription. Non-limiting examples of TetRs include tetR (e.g., SEQ ID NO: 26), and tetRKRAB (e.g., SEQ ID NO: 28). In some embodiments, a TetR is a TetR fusion (e.g., TRSID, which may be created by fusing TetR to a mSIN30interacting domain (SID) of Mad1). See, e.g., Zhang et al., J Biol Chem. 2001 Nov. 30: 276 (48): 45168-74.

The term "therapeutic sequence" as used herein is any transgene that encodes a therapeutic nucleic acid and/or protein, (including prophylactic nucleic acids and/or proteins and diagnostic nucleic acids and/or proteins). For example, a nonlimiting list of transgene sequences that are therapeutic sequences is described in O'Connor et al., Nat Rev Genet. 2006 Apr.: 7 (4): 261-76. Non-limiting examples of therapeutic proteins include antibodies, enzymes, kinases, hormones, growth factors, cytokines, plasma proteins, fusion proteins, membrane-lytic proteins and coagulation factors. In some embodiments, a therapeutic protein is an inflammatory agent. In some embodiments, a therapeutic protein is an anti-inflammatory agent. In some embodiments, a therapeutic protein is an immunomodulatory agent. In some embodiments, a therapeutic protein is an anti-cancer agent. In some embodiments, a therapeutic protein is a metabolic agent. In some embodiments, a therapeutic protein is an antiviral/virocidal agent. In some embodiments, a therapeutic protein is an antibacterial/bacteriocidal agent.

The term "tissue" refers to any biological tissue of a subject (including a group of cells, a body part, or an organ) or a part thereof, including blood and/or lymph vessels, which is the object to which a compound, particle, and/or composition of the invention is delivered. A tissue may be an abnormal or unhealthy tissue, which may need to be treated. A tissue may also be a normal or healthy tissue that is under a higher than normal risk of becoming abnormal or unhealthy, which may need to be prevented. In certain embodiments, the tissue is considered healthy but suboptimal for performance or survival in current or future conditions. For example, in agricultural practice, environmental conditions including weather and growing conditions (e.g., nutrition) may benefit from any of the methods described herein. In certain embodiments, the tissue is the central nervous system. In certain embodiments, the tissue refers to tissue from the In certain embodiments, the cell or tissue is from eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine. In certain embodiments, the tissue is damaged (e.g., due to a congenital defect, an injury, an accident, or an iatrogenic injury) and/or is aged tissue. In certain embodiments, the tissue is a deep tissue that is reachable with a fiber optic probe.

The term "tissue repair" in the context of damaged tissue refers to restoration of tissue architecture, function following tissue damage, or a combination thereof. Tissue repair includes tissue regeneration, cell growth, tissue replacement, and/or rewiring of existing tissue (reprogramming).

The term "tissue regeneration" refers to production of new tissue or cells within a tissue that are the same type as the tissue of interest (e.g., same type as the damaged tissue or cell). In some embodiments, the methods provided herein promote organ regeneration.

The term "tissue replacement" refers to production of a different type of tissue compared to the tissue of interest (e.g., connective tissue to replace damaged tissue).

As used herein, the terms "treatment," "treat," and "treating" refer to reversing, alleviating, delaying the onset of, or inhibiting the progress of a disease or disorder, or one or more symptoms thereof, as described herein. In certain embodiments, treatment may be administered after one or more symptoms have developed. In other embodiments, treatment may be administered in the absence of symptoms. For example, treatment may be administered to a susceptible individual prior to the onset of symptoms or may be treated with another damaging agent (e.g., in light of a history of symptoms, in light of genetic or other susceptibility factors, a disease therapy or any combination thereof). Treatment may also be continued after symptoms have resolved, for example, to prevent or delay their recurrence.

The term "variant" or "mutant" refers to a sequence that comprises a modification relative to a wild-type sequence (e.g., rtTA3 sequence). Non-limiting modifications in an amino acid sequence include insertions, deletions, truncation mutations and point mutations. Non-limiting modifications to nucleic acid sequences include frameshift mutations, nucleotide insertions, and nucleotide deletions.

The term "WPRE" refers to a Woodchuck Hepatitis Virus (WHP) Posttranscriptional Regulatory Element (WPRE). WPREs create tertiary structures in nucleic acids (e.g., expression vectors) and are capable of enhancing transgene expression (e.g., from a viral vector). In certain embodiments, a WPRE sequence is at least 70% (e.g., at least 75%, at least 80%, at least 85%, at least 90%, at least 95%, at least 98%, at least 99%, or at least 100%) identical to SEQ ID NO: 21.

These and other exemplary substituents are described in more detail in the Detailed Description, Examples, and claims. The invention is not intended to be limited in any manner by the above exemplary listing of substituents.

BRIEF DESCRIPTION OF THE DRAWINGS

FIGS. 2A-2M include a series of schematics mapping the features shown in FIG. 1 onto the nucleic acid sequence of the vector encoding rtTA4 (SEQ ID NOs: 17 and 38, top and bottom rows respectively).

FIG. 3 shows the location and size of each feature depicted in FIGS. 2A-2M.

FIG. 4A is a non-limiting example of a Tet-On system comprising two nucleic acids. The first nucleic acid comprises a UBC promoter operably linked to sequences that encode rtTA3, a self-cleaving peptide (2A peptide), and mKate (far-red fluorescent protein) (FIG. 4A, top). The second nucleic acid encodes an inducible promoter with a tetracycline-responsive element (TRE) (TRE3G promoter, SEQ ID NO: 7) that is operably linked to GFP (FIG. 4A, bottom). DOX indicates doxycycline. FIG. 4B shows a western blot of liver samples from mice that were treated with (1) no AAVs, (2) AAVs harboring an AAV vector that comprises the first nucleic acid in FIG. 4A, and AAVs harboring an AAV vector that comprises the second nucleic acid in FIG. 4A in the absence of doxycycline (DOX), or (3) the AAVs of (2) in the presence of doxycycline (DOX). mKate, GFP, and actin expression is shown.

FIG. 5A is a schematic depicting a Tet-On system reporter system with rtTA4. The top portion of the schematic shows a nucleic acid, in which a promoter sequence operably linked to a sequence encoding rtTA4. The bottom potion of the schematic shows a second nucleic acid, in which a TRE3G promoter is operably linked to a sequence encoding luciferase. FIG. 5B is a graph showing the effect of doxycycline (DOX, ng/ml) on the production of luciferase in a Tet-On reporter system using rtTA3 compared to a Tet-On reporter system using rtTA4. Luciferase production is measured in luminescence/protein. The baseline level of luminescence/protein in the absence of any rtTA is shown.

FIG. 6A is a graph showing the effect of doxycycline on expression in a Tet-On reporter system, in which rtTA3 expression is driven by a Desmin promoter and luciferase expression is controlled by a TRE3G promoter. FIG. 6B is a graph showing the effect of doxycycline on expression in a Tet-On reporter system, in which with rtTA4 expression is driven by a Desmin promoter and luciferase expression is controlled by a TRE3G promoter. FIG. 6C is a graph showing the length of time for doxycycline withdrawal needed to reduce luciferase expression in a Tet-On reporter system with rtTA3 compared to that in a Tet-On reporter system with rtTA4. In both reporter systems, expression of the rtTA is driven by a UBC promoter, and expression of luciferase is controlled by a TRE3G promoter.

FIGS. 8A-8C include data showing that a Tet-On system comprising rtTA4 (SEQ ID NO: 13) has low leakiness in the liver of mice. FIG. 8A is a series of immunofluorescence images showing expression of KLF4 in the livers of mice that have been administered AAVs harboring nucleic acids shown in FIG. 8B in the absence of doxycycline (no DOX) and in the presence of doxycycline (with DOX). DAPI is a nuclear stain that was used to visualize cells.

FIG. 8B is a schematic depicting the two nucleic acids that were administered to mice in AAV9 viruses. FIG. 8C is a western blot of liver samples from mice that received the constructs depicted in FIG. 8B and were treated with no doxycycline or with doxycycline. OCT4, KLF4, and SOX2 levels were detected as indicated using antibodies. Actin is shown as a loading control.

FIG. 14 shows body weight of WT mice, OSK transgenic mice, and AAV-mediated OSK-expressing mice ($1.0 \times 10^{12}$ gene copies) with or without doxycycline induction in the first 4 weeks (n=5, 3, 6, 4, 6, 3, respectively).

FIG. 15A shows AAV9 expression in the liver compared to transgenic mice. FIG. 15B shows the body weight of WT mice and AAV-mediated OSK-expressing mice ($1.0 \times 10^{12}$ gene copies total) with or without doxycycline in the following 9 months after first 4 weeks (n=5, 3, 6, 4, respectively). FIG. 15C shows AAV-UBC-rtTA and AAV-TRE-Luc vectors used for measuring tissue distribution. FIG. 15D shows luciferase imaging of WT mice at 2 months after retro-orbital injections of AAV9-UBC-rtTA and AAV9-TRE-Luc ($1.0 \times 10^{12}$ gene copies total). Doxycycline was delivered in drinking water (1 mg/mL) for 7 days to the mouse shown on the right. FIG. 15E shows luciferase imaging of eye (Ey), brain (Br), pituitary gland (Pi), heart (He), thymus (Th), lung (Lu), liver (Li), kidney (Ki), spleen (Sp), pancreas (Pa), testis (Te), adipose (Ad), muscle (Mu), spinal cord (SC), stomach (St), small intestine (In), and cecum (Ce) 2 months after retro-orbital injection of AAV9-UBC-rtTA and AAV9-TRE-Luc followed by treatment with doxycycline for 7 days. The luciferase signal is primarily in liver. Imaging the same tissues with a longer exposure time (FIG. 15E, lower panel) revealed lower levels of luciferase signal in pancreas (liver was removed).

DETAILED DESCRIPTION OF CERTAIN EMBODIMENTS OF THE INVENTION

Figure 1:
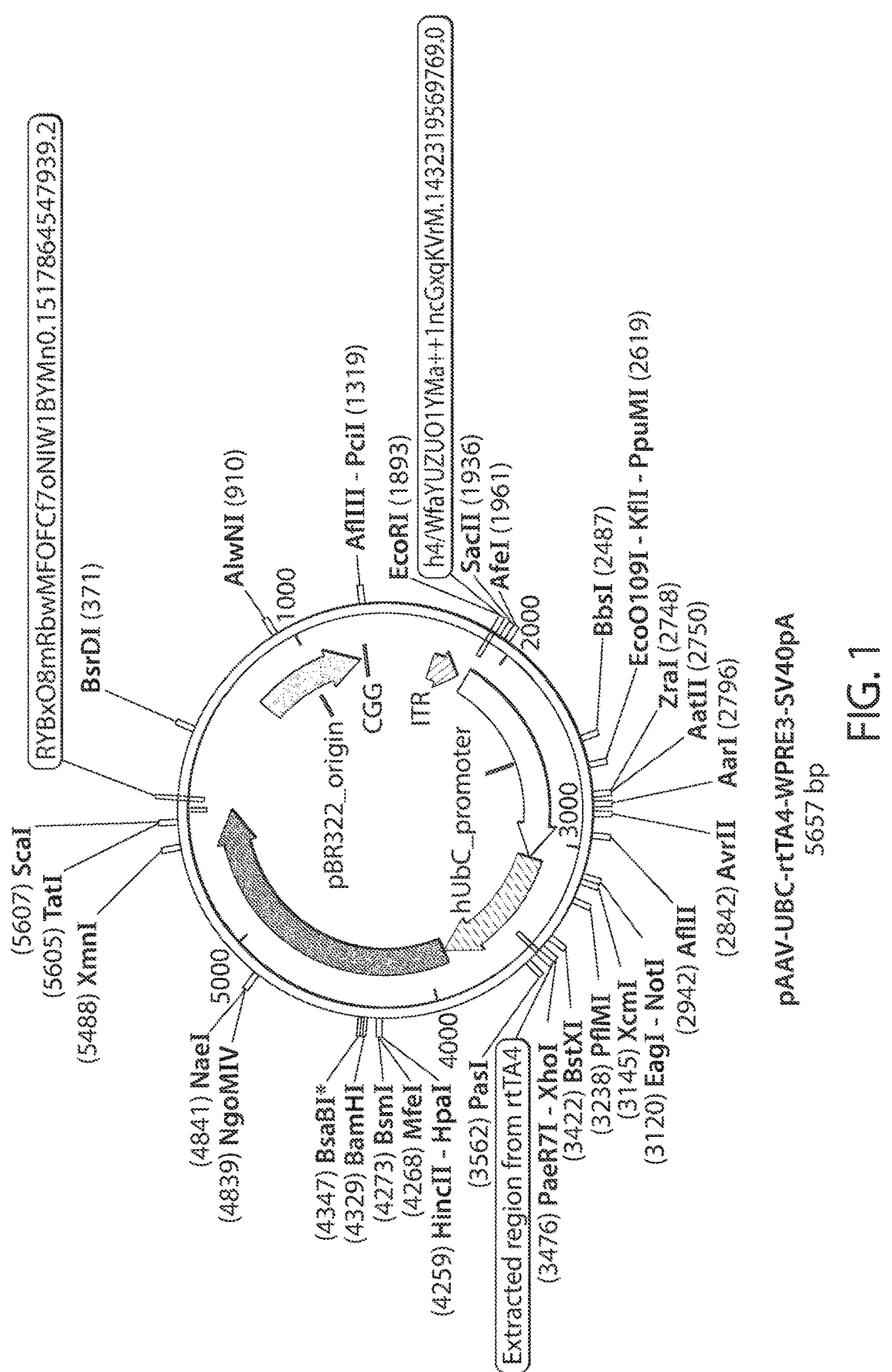
FIG. 1 is a vector map showing features in an adeno-associated virus (AAV) vector encoding reverse tetracycline-transactivator 4 (rtTA4). Ubc is a constitutive promoter that is operably linked to the nucleic acid encoding rtTA4. SV40 pA is an SV40-derived terminator sequence. The sequence of this vector is provided in SEQ ID NO: 17.
Figure 2B:
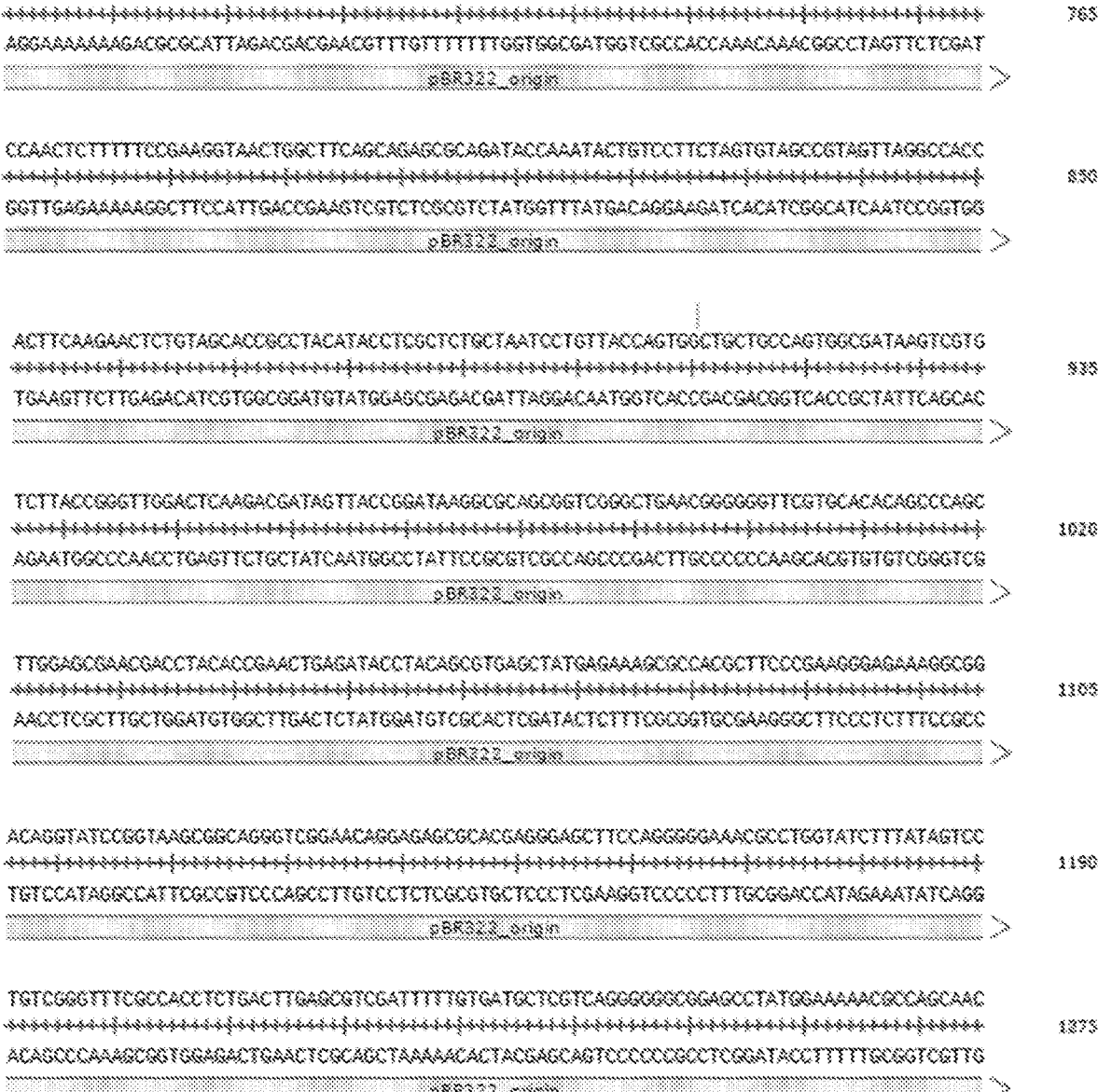
Figure 2C:
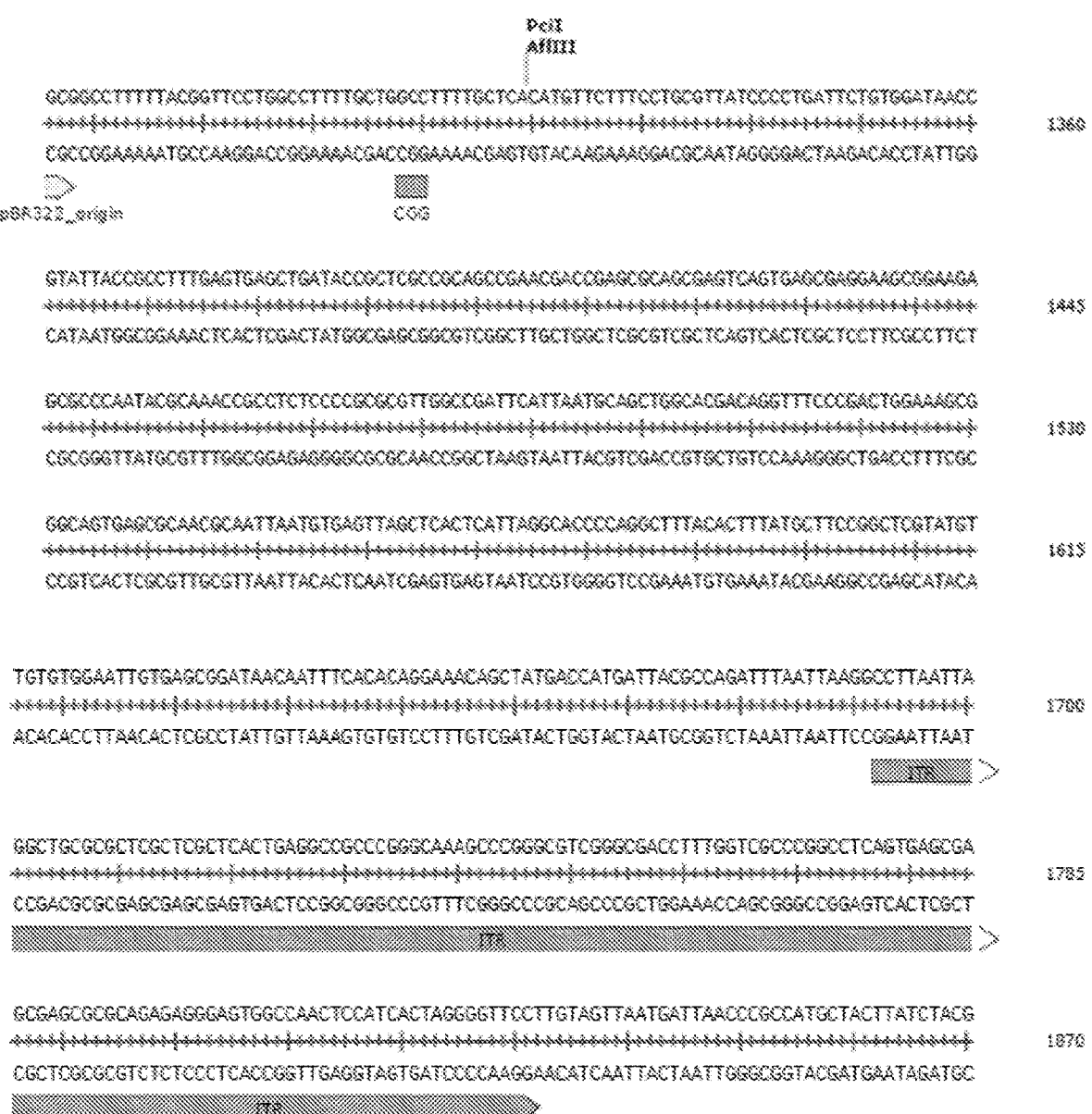
Figure 2D:
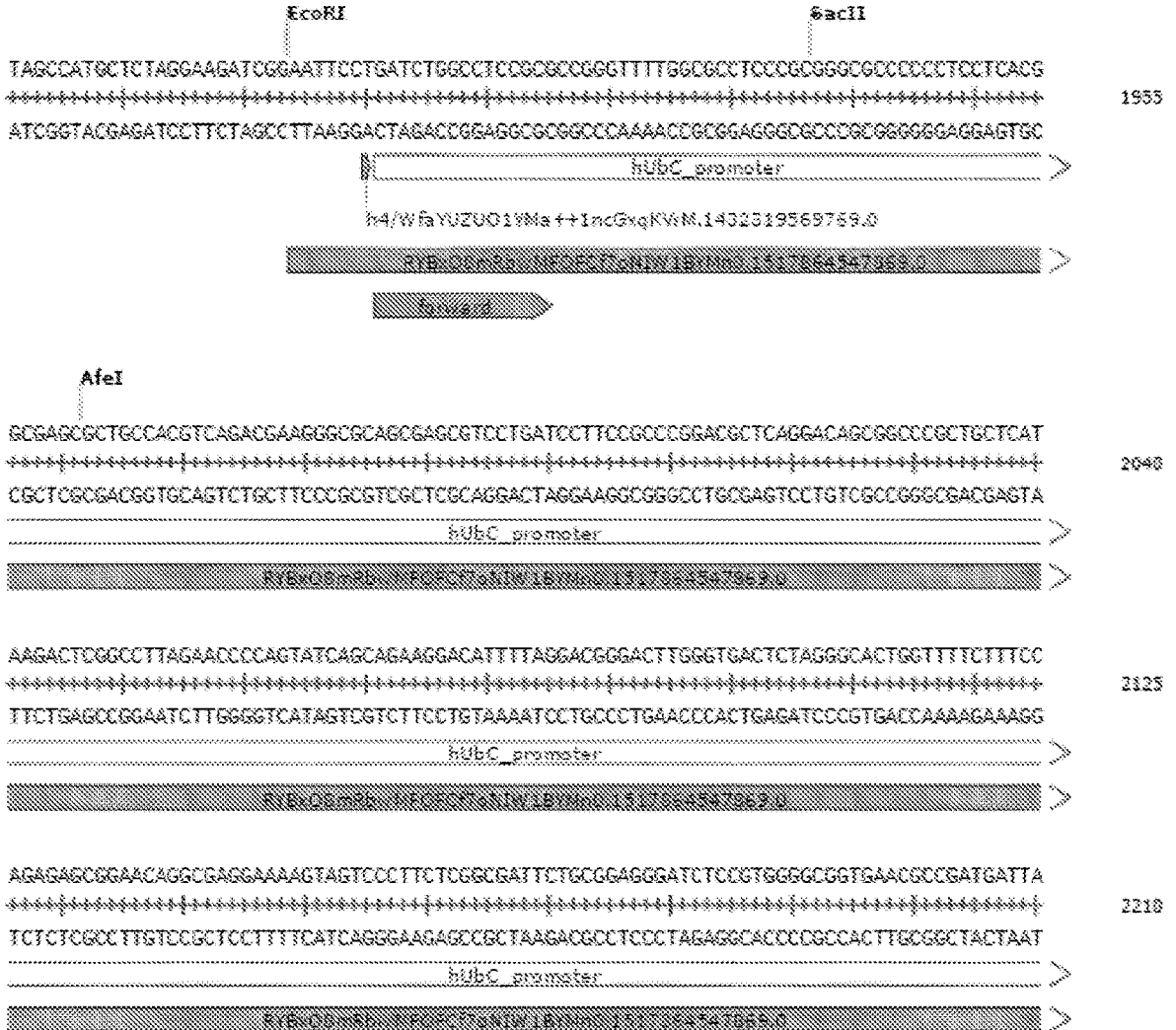
Figure 2E:
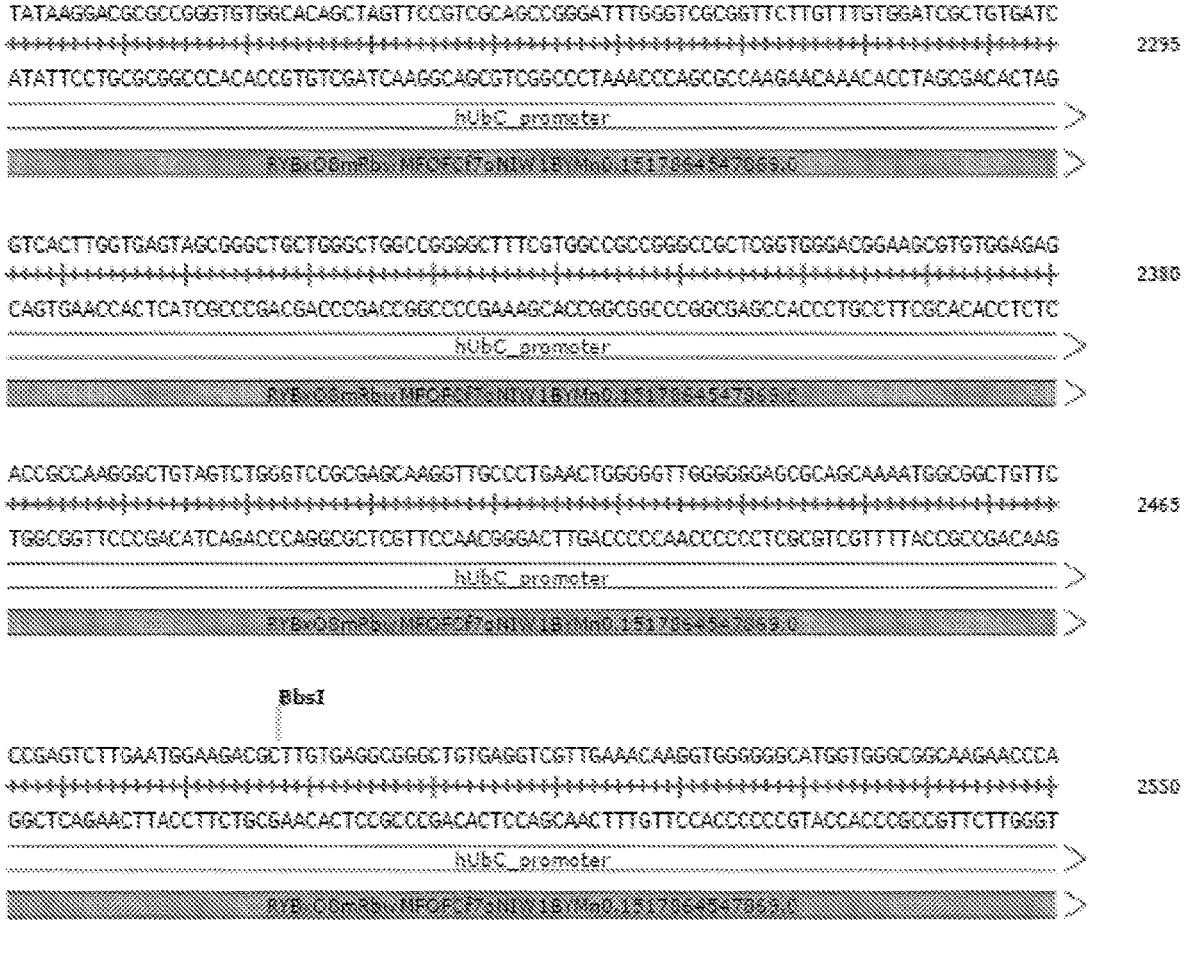
Figure 2F:
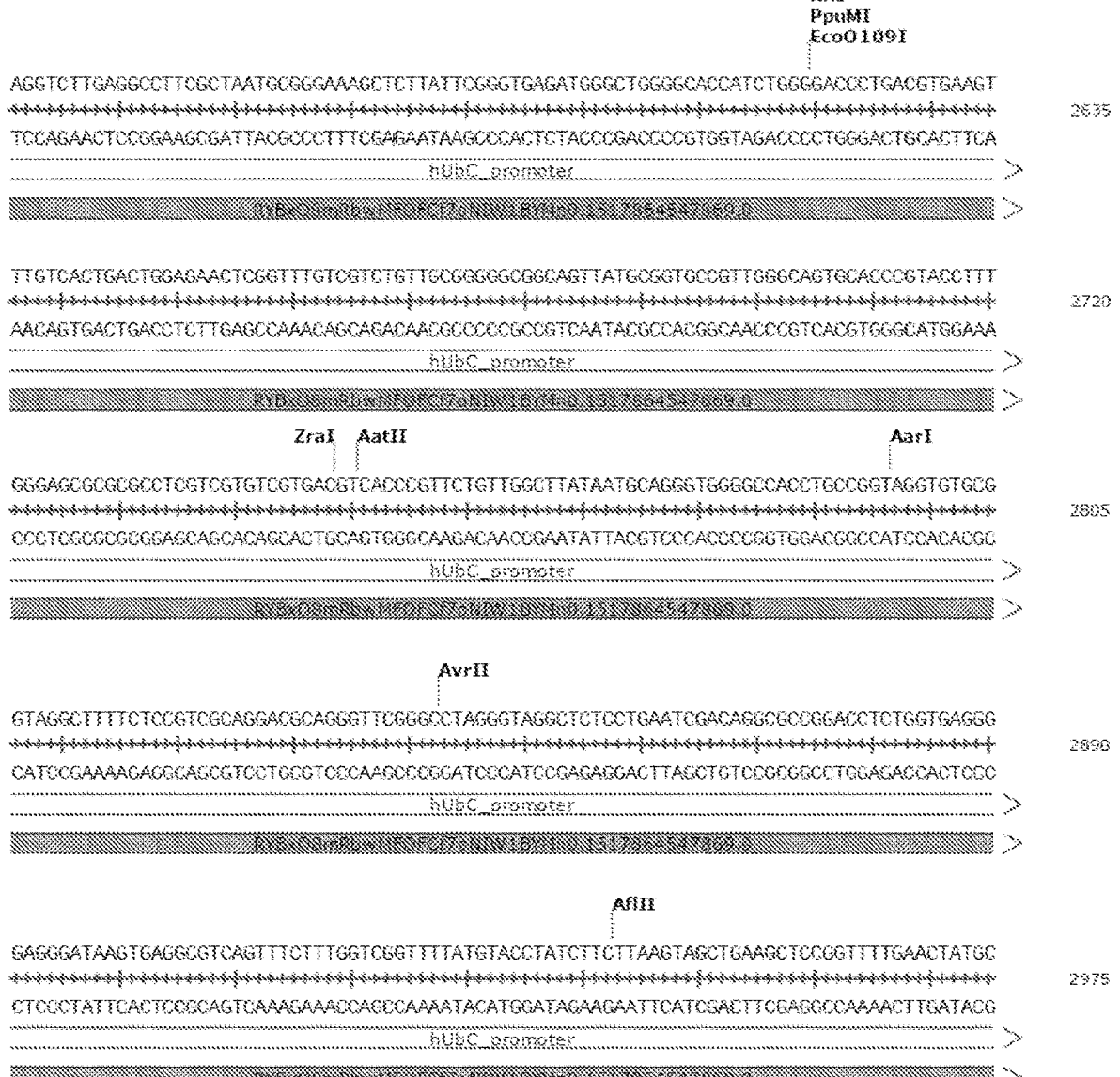
Figure 2G:
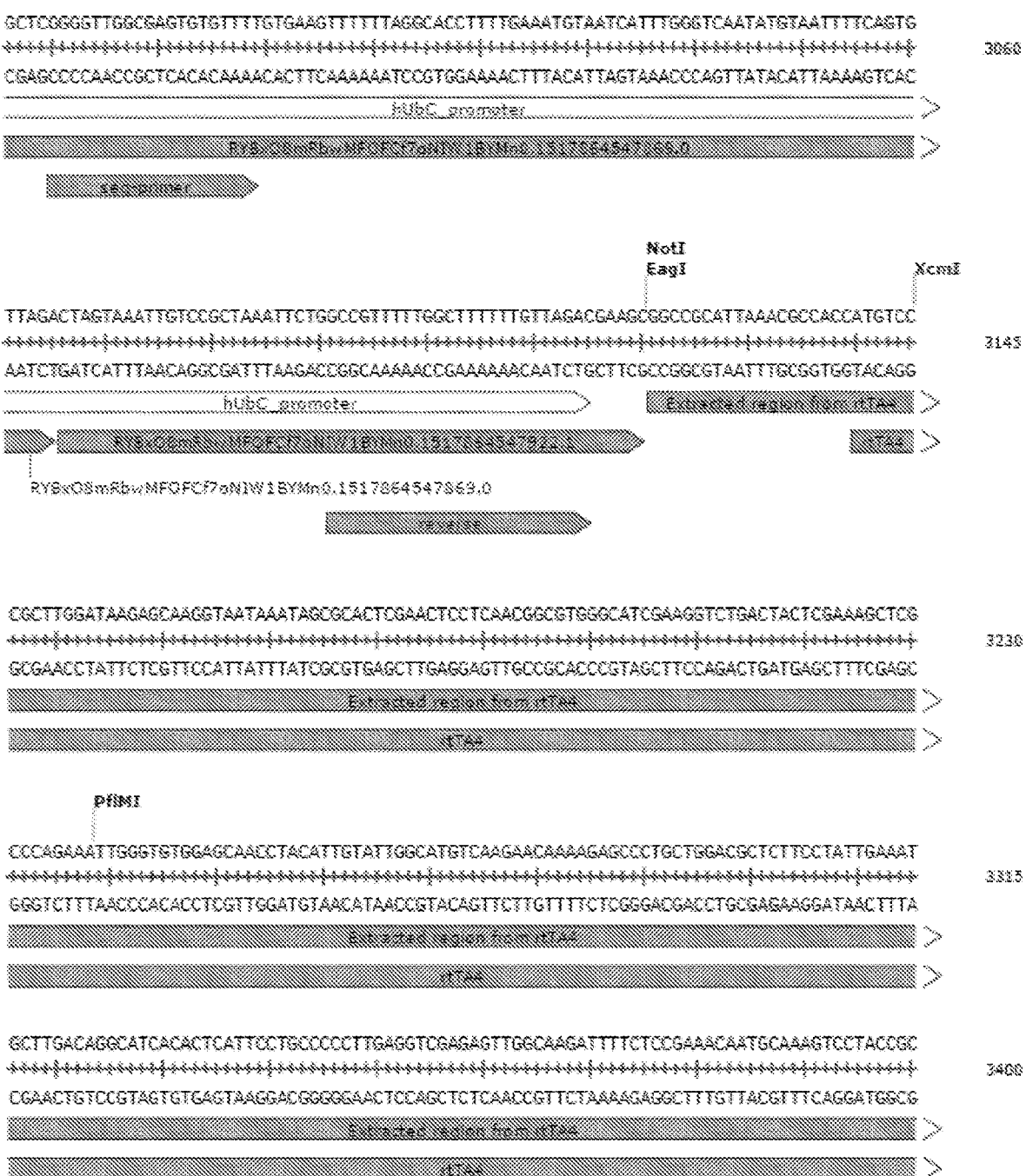
Figure 2H:
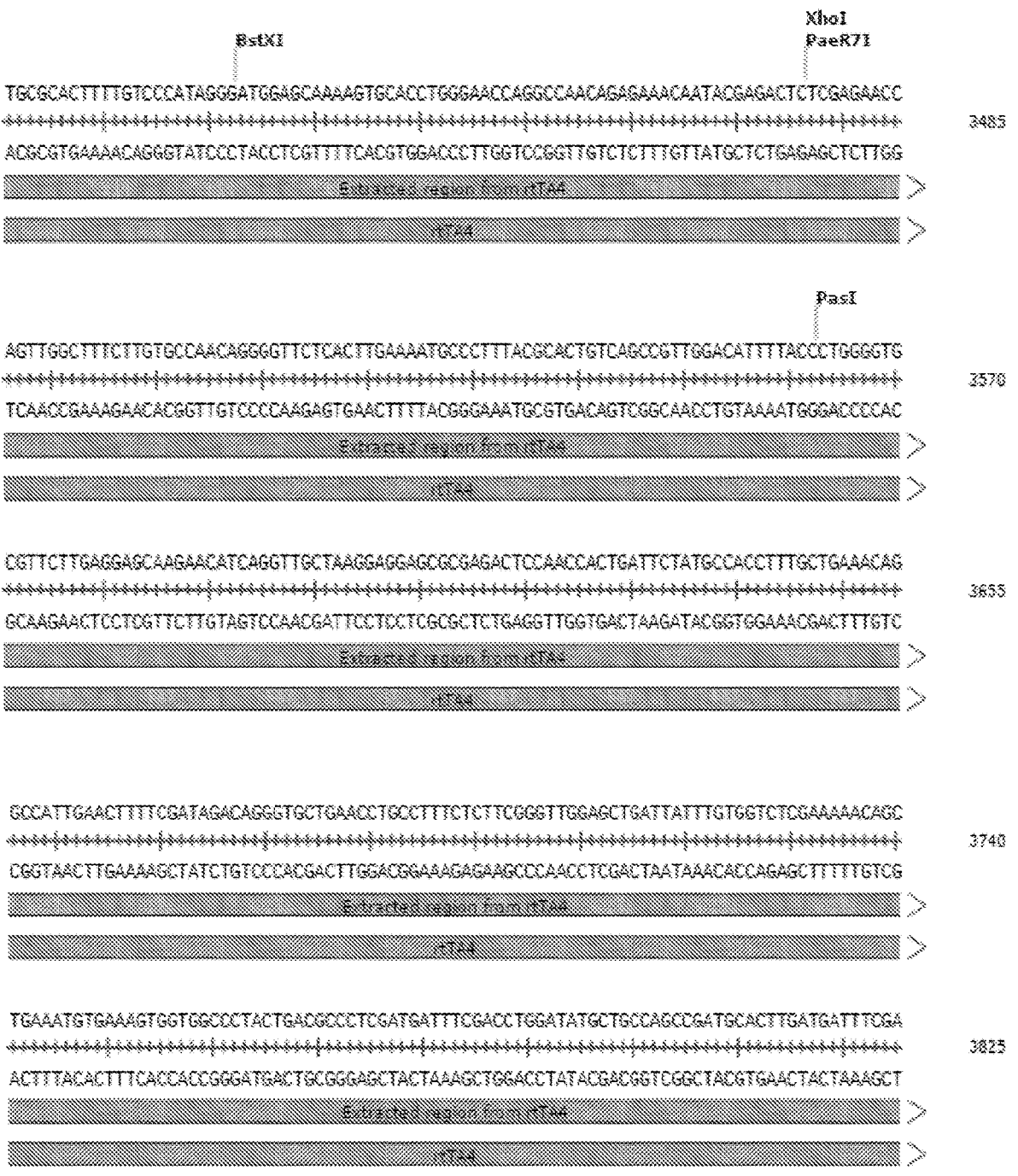
Figure 2I:
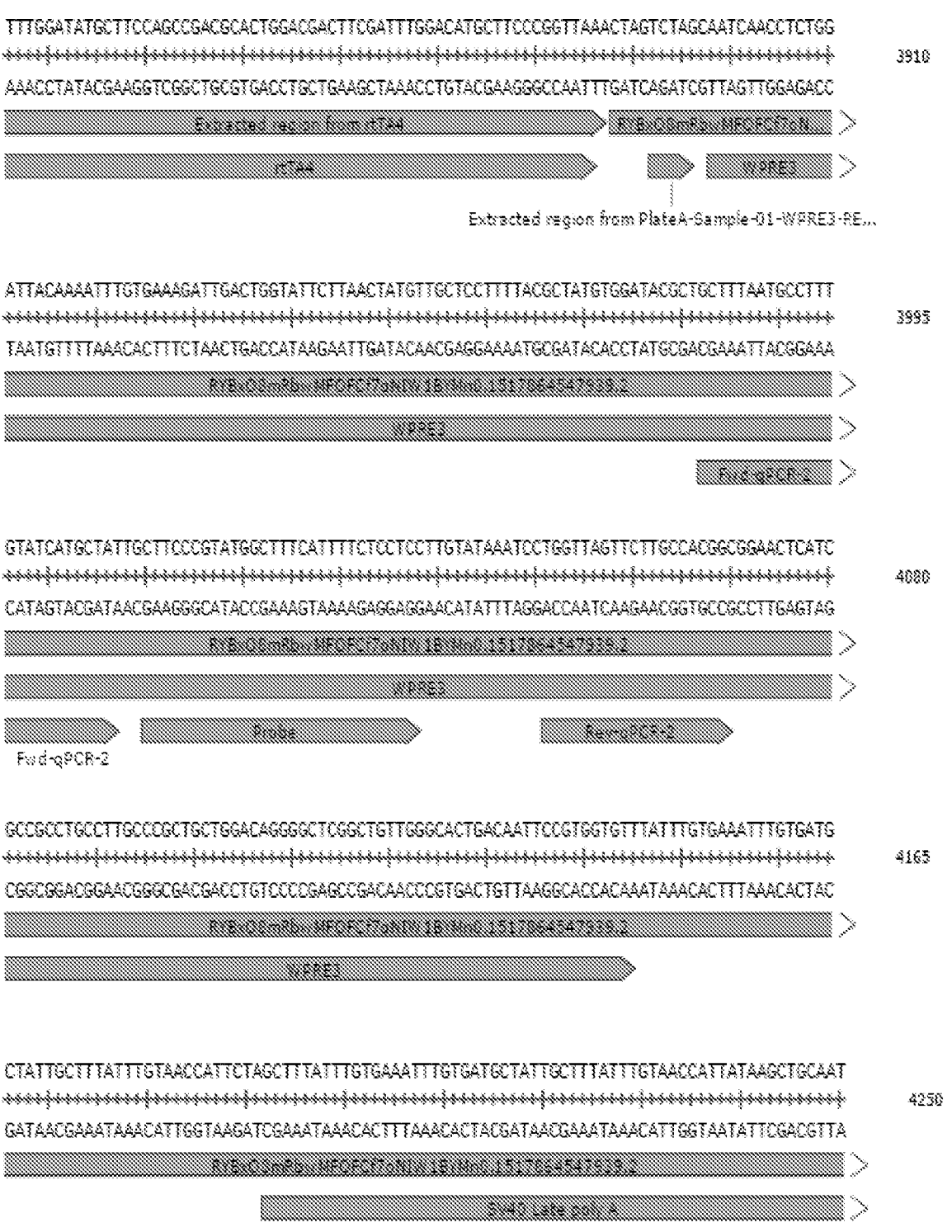
Figure 2J:
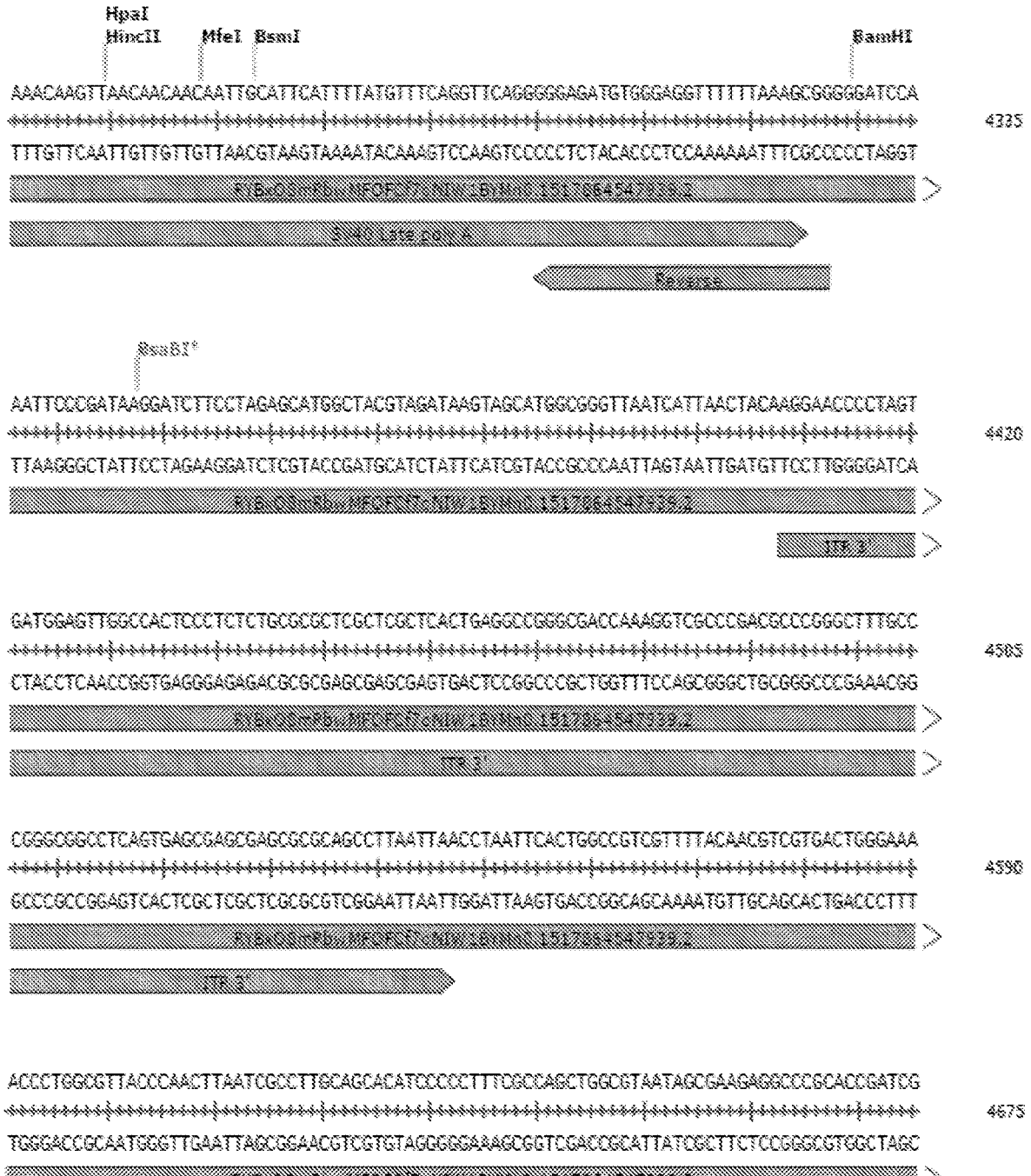
Figure 2K:
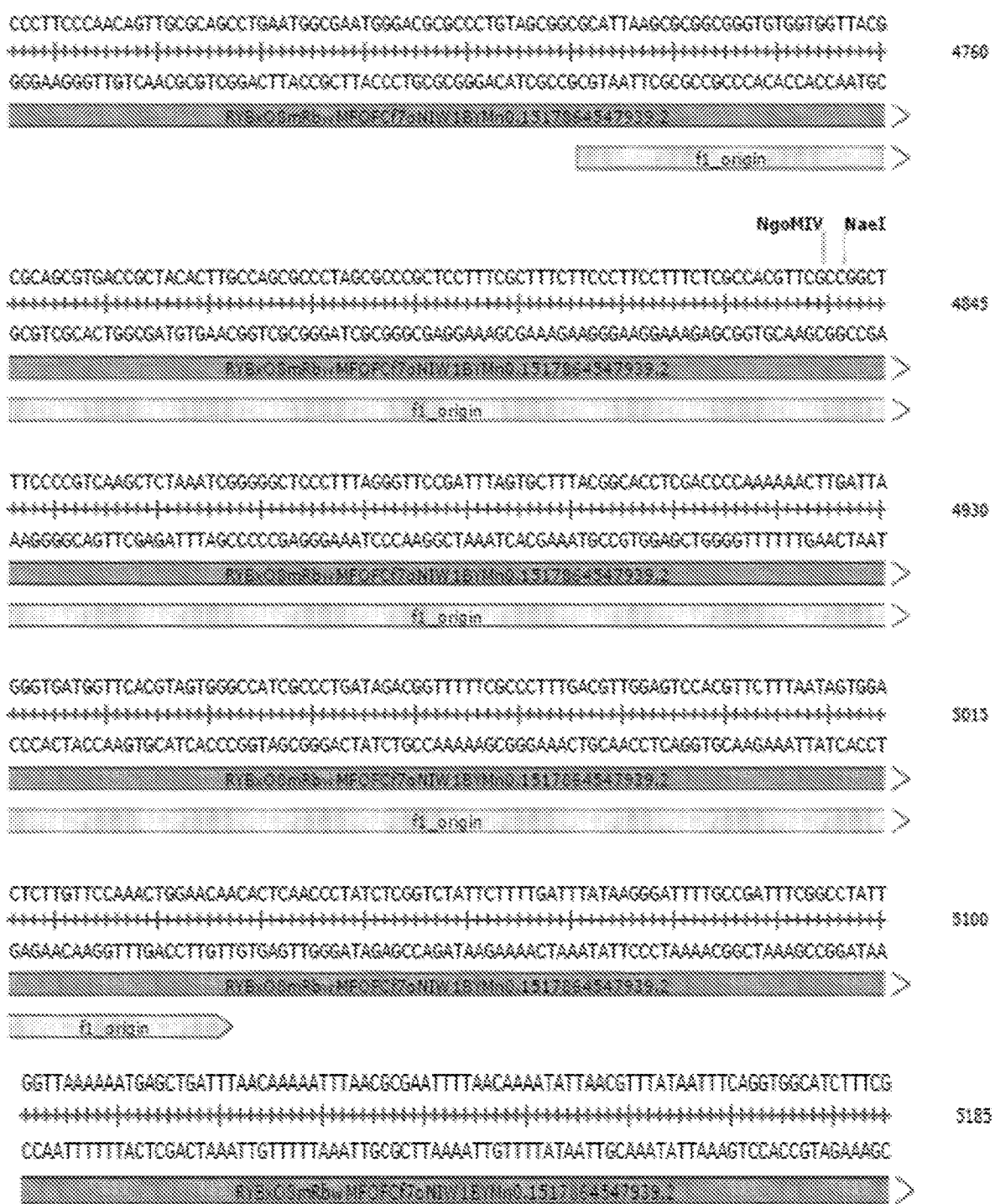
Figure 2L:
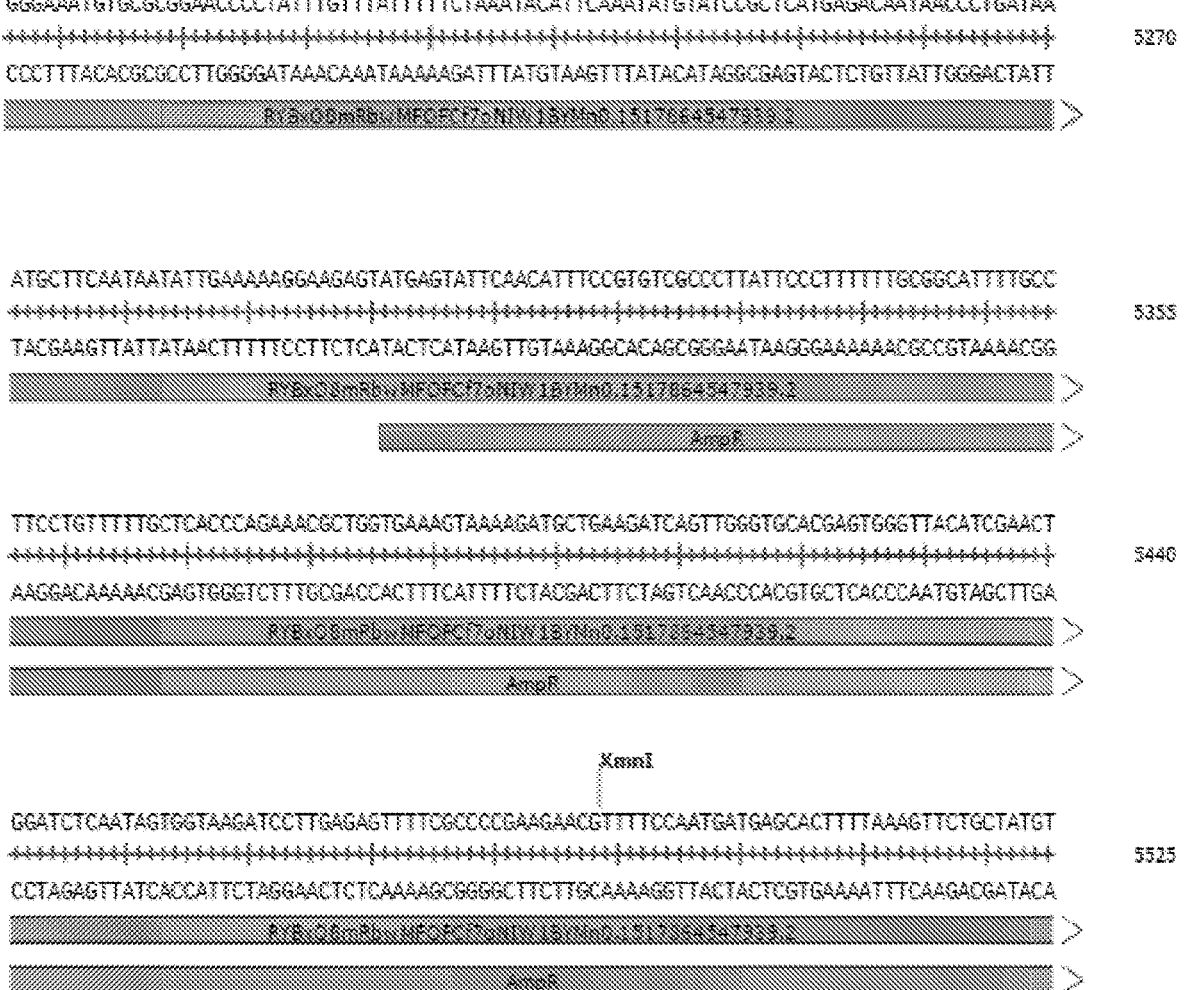
Figure 2M:

The present disclosure is based, at least in part, on the unexpected results demonstrating that four mutations corresponding to residues G72, G12, F67, and R171 in rtTA3 (SEQ ID NO: 11) produced a mutant rtTA (referred to herein as rtTA4) that had lower leakiness as compared to rtTA3 and improved sensitivity to tetracycline withdrawal. Whereas existing rtTA3 Tet-On systems are leaky (FIG. 4B) in vivo (e.g., in the liver of mice), the rtTA4 system described herein did not induce detectable transgene expression (e.g., in the livers of mice).

As shown herein, artTA4 sequence (e.g., SEQ ID NO: 13) was less leaky than rtTA3 (SEQ ID NO: 11), and in the absence of a tetracycline (e.g., doxycycline), rtTA4 did not induce detectable transgene expression in the liver, whereas rtTA3 induced transgene expression, even in the absence of a tetracycline (e.g., doxycycline). Furthermore, a Tet-On system with rtTA4 turned off 4-12 times faster than rtTA3. In certain embodiments, the rtTA4 Tet-On system described herein is further regulated by a tetR (tetRKRAB), which can bind to the TRE promoter in the absence of a tetracycline (e.g., doxycycline), preventing binding of rtTA and thereby further repressing gene expression.

Accordingly, provided herein, in some embodiments, are mutant rtTAs (e.g., rtTA4), engineered nucleic acids (e.g., expression vectors), recombinant viruses, systems, kits, and compositions comprising the same and methods of regulating gene expression using the same. Any of the mutant rtTAs, nucleic acids (e.g., engineered nucleic acids, including expression vectors) comprising a mutant rtTA, recombinant viruses, systems, kits, and compositions comprising the same may be useful in regulating gene expression, inducing cellular reprogramming, tissue repair, tissue regeneration, organ regeneration, reversing aging, treating a disease (e.g., acute injuries, neurodegenerative disease, chronic diseases, proliferative diseases, cardiovascular diseases, genetic diseases, inflammatory diseases, autoimmune diseases, neurological diseases, hematological diseases, painful conditions, psychiatric disorders, metabolic disorders, cancers, aging, age-related diseases, and diseases affecting any tissue in a subject), or any combination thereof Mutant Reverse Tetracycline Transactivators (rtTAs)

Aspects of the present disclosure provide mutant reverse tetracycline transactivators (rtTAs) that are capable of activating expression of genes from an operably linked tetracycline-responsive element (TRE) (e.g., a TRE3G, a TRE2, or a P tight promoter) in the presence of a tetracycline (e.g., doxycycline).

A mutant rtTA of the present disclosure comprises at least 1, 2, 3, 4, 5, 6, 7, 8, 9, 10, 11, 12, 13, 14, 15, 16, 17, 18, 19, 20, 30, 40, 50, 60, 70, 80, 90, or 100 transactivation domains. Non-limiting examples of transactivation domains include VP64, P65. RTA and MPH MS2-P65-HSF1. In some embodiments, a nucleotide sequence encoding VP64 comprises a sequence that is at least 70% (e.g., at least 75%, 80%, 85%, 90%, 95%, 98%, 99%, or 100%) identical to SEQ ID NO: 34. In some embodiments, an amino acid sequence encoding VP64 comprises a sequence that is at least 70% (e.g., at least 75%, 80%, 85%, 90%, 95%, 98%, 99%, or 100%) identical to the amino acid sequence encoded by SEQ ID NO: 34. In some embodiments, a nucleotide sequence encoding P65 comprises a sequence that is at least 70% (e.g., at least 75%, 80%, 85%, 90%, 95%, 98%, 99%, or 100%) identical to SEQ ID NO: 35. In some embodiments, an amino acid sequence encoding P65 comprises a sequence that is at least 70% (e.g., at least 75%, 80%, 85%, 90%, 95%, 98%, 99%, or 100%) identical to the amino acid sequence encoded by SEQ ID NO: 35. In some embodiments, a nucleotide sequence encoding RTA comprises a sequence that is at least 70% (e.g., at least 75%, 80%, 85%, 90%, 95%, 98%, 99%, or 100%) identical to SEQ ID NO: 36. In some embodiments, an amino acid sequence encoding RTA comprises a sequence that is at least 70% (e.g., at least 75%, 80%, 85%, 90%, 95%, 98%, 99%, or 100%) identical to the amino acid sequence encoded by SEQ ID NO: 36. In some embodiments, a nucleotide sequence encoding MPH MS2-P65-HSF1 comprises a sequence that is at least 70% (e.g., at least 75%, 80%, 85%, 90%, 95%, 98%, 99%, or 100%) identical to SEQ ID NO: 37. In some embodiments, an amino acid sequence encoding MPH MS2-P65-HSF1 comprises a sequence that is at least 70% (e.g., at least 75%, 80%, 85%, 90%, 95%, 98%, 99%, or 100%) identical to the amino acid sequence encoded by SEQ ID NO: 37.

The mutant rtTAs (e.g., rtTA4) of the present disclosure comprise mutations at positions corresponding to the following residues in SEQ ID NO: 11: G72; G12; F67; and R171. SEQ ID NO: 11 is a non-limiting example of a rtTA3 sequence. Non-limiting examples of mutations include point mutations, truncation mutations, deletions or insertions.

Non-limiting mutations at positions corresponding to residue G12 in SEQ ID NO: 11 include alanine (A), arginine (R), asparagine (N), aspartic acid (D), cysteine (C), glutamine (Q), glutamic acid (E), histidine (H), isoleucine (I), lysine (K), methionine (M), phenylalanine (F), proline (P), serine(S), threonine (T), tryptophan (W), tyrosine (Y), and valine (V).

Non-limiting mutations at positions corresponding to residue G72 in SEQ ID NO: 11 include alanine (A), arginine (R), asparagine (N), aspartic acid (D), cysteine (C), glutamine (Q), glutamic acid (E), histidine (H), isoleucine (I), lysine (K), methionine (M), phenylalanine (F), proline (P), serine(S), threonine (T), tryptophan (W), tyrosine (Y), and valine (V).

Non-limiting mutations at positions corresponding to residue F67 in SEQ ID NO: 11 include alanine (A), arginine (R), asparagine (N), aspartic acid (D), cysteine (C), glutamine (Q), glutamic acid (E), glycine (G), histidine (H), isoleucine (I), lysine (K), methionine (M), proline (P), serine(S), threonine (T), tryptophan (W), tyrosine (Y), and valine (V).

Non-limiting mutations at positions corresponding to residue F67 in SEQ ID NO: 11 include alanine (A), asparagine (N), aspartic acid (D), cysteine (C), glutamine (Q), glutamic acid (E), glycine (G), histidine (H), isoleucine (I), lysine (K), methionine (M), proline (P), phenylalanine (F), serine(S), threonine (T), tryptophan (W), tyrosine (Y), and valine (V).

Non-limiting mutations at positions corresponding to residue F67 in SEQ ID NO: 11 include alanine (A), arginine (R), asparagine (N), aspartic acid (D), cysteine (C), glutamine (Q), glutamic acid (E), glycine (G), histidine (H), isoleucine (I), lysine (K), methionine (M), proline (P), serine(S), threonine (T), tryptophan (W), tyrosine (Y), and valine (V).

The mutation at G72; G12; F67; and/or R171 may be a mutation to an amino acid with a charged side chain (e.g., arginine, histidine, lysine, aspartic acid, or glumatic acid). The amino acid may comprise a negatively charged side chain (e.g., aspartic acid or glutamic acid). The amino acid may comprise a positively charged side chain (arginine, histidine or lysine).

The mutation at G72; G12; F67; and/or R171 may be a mutation to an amino acid comprising a polar uncharged side chain (e.g., serine, threonine, asparagine, glutamine) or a comprising a hydrophobic side chain (e.g., alanine, valine, isoleucine, leucine, methionine, phenylalanine, tyrosine, or tryptophan).

The mutation at G72; G12; F67; and/or R171 may be to an amino acid comprising an aromatic ring (e.g., phenylalanine, tyrosine, or tryptophan).

In certain embodiments, a nucleic acid encoding rtTA4 comprises a sequence that is at least 70% (e.g., at least 75%, at least 80%, at least 85%, at least 90%, at least 95%, at least 98%, at least 99%, or at least 100%) identical to SEQ ID NO: 12 and/or encodes a protein with a mutation at the following residues corresponding to the following positions in rtTA3 (SEQ ID NO: 11): G72; G12; F67; and R171. ArtTA4 nucleic acid sequence may consist of SEQ ID NO: 12.

In certain embodiments, an amino acid sequence encoding rtTA4 comprises a sequence that is at least 70% (e.g., at least 75%, at least 80%, at least 85%, at least 90%, at least 95%, at least 98%, at least 99%, or at least 100%) identical to SEQ ID NO: 13 and/or encodes a protein with mutations at the following residues corresponding to the following positions in rtTA3 (SEQ ID NO: 11): G72; G12; F67; and R171.

In certain embodiments, a mutant rtTA comprises at least another mutation in a position corresponding to rtTA3 (SEQ ID NO: 11) in addition to the mutations corresponding to residues G72; G12; F67; and R171 in SEQ ID NO: 11. In certain embodiments, a mutant rtTA comprises at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 80, 90, 100, 110, 120, 130, 140, 150, 160, 170, 180, 190, 200, 210, 220, 230, or 240 additional mutations corresponding to a position that is not residues G72, G12, F67 and R171 in SEQ ID NO: 11.

It should be appreciated that any rtTA (e.g., rtTA3 or M2-rtTA) could be used as the reference sequence to be mutated. For example, a mutant rtTA of the present disclosure may comprise mutations corresponding to residues G72; G12; F67; and R171 of SEQ ID NO: 11, but otherwise comprise amino acid sequences present in M2-rtTA. In certain embodiments, in addition to the mutations corresponding to residues G72; G12; F67; and R171 of SEQ ID NO: 11, artTA of the present disclosure may comprise at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 80, 90, 100, 110, 120, 130, 140, 150, 160, 170, 180, 190, 200, 210, 220, 230, or 240 additional mutations corresponding to positions that are not residues G72, G12, F67 and R171 in SEQ ID NO: 11.

In certain embodiments, a rtTA4 amino acid sequence comprises the following mutations relative to rtTA3: a valine (V) or proline (P) mutation at a residue corresponding to position G72 in SEQ ID NO: 11, a serine(S) mutation at a residue corresponding to position G12 in SEQ ID NO: 11, a serine(S) mutation at a residue corresponding to position F67 in SEQ ID NO: 11, and an lysine (K) mutation at a residue corresponding to position R171 in SEQ ID NO: 11. A rtTA4 amino acid sequence may consist of SEQ ID NO: 13.

Any suitable sequence alignment algorithm may be used to align two sequences of interest (e.g., a rtTA4 of the present disclosure with rtTA3 set forth as SEQ ID NO: 11) to identify the corresponding residue position in rtTA3. As a non-limiting example, SEQ ID NO: 13 (amino acid sequence of rtTA4) may be aligned to SEQ ID NO: 11 (amino acid sequence of rtTA3) using Clustal Omega (see e.g., Larkin et al., Bioinformatics. 2007 Nov. 1;23 (21): 2947-8). In the exemplary alignment below, position 12 (glycine) in SEQ ID NO: 11 is mutated to serine in SEQ ID NO: 13, position 72 (glycine) in SEQ ID NO: 11 is mutated to valine in SEQ ID NO: 13, position 67 (phenylalanine) in SEQ ID NO: 11 is mutated to serine in SEQ ID NO: 13, position 171 (arginine) in SEQ ID NO: 11 is mutated to lysine in SEQ ID NO: 13.

```
SEQIDNO11  MSRLDKSKVINGALELLNGVGIEGLTTRKLAQKLGVEQPTLYWHVKNKRALLDALPIEML   60

SEQIDNO13  MSRLDKSKVINSALELLNGVGIEGLTTRKLAQKLGVEQPTLYWHVKNKRALLDALPIEML   60
           ***********.************************************************

SEQIDNO11  DRHHTHFCPLEGESWQDFLRNNAKSYRCALLSHRDGAKVHLGTRPTEKQYETLENQLAFL  120

SEQIDNO13  DRHHTHSCPLEVESWQDFLRNNAKSYRCALLSHRDGAKVHLGTRPTEKQYETLENQLAFL  120
           ***** **** *************************************************

SEQIDNO11  CQQGFSLENALYALSAVGHFTLGCVLEEQEHQVAKEERETPTTDSMPPLLRQAIELFDRQ  180

SEQIDNO13  CQQGFSLENALYALSAVGHFTLGCVLEEQEHQVAKEERETPTTDSMPPLLKQAIELFDRQ  180
           **************************************************.*********

SEQIDNO11  GAEPAFLFGLELIICGLEKQLKCESGGPTDALDDFDLDMLPADALDDFDLDMLPG-----  235

SEQIDNO13  GAEPAFLFGLELIICGLEKQLKCESGGPTDALDDFDLDMLPADALDDFDLDMLPADALDD  240
           ******************************************************.

SEQIDNO11  --------                                                     235

SEQIDNO13  FDLDMLPG                                                     248
```

It should be understood, that the present disclosure encompasses rtTA4 variants that comprise mutations at the following residues corresponding to the following positions in rtTA3 (SEQ ID NO: 11): G72; G12; F67; and R171. Such a rtTA4 variant may comprise a sequence that is at least 70%, 75%, 80%, 85%, 90%, 91%, 92%, 93%, 94%, 95%, 96%, 97%, 98%, 99%, but less than 100% sequence identical to SEQ ID NO: 13.

The term "sequence identity," as known in the art, refers to a relationship between the sequences of two polypeptides or two polynucleotides, as determined by sequence comparison (alignment). In some embodiments, sequence identity is determined across the entire length of a mutant rtTA (e.g., rtTA4) sequence. In some embodiments, sequence identity is determined over a region (e.g., a stretch of amino acids or nucleotides such as 10, 20, 30, 40, 50, etc. amino acids or nucleotides) of a mutant rtTA (e.g., rtTA4).

Identity can also refer to the degree of sequence relatedness between two sequences as determined by the number of matches between strings of two or more residues (e.g., nucleotides or amino acid residues). Identity measures the percent of identical matches between the smaller of two or more sequences with gap alignments (if any) addressed by a particular mathematical model or computer program (e.g., "algorithms").

Identity of related polypeptides or nucleic acid sequences can be readily calculated by any of the methods known to one of ordinary skill in the art. The "percent identity" of two sequences (e.g., nucleic acid or amino acid sequences) may, for example, be determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the NBLAST® and XBLAST® programs (version 2.0) of Altschul et al., *J. Mol. Biol.* 215:403-10, 1990. BLAST® protein searches can be performed, for example, with the XBLAST program, score=50, wordlength=3 to obtain amino acid sequences homologous to the protein molecules of the invention. Where gaps exist between two sequences, Gapped BLAST® can be utilized, for example, as described in Altschul et al., *Nucleic Acids Res.* 25 (17): 3389-3402, 1997. When utilizing BLAST® and Gapped BLAST® programs, the default parameters of the respective programs (e.g., XBLAST® and NBLAST®) can be used, or the parameters can be adjusted appropriately as would be understood by one of ordinary skill in the art.

Another local alignment technique which may be used, for example, is based on the Smith-Waterman algorithm (Smith, T. F. & Waterman, M. S. (1981) "Identification of common molecular subsequences." *J. Mol. Biol.* 147:195-197). A general global alignment technique which may be used, for example, is the Needleman-Wunsch algorithm (Needleman, S. B. & Wunsch, C. D. (1970) "A general method applicable to the search for similarities in the amino acid sequences of two proteins." *J. Mol. Biol.* 48:443-453), which is based on dynamic programming.

More recently, a Fast Optimal Global Sequence Alignment Algorithm (FOGSAA) was developed that purportedly produces global alignment of nucleic acid and amino acid sequences faster than other optimal global alignment methods, including the Needleman-Wunsch algorithm. In some embodiments, the identity of two polypeptides is determined by aligning the two amino acid sequences, calculating the number of identical amino acids, and dividing by the length of one of the amino acid sequences. In some embodiments, the identity of two nucleic acids is determined by aligning the two nucleotide sequences and calculating the number of identical nucleotide and dividing by the length of one of the nucleic acids.

For multiple sequence alignments, computer programs including Clustal Omega (Sievers et al., *Mol Syst Biol.* 2011 Oct. 11:7:539) may be used.

In some embodiments, a protein encoding a mutant rtTA (e.g., rtTA4) is fused to a protein transduction domain. Without being bound by a particular theory, a protein transduction domain facilitate delivery of a cargo (e.g., a protein, nucleic acids, nanoparticles, viral particles, etc.) across cellular membranes. Protein transduction domains include cationic peptides, hydrophobic peptides, and/or a cell specific peptides. See, e.g., Zhou et al., Cell Stem Cell. 2009 May 8: 4 (5): 381-4; Zahid et al., Curr Gene Ther. 2012 Oct.: 12 (5): 374-80.

In some embodiments, a protein is formulated in a nanoparticle for delivery. In some embodiments, a chitosan polymeric nanoparticle is loaded with mutant rtTA (e.g., rtTA4) protein. See, e.g., Tammam et al., Oncotarget. 2016 Jun. 21;7 (25): 37728-37739.

Nucleic Acids (e.g., Engineered Nucleic Acids) Encoding a Mutant rtTA

Any of the nucleic acid sequences encoding a recombinant rtTAs (e.g., rtTA4) described herein may be cloned into an expression vector. A nucleic acid (e.g., engineered nucleic acid) of the present disclosure may be present on a viral or non-viral vector. Suitable non-viral vectors include, but are not limited to, plasmid DNA or RNA (e.g., mRNA). In some embodiments, plasmid DNA may be incorporated into a nanoparticle and/or fused to a potein transduction domain (PTD). See above.

As a non-limiting example, the engineered nucleic acids (e.g., expression vectors) of the present disclosure (e.g., RNA, including mRNA, or DNA (e.g., plasmid DNA) of the present disclosure may be formulated in a nanoparticle for delivery. See, e. g., Dong et al., Nano Lett. 2016 Feb. 10;16 (2): 842-8. In some embodiments, the nanoparticle comprises acetylated galactose. See, e.g., Lozano-Torres et al., J Am Chem Soc. 2017 Jul. 5;139 (26): 8808-8811. In some embodiments, the engineered nucleic acids (e.g., expression vectors) (e.g., RNA, including mRNA, or DNA) is electroporated or transfected into a cell. In certain embodiments, the engineered nucleic acids are delivered as a naked nucleic acid (e.g., naked DNA or naked RNA).

Nonlimiting examples of viral vectors include lentivirus, adenovirus, alphavirus, vaccinia virus, retrovirus, herpes virus, and AAV vectors. Any of the recombinant rtTAs using methods known in the art. Expression vectors containing the necessary elements for expression are commercially available and known to one of ordinary skill in the art (see, e.g., Sambrook et al., *Molecular Cloning: A Laboratory Manual*, Fourth Edition, Cold Spring Harbor Laboratory Press, 2012). See also, e.g., general techniques below. Non-limiting examples of elements on a nucleic acid (e.g., an engineered nucleic acid, including an expression vector) include promoters, nucleic acid sequences operably linked to a promoter (e.g., an open-reading frame), a terminator sequence, a separator sequence, or a WPRE sequence. A vector may comprise one or more of these elements.

In certain embodiments, the nucleic sequence encoding a mutant rtTA is codon-optimized, for example, for expression in a particular host cell. In certain embodiments the sequence encoding a mutant rtTA is codon-optimized for expression in a mammalian cell. In certain embodiments the sequence encoding a mutant rtTA is codon-optimized for expression in a human cell. In certain embodiments, a sequence encoding a mutant rtTA is at least 70% (e.g., 75%, 80%, 85%, 90%, 95%, 98%, 99%, or 100%) identical to SEQ ID NO: 12.

The engineered nucleic acids (e.g., expression vectors) encoding a mutant rtTA (e.g., rtTA4) of the present disclosure comprise a promoter that is operably linked to the nucleic acid encoding rtTA. The promoter may be a constitutive promoter (e.g., CP1, CMV, EF1a, SV40, PGK1. Ubc, human beta actin, CAG, Ac5, polyhedrin, TEF1, GDS, CaM3 5S, Ubi, H1, or U6 promoter). A Ubc promoter may comprise a sequence that is at least 70% (e.g., at least 75%, 80%, 85%, 90%, 95%, 98%, 99%, or 100%) identical to SEQ ID NO: 18.

To allow for tissue-specific expression of a mutant tTA, the promoter may be tissue-specific (e.g., an eye-specific promoter, a bone-specific promoter, a lung-specific promoter, a breast-specific promoter, a pancreas-specific promoter, a muscle-specific promoter, a liver-specific promoter, a skin-specific promoter, a heart-specific promoter, a brain-specific promoter, a nerve tissue-specific promoter, a kidney-specific promoter, a testes-specific promoter, an ovary-specific promoter, or an intestine-specific promoter). In certain embodiments, the muscle-specific promoter is a desmin promoter. In some embodiments, a desmin promoter comprises a sequence that is at least 70% (e.g., 75%, 80%, 85%, 90%, 95%, 98%, 99%, or 100%) identical to SEQ ID NO: 29.

As will be appreciated by a person of ordinary skill in the art, the promoter operably linked to a nucleic acid encoding a mutant rtTA may be selected based on the host cell for expression. For example, a mammalian promoter may be used to drive expression of a mutant rtTA in a mammalian cell. A eukaryotic promoter may be used to drive expression of rtTA in a eukaryotic cell. A prokaryotic promoter may be used to drive expression of rtTA in a prokaryotic cell. A tissue specific promoter may be used to express a mutant rtTA in a tissue of interest within a subject.

In certain embodiments, a nucleic acid (e.g., engineered nucleic acid) sequence encoding a mutant rtTA is codon optimized for expression in a particular host cell. For example, a nucleic acid (e.g., engineered nucleic acid) encoding a mutant rtTA may be optimized for expression in a eukaryotic cell (e.g., a mammalian cell) or a prokaryotic cell.

The nucleic acid (e.g., engineered nucleic acid, including an expression vector) encoding the mutant rtTA may further comprise a Woodchuck Hepatitis Virus (WHP) Posttranscriptional Regulatory Element (WPRE), which may be useful in enhancing transgene gene expression (e.g., from a viral vector). In certain embodiments, a WPRE sequence is at least 70% (e.g., at least 75%, at least 80%, at least 85%, at least 90%, at least 95%, at least 98%, at least 99%, or at least 100%) identical to SEQ ID NO: 21. In certain embodiments, a WPRE sequence is located downstream of the nucleic acid encoding a mutant rtTA (e.g., rtTA4).

A terminator sequence may be used to designate the end of a transcript (cause transcription to stop). Non-limiting examples of mammalian terminator sequences include bovine growth hormone terminator, and viral termination sequences such as, for example, the SV40 terminator, spy, yejM, secG-leuU, thrl ABC, rrnB T1, hisL.GDCBHAF1, metZWV, rrnC, xapR, aspA, and arcA terminator. In certain embodiments, the terminator sequence is SV40 and comprises a sequence that is at least 70% (e.g., at least 75%, 80%, 85%, 90%, 95%, 98%, 99%, or 100%) identical to SEQ ID NO: 8.

A nucleic acid (e.g., an engineered nucleic acid, including an expression vector) encoding a mutant rtTA (e.g., rtTA4) may further encode a tetracycline repressor (TetR), which prevents gene expression from promoters comprising a TRE in the absence of a tetracycline (e.g., doxycycline). In the presence of tetracycline, TetRs cannot bind promoters comprising a TRE, and TetR cannot prevent transcription. Non-limiting examples of TetRs include TetR, TRSID, and tetRKRAB. In some embodiments, a TetR (e.g., TetR) is encoded by a nucleic acid comprising a sequence that is at least 70% (e.g., at least 75%, at least 80%, at least 85%, at least 90%, at least 95%, at least 98%, at least 99%, or at least 100%) identical to SEQ ID NO: 25. In some embodiments, a TetR (e.g., TetR) comprises a sequence that is at least 70% (e.g., at least 75%, at least 80%, at least 85%, at least 90%, at least 95%, at least 98%, at least 99%, or at least 100%) identical to SEQ ID NO: 26. In some embodiments, a TetR (e.g., tetRKRAB) is encoded by a nucleic acid comprising a sequence that is at least 70% (e.g., at least 75%, at least 80%, at least 85%, at least 90%, at least 95%, at least 98%, at least 99%, or at least 100%) identical to SEQ ID NO: 27. In some embodiments, a TetR (e.g., tetRKRAB) comprises a sequence that is at least 70% (e.g., at least 75%, at least 80%, at least 85%, at least 90%, at least 95%, at least 98%, at least 99%, or at least 100%) identical to SEQ ID NO: 28. A TetR may decrease transgene expression from a promoter by at least 10%, at least 20%, at least 30%, at least 40%, at least 50%, at least 60%, at least 70%, at least 80%, at least 90%, or 100%) in the absence of a tetracycline (e.g., doxycycline) as compared to in the presence of a tetracycline. Gene expression may be measured using any suitable method including assessment of protein levels and RNA levels.

A nucleic acid (e.g., an engineered nucleic acid, including an expression vector) may further comprise a separator sequence (e.g., an IRES or a polypeptide cleavage signal). Exemplary polypeptide cleavage signals include 2A peptides (e.g., T2A, P2A, E2A, and F2A). A 2A peptide may comprise a sequence that is at least 70% (e.g., at least 75%, 80%, 85%, 90%, 95%, 98%, 99%, or 100%) identical to SEQ ID NO: 9. For expression vectors encoding more than one transgene (e.g., a mutant rtTA and a tetR (e.g., tetRKRAB), each transgene may be operably linked to a different promoter or to the same promoter. The transgenes may be separated (e.g., an IRES or a polypeptide cleavage signal) on the expression vector. Expression of the nucleic acid results in separate amino acid sequences encoding each protein of interest.

In some embodiments, a nucleic acid (e.g., an engineered nucleic acid, including an expression vector) encoding a mutant rtTA (e.g., rtTA4) may comprise a sequence that is at least 70% (e.g., 75%, 80%, 85%, 90%, 95%, 98%, 99%, or 100%) identical to pAAV-UBC-rtTA4-WPRE3-SV40 pA (SEQ ID NO: 17). In some embodiments, a nucleic acid (e.g., an engineered nucleic acid, including an expression vector) encoding a mutant rtTA (e.g., rtTA4) consists of SEQ ID NO: 17. In some embodiments, a nucleic acid (e.g., an engineered nucleic acid, including an expression vector) encoding a mutant rtTA (e.g., rtTA4) may comprise a sequence that is at least 70% (e.g., 75%, 80%, 85%, 90%, 95%, 98%, 99%, or 100%) identical to desmin-rtTA4 vector (SEQ ID NO: 30). In some embodiments, a nucleic acid (e.g., an engineered nucleic acid, including an expression vector) encoding a mutant rtTA (e.g., rtTA4) consists of SEQ ID NO: 30.

Vectors of the invention may further comprise a marker sequence for use in the identification of cells that have or have not been transformed or transfected with the vector. Markers include, for example, genes encoding proteins that increase or decrease either resistance or sensitivity to antibiotics (e.g., ampicillin resistance genes, kanamycin resistance genes, neomycin resistance genes, tetracycline resistance genes and chloramphenicol resistance genes) or other compounds, genes encoding enzymes with activities detectable by standard assays known in the art (e.g., B-galactosidase, luciferase or alkaline phosphatase), and genes that visibly affect the phenotype of transformed or transfected cells, hosts, colonies or plaques (e.g., green fluorescent protein). In some embodiments, the vectors used herein are capable of autonomous replication and expression of the structural gene products present in the DNA segments to which they are operably linked.

In some embodiments, the nucleic acid (e.g., an engineered nucleic acid, including an expression vector) encoding the rtTA is a viral vector (e.g., lentivirus vector, adenovirus vector, alphavirus vector, vaccinia virus vector, herpes virus vector, adeno-associated virus (AAV) vector). An AAV vector, as used herein, generally comprises ITRs flanking an expression cassette (e.g., a nucleic acid comprising a promoter sequence operably linked to a sequence encoding a mutant rtTA, including rtTA4).

In certain embodiments, the number of base pairs between two ITRs in an AAV vector of the present disclosure is less than 5 kilobases (kb) (e.g., less than 4.9 kb, less than 4.8 kb, less than 4.7 kb, less than 4.6 kb, less than 4.5 kb, less than 4.4 kb, less than 4.3 kb, less than 4.2 kb, less than 4.1 kb, less than 4 kb, less than 3.5 kb, less than 3 kb, less than 2.5 kb, less than 2 kb, less than 1.5 kb, less than 1 kb, or less than 0.5 kb). In certain embodiments, an AAV vector with a distance of less than 4.7 kb between two ITRs is capable of being packaged into virus at a titer of at least $0.5\times10^{10}$ particle forming units per ml (pfu/ml), at least $1\times10^{10}$ pfu/ml, at least $5\times10^{10}$ pfu/ml, at least $1\times10^{11}$ pfu/ml, at least $5\times10^{11}$ pfu/ml, at least $1\times10^{12}$ pfu/ml, at least $2\times10^{12}$ pfu/ml, at least $3\times10^{12}$ pfu/ml, at least $4\times10^{12}$ pfu/ml, at least $5\times10^{12}$ pfu/ml, at least $6\times10^{12}$ pfu/ml, at least $7\times10^{12}$ pfu/ml, at least $8\times10^{12}$ pfu/ml, at least $9\times10^{12}$ pfu/ml, or at least $1\times10^{13}$ pfu/ml.

In certain embodiments, the infection efficiency of a recombinant virus (e.g., lentivirus, adenovirus, alphavirus, vaccinia virus, retrovirus, herpes virus, or AAV) harboring a mutant rtTA (e.g., rtTA4) vector of the present disclosure in cells (e.g., animal cells, including mammalian cells) is at least 20% (e.g., at least 30%, at least 40%, at least 50%, at least 60%, at least 70%, at least 80%, or at least 90%, or 100%).

In certain embodiments, a nucleic acid (e.g., an engineered nucleic acid, including an expression vector) of the present disclosure is at least 1 kilobase (kb) (e.g., at least 1 kb, 2 kb, 3 kb, 4 kb, 5 kb, 6 kb, 7 kb, 8 kb, 9 kb, 10 kb, 50 kb, or 100 kb). In certain embodiments, a nucleic acid (e.g., an engineered nucleic acid, including an expression vector) of the present disclosure is less than 10 kb (e.g., less than 9 kb, less 8 kb, less than 7 kb, less than 6 kb, less than 5 kb, less than 4 kb, less than 3 kb, less than 2 kb, or less than 1 kb).

Inducible Expression Vectors Encoding a Transgene

Any of the mutant rtTAs described herein may be used to promote expression of a transgene that is operably linked to an inducible promoter. In certain embodiments, a nucleic acid (e.g., an engineered nucleic acid, including an expression vector) encoding a mutant rtTA also comprises the transgene operably linked to an inducible promoter. In certain embodiments, a nucleic acid (e.g., an engineered nucleic acid, including an expression vector) encoding a mutant rtTA is separate from a nucleic acid (e.g., an engineered nucleic acid, including an expression vector) encoding a transgene operably linked to the inducible promoter. A mutant rtTA may drive expression of at least 1 inducible promoter comprising a Tet-O sequence. A mutant rtTA may drive expression of at least 2, 3, 4, 5, 6, 7, 8, 9, 10, 20, 30, 40, 50, 60, 70, 80, 90, or 100 inducible promoter comprising a Tet-O sequence.

It should be appreciated that one inducible promoter comprising a Tet-O sequence may be operably linked to at least 1, 2, 3, 4, 5, 6, 7, 8, 9, 10, 11, 12, 13, 14, 15, 16, 17, 18, 19, 20, 30, 40, 50, 60, 70, 80, 90, or 100 transgene sequences.

Suitable expression vectors encoding a transgene for use with a mutant rtTA of the present disclosure comprise an inducible promoter that comprise at least one Tet-O sequence (e.g., a TRE promoter) (e.g., an inducible promoter may comprise at least 1, 2, 3, 4, 5, 6, 7, 8, 9, 10, 11, 12, 13, 14, 15, 16, 17, 18, 19, 20 30, 40, 50, 60, 70, 80, 90, or all Tet-O sequences). A TRE promoter of the present disclosure may comprise a sequence that is at least 70% (e.g., at least 75%, at least 80%, at least 85%, at least 90%, at least 95%, at least 98%, at least 99%, or 100%) identical to SEQ ID NO: 7. The TRE promoter often comprises a minimal promoter, which cannot promote transcription in the absence of upstream enhancers that are present in the TRE promoter. A minimal promoter may be a minimal CMV promoter (e.g., a sequence that is at least 70%, at least 75%, at least 80%, at least 85%, at least 90%, at least 95%, at least 98%, at least 99%, or 100% identical to SEQ ID NO: 20). For example, a TRE promoter may be a TRE3G promoter (e.g., a sequence that is at least 70% (e.g., at least 75%, at least 80%, at least 85%, at least 90%, at least 95%, at least 98%, at least 99%, or 100%) identical to SEQ ID NO: 7). For example, a TRE promoter may be a TRE3G promoter (e.g., a sequence that is at least 70% (e.g., at least 75%, at least 80%, at least 85%, at least 90%, at least 95%, at least 98%, at least 99%, or 100%) identical to SEQ ID NO: 7). In some embodiments, the TRE promoter is a TRE2 or P tight promoter. In some embodiments, a TRE promoter is a TRE2 promoter and comprises a sequence that is at least 70%, least 75%, at least 80%, at least 85%, at least 90%, at least 95%, at least 98%, at least 99%, or at least 100% identical to SEQ ID NO: 23. In some embodiments, a TRE promoter is a P tight promoter and comprises a sequence that is at least 70%, least 75%, at least 80%, at least 85%, at least 90%, at least 95%, at least 98%, at least 99%, or at least 100% identical to SEQ ID NO: 24.

The inducible expression vectors of the present disclosure comprise at least 1 (e.g., 2, 3, 4, 5, 6, 7, 8, 9, 10, 20, 30, 40, 50, 60, 70, 80, 90, or 100) transgenes. A transgene may encode any gene (e.g., a protein-encoding gene, a gene-targeting nucleic acid, and/or a therapeutic gene). Non-limiting examples of genes include wild-type genes that are mutated in a genetic disease. In certain embodiments, the genes are transcription factors. In certain embodiments, the transgene encodes OCT4, SOX2, KLF4, or homologs or variants (e.g., functional variants) thereof, alone or in combination. In certain embodiments, an engineered nucleic acid encodes c-Myc. In certain embodiments, an engineered nucleic acid does not encode c-Myc. In certain embodiments, an engineered nucleic acid does not encode a functional c-Myc because it lacks a c-Myc sequence. Assays to determine transcription factor (e.g., OCT4, SOX2, KLF4, c-Myc or any combination thereof) activity are known in the art and include cell-based transcription assays and in vitro transcription assays. Transcription factor expression may also be determined using other methods including enzyme-linked immunosorbent assays (ELISAs), western blots, and quantification of RNA (e.g., using reverse transcription polymerase chain reaction).

Non-limiting examples of genes include Tet1, Tet2, Nanog, SIRT1, SIRT2, SIRT3, SIRT4, SIRT5, SIRT6, SIRT7, FGF21, GDF15, GDF11, NF-kb, PCSK9, mTERT, HAS2, PDE4By358c, sIGFIr-FC, sIGF2r-FC, Fat-1, mTOR, Klotho, TFEB, Grin2b, DNMT1, AMPK, NRF2, NEU1, NGF, Bcat-1, FoxP2, ZAG, Adiponectin, and TFAM.

In some embodiments, the transgene encodes a gene-targeting nucleic acid. In some embodiments, the gene-targeting nucleic acid is complementary to the promoter and/or enhancer region of the endogenous locus of a gene. In some embodiments, the gene-targeting nucleic acid is complementary to the protein-coding region of a gene. In some embodiments, the gene-targeting nucleic acid is complementary to a RNA (e.g., mRNA). In some embodiments, the RNA (e.g., mRNA) encodes a protein.

In some embodiments, the gene-targeting nucleic acid is a small interfering RNA (siRNA), small hairpin RNA or short hairpin RNA (shRNA), microRNA (miRNA), guide RNA (gRNA), or an antisense RNA (asRNA). In some embodiments, the siRNA, shRNA, miRNA, or asRNA is capable of decrease expression of the target gene by at least 10%, 20%, 30%, 40%, 50%, 60%, 70%, 80%, 90%, or 100%.

In some embodiments, the guide RNA is a CRISPR guide RNA and can guide a Cas9 nuclease to an endogenous location in the genome. The guide RNA and CRISPR system may be used to knockout expression of a gene or activate expression of a gene. When used with a donor template, the guide RNA and CRISPR system may also be used to knockin an allele or gene of interest. Methods of using CRISPR systems and considerations for guide RNA design are known in the art. Numerous web-based tools are available for designing guide RNAs. For example, a non-limiting example available from MIT (e.g., crispr.mit.edu) and from the Broad Institute (portals.broadinstitute.org/gpp/public/analysis-tools/sgrna-design). See also, e.g., Hsu et al., Cell. 2014 Jun. 5;157 (6): 1262-78; Sander et al., Nat Biotechnol. 2014 Apr.; 32 (4): 347-55; Doench et al., Nat Biotechnol. 2016 Feb.; 34 (2): 184-191.

In some embodiments the transgene encodes Cas9 and/or a nuclease-deficient Cas9 that is fused to a transcription activation complex (e.g., comprising VP64, P65, Rta, and/or MPH).

In general, a CRISPR-activating system comprises an enzymatically dead Cas9 nuclease (or nuclease-deficient Cas9 (dCas9)) fused to a transcription activation complex (e.g., comprising VP64, P65, Rta, and/or MPH). Non-limiting examples of sequences encoding VP64, P65, Rta, and/or MPH are provided below. A VP64, P65, Rta, or MPH may ccomprisecomprise a sequence that is at least 70% (e.g., 75%, 80%, 85%, 90%, 95%, 98%, 99%, or 100%) identical to any of the VP64, P65, Rta, and/or MPH sequences described herein. This Cas9 fusion protein may be referred to as a CRISPR activator. A guide RNA targeting the promoter and/or enhancer region of a gene of interest is used in a CRISPR-activating system to target the dCas9-transcription activation complex and drive expression of the endogenous gene.

In some embodiments, administration of an inducible nucleic acid (e.g., an engineered nucleic acid, including an expression vector) comprising a TRE promoter operably linked to a transgene encoding Cas9 and/or a guide RNA targeting an endogenous gene of interest results in decrease expression of the target gene by at least 10%, 20%, 30%, 40%, 50%, 60%, 70%, 80%, 90%, or 100%. In some embodiments, the Cas9 and the guide RNA are located on two separate expression vectors. In some embodiments, administration of an inducible nucleic acid (e.g., an engineered nucleic acid, including an expression vector) comprising a TRE promoter operably linked to a transgene encoding dCas9 fused to an activator complex and/or a guide RNA targeting a promoter and/or enhancer region of an endogenous gene of interest results increasing expression of the operably linked gene by 10%, 20%, 30%, 40%, 50%, 60%, 70%, 80%, 90%, 100%, 150%, 200%, 300%, 400%, 500%, 600%, 700%, 800%, 900%, or 1000%.

The transgenes of the present disclosure (e.g., transgene encoding a protein, a therapeutic sequence, a gene-targeting nucleic acid, a nucleic acid encoding OCT4, SOX2, KLF4, c-Myc, transcription factors, or homologs or variants thereof, including mammalian OCT4, mammalian SOX2, and mammalian KLF4) may be encoded by a single nucleic acid, or a single nucleic acid may encode two or more transgenes (e.g., each operably linked to a different promoter, or all operably linked to the same promoter). For example, in certain embodiments, a nucleic acid may encode OCT4; SOX2; c-Myc; KLF4; OCT4 and SOX2; OCT4 and KLF4; SOX2 and KLF4; or OCT4, SOX2, and KLF4, OCT4, c-Myc, and SOX2; OCT4, c-Myc, and KLF4; SOX2, c-Myc, and KLF4; or OCT4, SOX2, c-Myc, and KLF4, in any order.

In certain embodiments, a nucleic acid (e.g., an engineered nucleic acid, including an expression vector) encodes at least one (e.g., 2, 3, 4, 5, 6, 7, 8, 9, 10, 11, 12, 13, 14, 15, 16, 17, 18, 19, 20, 30, 40, 50, 60, 70, 80, 90, or 100) transgene.

In certain embodiments, a transgene encodes a protein. In certain embodiments, the protein is a human protein. In certain embodiments, the protein is a non-human protein (for example, mammals (e.g., primates (e.g., cynomolgus monkeys, rhesus monkeys); commercially relevant mammals, such as cattle, pigs, horses, sheep, goats, cats, and/or dogs) and birds (e.g., commercially relevant birds, such as chickens, ducks, geese, and/or turkeys). If two or more of the transgenes are on one vector, they may be in any order. Ther words "first," "second," and "third" are not meant to imply an order of the genes on the vector.

In certain embodiments, a transgene encodes a therapeutic sequence. Therapeutic sequences may also be referred to as genes that suitable for gene therapy in the art. Non-limiting examples of therapeutic proteins include antibodies, enzymes, kinases, hormones, growth factors, cytokines, plasma proteins, fusion proteins, membrane-lytic proteins and coagulation factors. In some embodiments, a therapeutic protein is an inflammatory agent. In some embodiments, a therapeutic protein is an anti-inflammatory agent. In some embodiments, a therapeutic protein is an immunomodulatory agent. In some embodiments, a therapeutic protein is an anti-cancer agent. In some embodiments, a therapeutic protein is a metabolic agent. In some embodiments, a therapeutic protein is an antiviral/virocidal agent. In some embodiments, a therapeutic protein is an antibacterial/bacteriocidal agent.

The transgenes described herein (e.g., a therapeutic sequence, a gene-targeting nucleic acid) may comprise one or more amino acid substitutions. Variants can be prepared according to methods for altering polypeptide sequences known to one of ordinary skill in the art such as those found in references which compile such methods, e.g. *Molecular Cloning: A Laboratory Manual*, J. Sambrook, et al., eds., Second Edition, Cold Spring Harbor Laboratory Press, Cold Spring Harbor, New York, 1989, or *Current Protocols in Molecular Biology*, F. M. Ausubel et al., eds., John Wiley & Sons, Inc., New York. Conservative substitutions of amino acids include substitutions made amongst amino acids within the following groups: (a) M. I. L. V; (b) F, Y, W; (c) K. R. H; (d) A, G; (e) S. T: (f) Q, N; and (g) E, D.

Expression vectors containing the necessary elements for expression are commercially available and known to one of ordinary skill in the art (see, e.g., Sambrook et al., *Molecular Cloning: A Laboratory Manual*, Fourth Edition, Cold Spring Harbor Laboratory Press, 2012).

In certain embodiments, a nucleic acid (e.g., an engineered nucleic acid, including an expression vector) comprising a transgene (e.g., a protein-encoding gene, a gene-targeting nucleic acid, and/or a therapeutic gene) is present on a viral vector (e.g., AAV vector). An AAV vector, as used herein, generally comprises ITRs flanking an expression cassette (e.g., a nucleic acid comprising a TRE promoter operably linked to a transgene (e.g., a therapeutic sequence, a gene-targeting nucleic acid and/or a protein-encoding sequence)).

In certain embodiments, a nucleic acid (e.g., an engineered nucleic acid, including an expression vector) comprising a transgene (e.g., a protein-encoding gene, a gene-targeting nucleic acid, and/or a therapeutic gene) is present on a non-viral vector (e.g., a plasmid for transient transfection).

In certain embodiments, the number of base pairs between two ITRs in an AAV vector of the present disclosure is less than 5 kilobases (kb) (e.g., less than 4.9 kb, less than 4.8 kb, less than 4.7 kb, less than 4.6 kb, less than 4.5 kb, less than 4.4 kb, less than 4.3 kb, less than 4.2 kb, less than 4.1 kb, less than 4 kb, less than 3.5 kb, less than 3 kb, less than 2.5 kb, less than 2 kb, less than 1.5 kb, less than 1 kb, or less than 0.5 kb). In certain embodiments, an AAV vector with a distance of less than 4.7 kb between two ITRs is capable of being packaged into virus at a titer of at least $0.5 \times 10^{10}$ particle forming units per ml (pfu/ml), at least $1 \times 10^{10}$ pfu/ml, at least $5 \times 10^{10}$ pfu/ml, at least $1 \times 10^{11}$ pfu/ml, at least $5 \times 10^{11}$ pfu/ml, at least $1 \times 10^{12}$ pfu/ml, at least $2 \times 10^{12}$ pfu/ml, at least $3 \times 10^{12}$ pfu/ml, at least $4 \times 10^{12}$ pfu/ml, at least $5 \times 10^{12}$ pfu/ml, at least $6 \times 10^{12}$ pfu/ml, at least $7 \times 10^{12}$ pfu/ml, at least $8 \times 10^{12}$ pfu/ml, at least $9 \times 10^{12}$ pfu/ml, or at least $1 \times 10^{13}$ pfu/ml.

In certain embodiments, a nucleic acid (e.g., an engineered nucleic acid, including an expression vector) of the present disclosure is at least 1 kilobase (kb) (e.g., at least 1 kb, 2 kb, 3 kb, 4 kb, 5 kb, 6 kb, 7 kb, 8 kb, 9 kb, 10 kb, 50 kb, or 100 kb). In certain embodiments, a nucleic acid (e.g., an engineered nucleic acid, including an expression vector) of the present disclosure is less than 10 kb (e.g., less than 9 kb, less 8 kb, less than 7 kb, less than 6 kb, less than 5 kb, less than 4 kb, less than 3 kb, less than 2 kb, or less than 1 kb).

Without being bound by a particular theory, a nucleic acid (e.g., an engineered nucleic acid, including an expression vector) (e.g., an AAV vector) that encodes multiple transgenes (e.g., protein-encoding sequences, a gene-targeting nucleic acid, and/or therapeutic sequences) under one promoter results in more efficient transduction of all transgenes in vivo compared to separate nucleic acids encoding one or two of the transgenes. In certain embodiments, the infection efficiency of a recombinant virus (e.g., lentivirus, adenovirus, alphavirus, vaccinia virus, retrovirus, herpes virus, or AAV) harboring a transgene vector of the present disclosure in cells (e.g., eukaryotic cells or prokaryotic cells) is at least 20% (e.g., at least 30%, at least 40%, at least 50%, at least 60%, at least 70%, at least 80%, or at least 90%, or 100%).

Recombinant Viruses

Aspects of the present disclosure provide recombinant viruses (e.g., lentiviruses, adenoviruses, herpes viruses, alphaviruses, vaccinia viruses, retroviruses, or AAVs). The recombinant viruses (e.g., lentivirus, adenovirus, alphavirus, vaccinia virus, retrovirus, herpes virus, or AAV) may harbor a nucleic acid (e.g., an engineered nucleic acid, including an expression vector) encoding a mutant rtTA, an inducible nucleic acid (e.g., an engineered nucleic acid, including an expression vector) comprising a transgene (e.g., a therapeutic sequence, a gene-targeting nucleic acid, and/or a protein encoding sequence), or a combination thereof.

In certain embodiments, recombinant virus is a recombinant AAV. In some embodiments, a recombinant AAV has tissue-specific targeting capabilities, such that a transgene of the AAV will be delivered specifically to one or more predetermined tissue(s). Generally, the AAV capsid is a relevant factor in determining the tissue-specific targeting capabilities of an AAV. An AAV capsid may comprise an amino acid sequence derived from AAV1, AAV2, AAV3, AAV4, AAV5, AAV6, AAV7, AAV8, AAV9, AAV10, AAV11, and variants thereof. Non-limiting examples of the tissue-specificity of AAV serotypes are provided in Table 1. An "x" indicates that the indicated AAV serotype is capable of delivering a transgene to a specific tissue.

TABLE 1

Non-limiting examples of AAV serotypes and their utility in specific tissues.

| | Relevant Tissue | | | | | | | | |
| AAV serotype | Liver | Heart | Muscle (e.g., Skeletal Muscle) | Eye | Central Nervous System (CNS) | Central Nervous System (Blood-brain barrier) | Pancreas | Lung | Immune System (T-cells, B-cells and Dendritic Cells) |
|---|---|---|---|---|---|---|---|---|---|
| AAV1 | | x | x | | x | | | | |
| AAV2 | x | | x | x | x | | | | |
| AAV3 | x | | x | x | | | | x | |
| AAV4 | | | x | x | x | | | | |
| AAV5 | | | | x | x | | x | x | |
| AAV6 (e.g., AAV6.2) | | x | x | | | | | x | x |
| AAV7 | x | | x | | | | | | |
| AAV8 | x | | x | | x | | x | | |
| AAV9 | x | x | x | x | x | x | x | x | |
| AAV10 (e.g., AAVrh10) | x | x | x | x | x | x | x | x | |
| AAVDJ | x | | x | | x | | | | |
| AAVPHP.B | | | | | x | x | | | |

Recombinant AAVs comprising a particular capsid protein may be produced using any suitable method. See, e.g., U.S. Patent Application Publication, US 2003/0138772, which is incorporated herein by reference. AAV capsid protein sequences also known in the art. See, e.g., Published PCT Application, WO 2010/138263, which is incorporated herein by reference. Generally, recombinant AAV is produced in a host cell with the following components: (1) a nucleic acid sequence encoding an AAV capsid protein or a fragment thereof, (2) a nucleic acid encoding a functional rep gene, (3) a recombinant AAV vector comprising AAV inverted terminal repeats flanking a transgene (e.g., a sequence encoding a protein, a gene targeting nucleic acid, and/or a therapeutic sequence), and (4) helper functions that allow for packaging of the recombinant AAV vector into AAV capsid proteins. In certain embodiments, the helper functions are introduced via a helper vector that is known in the art.

In some instances, a suitable host cell line (e.g., HEK293T cells) may be used for producing a recombinant AAV disclosed herein following routine practice. One or more expression vectors encoding one or more of the components described above may be introduced into a host cell by exogenous nucleic acids, which can be cultured under suitable conditions allowing for production of AAV particles. When needed, a helper vector can be used to facilitate replication, to facilitate assembly of the AAV particles, or any combination thereof. In certain embodiments, the recombinant AAV vector is present on a separate nucleic acid from the other components (e.g., a nucleic acid sequence encoding an AAV capsid protein or a fragment thereof, a nucleic acid encoding a functional rep gene, and helper functions that allow for packaging of the recombinant AAV vector into AAV capsid proteins. In certain embodiments, a host cell may stably express one or more components needed to produce AAV virus. In that case, the remaining components may be introduced into the host cell. The supernatant of the cell culture may be collected, and the viral particles contained therein can be collected via routine methodology.

The compositions of the disclosure may comprise any of the recombinant viruses (e.g., lentivirus, adenovirus, alphavirus, vaccinia virus, retrovirus, herpes virus, or AAV) described herein alone, or in combination with one or more other recombinant viruses (e.g., a second AAV encoding having one or more different transgenes). In some embodiments, a composition comprises 1, 2, 3, 4, 5, 6, 7, 8, 9, 10, or more different viruses (e.g., lentivirus, adenovirus, alphavirus, vaccinia virus, retrovirus, herpes virus, or AAV) each having one or more different transgenes.

In some embodiments, a composition further comprises a pharmaceutically acceptable carrier. Suitable carriers may be readily selected by one of skill in the art in view of the indication for which the recombinant virus (e.g., lentivirus, adenovirus, alphavirus, vaccinia virus, retrovirus, herpes virus, or AAV) is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the recombinant virus (e.g., lentivirus, adenovirus, alphavirus, vaccinia virus, retrovirus, herpes virus, or AAV) and carrier(s), other pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The recombinant viruses (e.g., lentivirus, adenovirus, alphavirus, vaccinia virus, retrovirus, herpes virus, or AAV) are administered in sufficient amounts to transfect the cells of a desired tissue (e.g., ocular tissue, such as corneal tissue) and to provide sufficient levels of gene transfer and expression without undue adverse effects. Examples of pharmaceutically acceptable routes of administration include, but are not limited to, direct delivery to the selected organ (e.g., intrastromal delivery to the eye), oral, inhalation (including intranasal and intratracheal delivery), intraocular, intravenous, intramuscular, subcutaneous, intradermal, intratumoral, and other parental routes of administration. Routes of administration may be combined, if desired.

The dose of recombinant virus (e.g., lentivirus, adenovirus, alphavirus, vaccinia virus, herpes virus, or AAV) virions required to achieve a particular therapeutic effect, e.g., the units of dose in genome copies/per kilogram of body weight (GC/kg), will vary based on several factors including, but not limited to: the route of recombinant virus (e.g., lentivirus, adenovirus, alphavirus, vaccinia virus, retrovirus, herpes virus, or AAV) virion administration, the level of gene or RNA expression required to achieve a therapeutic effect, the specific disease or disorder being treated, and the stability of the gene or RNA product. One of skill in the art can readily determine a recombinant virus (e.g., lentivirus, adenovirus, alphavirus, vaccinia virus, retrovirus, herpes virus, or AAV virion) dose range to treat a patient having a particular disease or disorder based on the aforementioned factors, as well as other factors.

An effective amount of a recombinant virus (e.g., lentivirus, adenovirus, alphavirus, vaccinia virus, retrovirus, herpes virus, or AAV) is an amount sufficient to target infect an animal, target a desired tissue. In some embodiments, an effective amount of an recombinant virus (e.g., lentivirus, adenovirus, alphavirus, vaccinia virus, retrovirus, herpes virus, or AAV) is an amount sufficient to produce a stable somatic transgenic animal model. The effective amount will depend primarily on factors such as the species, age, weight, health of the subject, and the tissue to be targeted, and may thus vary among animal and tissue. For example, an effective amount of the recombinant virus (e.g., lentivirus, adenovirus, alphavirus, vaccinia virus, retrovirus, herpes virus, or AAV) is generally in the range of from about 1 ml to about 100 ml of solution containing from about $10^9$ to $10^{16}$ genome copies. In some cases, a dosage between about $10^{11}$ to $10^{13}$ recombinant virus (e.g., lentivirus, adenovirus, alphavirus, vaccinia virus, retrovirus, herpes virus, or AAV) genome copies is appropriate. In certain embodiments, $10^{10}$ or $10^{11}$ recombinant virus (e.g., lentivirus, adenovirus, alphavirus, vaccinia virus, retrovirus, herpes virus, or AAV) genome copies is effective to target ocular tissue (e.g., retinal tissue). In some cases, stable transgenic animals are produced by multiple doses of a recombinant virus (e.g., lentivirus, adenovirus, alphavirus, vaccinia virus, retrovirus, herpes virus, or AAV).

In some embodiments, a dose of recombinant virus (e.g., lentivirus, adenovirus, alphavirus, vaccinia virus, retrovirus, herpes virus, or AAV) is administered to a subject no more than once per calendar day (e.g., a 24-hour period). In some embodiments, a dose of recombinant virus (e.g., lentivirus, adenovirus, alphavirus, vaccinia virus, retrovirus, herpes virus, or AAV) is administered to a subject no more than once per 2, 3, 4, 5, 6, or 7 calendar days. In some embodiments, a dose of recombinant virus (e.g., lentivirus, adenovirus, alphavirus, vaccinia virus, retrovirus, herpes virus, or AAV) is administered to a subject no more than once per calendar week (e.g., 7 calendar days). In some embodiments, a dose of recombinant virus (e.g., lentivirus, adenovirus, alphavirus, vaccinia virus, retrovirus, herpes virus, or AAV) is administered to a subject no more than bi-weekly (e.g., once in a two calendar week period). In some embodiments, a dose of recombinant virus (e.g., lentivirus, adenovirus, alphavirus, vaccinia virus, retrovirus, herpes virus, or AAV) is administered to a subject no more than once per calendar month (e.g., once in 30 calendar days). In some embodiments, a dose of recombinant virus (e.g., lentivirus, adenovirus, alphavirus, vaccinia virus, retrovirus, herpes virus, or AAV) is administered to a subject no more than once per six calendar months. In some embodiments, a dose of recombinant virus (e.g., lentivirus, adenovirus, alphavirus, vaccinia virus, retrovirus, herpes virus, or AAV) is administered to a subject no more than once per calendar year (e.g., 365 days or 366 days in a leap year).

In some embodiments, recombinant virus (e.g., lentivirus, adenovirus, alphavirus, vaccinia virus, retrovirus, herpes virus, or AAV) compositions are formulated to reduce aggregation of AAV particles in the composition, particularly where high recombinant virus (e.g., lentivirus, adenovirus, alphavirus, vaccinia virus, retrovirus, herpes virus, or AAV) concentrations are present (e.g., ~$10^{13}$ GC/ml or more). Appropriate methods for reducing aggregation of may be used, including, for example, addition of surfactants, pH adjustment, salt concentration adjustment, etc. (See, e.g., Wright F R, et al., Molecular Therapy (2005) 12, 171-178, the contents of which are incorporated herein by reference.)

In some embodiments, a nucleic acid is delivered non-virally (e.g., not on a viral vector and/or not in a virus). In some embodiments, a nucleic acid (e.g., RNA or DNA) encoding a transgene operably linked to a TRE promoter and/or a mutant rtTA (e.g., rtTA4) is administered in a liposome. In some embodiments, the nucleic acid is RNA (e.g., mRNA). In some embodiments, a nucleic acid (e.g., RNA or DNA) encoding a transgene operably linked to a TRE promoter and/or a mutant rtTA (e.g., rtTA4) is administered in a nanoparticle.

Systems and Recombinant Cells Comprising a Mutant rtTA or a Nucleic Acid (e.g., an Engineered Nucleic Acid, Including an Expression Vector) Thereof Aspects of the present disclosure also provide systems or cells comprising a mutant rtTA (e.g., rtTA protein) and/or a nucleic acid (e.g., an engineered nucleic acid, including an expression vector) encoding a mutant rtTA thereof. The cells may be eukaryotic or prokaryotic and may be from any tissue (e.g., ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine).

In certain embodiments, a system or cell comprises a nucleic acid (e.g., an engineered nucleic acid, including an expression vector) encoding both a mutant rtTA and a transgene operably linked to an inducible promoter that comprises a Tet-O sequence. In certain embodiments, a system or cell comprises a nucleic acid (e.g., an engineered nucleic acid, including an expression vector) encoding a mutant rtTA and a second nucleic acid (e.g., an engineered nucleic acid, including an expression vector) comprising a transgene operably linked to an inducible promoter that comprises a Tet-O sequence. In certain embodiments, a system or cell comprises multiple (e.g., at least 1, 2, 3, 4, 5, 6, 7, 8, 9, 10, 20, 30, 40, 50, 60, 70, 80, 90, or 100) expression vectors encoding one or more transgenes (e.g., at least 1, 2, 3, 4, 5, 6, 7, 8, 9, 10, 20, 30, 40, 50, 60, 70, 80, 90, or 100 transgenes).

In some embodiments, a nucleic acid encoding a mutant rtTA (e.g., rtTA4) and/or a TRE promoter (e.g., TRE3G, TRE2, and/or P tight) is integrated into the genome of a cell. In some embodiments, a nucleic acid encoding a mutant rtTA (e.g., rtTA4) and/or a TRE promoter (e.g., TRE3G, TRE2, and/or P tight) is integrated into the genome of a subject (e.g., to create a transgenic subject). Any suitable method may be used to integrate a nucleic acid encoding a mutant rtTA (e.g., rtTA4) and/or a TRE promoter. See, e.g., Cho et al., Curr Protoc Cell Biol. 2009 Mar.; CHAPTER:

Unit-19.11. In some embodiments, a mutant rtTA and/or TRE promoter is knocked in to a cell or into a subject using CRISPR. See, e.g., Aida et al., Genome Biol. 2015 Apr. 29:16:87. As a non-limiting example, rtTA may be integrated into the rosa 26 locus in a mouse and/or TRE may be integrated into the Colla1 locus.

In some embodiments, a recombinant cell is produced ex vivo and administered to a subject in need thereof.

Compositions (e.g., Pharmaceutical Compositions)

Aspects of the present disclosure provide compositions comprising any of the mutant rtTAs, recombinant cells, nucleic acids (e.g., engineered nucleic acids, expression vectors, plasmid DNA, and/or RNA) encoding a rtTA, inducible vectors encoding a transgene, recombinant viruses encoding a rtTA and/or a transgene, or combinations thereof. Any of the mutant rtTAs, recombinant cells, nucleic acids (e.g., engineered nucleic acids, expression vectors, plasmid DNA, and/or RNA) encoding a rtTA, inducible vectors encoding a transgene, recombinant viruses encoding a rtTA and/or a transgene, or combinations thereof may be formulated into a pharmaceutical composition with a pharmaceutically acceptable excipient. Formulation of pharmaceutically-acceptable excipients and carrier solutions is well-known to those of skill in the art, as is the development of suitable dosing and treatment regimens for using the particular compositions described herein in a variety of treatment regimens. Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In some embodiments, the mutant rtTAs, recombinant cells, nucleic acids (e.g., engineered nucleic acids, expression vectors, plasmid DNA, and/or RNA) encoding a rtTA, inducible vectors encoding a transgene, and/or recombinant viruses described herein are suitably formulated pharmaceutical compositions disclosed herein are delivered directly to target tissue and/or organ in a subject, e.g., direct to eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine.

However, in certain circumstances it may be desirable to separately or in addition deliver the recombinant viruses, recombinant cells, nucleic acids (e.g., engineered nucleic acids), and/or mutant rtTA (e.g., rtTA4) via another route, e.g., intravenously, intradermally, intraarterially, intralesionally, intratumorally, intracranially, intraarticularly, intraprostaticaly, intrapleurally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, systemically, injection, infusion, continuous infusion, localized perfusion bathing target cells directly, via a catheter, in creams, in lipid compositions (e.g., liposomes).

In some embodiments, the administration modalities as described in U.S. Pat. Nos. 5,543,158; 5,641,515 and 5,399, 363 (each specifically incorporated herein by reference in its entirety) may be used to deliver recombinant virus (e.g., lentivirus, adenovirus, alphavirus, vaccinia virus, retrovirus, herpes virus, or AAV). In some embodiments, a preferred mode of administration is by intrastromal injection.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a suitable sterile aqueous medium may be employed. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active recombinant virus (e.g., lentivirus, adenovirus, alphavirus, vaccinia virus, retrovirus, herpes virus, or AAV) in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The recombinant virus (e.g., lentivirus, adenovirus, alphavirus, vaccinia virus, retrovirus, herpes virus, or AAV) compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

A carrier includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions.

Delivery vehicles such as liposomes, nanocapsules, microparticles, microspheres, lipid particles, vesicles, and the like, may be used for the introduction of compositions of the present disclosure into suitable host cells. As a non-limiting example, the recombinant virus (e.g., lentivirus, adenovirus, alphavirus, vaccinia virus, retrovirus, herpes virus, or AAV) vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids (e.g., engineered nucleic acids, including expression vectors) or the recombinant virus (e.g., lentivirus, adenovirus, alphavirus, vaccinia virus, retrovirus, herpes virus, or AAV) constructs disclosed herein. The formation and use of liposomes is generally known to those of skill in the art. Recently, liposomes were developed with improved serum stability and circulation half-times (U.S. Pat. No. 5,741, 516). Further, various methods of liposome and liposome like preparations as potential drug carriers have been described (U.S. Pat. Nos. 5,567,434; 5,552,157; 5,565,213; 5,738,868 and 5,795,587; each of which is incorporated herein by reference).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500.ANG., containing an aqueous solution in the core.

Alternatively, nanocapsule formulations of the recombinant virus (e.g., lentivirus, adenovirus, alphavirus, vaccinia virus, retrovirus, herpes virus, or AAV) may be used. Nanocapsules can generally entrap substances in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use.

Kits and Related Compositions

The agents described herein may, in some embodiments, be assembled into pharmaceutical or diagnostic or research kits to facilitate their use in therapeutic, diagnostic or research applications. A kit may include one or more containers housing the components of the disclosure and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

In some embodiments, the instant disclosure relates to a kit comprising a nucleic acid (e.g., an engineered nucleic acid, including an expression vector) encoding mutant rtTA (e.g., rtTA4), which may be useful, for example for producing a recombinant virus (e.g., lentivirus, adenovirus, alphavirus, vaccinia virus, retrovirus, herpes virus, or AAV). The kit may comprise a container housing the nucleic acid (e.g., an engineered nucleic acid, including an expression vector) encoding mutant rtTA (e.g., rtTA4). The kit may further comprise a second container housing a nucleic acid (e.g., an engineered nucleic acid, including an expression vector) encoding a transgene (e.g., a gene associated a disease, such as retinal disease). In certain embodiments, the transgene is a sequence encoding a protein, a gene-targeting nucleic acid, and/or a therapeutic sequence. In some embodiments, the kit further comprises instructions for producing recombinant virus (e.g., lentivirus, adenovirus, alphavirus, vaccinia virus, retrovirus, herpes virus, or AAV).

In some embodiments, the instant disclosure relates to a kit comprising a container housing any of the engineered nucleic acids (e.g., expression vectors) or recombinant viruses described herein. For example, the kit may comprise a nucleic acid (e.g., an engineered nucleic acid, including an expression vector) or recombinant virus encoding an inducing agent. In some embodiments, a nucleic acid (e.g., an engineered nucleic acid, including an expression vector) a mutant rtTA4 comprises a sequence that is at least 70% identical to SEQ ID NO: 17. In some embodiments, the nucleic acid (e.g., an engineered nucleic acid, including an expression vector) encoding an inducing agent consists of a sequence that is at least 70% identical to SEQ ID NO: 17. In some embodiments, a nucleic acid (e.g., an engineered nucleic acid, including an expression vector) a mutant rtTA4 comprises a sequence that is at least 70% identical to desmin-rtTA4 (SEQ ID NO: 30). In some embodiments, the nucleic acid (e.g., an engineered nucleic acid, including an expression vector) encoding an inducing agent consists of a sequence that is at least 70% identical to desmin-rtTA4 (SEQ ID NO: 30). The kit may further comprise a nucleic acid (e.g., an engineered nucleic acid, including an expression vector) or recombinant virus encoding any transgene (e.g., therapeutic sequence, a gene-targeting nucleic acid, and/or sequence encoding a protein) operably linked to a promoter comprising a Tet-O (e.g., a TRE promoter). A non-limiting example of a vector encoding a transgene (e.g., multiple transgenes) is provided in SEQ ID NO: 16. In some embodiments, the nucleic acid (e.g., an engineered nucleic acid, including an expression vector) encoding a transgene comprises SEQ ID NO: 16.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to an animal, such as a syringe, topical application devices, or iv needle tubing and bag, particularly in the case of the kits for producing specific somatic animal models.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

Therapeutic Applications

Any of the compositions (e.g., pharmaceutical compositions) comprising a mutant rtTA (e.g., rtTA4), a nucleic acid (e.g., an engineered nucleic acid, including an expression vector) encoding a mutant rtTA, an inducible nucleic acid (e.g., an engineered nucleic acid, including an expression vector) encoding a transgene, a recombinant virus encoding a mutant rtTA or a transgene that is operably linked to an inducible promoter encoding described herein may be used to regulate (e.g., inhibit or induce) cellular reprogramming, tissue repair, tissue regeneration, treating a disease, organ regeneration, reversing aging, or any combination thereof. The compositions may be useful in regulating cellular reprogramming, tissue repair, tissue survival, tissue regeneration, tissue growth, tissue function, organ regeneration, organ survival, organ function, or any combination thereof. Regulating may comprise inducing cellular reprogramming, reversing aging, improving tissue function, improving organ function, tissue repair, tissue survival, tissue regeneration, tissue growth, angiogenesis, scar formation, the appearance of aging, organ regeneration, organ survival, altering the taste and quality of agricultural products derived from animals, treating a disease, or any combination thereof, in vivo or in vitro may be administered to a cell, tissue, or organ that is in vivo (e.g., part of a subject), or may be administered to a cell, tissue, or organ ex vivo. As used herein, regulating may refer to any type of modulation, including inducing or promoting, inhibiting, and/or stopping. Angiogenesis refers to growth of new blood vessels.

In some instances, a viral vector (e.g., lentivirus, adenovirus, alphavirus, vaccinia virus, retrovirus, herpes virus, or AAV vector) is administered in a recombinant virus (e.g., lentivirus, adenovirus, alphavirus, vaccinia virus, retrovirus, herpes virus, or AAV).

Without being bound by a particular theory, transient expression of one or more transgenes (e.g., OCT4, SOX2, KLF4, any transcription factor, any protein-encoding sequence, any gene-targeting nucleic acid, and/or any therapeutic sequence) may result in partial reprogramming of a cell. For example, partial reprogramming may induce a fully differentiated cell to become multipotent. In some instances, prolonged expression (e.g., continued expression for at least 1 day, at least 5 days, at least 1 week, or at least 1 month) of one or more transcription factors (e.g., any transcription factor, including OCT4, SOX2, KLF4, and/or c-MYC), results in full reprogramming of a cell. For example, a cell may be fully reprogrammed into a pluripotent cell (e.g., induced pluripotent cell).

To practice this embodiment, an effective amount of mutant rtTA (e.g., rtTA4 may be administered to a cell, tissue or a subject along with a nucleic acid (e.g., an engineered nucleic acid, including an expression vector) comprising a transgene to be expressed (a protein-encoding sequence, a gene-targeting nucleic acid, and/or a therapeutic sequence) operably linked to a TRE promoter (e.g., a TRE2, a P tight, or a TRE3G promoter). In certain embodiments, mutant rtTA (e.g., rtTA4) is administered as a protein. In certain embodiments, mutant rtTA (e.g., rtTA4) is administered in a nucleic acid (e.g., an engineered nucleic acid, including an expression vector)

In some embodiments, a nucleic acid (e.g., engineered nucleic acid) encoding mutant rtTA4 and/or a transgene operably linked to a TRE promoter (e.g., TRE3G, a P tight, or a TRE2 promoter) is not a viral vector. For example, the nucleic acid may be a plasmid (e.g., plasmid DNA) or RNA (e.g., mRNA). As a non-limiting example, the engineered nucleic acids (e.g., RNA, including mRNA, or DNA) of the present disclosure may be formulated in a nanoparticle for delivery. See, e. g., Dong et al., Nano Lett. 2016 Feb. 10;16 (2): 842-8. In some embodiments, the nanoparticle comprises acetylated galactose. See, e.g., Lozano-Torres et al., J Am Chem Soc. 2017 Jul. 5;139 (26): 8808-8811. In some embodiments, an engineered nucleic acids (e.g., RNA, including mRNA, or DNA) is electroporated or transfected into a cell. In certain embodiments, the engineered nucleic acids are delivered as a naked nucleic acid (e.g., naked DNA or naked RNA). In some embodiments, a naked nucleic acid is plasmid DNA. In some embodiments, a nucleic acid (e.g., engineered nucleic acid) is administered in a liposome.

In some embodiments, a nucleic acid (e.g., engineered nucleic acid) encoding mutant rtTA4 and/or encoding a transgene operably linked to a TRE promoter (e.g., e.g., TRE3G, a P tight, or a TRE2 promoter) is a viral vector. Non-limiting examples of viral vectors include lentivirus vector, adenovirus vector, alphavirus vector, vaccinia virus vector, herpes virus vector, adenovirus (AAV) vector.

In certain embodiments, a nucleic acid (e.g., engineered nucleic acid encoding a mutant rtTA (e.g., rtTA4)) is administered in a virus (e.g., lentivirus, adenovirus, alphavirus, vaccinia virus, retrovirus, herpes virus, or AAV). In certain embodiments, the nucleic acid (e.g., an engineered nucleic acid, including an expression vector) comprising a transgene operably linked to a TRE promoter (e.g., TRE3G, a P tight, or a TRE2 promoter) is administered in a virus (e.g., lentivirus, adenovirus, alphavirus, vaccinia virus, retrovirus, herpes virus, or AAV)

A suitable amount of tetracycline (e.g., doxycycline) may be added to drive expression from the TRE promoter (e.g. TRE3G, P tight, or a TRE2 promoter). The suitable amount of tetracycline to be added may be determined by one of ordinary skill in the art and may depend on factors, including the type of pharmaceutical excipient (if any), the type of cell, the type of tissue, or any characteristic of a subject (e.g., weight, medical history, genetics, etc.).

In some embodiments, tetracycline is administered intravenously, intradermally, intraarterially, intralesionally, intratumorally, intracranially, intraarticularly, intraprostaticaly, intrapleurally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, systemically, injection, infusion, continuous infusion, localized perfusion bathing target cells directly, via a catheter, in creams, or in lipid compositions.

In some embodiments, a recombinant virus and/or expression vector encoding a mutant rtTA and/or a transgene operably linked to a TRE promoter is administered systemically. In some embodiments, the, a recombinant virus and/or expression vector encoding a mutant rtTA and/or a transgene operably linked to a TRE promoter is administered locally (e.g., directly to a tissue or organ of interest, including eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine).

In some embodiments, the virus and/or expression vector is administered with tetracycline (e.g., doxycycline). In some embodiments, the virus and/or expression vector comprising a TRE promoter is administered separately from tetracycline (e.g., doxycycline). For example, any of the viruses and/or expression vectors comprising a TRE promoter described herein may be administered systemically and the tetracycline may be administered locally (e.g., to an organ or tissue of interest). In some embodiments, any of the viruses and/or expression vectors comprising a TRE promoter described herein may be administered locally (e.g., to directly to a tissue or organ of interest, including eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine) and the tetracycline and/or mutant rtTA (e.g., mutant rtTA protein or nucleic acid encoding a mutant rtTA) may be administered systemically. As a non-limiting example, a virus and/or expression vector comprising a TRE promoter is administered directly (e.g., injected) into the eye of a subject and the tetracycline (e.g., doxycycline) and/or mutant rtTA (e.g., mutant rtTA protein or nucleic acid encoding a mutant rtTA) is administered systemically (e.g., orally as a pill). In some embodiments the nucleic acid (e.g., engineered nucleic acid) comprising a TRE promoter is administered to a subject in the same route as the mutant rtTA (e.g., mutant rtTA protein or nucleic acid encoding a mutant rtTA). In some embodiments, the nucleic acid (e.g., engineered nucleic acid) comprising a TRE promoter is administered to a subject in a different route as the mutant rtTA (e.g., mutant rtTA protein or nucleic acid encoding a mutant rtTA).

In certain embodiments of the present disclosure, the method further comprises withdrawing tetracycline (e.g., doxycycline) from a cell, tissue, or subject after administration of tetracycline, which may be useful in stopping expression of a transgene. Tetracycline may be withdrawn at least 1 hour, at least 2 hours, at least 3 hours, at least 4 hours, at least 5 hours, at least 10 hours, at least 24 hours, at 2 days, at least 3 days, at least 4 days, at least 5 days, at least 6 days, at least 1 week, at least 2 weeks, at least 3 weeks, at least 1 month, or at least 1 year after tetracycline administration. In certain embodiments, withdrawal of tetracycline results in a detectable decrease in transgene expression (e.g., at least 5%, at least 10%, at least 20%, at least 30%, at least 40%, at least 50%, at least 60%, at least 70%, at least 80%, at least 90%, or 100% decrease). For example, decrease in transgene expression may be detectable at least 1 hour, at least 2 hours, at least 3 hours, at least 4 hours, at least 5 hours, at least 10 hours, at least 24 hours, at 2 days, at least 3 days, at least 4 days, at least 5 days, at least 6 days, at least 1 week, at least 2 weeks, at least 3 weeks, at least 1 month, or at least 1 year after tetracycline withdrawal.

Without being bound by a particular theory, the four mutations in rtTA4 (mutations at positions corresponding to G12, F67, R171, or G72 in SEQ ID NO: 11, for example G12S, G72V or G72P, F67S, and R171K) result in lower leakiness as compared to rtTA3 (SEQ ID NO: 11) because the mutations decrease rtTA4's binding affinity for the promoter in the absence of tetracycline. In some embodiments, the amount of transgene expression with rtTA4 (e.g., SEQ ID NO: 13) is at least 10%, 20%, 30%, 40%, 50%, 60%, 70%, 80%, 90%, or 100% less than the amount of transgene expression detected with rtTA3 (e.g., SEQ ID NO: 11) in the absence of tetracycline (e.g., doxycycline). Without being bound by a particular theory, the four mutations in rtTA4 (mutations at positions corresponding to G12, F67, R171, or G72 in SEQ ID NO: 11, for example G12S. G72V or G72P. F67S, and R171K) result in a greater sensitivity to tetracycline withdrawal as compared to rtTA3 (SEQ ID NO: 11) because the mutations decrease rtTA's binding affinity for tetracycline. In some embodiments, the amount of transgene expression with rtTA4 (e.g., SEQ ID NO: 13) decreases at least 2 times, 3 times, 4 times, 5 times, 6 times, 7 times, 8 times, 9 times, 10 times, 20 times, 30 times, 40 times, 50 times, 60 times, 70 times, 80 times, 90 times, or 100 times faster, when tetracycline (e.g., doxycycline) is withdrawn for a given amount of time compared to the amount of transgene expression with rtTA3 (e.g., SEQ ID NO: 11).

Administration of a nucleic acid (e.g., an engineered nucleic acid, including an expression vector) encoding a mutant rtTA (e.g., rtTA4), a nucleic acid (e.g., an engineered nucleic acid, including an expression vector) comprising a TRE promoter (e.g., TRE3G, TRE2, or a P tight promoter) operably linked to a transgene (e.g., a therapeutic sequence, a gene-targeting nucleic acid, and/or a protein-encoding sequence), and tetracycline increases expression of the transgene by at least 10%, at least 20%, at least 30%, at least 40%, at least 50%, at least 60%, at least 70%, at least 80%, at least 90%, at least 100%, at least 200%, at least 300%, at least 400%, at least 500%, at least 500%, at least 600%, at least 700%, at least 800%, at least 900%, or at least 1,000% in a cell. Gene expression may be determined by routine methods including enzyme-linked immunosorbent assays (ELISAs), western blots, and quantification of RNA (e.g., reverse transcription polymerase chain reaction).

A pharmaceutical composition described herein may be administered to a subject in need thereof. Non-limiting examples of subjects include any animal (e.g., mammals, including humans). A subject may be suspected of having, be at risk for or have a condition. For example, the condition may be an injury or a disease and the condition may affect any tissue (e.g., ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine). Non-limiting examples of conditions, diseases, and disorders include acute injuries, neurodegenerative disease, chronic diseases, proliferative diseases, cardiovascular diseases, genetic diseases, inflammatory diseases, autoimmune diseases, neurological diseases, hematological diseases, painful conditions, psychiatric disorders, metabolic disorders, cancers, aging, age-related diseases, and diseases affecting any tissue in a subject. In some embodiments, the disease is an ocular disease.

In certain embodiments, the condition is aging. All animals typically go through a period of growth and maturation followed by a period of progressive and irreversible physiological decline ending in death. The length of time from birth to death is known as the life span of an organism, and each organism has a characteristic average life span. Aging is a physical manifestation of the changes underlying the passage of time as measured by percent of average life span.

In some cases, characteristics of aging can be quite obvious. For example, characteristics of older humans include skin wrinkling, graying of the hair, baldness, and cataracts, as well as hypomelanosis, osteoporosis, cerebral cortical atrophy, lymphoid depletion, thymic atrophy, increased incidence of diabetes type II, atherosclerosis, cancer, and heart disease. Nehlin et al. (2000). *Annals NY Acad Sci* 980:176-79. Other aspects of mammalian aging include weight loss, lordokyphosis (hunchback spine), absence of vigor, lymphoid atrophy, decreased bone density, dermal thickening and subcutaneous adipose tissue, decreased ability to tolerate stress (including heat or cold, wounding, anesthesia, and hematopoietic precursor cell ablation), liver pathology, atrophy of intestinal villi, skin ulceration, amyloid deposits, and joint diseases. Tyner et al. (2002), Nature 415:45-53.

Those skilled in the art will recognize that the aging process is also manifested at the cellular level, as well as in mitochondria. Cellular aging is manifested in loss of doubling capacity, increased levels of apoptosis, changes in differentiated phenotype, and changes in metabolism, e.g., decreased levels of protein synthesis and turnover.

Given the programmed nature of cellular and organismal aging, it is possible to evaluate the "biological age" of a cell or organism by means of phenotypic characteristics that are correlated with aging. For example, biological age can be deduced from patterns of gene expression, resistance to stress (e.g., oxidative or genotoxic stress), rate of cellular proliferation, and the metabolic characteristics of cells (e.g., rates of protein synthesis and turnover, mitochondrial function, ubiquinone biosynthesis, cholesterol biosynthesis, ATP levels within the cell, levels of a Krebs cycle intermediate in the cell, glucose metabolism, nucleic acid metabolism, ribosomal translation rates, etc.). As used herein, "biological age" is a measure of the age of a cell or organism based upon the molecular characteristics of the cell or organism. Biological age is distinct from "temporal age," which refers to the age of a cell or organism as measured by days, months, and years.

The rate of aging of an organism, e.g., an invertebrate (e.g., a worm or a fly) or a vertebrate (e.g., a rodent, e.g., a mouse) can be determined by a variety of methods, e.g., by one or more of: a) assessing the life span of the cell or the organism; (b) assessing the presence or abundance of a gene transcript or gene product in the cell or organism that has a biological age-dependent expression pattern: (c) evaluating resistance of the cell or organism to stress, e.g., genotoxic stress (e.g., etoposide, UV irradiation, exposure to a mutagen, and so forth) or oxidative stress; (d) evaluating one or more metabolic parameters of the cell or organism; (e) evaluating the proliferative capacity of the cell or a set of cells present in the organism; and (f) evaluating physical appearance or behavior of the cell or organism. In one example, evaluating the rate of aging includes directly measuring the average life span of a group of animals (e.g., a group of genetically matched animals) and comparing the resulting average to the average life span of a control group of animals (e.g., a group of animals that did not receive the test compound but are genetically matched to the group of animals that did receive the test compound). Alternatively, the rate of aging of an organism can be determined by measuring an age-related parameter. Examples of age-related parameters include: appearance, e.g., visible signs of age; the expression of one or more genes or proteins (e.g., genes or proteins that have an age-related expression pattern): resistance to oxidative stress; metabolic parameters (e.g., protein synthesis or degradation, ubiquinone biosynthesis, cholesterol biosynthesis, ATP levels, glucose metabolism, nucleic acid metabolism, ribosomal translation rates, etc.); and cellular proliferation (e.g., of retinal cells, bone cells, white blood cells, etc.).

The methods may be used to prevent or alleviate neurodegeneration and peripheral neuropathies associated. Neurodegenerative diseases include Parkinson's disease, Alzheimer's disease, multiple sclerosis, amniotropic lateral sclerosis (ALS), Huntington's disease, and muscular dystrophy. Neurodegeneration may be quantified using any method known in the art. For example, the executive function of an individual may be determined (Moreira et al., Front Aging Neurosci. 2017 Nov. 9; 9:369).

Additional age-related conditions which may be treated include heart failure, stroke, diabetes, osteoporosis, arthritis, hearing loss (partial or total), eye-related conditions (e.g., poor eye sight or retinal disease), glaucoma, and cancer. In certain embodiments, the disease is a retinal disease (e.g., macular degeneration). The condition may be a retinal disease, cancer, aging, an age-related disease, injury, or a neurodegenerative disease. In certain embodiments, the cell or tissue is from eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine. In certain embodiments, the tissue is damaged (e.g., due to an injury, an accident, or an iatrogenic injury) and/or is aged tissue. In certain embodiments, the tissue may be considered healthy but suboptimal for performance or survival in current or future conditions (e.g., in agriculture or adverse conditions including toxic therapies, sun exposure, or travel outside the earth's atmosphere).

For example, the condition may be an injury or a disease and the condition may affect any tissue (e.g., eye, ear, bone, lung, breast, pancreas, muscle, heart, liver, skin, brain, nerve tissue, or intestine). Non-limiting examples of conditions, diseases, and disorders include acute injuries, neurodegenerative diseases, chronic diseases, cancers, aging, age-related diseases, and diseases affecting any tissue in a subject.

In some embodiments, any of the mutant rtTA4, nucleic acids (e.g., engineered nucleic acids) encoding rtTA4, nucleic acids comprising a TRE promoter operably linked to a transgene sequence, recombinant viruses, and/or recombinant cells may be used to treat a disease that affects a non-human subject (e.g., a disease affecting livestock, domesticated pets, and/or other non-human animals). For example, the disease may be a cattle disease, a primate (e.g., cynomolgus monkeys, rhesus monkeys) disease, a disease affecting a commercially relevant animal, such as cattle, pigs, horses, sheep, goats, cats, and/or dogs) and/or a disease affecting birds (e.g., commercially relevant birds, such as chickens, ducks, geese, and/or turkeys). For example, any of the, any of the mutant rtTA4, nucleic acids (e.g., engineered nucleic acids) encoding rtTA4, nucleic acids comprising a TRE promoter operably linked to a transgene sequence, recombinant viruses, and/or recombinant cells described herein may be used to promote wound healing, treat an injury (e.g., broken bones, bleeding out gun shot injury, and/or reduce scarring during surgery). In some embodiments, surgery includes cesarean.

Methods for identifying subjects suspected of having a condition may include physical examination, subject's family medical history, subject's medical history, biopsy, genetic testing, or a number of imaging technologies such as ultrasonography, computed tomography, magnetic resonance imaging, magnetic resonance spectroscopy, or positron emission tomography.

Effective amounts of the nucleic acids (e.g., engineered nucleic acids, including expression vectors), viruses (e.g., lentivirus, adenovirus, alphavirus, vaccinia virus, retrovirus, herpes virus, or AAV) or compositions thereof vary, as recognized by those skilled in the art, depending on route of administration, excipient usage, and co-usage with other active agents. The quantity to be administered depends on the subject to be treated, including, for example, the age of the subject, the gravity of the condition, the weight of the subject, the genetics of the subject, the cells, tissue, or organ to be targeted, or any combination thereof.

Using a mutant rtTA disclosed herein, expression of one or more transgenes (e.g., a therapeutic sequence, a gene-targeting nucleic acid, and/or a protein-encoding sequence) may result in reprogramming of a cell, tissue repair, tissue regeneration, organ regeneration, reversal of aging, infectious disease, prevention of a disease, treatment of a disease or any combination thereof. Cellular reprogramming may be determined by determining the extent of differentiation of a cell (e.g., by determining the expression of one or more lineage markers or pluripotency markers, including OCT4, KLF4, SOX2, NANOG, ESRRB, NR4A2, and C/EBPa). The differentiation potential of a cell may also be determined using routine differentiation assays. Tissue repair may be determined by tissue replacement and tissue regeneration assays. For example, tissue replacement assays include wound healing assays. Tissue regeneration may be determined by quantifying a particular cell type following transgene expression (e.g., expression of one or more transcription factors, including OCT4, KLF4, and SOX2) compared to before transgene expression. In some instances, the methods described herein promote organ regeneration.

These and other aspects of the present invention will be further appreciated upon consideration of the following Examples, which are intended to illustrate certain particular embodiments of the invention but are not intended to limit its scope, as defined by the claims.

General Techniques

The practice of the present disclosure will employ, unless otherwise indicated, conventional techniques of molecular biology (including recombinant techniques), microbiology, cell biology, biochemistry and immunology, which are within the skill of the art. Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995). Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

These and other aspects of the present invention will be further appreciated upon consideration of the following Examples, which are intended to illustrate certain particular embodiments of the invention but are not intended to limit its scope, as defined by the claims.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

Example 1: Development of a Mutant Reverse Tetracycline Transactivator (rtTA) with Low Leakiness and Improved Reaction Time with Doxycycline Withdrawal in a Tet-on System In Vitro A mutant reverse tetracycline transactivator (rtTA) was engineered using routine cloning techniques. An exemplary mutant rtTA (rtTA4) comprises four mutations (G12S, F67S, G72V, and R171K) as compared to rtTA3 (SEQ ID NO: 11). A rtTA comprising four mutations at positions G12, F67, G72, and R171 of rtTA3 (SEQ ID NO: 11) is referred to as rtTA4 herein. rtTA4 (SEQ ID NO: 13) comprises three VP16 transactivation domains, while rtTA3 (SEQ ID NO: 11) comprises two VP 16 transactivation domains.

A nucleic sequence (SEQ ID NO: 12) encoding rtTA4 (SEQ ID NO: 13) was cloned into an AAV vector using routine methods. The pAAV-UBC-rtTA4-WPRE3-SV40 pA (SEQ ID NO: 17) vector is depicted in FIG. 1, FIGS. 2A-2M, and FIG. 3. FIG. 1 is a vector map showing features in an AAV vector encoding rtTA4. UBC is a constitutive promoter that is operably linked to the nucleic acid encoding rtTA4. SV40 pA is an SV40-derived terminator sequence. FIGS. 2A-2M include a series of schematics mapping the features shown in FIG. 1 onto the nucleic acid sequence of the vector encoding rtTA4. FIG. 3 shows the location and size of each feature depicted in FIGS. 2A-2M.

The pAAV-UBC-rtTA4-WPRE3-SV40 pA vector (SEQ ID NO: 17) comprises two inverted terminal repeats (ITRs) flanking a sequence encoding a UBC promoter operably linked to a nucleic acid sequence encoding rtTA4 (SEQ ID NO: 12). The AAV vector further comprises a WPRE3 sequence (SEQ ID NO: 21) and a SV40 terminator sequence (SEQ ID NO: 8). The location of restriction enzyme digestion sites are shown in Table 2 below.

TABLE 2

Restriction enzyme digestion sites in pAAV-UBC-rtTA4-WPRE3-SV40pA (SEQ ID NO: 17).

| Enzyme | Sites | Location |
|---|---|---|
| AarI | 1 | 2796 |
| AatII | 1 | 2750 |
| AfeI | 1 | 1961 |
| AflII | 1 | 2942 |
| AflIII | 1 | 1319 |
| AlwNI | 1 | 910 |
| AvrII | 1 | 2842 |
| BamHI | 1 | 4329 |
| BbsI | 1 | 2487 |
| BsaBI | 1* | 4347* |
| BsmI | 1 | 4273 |
| BsrDI | 1 | 371 |
| BstXI | 1 | 3422 |
| EagI | 1 | 3120 |
| EcoO109I | 1 | 2619 |
| EcoRI | 1 | 1893 |
| HincII | 1 | 4259 |
| HpaI | 1 | 4259 |
| KflI | 1 | 2619 |
| MfeI | 1 | 4268 |
| NaeI | 1 | 4841 |
| NgoMIV | 1 | 4839 |
| NotI | 1 | 3120 |
| PaeR7I | 1 | 3476 |

TABLE 2-continued

Restriction enzyme digestion sites in pAAV-UBC-rtTA4-WPRE3-SV40pA (SEQ ID NO: 17).

| Enzyme | Sites | Location |
|---|---|---|
| PasI | 1 | 3562 |
| PciI | 1 | 1319 |
| PflMI | 1 | 3238 |
| PpuMI | 1 | 2619 |
| SacII | 1 | 1936 |
| ScaI | 1 | 5607 |
| TatI | 1 | 5605 |
| XcmI | 1 | 3145 |
| XhoI | 1 | 3476 |
| XmnI | 1 | 5488 |
| ZraI | 1 | 2748 |

Figure 4A:
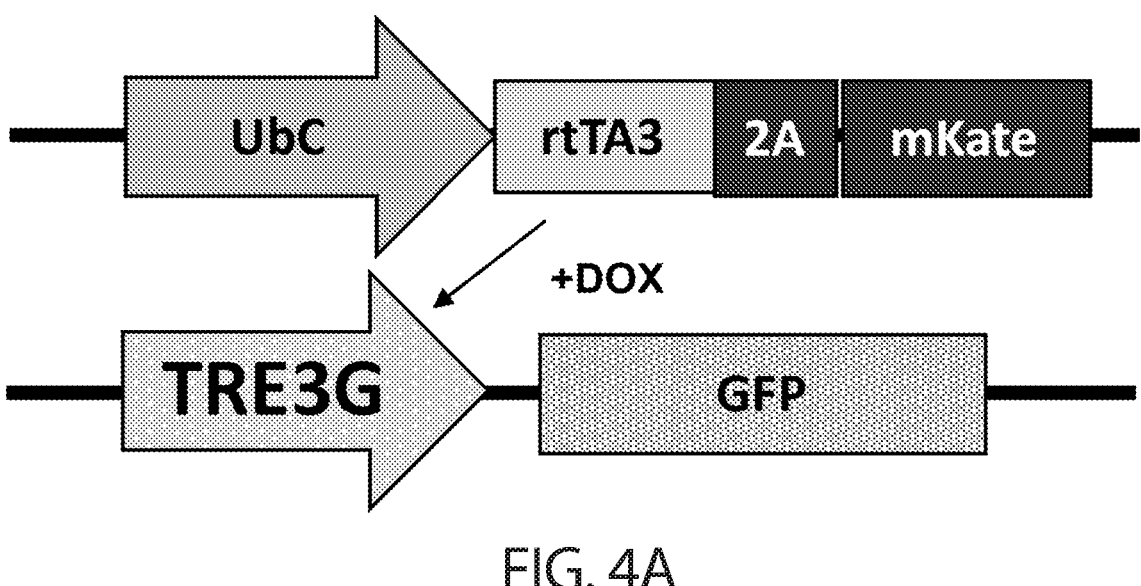
FIGS. 4A-4B include data showing that a tetracycline-on (Tet-On) system with rtTA3 (SEQ ID NO: 11) as the inducing agent is leaky in vivo.
Figure 4B:
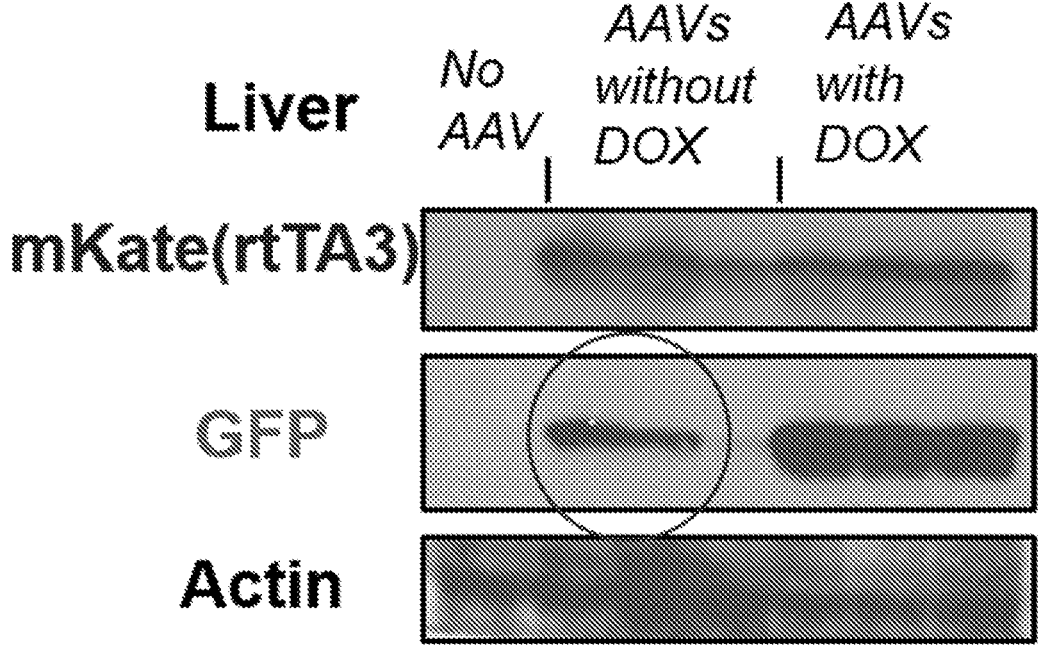

As shown in FIGS. 4A-4B, rtTA3 (SEQ ID NO: 11) is leaky and induced expression of a transgene that was operably linked to a tetracycline inducible promoter even in the absence of doxycycline. A nucleic acid sequence encoding rtTA3 is provided as SEQ ID NO: 10. FIG. 4A is a schematic depicting two nucleic acids that were used in this experiment. One nucleic acid encoded a UBC promoter operably linked to (1) a nucleic acid (SEQ ID NO: 12) encoding rtTA4 (SEQ ID NO: 13), (2) a nucleic acid encoding a 2A peptide, and (3) a nucleic acid encoding mKate (a far-red fluorescent protein). mKate expression was used as a readout of rtTA3 expression (FIG. 4B). The second nucleic acid encoded GFP under the control of a TRE3G (SEQ ID NO: 7) promoter. GFP should only be expressed in the presence of doxycycline (DOX) as shown in FIG. 4A.

Next, the vectors shown in FIG. 4A were tested in vivo. AAV harboring the UBC-rtTA3 vector depicted in the top portion of FIG. 4A and AAV harboring the TRE3G-GFP promoter depicted in the bottom portion of FIG. 4B were administered to mice. No AAV administration was used as a control. Mice were treated without doxycycline (DOX) or with DOX. Liver samples were then analyzed using a western blot using relevant antibodies to determine mKate expression (readout of rtTA3 expression), GFP expression, and actin expression. As shown in FIG. 4B, GFP expression was detected even in the absence of doxycycline. Therefore, rtTA3 is leaky in vivo.

Figures 5A, 5B:
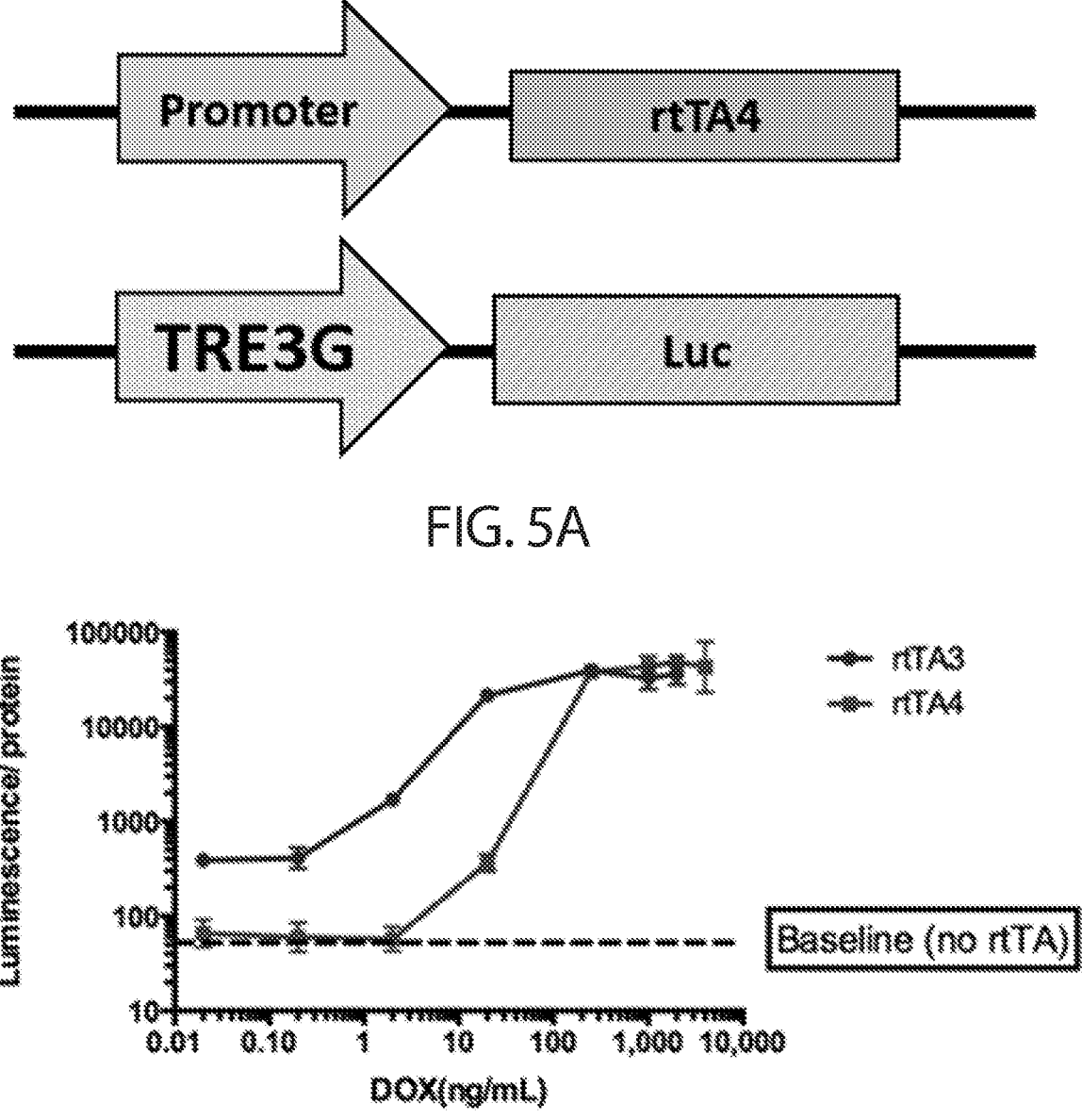
FIGS. 5A-5B show that a tetracycline-on (Tet-On) system with rtTA4 (SEQ ID NO: 13) is less leaky than the same system with rtTA3.

To determine whether rtTA4 is less leaky and more sensitive to doxycycline compared to rtTA3, a Tet-On luciferase reporter system was used. FIG. 5A is a schematic representation of two of the nucleic acids used in this experiment. The first nucleic acid comprises a promoter driving expression of a rtTA (FIG. 5A, top). rtTA4 is depicted in FIG. 5A, but rtTA4 was substituted with rtTA3 in the Tet-On luciferase reporter system that was used to test rtTA3. The second nucleic acid (TRE3G-Luc) comprises a TRE3G promoter operably linked to a nucleic acid sequence encoding luciferase (luc) (FIG. 5A, bottom). The Tet-On reporter system encoding rtTA4 or rtTA3 was introduced into 293T cells with the vectors alone and the cells were treated with increasing concentrations of doxycycline. Luciferase expression was determined by measuring luminescence/protein. As shown in FIG. 5B, the level of luminescence/protein was low when the level of doxycycline was low (0.01 to 1 ng/ml). The level of luminescence/protein with rtTA4 at these low levels of doxycycline was the same as baseline levels in the absence of any rtTA (baseline indicated with dotted line in FIG. 5B). The level of luminescence/protein increased with increasing levels of doxycycline in the Tet-On system with rtTA4 (FIG. 5B). In contrast, the level of luminescence/protein was significantly higher than baseline with rtTA3 even at low levels of doxycycline (e.g., 0.01 to 1 ng/ml DOX). These results suggest that rtTA4 is less leaky than rtTA3 (does not induce detectable transgene expression in the absence of doxycycline), but is capable of inducing transgene expression in the presence of increasing concentrations of doxycycline.

Figure 6A:
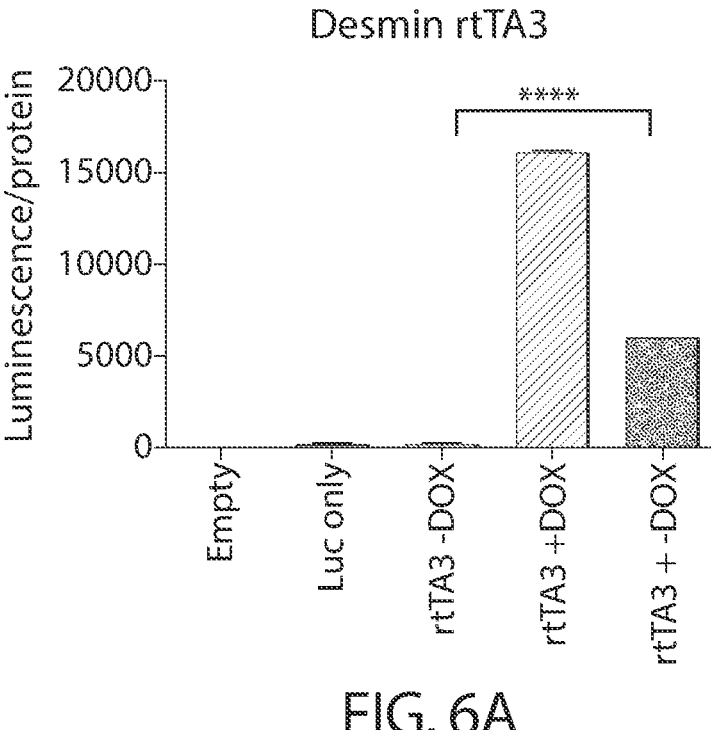
FIGS. 6A-6C include a series of graphs showing that a Tet-On system with rtTA4 turns off faster in response to doxycycline withdrawal compared to a Tet-On system with rtTA3. A DOX-inducible luciferase reporter system was used, and luciferase production was measured in luminescence/protein. +DOX indicates doxycycline treatment, −DOX indicates absence of doxycycline treatment, +-DOX indicates doxycycline treatment followed by doxycycline withdrawal.
Figure 6B:
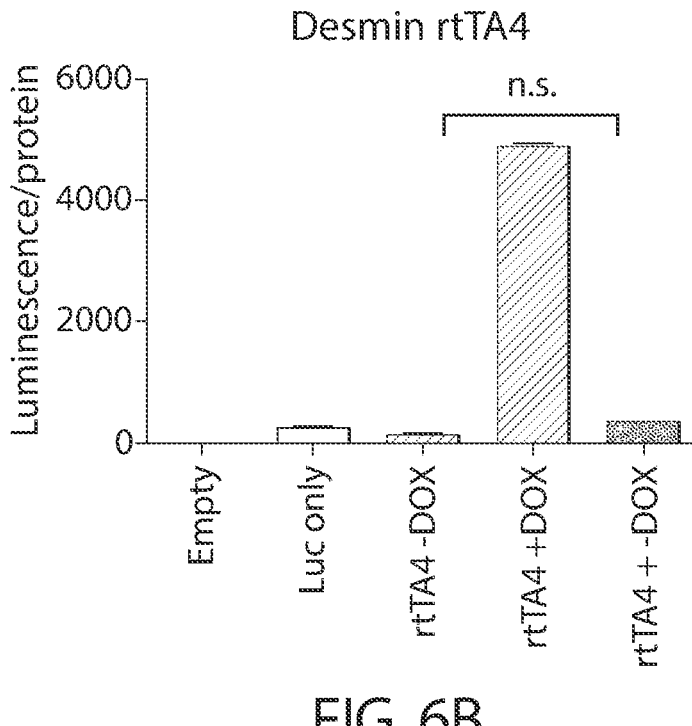

To compare the sensitivity of rtTA4 and rtTA3 to doxycycline withdrawal, Tet-On luciferase reporter systems similar to the one depicted in FIG. 5A were used. For the results shown in FIG. 6A, a TRE3G-luc vector and a vector encoding rtTA3 under the control of a desmin promoter were introduced into 293T cells. Cells received an empty vector or the TRE3G-luc vector only as controls. Cells harboring both the TRE3G-luc vector and the vector encoding rtTA3 under the desmin-promoter were treated (1) without doxycycline (−DOX), (2) with doxycycline (+DOX), or (3) with doxycycline and then doxycycline was withdrawn (+-DOX). As shown in FIG. 6A, the level of luminescence/protein detected with treatment (3) was significantly higher than the level of luminescence/protein with treatment (1). These results suggest that rtTA3 is leaky. In contrast, as shown in FIG. 6B, when the same experiment was conducted with rtTA4, doxycycline withdrawal significantly decreased the amount of luminescence/protein detected to a level that was comparable to the level detected in cells that never received doxycycline. Therefore, rtTA4 is more responsive to doxycycline withdrawal compared to rtTA3.

Figure 6C:
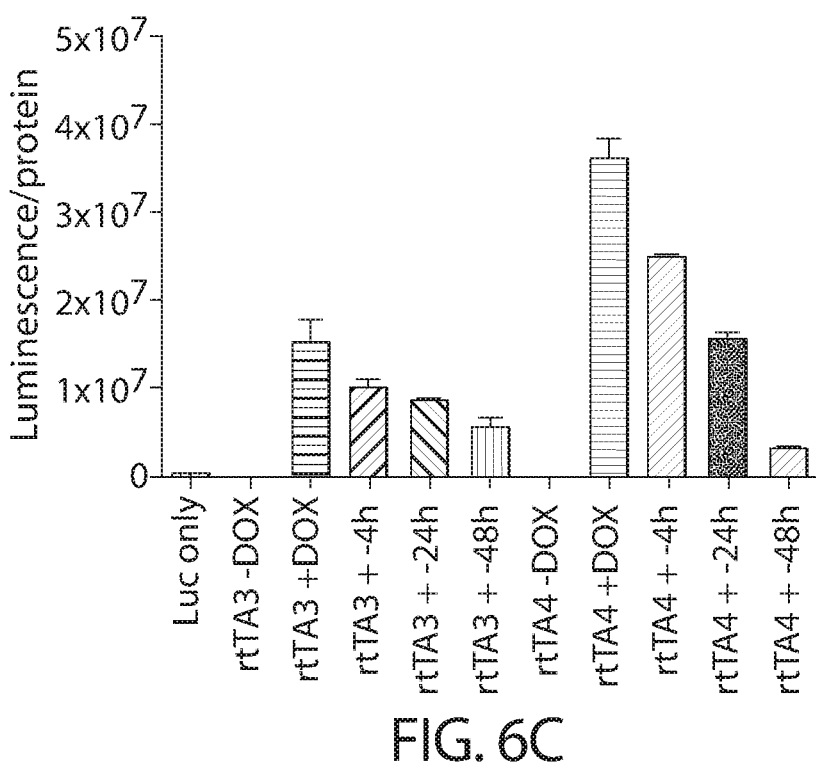
Figure 7:
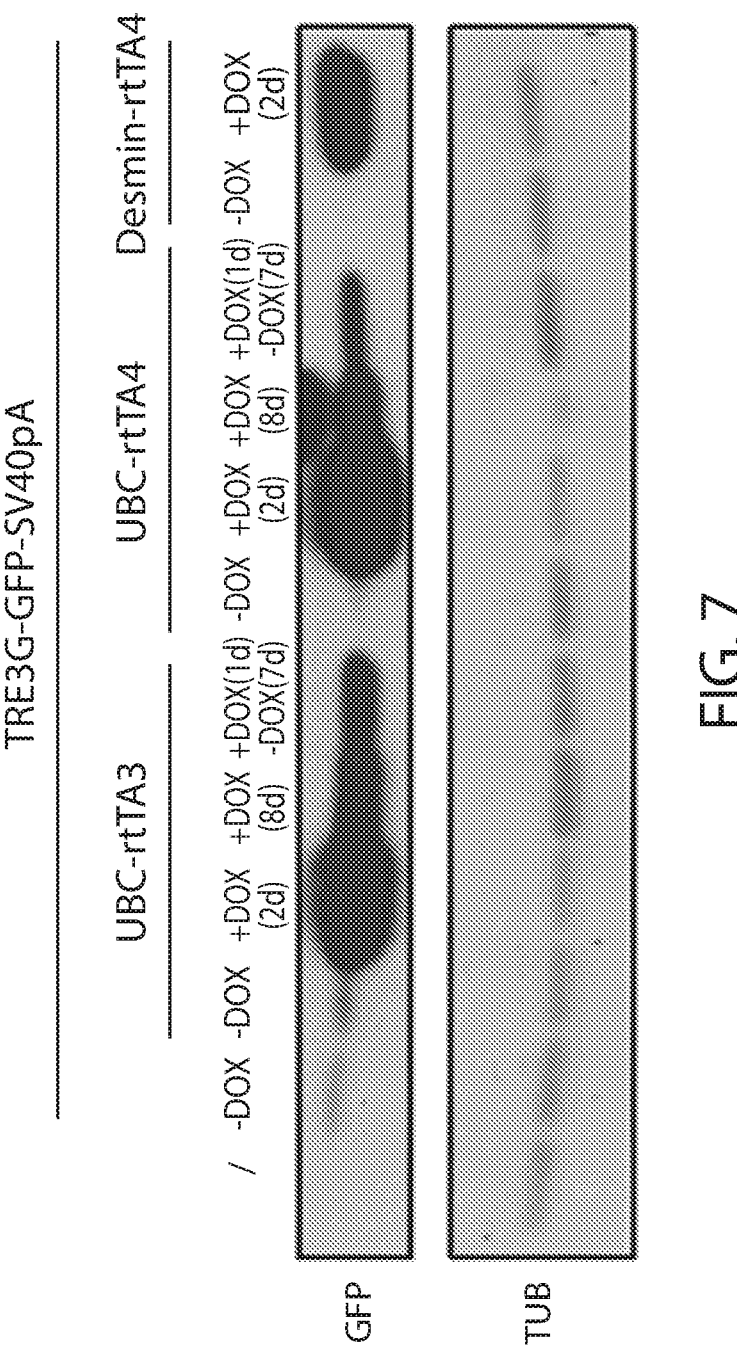
FIG. 7 is a western blot comparing the effects of doxycycline treatment and withdrawal on transgene expression induced by rtTA3 (SEQ ID NO: 11) and rtTA4 (SEQ ID NO: 13) in 293T cells. The nucleic acid sequence (SEQ ID NO: 10) encoding rtTA3 was operably linked to a UBC promoter (SEQ ID NO: 18), while rtTA4 was operably linked to a UBC promoter (SEQ ID NO: 18) or a desmin promoter (SEQ ID NO: 29).

To compare the length of time needed for doxycycline withdrawal to turn off expression of a transgene with rtTA4 compared to rtTA3, Tet-On luciferase reporter systems comprising a TRE3G-luc vector and a vector encoding one of the rtTA proteins was introduced into 293T cells. TRE3G-luc vector was introduced into cells alone as a control. The level of luminescence/protein in the absence of any doxycycline treatment (−DOX) was also determined for the rtTA3 and for the rtTA4 system (FIG. 6C). Cells with either the rtTA3 Tet-On system or the rtTA4 Tet-On system were subsequently treated with doxycycline (+DOX), or doxycycline followed by doxycycline withdrawal (+-) for the number of hours as indicated (FIG. 6C). rtTA4 was capable of turning off transgene expression faster than rtTA3 (FIG. 6C). As shown in FIGS. 6A-6C, rtTA4 turns off 4-12 times faster than rtTA3 with both Desmin promoter and Ubc promoter.

rtTA4 was further tested in Tet-On systems in mammalian 293T cells. A TRE3G-GFP-SV40 pA AAV vector and second AAV vector with (1) a sequence encoding rtTA3 operably linked to a UBC promoter, (2) a sequence encoding rtTA4 operably linked to a UBC promoter, or (3) a sequence encoding rtTA4 operably linked to a desmin promoter were introduced into 293T cells (FIG. 7). Cells were then treated in the absence of doxycycline (−DOX), in the presence of doxycycline (+DOX), or in the presence of DOX (+DOX) followed by doxycycline withdrawal (−DOX). As shown in FIG. 7, whereas rtTA3 induced GFP expression even in the absence of doxycycline, rtTA4 did not. Furthermore, removal of DOX for seven days after one day of doxycycline treatment resulted in lower GFP expression in the UBC-rtTA4 system compared to the UBC-rtTA3 system. Therefore, Tet-On systems comprising AAV vectors encoding rtTA4 successfully induced transgene expression in mammalian cells, had lower leakiness compared to the same systems with rtTA3 and showed quicker inhibition of transgene expression following doxycycline removal.

Figure 8B:
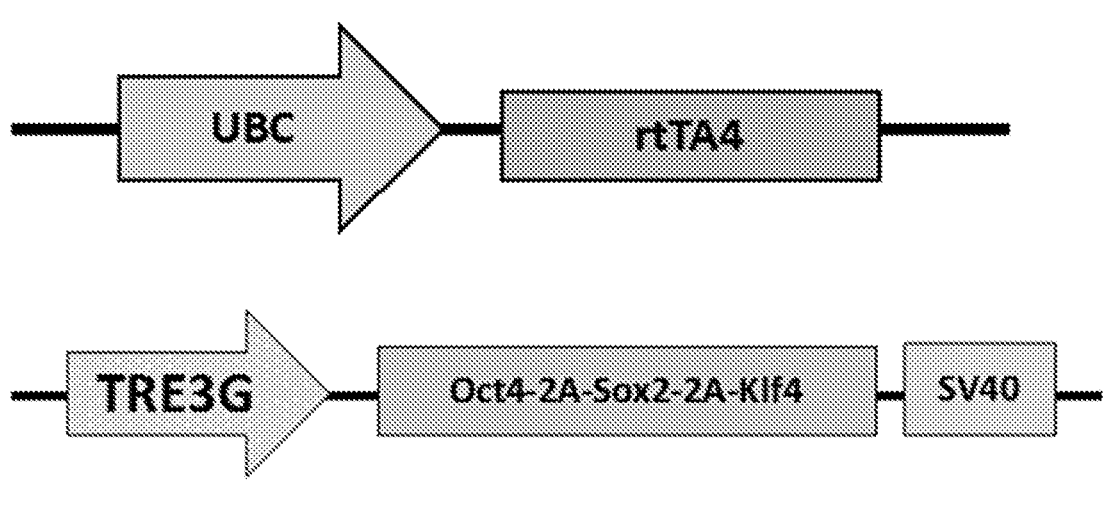
Figure 8C:
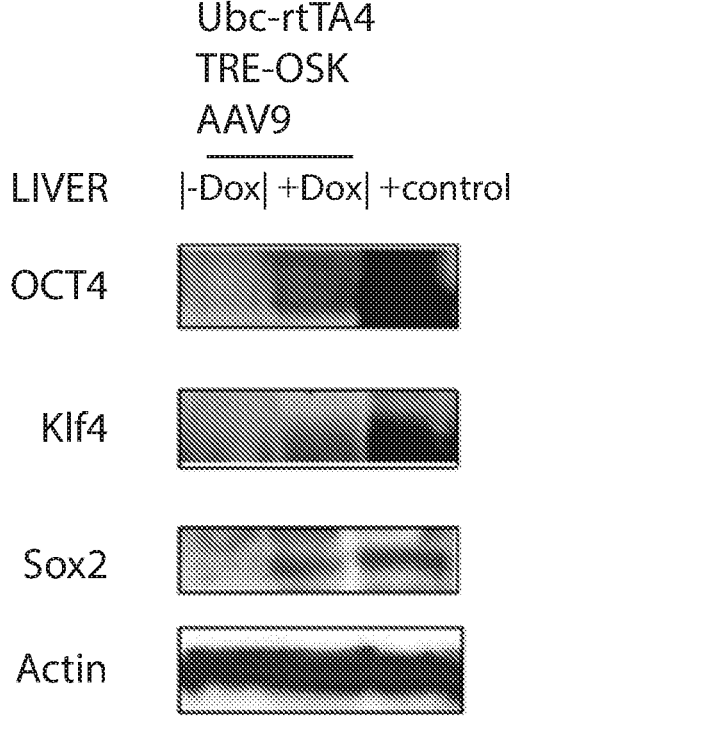
Figure 9:
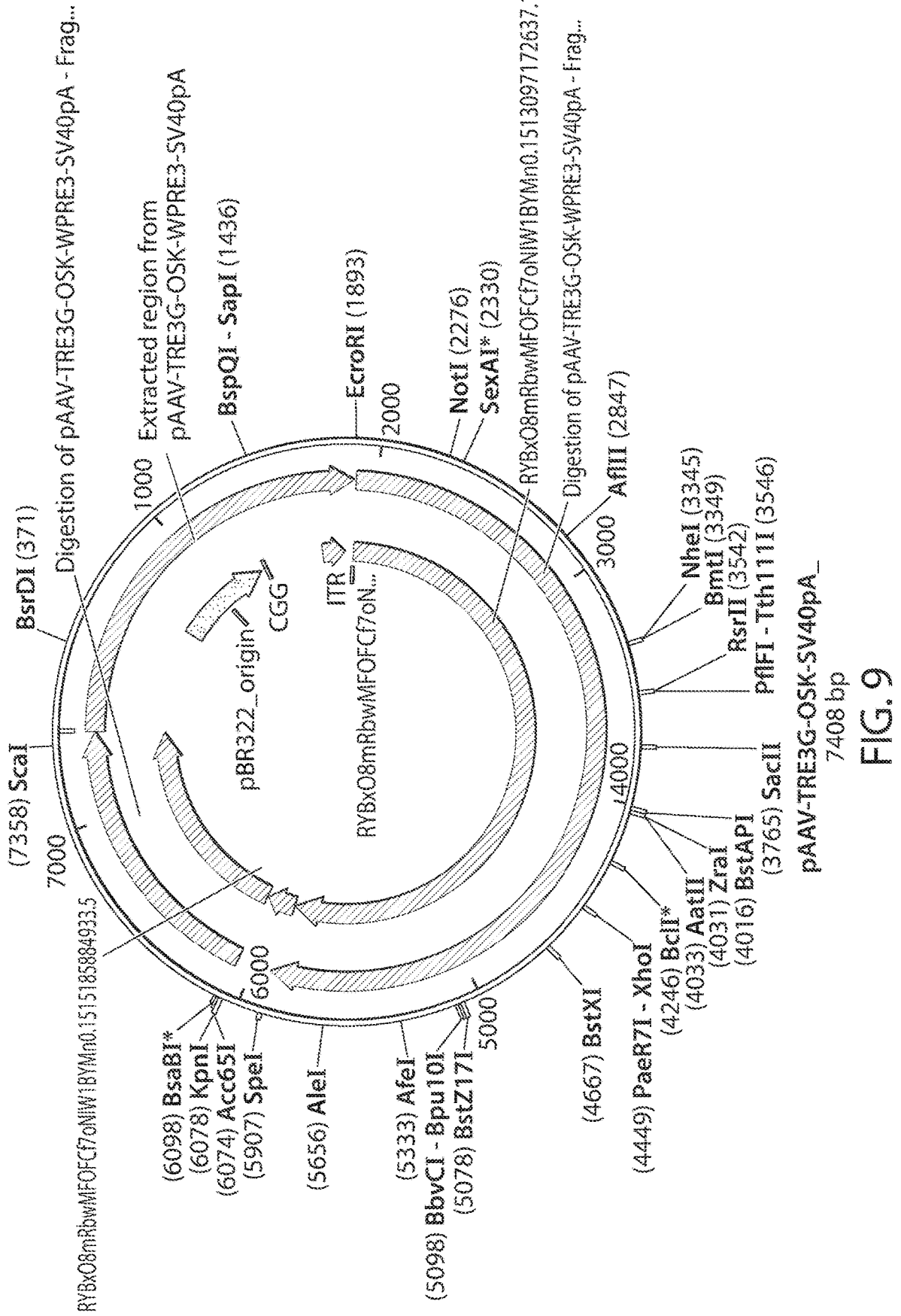
FIG. 9 is a vector map depicting a non-limiting example of an inducible AAV vector (TRE3G-OSK-SV40 pA, SEQ ID NO: 16) encoding Oct4, SOX2, and KLF4, which may be used in combination with any of the rtTA4 vectors described herein.

Example 2: An AAV Vector Encoding Mutant Reverse Tetracycline Transactivator (rtTA) Showed Low Leakiness in the Liver of Mice A Tet-On system comprising rtTA4 (SEQ ID NO: 13) was also tested in vivo using recombinant AAV9 viruses. Two AAV vectors comprising components shown in FIG. 8B were used. AAV virus encoding rtTA4 operably linked to a UBC promoter (pAAV-UBC-rtTA4-WPRE3-SV40 pA vector is provided as SEQ ID NO: 17) and AAV virus encoding an AAV TRE3G-OSK-SV40 pA vector (SEQ ID NO: 16) with a vector map depicted in FIG. 9 were administered to mice. Mice were treated without doxycycline or with doxycycline and liver samples were collected. As shown in the immunofluorescence images of FIG. 8A, in the absence of doxycycline, KLF4 expression was not detectable in the liver. When mice were treated with doxycycline through their drinking water, KLF4 expression was detected in the liver (FIG. 8A). These results were also evident by western blot using antibodies against OCT4, KLF4, and SOX2 to determine expression of these protein (FIG. 8C). Actin was used as a loading control (FIG. 8C). OCT4, KLF4, and SOX2 were only detected in the liver when mice were treated with doxycycline (FIG. 8C).

Example 3: Development of a Tet-on System Combining a Tetracycline Repressor and rtTA4

Figure 10:
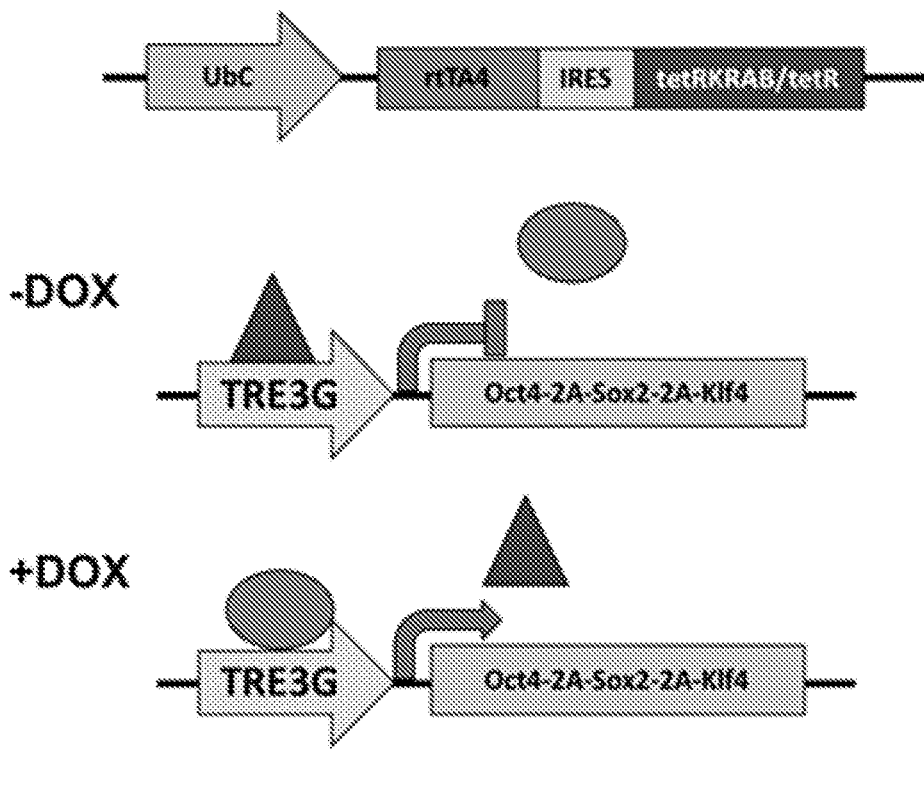
FIG. 10 is a schematic showing a non-limiting example of an inducible expression system combining an rtTA (e.g., rtTA4) and a tetracycline repressor (tetR, e.g., tetRKRAB). The triangle represents tetR (e.g., tetRKRAB) protein and the circle represents rtTA4 protein.
Figure 11:
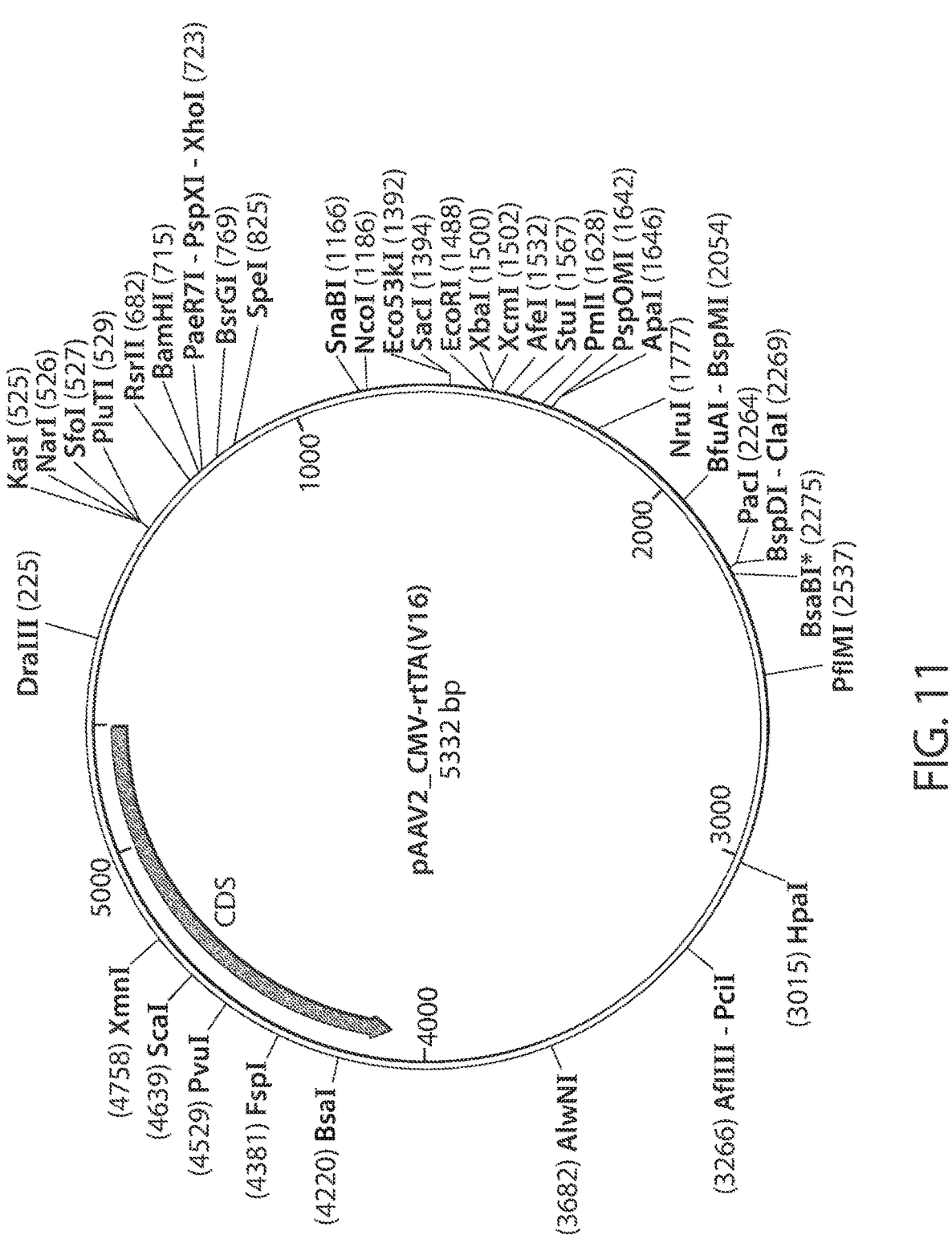
FIG. 11 is a vector map of pAAV2_CMV_ItTA (VP16) (SEQ ID NO: 31). This vector is a non-limiting example of a vector encoding rtTA.
Figure 12:
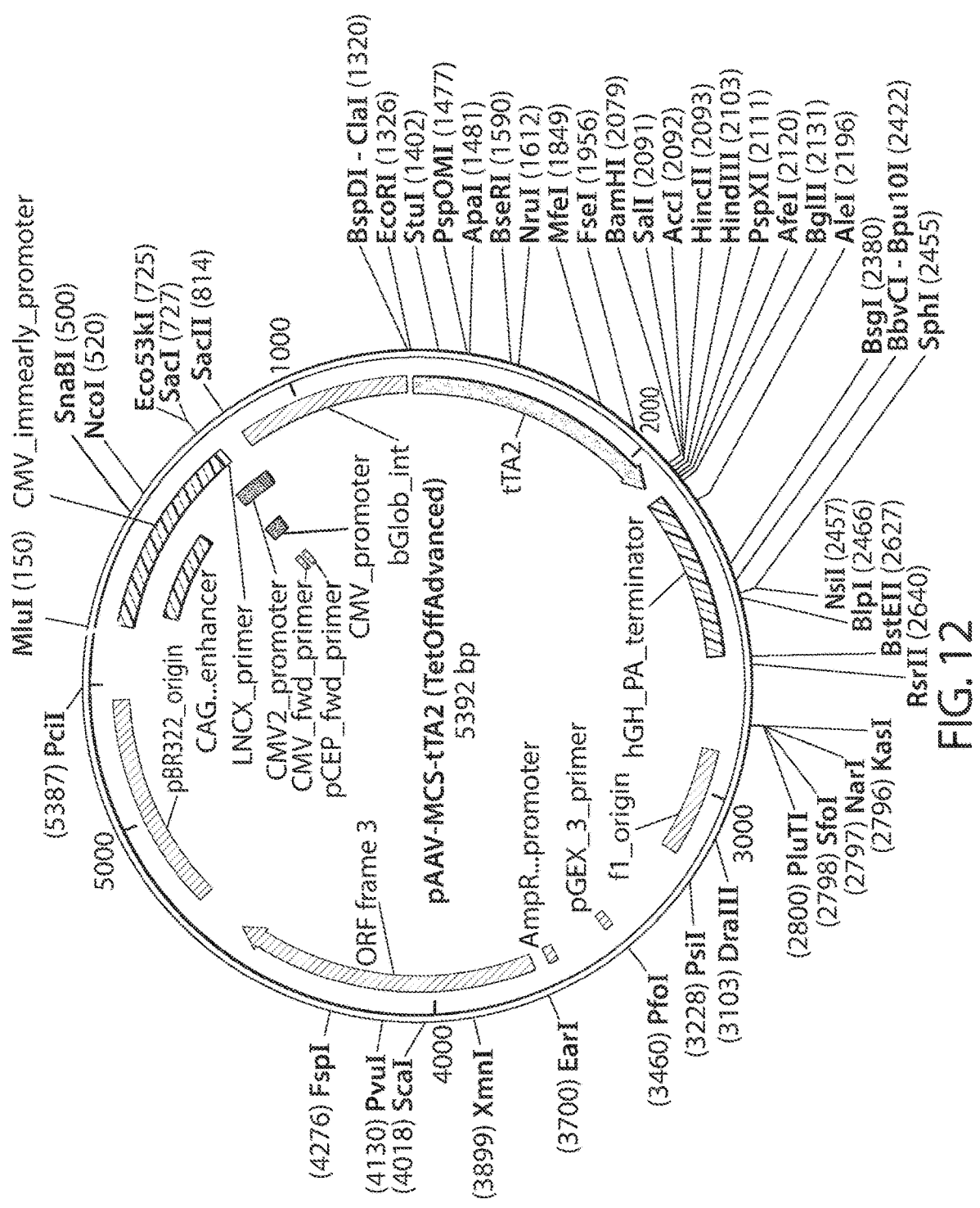
FIG. 12 is a vector map of pAAV-MCS-tTA2 (or CAG-tTA) (SEQ ID NO: 32). This vector is a non-limiting example of a vector encoding tTA under a CAG promoter.
Figure 13:
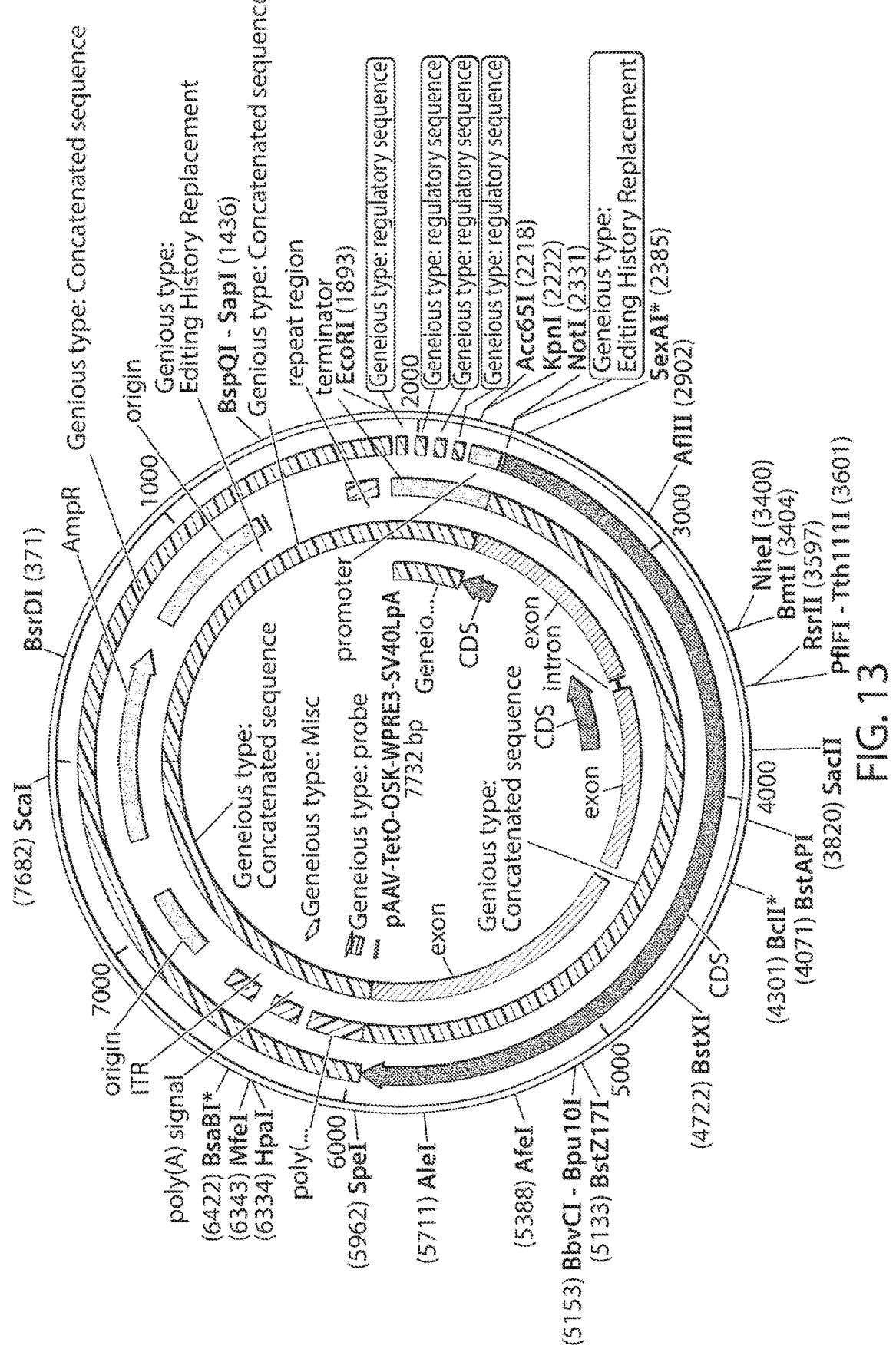
FIG. 13 is a vector map of p-AAV-TetO-OSK-WPRE3-SV50LpA (TRE2-OSK, pAAV-TRE2-OSK-SV40LpA, or TRE2-OSK) (SEQ ID NO: 33). This vector is a non-limiting example of an AAV vector comprising a nucleic acid (e.g., engineered nucleic acid) sequence that is greater than 4.7 kb between the two ITRs in the vector.

To further reduce the background binding of rtTA to TRE operator in the absence of DOX, we have developed a double insurable system of rtTA and tetR (tetRKRAB) (FIG. 10). tetR or tetRKRAB can binds to TRE operator in the absence of DOX, prevent the binding of rtTA and repress the activity of TRE. When adding DOX into system, tetR or tetRKRAB leave the TRE element and expose it to binding of rtTA to activate the expression of gene downstream of TRE. Putting this rtTA-IRES-tetRKRAB or rtTA-IRES-tetR under a continuous expressive promoter like UBC, CAG, or tissue specific promoters, allows for tight control of protein expression was achieved in a whole animal or a specific tissue.

Example 4. Use of rtTA4 to Control Gene Expression In Vivo

Figure 14:
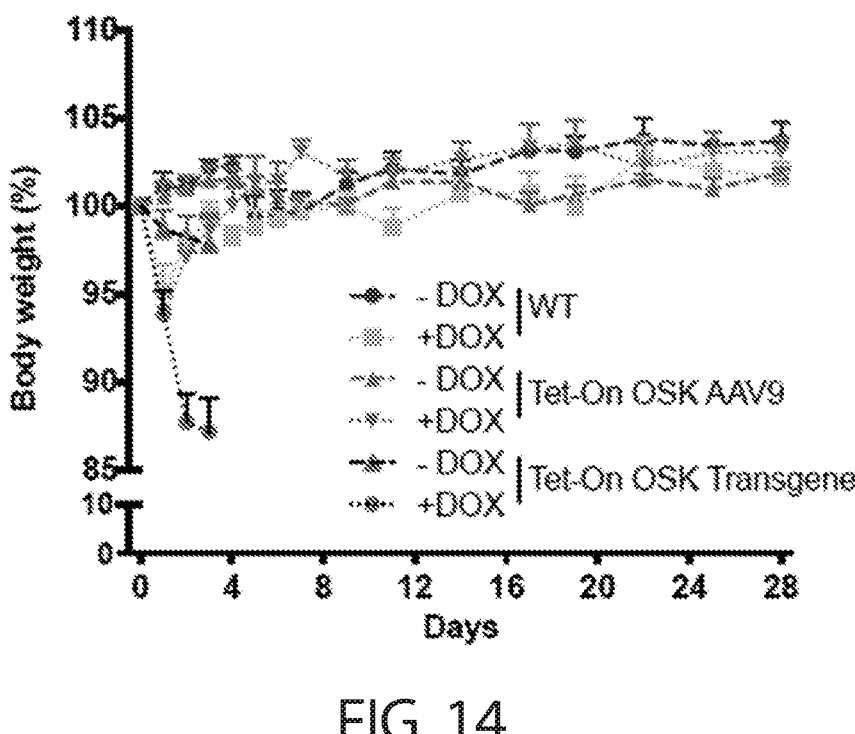
FIG. 14 shows that partial reprogramming with AAV-delivered polycistronic OSK under the control of rtTA4 is non-toxic.
Figure 15A:
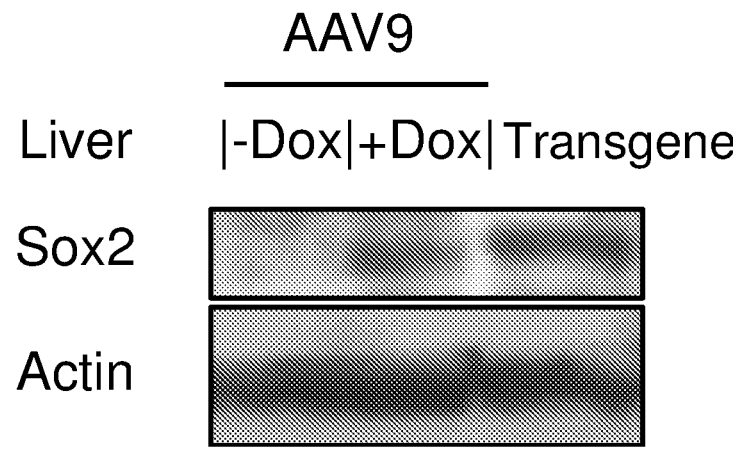
FIGS. 15A-15E shows that rtTA4 may be used in vivo to control OSK expression.
Figures 15B, 15C:
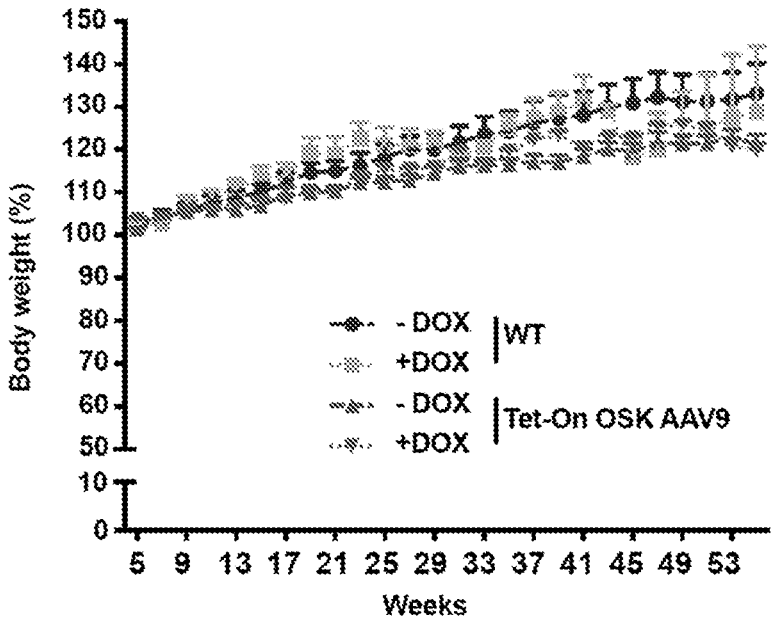
Figure 15D:
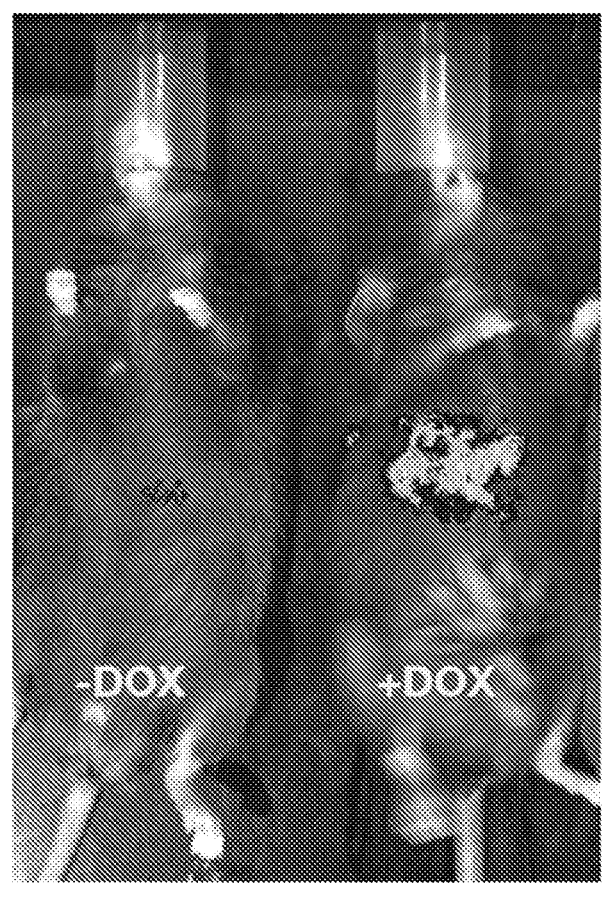
Figure 15E:
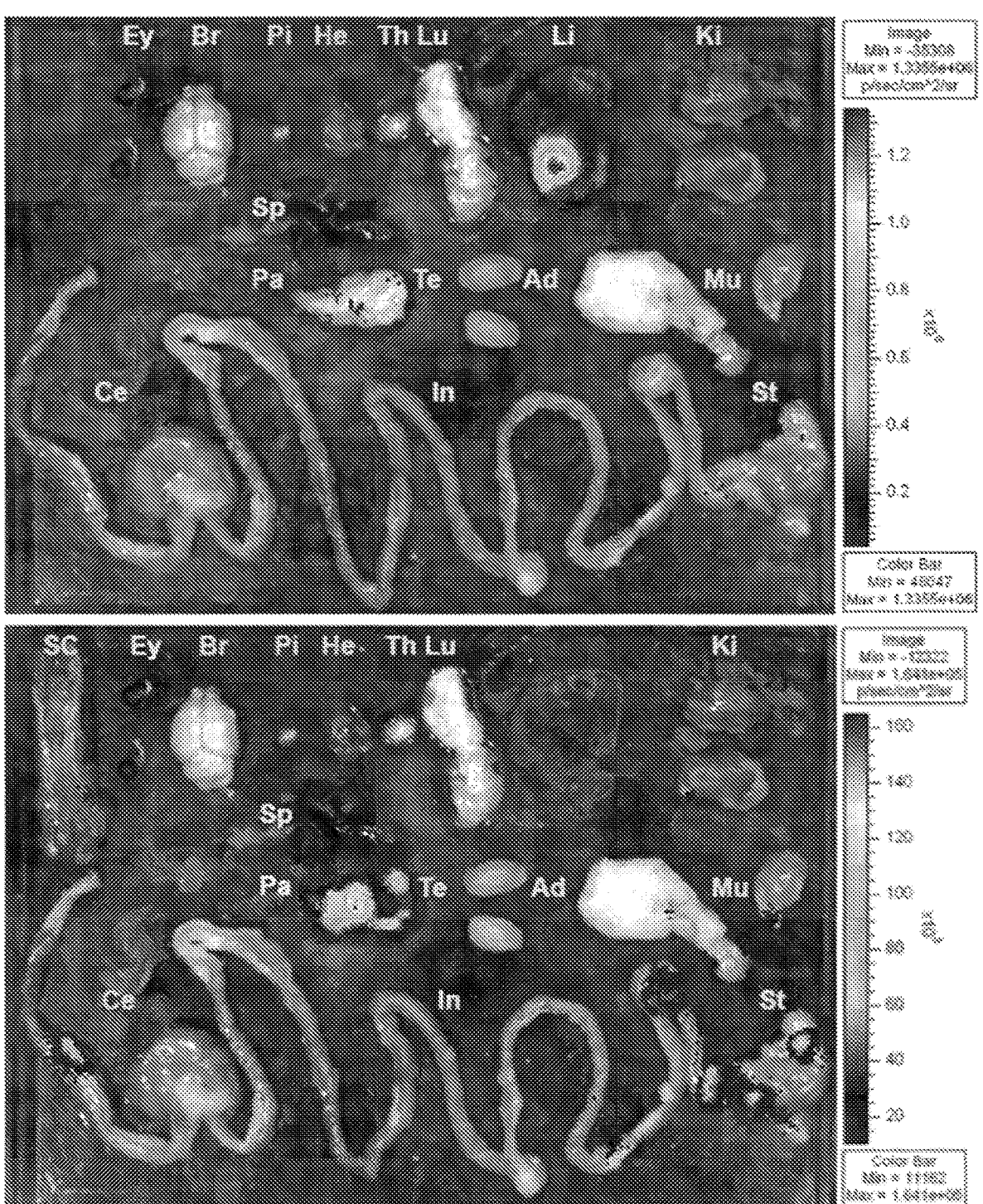

To determine whether the rtTA4 system can function in vivo, two AAVs (UBC-rtTA4 and TRE-Luc or TRE-OSK) were delivered through retro-orbital injections to mice. The 5-month-old C57BL/6J mice infected with rtTA4 and TRE-OSK AAV9s. In the absence of DOX treatment, no expression from the TRE promoter was detected (FIG. 15A). However, robust expression in tissues like liver and pancreas was observed with DOX treatment, such that the induced levels were comparable to those of transgenic mice (FIG. 15A). Surprisingly, continuous induction of OSK for over a year had no discernable negative effect on the mice for over a year (FIG. 14 and FIG. 15B). Without being bound by a particular theory, there was ostensibly no discernable negative effect on the mice because high-level expression in the intestine was avoided (FIGS. 15C-15E), thus avoiding the dysplasia and weight loss seen in other studies, including Abad et al., Nature 502, 340-345, doi: 10.1038/nature12586 (2013). Therefore, the rtTA4 system allows for spatial and temporal control of gene expression in vivo.

Methods

Mouse Lines

C57BL6/J wild type mice are purchased from Jackson Laboratory (000664) for optic nerve crush and glaucoma model experiment. For ageing experiment, females from NIA Aged Rodent Colonies (www.nia.nih.gov/research/dab/aged-rodent-colonies-handbook) are used. Colla1-tetOP-OKS-mCherry/Rosa26-M2rtTA alleles are described in Bar-Nur et al., Nat Methods, 2014. 11 (11): p. 1170-6. All animal work was approved by Harvard Medical School, Boston Children's Hospital, Mass Eye and Ear Institutional animal care and use committees.

Production of AAVs

Vectors of AAV-TRE-OSK were made by cloning mouse Oct4, Sox2 and Klf4 cDNA into an AAV plasmid consisting of the a Tet Response Element (TRE3G promoter) and SV40 element. The other vectors were directly chemically synthesized. All pAAVs, as listed in Table 6, were then packaged into AAVs of serotype 2/2 or 2/9 (titers: >5×10$^{12}$ genome copies per milliliter). Adeno associated viruses were produced by Boston Children's Hospital Viral Core.

Systemical Delivery of AAV9 to Internal Organs

Expression in internal organs was achieved through retro-orbital injection of AAV9 (3×10$^{11}$ TRE-OSK plus 7×10$^{11}$ UBC-rtTA4). 1 mg/mL doxycycline was treated 3 weeks post injection continuously to induce OSK expression.

Example 5. Non-Limiting Examples of Sequences

```
Nucleotide sequence encoding OCT4
(no stop codon): (SEQ ID NO: 1):
ATGGCTGGACACCTGGCTTCAGACTTCGCCTTCTCACCCC
CACCAGGTGGGGGTGATGGGTCAGCAGGGCTGGAGCCGGG
CTGGGTGGATCCTCGAACCTGGCTAAGCTTCCAAGGGCCT
CCAGGTGGGCCTGGAATCGGACCAGGCTCAGAGGTATTGG
GGATCTCCCCATGTCCGCCCGCATACGAGTTCTGCGGAGG
GATGGCATACTGTGGACCTCAGGTTGGACTGGGCCTAGTC
CCCCAAGTTGGCGTGGAGACTTTGCAGCCTGAGGGCCAGG
CAGGAGCACGAGTGGAAAGCAACTCAGAGGGAACCTCCTC
TGAGCCCTGTGCCGACCGCCCCAATGCCGTGAAGTTGGAG
AAGGTGGAACCAACTCCCGAGGAGTCCCAGGACATGAAAG
CCCTGCAGAAGGAGCTAGAACAGTTTGCCAAGCTGCTGAA
GCAGAAGAGGATCACCTTGGGGTACACCCAGGCCGACGTG
GGGCTCACCCTGGGCGTTCTCTTTGGAAAGGTGTTCAGCC
AGACCACCATCTGTCGCTTCGAGGCCTTGCAGCTCAGCCT
TAAGAACATGTGTAAGCTGCGGCCCCTGCTGGAGAAGTGG
GTGGAGGAAGCCGACAACAATGAGAACCTTCAGGAGATAT
GCAAATCGGAGACCCTGGTGCAGGCCCGGAAGAGAAAGCG
AACTAGCATTGAGAACCGTGTGAGGTGGAGTCTGGAGACC
ATGTTTCTGAAGTGCCCGAAGCCCTCCCTACAGCAGATCA
CTCACATCGCCAATCAGCTTGGGCTAGAGAAGGATGTGGT
TCGAGTATGGTTCTGTAACCGGCGCCAGAAGGGCAAAAGA
```

66

-continued

```
TCAAGTATTGAGTATTCCCAACGAGAAGAGTATGAGGCTA
CAGGGACACCTTTCCCAGGGGGGGCTGTATCCTTTCCTCT
GCCCCCAGGTCCCCACTTTGGCACCCCAGGCTATGGAAGC
CCCCACTTCACCACACTCTACTCAGTCCCTTTTCCTGAGG
GCGAGGCCTTTCCCTCTGTTCCCGTCACTGCTCTGGGCTC
TCCCATGCATTCAAAC

Amino acid sequence encoding OCT 4:
(SEQ ID NO: 2):
MAGHLASDFAFSPPPGGGDGSAGLEPGWVDPRTWLSFQGP
PGGPGIGPGSEVLGISPCPPAYEFCGGMAYCGPQVGLGLV
PQVGVETLQPEGQAGARVESNSEGTSSEPCADRPNAVKLE
KVEPTPEESQDMKALQKELEQFAKLLKQKRITLGYTQADV
GLTLGVLFGKVFSQTTICRFEALQLSLKNMCKLRPLLEKW
VEEADNNENLQEICKSETLVQARKRKRTSIENRVRWSLET
MFLKCPKPSLQQITHIANQLGLEKDVVRVWFCNRRQKGKR
SSIEYSQREEYEATGTPFPGGAVSFPLPPGPHFGTPGYGS
PHFTTLYSVPFPEGEAFPSVPVTALGSPMHSN Nucleotide sequence encoding SOX2
(no stop codon): (SEQ ID NO: 3):
ATGTATAACATGATGGAGACGGAGCTGAAGCCGCCGGGCC
CGCAGCAAGCTTCGGGGGGCGGCGGCGGAGGAGGCAACGC
CACGGCGGCGGCGACCGGCGGCAACCAGAAGAACAGCCCG
GACCGCGTCAAGAGGCCCATGAACGCCTTCATGGTATGGT
CCCGGGGGCAGCGGCGTAAGATGGCCCAGGAGAACCCCAA
GATGCACAACTCGGAGATCAGCAAGCGCCTGGGCGCGGAG
TGGAAACTTTTGTCCGAGACCGAGAAGCGGCCGTTCATCG
ACGAGGCCAAGCGGCTGCGCGCTCTGCACATGAAGGAGCA
CCCGGATTATAAATACCGGCCGCGGCGGAAAACCAAGACG
CTCATGAAGAAGGATAAGTACACGCTTCCCGGAGGCTTGC
TGGCCCCCGGCGGGAACAGCATGGCGAGCGGGGTTGGGGT
GGGCGCCGGCCTGGGTGCGGGCGTGAACCAGCGCATGGAC
AGCTACGCGCACATGAACGGCTGGAGCAACGGCAGCTACA
GCATGATGCAGGAGCAGCTGGGCTACCCGCAGCACCCGGG
CCTCAACGCTCACGGCGCGGCACAGATGCAACCGATGCAC
CGCTACGACGTCAGCGCCCTGCAGTACAACTCCATGACCA
GCTCGCAGACCTACATGAACGGCTCGCCCACCTACAGCAT
GTCCTACTCGCAGCAGGGCACCCCCGGTATGGCGCTGGGC
TCCATGGGCTCTGTGGTCAAGTCCGAGGCCAGCTCCAGCC
CCCCCGTGGTTACCTCTTCCTCCCACTCCAGGGCGCCCTG
CCAGGCCGGGGACCTCCGGGACATGATCAGCATGTACCTC
CCCGGCGCCGAGGTGCCGGAGCCCGCTGCGCCCAGTAGAC
```

-continued

TGCACATGGCCCAGCACTACCAGAGCGGCCCCGGTGCCCGG

CACGGCCATTAACGGCACACTGCCCCTGTCGCACATG

Amino acid sequence encoding SOX2
(translated): (SEQ ID NO: 4)
MYNMMETELKPPGPQQASGGGGGGGNATAAATGGNQKNSP

DRVKRPMNAFMVWSRGQRRKMAQENPKMHNSEISKRLGAE

WKLLSETEKRPFIDEAKRLRALHMKEHPDYKYRPRRKTKT

LMKKDKYTLPGGLLAPGGNSMASGVGVGAGLGAGVNQRMD

SYAHMNGWSNGSYSMMQEQLGYPQHPGLNAHGAAQMQPMH

RYDVSALQYNSMTSSQTYMNGSPTYSMSYSQQGTPGMALG

SMGSVVKSEASSSPPVVTSSSHSRAPCQAGDLRDMISMYL

PGAEVPEPAAPSRLHMAQHYQSGPVPGTAINGTLPLSHM

Nucleotide sequence encoding KLF4
(no stop codon): (SEQ ID NO: 5):
ATGAGGCAGCCACCTGGCGAGTCTGACATGGCTGTCAGCG

ACGCTCTGCTCCCGTCCTTCTCCACGTTCGCGTCCGGCCC

GGCGGGAAGGGAGAAGACACTGCGTCCAGCAGGTGCCCCG

ACTAACCGTTGGCGTGAGGAACTCTCTCACATGAAGCGAC

TTCCCCCACTTCCCGGCCGCCCCTACGACCTGGCGGCGAC

GGTGGCCACAGACCTGGAGAGTGGCGGAGCTGGTGCAGCT

TGCAGCAGTAACAACCCGGCCCTCCTAGCCCGGAGGGAGA

CCGAGGAGTTCAACGACCTCCTGGACCTAGACTTTATCCT

TTCCAACTCGCTAACCCACCAGGAATCGGTGGCCGCCACC

GTGACCACCTCGGCGTCAGCTTCATCCTCGTCTTCCCCAG

CGAGCAGCGGCCCTGCCAGCGCGCCCTCCACCTGCAGCTT

CAGCTATCCGATCCGGGCCGGGGGTGACCCGGGCGTGGCT

GCCAGCAACACAGGTGGAGGGCTCCTCTACAGCCGAGAAT

CTGCGCCACCTCCCACGGCCCCCTTCAACCTGGCGGACAT

CAATGACGTGAGCCCCTCGGGCGGCTTCGTGGCTGAGCTC

CTGCGGCCGGAGTTGGACCCAGTATACATTCCGCCACAGC

AGCCTCAGCCGCCAGGTGGCGGGCTGATGGGCAAGTTTGT

GCTGAAGGCGTCTCTGACCACCCCTGGCAGCGAGTACAGC

AGCCCTTCGGTCATCAGTGTTAGCAAAGGAAGCCCAGACG

GCAGCCACCCCGTGGTAGTGGCGCCCTACAGCGGTGGCCC

GCCGCGCATGTGCCCCAAGATTAAGCAAGAGGCGGTCCCG

TCCTGCACGGTCAGCCGGTCCCTAGAGGCCCATTTGAGCG

CTGGACCCCAGCTCAGCAACGGCCACCGGCCCAACACACA

CGACTTCCCCCTGGGGCGGCAGCTCCCCACCAGGACTACC

CCTACACTGAGTCCCGAGGAACTGCTGAACAGCAGGGACT

GTCACCCTGGCCTGCCTCTTCCCCCAGGATTCCATCCCCA

TCCGGGGCCCAACTACCCTCCTTTCCTGCCAGACCAGATG

CAGTCACAAGTCCCCTCTCTCCATTATCAAGAGCTCATGC

-continued

CACCGGGTTCCTGCCTGCCAGAGGAGCCCAAGCCAAAGAG

GGGAAGAAGGTCGTGGCCCCGGAAAAGAACAGCCACCCAC

ACTTGTGACTATGCAGGCTGTGGCAAAACCTATACCAAGA

GTTCTCATCTCAAGGCACACCTGCGAACTCACACAGGCGA

GAAACCTTACCACTGTGACTGGGACGGCTGTGGGTGGAAA

TTCGCCCGCTCCGATGAACTGACCAGGCACTACCGCAAAC

ACACAGGGCACCGGCCCTTTCAGTGCCAGAAGTGCGACAG

GGCCTTTTCCAGGTCGGACCACCTTGCCTTACACATGAAG

AGGCAC

Amino acid sequence encoding KLF4
(translated): (SEQ ID NO: 6):
MRQPPGESDMAVSDALLPSFSTFASGPAGREKTLRPAGAP

TNRWREELSHMKRLPPLPGRPYDLAATVATDLESGGAGAA

CSSNNPALLARRETEEFNDLLLDLDFILSNSLTHQESVAAT

VTTSASASSSSSPASSGPASAPSTCSFSYPIRAGGDPGVA

ASNTGGGLLYSRESAPPPTAPFNLADINDVSPSGGFVAEL

LRPELDPVYIPPQQPQPPGGGLMGKFVLKASLTTPGSEYS

SPSVISVSKGSPDGSHPVVVAPYSGGPPRMCPKIKQEAVP

SCTVSRSLEAHLSAGPQLSNGHRPNTHDFPLGRQLPTRTT

PTLSPEELLNSRDCHPGLPLPPGFHPHPGPNYPPFLPDQM

QSQVPSLHYQELMPPGSCLPEEPKPKRGRRSWPRKRTATH

TCDYAGCGKTYTKSSHLKAHLRTHTGEKPYHCDWDGCGWK

FARSDELTRHYRKHTGHRPFQCQKCDRAFSRSDHLALHMK

RH

TRE3G promoter sequence (non-limiting
example of a TRE promoter):
(SEQ ID NO: 7):
TTTACTCCCTATCAGTGATAGAGAACGTATGAAGAGTTTA

CTCCCTATCAGTGATAGAGAACGTATGCAGACTTTACTCC

CTATCAGTGATAGAGAACGTATAAGGAGTTTACTCCCTAT

CAGTGATAGAGAACGTATGACCAGTTTACTCCCTATCAGT

GATAGAGAACGTATCTACAGTTTACTCCCTATCAGTGATA

GAGAACGTATATCCAGTTTACTCCCTATCAGTGATAGAGA

ACGTATAAGCTTTAGGCGTGTACGGTGGGCGCCTATAAAA

GCAGAGCTCGTTTAGTGAACCGTCAGATCGCCTGGAGCAA

TTCCACAACACTTTTGTCTTATACCAACTTTCCGTACCAC

TTCCTACCCTCGTAAA

5V40-derived terminator sequence:
(SEQ ID NO: 8):
TGCGCGCAGCGGCCGACCATGGCCCAACTTGTTTATTGCA

GCTTATAATGGTTACAAATAAAGCAATAGCATCACAAATT

TCACAAATAAAGCATTTTTTTCACTGCATTCTAGTTGTGG

TTTGTCCAAACTCATCAATGTATCTTATCATGTCTGGATC

TCGGTACCG

-continued

T2A sequence (SEQ ID NO: 9):
GSGEGRGSLLTCGDVEENPGP

Nucleotide sequence encoding rtTA3
(with 2 VP16 domain at 3' end):
(SEQ ID NO: 10):
ATGTCTAGGCTGGACAAGAGCAAAGTCATAAACGGAGCTC

TGGAATTACTCAATGGTGTCGGTATCGAAGGCCTGACGAC

AAGGAAACTCGCTCAAAAGCTGGGAGTTGAGCAGCCTACC

CTGTACTGGCACGTGAAGAACAAGCGGGCCCTGCTCGATG

CCCTGCCAATCGAGATGCTGGACAGGCATCATACCCACTT

CTGCCCCCTGGAAGGCGAGTCATGGCAAGACTTTCTGCGG

AACAACGCCAAGTCATACCGCTGTGCTCTCCTCTCACATC

GCGACGGGGCTAAAGTGCATCTCGGCACCCGCCCAACAGA

GAAACAGTACGAAACCCTGGAAAATCAGCTCGCGTTCCTG

TGTCAGCAAGGCTTCTCCCTGGAGAACGCACTGTACGCTC

TGTCCGCCGTGGGCCACTTTACACTGGGCTGCGTATTGGA

GGAACAGGAGCATCAAGTAGCAAAAGAGGAAAGAGAGACA

CCTACCACCGATTCTATGCCCCCACTTCTGAGACAAGCAA

TTGAGCTGTTCGACCGGCAGGGAGCCGAACCTGCCTTCCT

TTTCGGCCTGGAACTAATCATATGTGGCCTGGAGAAACAG

CTAAAGTGCGAAAGCGGCGGGCCGACCGACGCCCTTGACG

ATTTTGACTTAGACATGCTCCCAGCCGATGCCCTTGACGA

TTTTGACCTTGACATGCTCCCCGGGTAA

Amino acid sequence encoding rtTA3:
(SEQ ID NO: 11):
MSRLDKSKVINGALELLNGVGIEGLTTRKLAQKLGVEQPT

LYWHVKNKRALLDALPIEMLDRHHTHFCPLEGESWQDFLR

NNAKSYRCALLSHRDGAKVHLGTRPTEKQYETLENQLAFL

CQQGFSLENALYALSAVGHFTLGCVLEEQEHQVAKEERET

PTTDSMPPLLRQAIELFDRQGAEPAFLFGLELIICGLEKQ

LKCESGGPTDALDDFDLDMLPADALDDFDLDMLPG

Nucleotide sequence encoding rtTA4
(with 3 VP16 domain at 3' end):
(SEQ ID NO: 12):
ATGTCCCGCTTGGATAAGAGCAAGGTAATAAATAGCGCAC

TCGAACTCCTCAACGGCGTGGGCATCGAAGGTCTGACTAC

TCGAAAGCTCGCCCAGAAATTGGGTGTGGAGCAACCTACA

TTGTATTGGCATGTCAAGAACAAAAGAGCCCTGCTGGACG

CTCTTCCTATTGAAATGCTTGACAGGCATCACACTCATTC

CTGCCCCCTTGAGGTCGAGAGTTGGCAAGATTTTCTCCGA

AACAATGCAAAGTCCTACCGCTGCGCACTTTTGTCCCATA

GGGATGGAGCAAAAGTGCACCTGGGAACCAGGCCAACAGA

GAAACAATACGAGACTCTCGAGAACCAGTTGGCTTTCTTG

TGCCAACAGGGGTTCTCACTTGAAAATGCCCTTTACGCAC

TGTCAGCCGTTGGACATTTTACCCTGGGGTGCGTTCTTGA

-continued

GGAGCAAGAACATCAGGTTGCTAAGGAGGAGCGCGAGACT

CCAACCACTGATTCTATGCCACCTTTGCTGAAACAGGCCA

TTGAACTTTTCGATAGACAGGGTGCTGAACCTGCCTTTCT

CTTCGGGTTGGAGCTGATTATTTGTGGTCTCGAAAAACAG

CTGAAATGTGAAAGTGGTGGCCCTACTGACGCCCTCGATG

ATTTCGACCTGGATATGCTGCCAGCCGATGCACTTGATGA

TTTCGATTTGGATATGCTTCCAGCCGACGCACTGGACGAC

TTCGATTTGGACATGCTTCCCGGTTAA

Amino acid sequence encoding rtTA4:
(SEQ ID NO: 13):
MSRLDKSKVINSALELLNGVGIEGLTTRKLAQKLGVEQPT

LYWHVKNKRALLDALPIEMLDRHHTHSCPLEVESWQDFLR

NNAKSYRCALLSHRDGAKVHLGTRPTEKQYETLENQLAFL

CQQGFSLENALYALSAVGHFTLGCVLEEQEHQVAKEERET

PTTDSMPPLLKQAIELFDRQGAEPAFLFGLELIICGLEKQ

LKCESGGPTDALDDFDLDMLPADALDDFDLDMLPADALDD

FDLDMLPG

Nucleotide sequence encoding
M2-rtTA (SEQ ID NO: 14):
ATGCCTTTGTATCATGCTATTGCTTCCCGTATGGCTTTCA

TTTTCTCCTCCTTGTATAAATCCTGGTTGCTGTCTCTTTA

TGAGGAGTTGTGGCCCGTTGTCAGGCAACGTGGCGTGGTG

TGCACTGTGTTTGCTGACGCAACCCCCACTGGTTGGGGCA

TTGCCACCACCTGTCAGCTCCTTTCCGGGACTTTCGCTTT

CCCCCTCCCTATTGCCACGGCGGAACTCATCGCCGCCTGC

CTTGCCCGCTGCTGGACAGGGGCTCGGCTGTTGGGCACTG

ACAATTCCGTGGTGTTGTCGGGGAAATCATCGTCCTTTCC

TTGGCTGCTCGCCTGTGTTGCCACCTGGATTCTGCGCGGG

ACGTCCTTCTGCTACGTCCCTTCGGCCCTCAATCCAGCGG

ACCTTCCTTCCCGCGGCCTGCTGCCGGCTCTGCGGCCTCT

TCCGCGTCTTCGCCTTCGCCCTCAGACGAGTCGGATCTCC

CTTTGGGCCGCCTCCCCGCATCGATACCGTCGACCTCGAG

ACCTAGAAAAACATGGAGCAATCACAAGTAGCAATACAGC

AGCTACCAATGCTGATTGTGCCTGGCTAGAAGCACAAGAG

GAGGAGGAGGTGGGTTTTCCAGTCACACCTCAGGTACCTT

TAAGACCAATGACTTACAAGGCAGCTGTAGATCTTAGCCA

CTTTTTAAAAGAAAAGGGGGGACTGGAAGGGCTAATTCAC

TCCCAACGAAGACAAGATATCCTTGATCTGTGGATCTACC

ACACACAAGGCTACTTCCCTGATTGGCAGAACTACACACC

AGGGCCAGGGATCAGATATCCACTGACCTTTGGATGGTGC

TACAAGCTAGTACCAGTTGAGCAAGAGAAGGTAGAAGAAG

CCAATGAAGGAGAGAACACCCGCTTGTTACACCCTGTGAG

CCTGCATGGGATGGATGACCCGGAGAGAGAAGTATTAGAG

-continued

TGGAGGTTTGACAGCCGCCTAGCATTTCATCACATGGCCC

GAGAGCTGCATCCGGACTGTACTGGGTCTCTCTGGTTAGA

CCAGATCTGA

Amino acid sequence encoding
M2-rtTA (SEQ ID NO: 15):
MPLYHAIASRMAFIFSSLYKSWLLSLYEELWPVVRQRGVV

CTVFADATPTGWGIATTCQLLSGTFAFPLPIATAELIAAC

LARCWTGARLLGTDNSVVLSGKSSSFPWLLACVATWILRG

TSFCYVPSALNPADLPSRGLLPALRPLPRLRLRPQTSRIS

LWAASPHRYRRPRDLEKHGAITSSNTAATNADCAWLEAQE

EEEVGFPVTPQVPLRPMTYKAAVDLSHFLKEKGGLEGLIH

SQRRQDILDLWIYHTQGYFPDWQNYTPGPGIRYPLTFGWC

YKLVPVEQEKVEEANEGENTRLLHPVSLHGMDDPEREVLE

WRFDSRLAFHHMARELHPDCTGSLWLDQI

Nucleic acid sequence of
pAAV-TRE3G-OSK-SV40pA
or TRE3G-OSK-SV40pA vector
(SEQ ID NO: 16):
TTATGCAGTGCTGCCATAACCATGAGTGATAACACTGCGG

CCAACTTACTTCTGACAACGATCGGAGGACCGAAGGAGCT

AACCGCTTTTTTGCACAACATGGGGGATCATGTAACTCGC

CTTGATCGTTGGGAACCGGAGCTGAATGAAGCCATACCAA

ACGACGAGCGTGACACCACGATGCCTGTAGTAATGGTAAC

AACGTTGCGCAAACTATTAACTGGCGAACTACTTACTCTA

GCTTCCCGGCAACAATTAATAGACTGGATGGAGGCGGATA

AAGTTGCAGGACCACTTCTGCGCTCGGCCCTTCCGGCTGG

CTGGTTTATTGCTGATAAATCTGGAGCCGGTGAGCGTGGG

TCTCGCGGTATCATTGCAGCACTGGGGCCAGATGGTAAGC

CCTCCCGTATCGTAGTTATCTACACGACGGGGAGTCAGGC

AACTATGGATGAACGAAATAGACAGATCGCTGAGATAGGT

GCCTCACTGATTAAGCATTGGTAACTGTCAGACCAAGTTT

ACTCATATATACTTTAGATTGATTTAAAACTTCATTTTTA

ATTTAAAAGGATCTAGGTGAAGATCCTTTTTGATAATCTC

ATGACCAAAATCCCTTAACGTGAGTTTTCGTTCCACTGAG

CGTCAGACCCCGTAGAAAAGATCAAAGGATCTTCTTGAGA

TCCTTTTTTTCTGCGCGTAATCTGCTGCTTGCAAACAAAA

AAACCACCGCTACCAGCGGTGGTTTGTTTGCCGGATCAAG

AGCTACCAACTCTTTTTCCGAAGGTAACTGGCTTCAGCAG

AGCGCAGATACCAAATACTGTCCTTCTAGTGTAGCCGTAG

TTAGGCCACCACTTCAAGAACTCTGTAGCACCGCCTACAT

ACCTCGCTCTGCTAATCCTGTTACCAGTGGCTGCTGCCAG

TGGCGATAAGTCGTGTCTTACCGGGTTGGACTCAAGACGA

TAGTTACCGGATAAGGCGCAGCGGTCGGGCTGAACGGGGG

-continued

GTTCGTGCACACAGCCCAGCTTGGAGCGAACGACCTACAC

CGAACTGAGATACCTACAGCGTGAGCTATGAGAAAGCGCC

ACGCTTCCCGAAGGGAGAAAGGCGGACAGGTATCCGGTAA

GCGGCAGGGTCGGAACAGGAGAGCGCACGAGGGAGCTTCC

AGGGGGAAACGCCTGGTATCTTTATAGTCCTGTCGGGTTT

CGCCACCTCTGACTTGAGCGTCGATTTTTGTGATGCTCGT

CAGGGGGGCGGAGCCTATGGAAAAACGCCAGCAACGCGGC

CTTTTTACGGTTCCTGGCCTTTTGCTGGCCTTTTGCTCAC

ATGTTCTTTCCTGCGTTATCCCCTGATTCTGTGGATAACC

GTATTACCGCCTTTGAGTGAGCTGATACCGCTCGCCGCAG

CCGAACGACCGAGCGCAGCGAGTCAGTGAGCGAGGAAGCG

GAAGAGCGCCCAATACGCAAACCGCCTCTCCCCGCGCGTT

GGCCGATTCATTAATGCAGCTGGCACGACAGGTTTCCCGA

CTGGAAAGCGGGCAGTGAGCGCAACGCAATTAATGTGAGT

TAGCTCACTCATTAGGCACCCCAGGCTTTACACTTTATGC

TTCCGGCTCGTATGTTGTGTGGAATTGTGAGCGGATAACA

ATTTCACACAGGAAACAGCTATGACCATGATTACGCCAGA

TTTAATTAAGGCCTTAATTAGGCTGCGCGCTCGCTCGCTC

ACTGAGGCCGCCCGGGCAAAGCCCGGGCGTCGGGCGACCT

TTGGTCGCCCGGCCTCAGTGAGCGAGCGAGCGCGCAGAGA

GGGAGTGGCCAACTCCATCACTAGGGGGTTCCTTGTAGTTA

ATGATTAACCCGCCATGCTACTTATCTACGTAGCCATGCT

CTAGGAAGATCGGAATTCTTTACTCCCTATCAGTGATAGA

GAACGTATGAAGAGTTTACTCCCTATCAGTGATAGAGAAC

GTATGCAGACTTTACTCCCTATCAGTGATAGAGAACGTAT

AAGGAGTTTACTCCCTATCAGTGATAGAGAACGTATGACC

AGTTTACTCCCTATCAGTGATAGAGAACGTATCTACAGTT

TACTCCCTATCAGTGATAGAGAACGTATATCCAGTTTACT

CCCTATCAGTGATAGAGAACGTATAAGCTTTAGGCGTGTA

CGGTGGGCGCCTATAAAAGCAGAGCTCGTTTAGTGAACCG

TCAGATCGCCTGGAGCAATTCCACAACACTTTTGTCTTAT

ACCAACTTTCCGTACCACTTCCTACCCTCGTAAAGCGGCC

GCGCCACCATGGCTGGACACCTGGCTTCAGACTTCGCCTT

CTCACCCCCACCAGGTGGGGGTGATGGGTCAGCAGGGCTG

GAGCCGGGCTGGGTGGATCCTCGAACCTGGCTAAGCTTCC

AAGGGCCTCCAGGTGGGCCTGGAATCGGACCAGGCTCAGA

GGTATTGGGGATCTCCCCATGTCCGCCCGCATACGAGTTC

TGCGGAGGGATGGCATACTGTGGACCTCAGGTTGGACTGG

GCCTAGTCCCCCAAGTTGGCGTGGAGACTTTGCAGCCTGA

GGGCCAGGCAGGAGCACGAGTGGAAAGCAACTCAGAGGGA

ACCTCCTCTGAGCCCTGTGCCGACCGCCCCAATGCCGTGA

-continued

```
AGTTGGAGAAGGTGGAACCAACTCCCGAGGAGTCCCAGGA

CATGAAAGCCCTGCAGAAGGAGCTAGAACAGTTTGCCAAG

CTGCTGAAGCAGAAGAGGATCACCTTGGGGTACACCCAGG

CCGACGTGGGGCTCACCCTGGGCGTTCTCTTTGGAAAGGT

GTTCAGCCAGACCACCATCTGTCGCTTCGAGGCCTTGCAG

CTCAGCCTTAAGAACATGTGTAAGCTGCGGCCCCTGCTGG

AGAAGTGGGTGGAGGAAGCCGACAACAATGAGAACCTTCA

GGAGATATGCAAATCGGAGACCCTGGTGCAGGCCCGGAAG

AGAAAGCGAACTAGCATTGAGAACCGTGTGAGGTGGAGTC

TGGAGACCATGTTTCTGAAGTGCCCGAAGCCCTCCCTACA

GCAGATCACTCACATCGCCAATCAGCTTGGGCTAGAGAAG

GATGTGGTTCGAGTATGGTTCTGTAACCGGCGCCAGAAGG

GCAAAAGATCAAGTATTGAGTATTCCCAACGAGAAGAGTA

TGAGGCTACAGGGACACCTTTCCCAGGGGGGGCTGTATCC

TTTCCTCTGCCCCCAGGTCCCCACTTTGGCACCCCAGGCT

ATGGAAGCCCCCACTTCACCACACTCTACTCAGTCCCTTT

TCCTGAGGGCGAGGCCTTTCCCTCTGTTCCCGTCACTGCT

CTGGGCTCTCCCATGCATTCAAACGCTAGCGGCAGCGGCG

CCACGAACTTCTCTCTGTTAAAGCAAGCAGGAGATGTTGA

AGAAAACCCCGGGCCTGCATGCATGTATAACATGATGGAG

ACGGAGCTGAAGCCGCCGGGCCCGCAGCAAGCTTCGGGGG

GCGGCGGCGGAGGAGGCAACGCCACGGCGGCGGCGACCGG

CGGCAACCAGAAGAACAGCCCGGACCGCGTCAAGAGGCCC

ATGAACGCCTTCATGGTATGGTCCCGGGGGCAGCGGCGTA

AGATGGCCCAGGAGAACCCCAAGATGCACAACTCGGAGAT

CAGCAAGCGCCTGGGCGCGGAGTGGAAACTTTTGTCCGAG

ACCGAGAAGCGGCCGTTCATCGACGAGGCCAAGCGGCTGC

GCGCTCTGCACATGAAGGAGCACCCGGATTATAAATACCG

GCCGCGGCGGAAAACCAAGACGCTCATGAAGAAGGATAAG

TACACGCTTCCCGGAGGCTTGCTGGCCCCCGGCGGGAACA

GCATGGCGAGCGGGGTTGGGGTGGGCGCCGGCCTGGGTGC

GGGCGTGAACCAGCGCATGGACAGCTACGCGCACATGAAC

GGCTGGAGCAACGGCAGCTACAGCATGATGCAGGAGCAGC

TGGGCTACCCGCAGCACCCGGGCCTCAACGCTCACGGCGC

GGCACAGATGCAACCGATGCACCGCTACGACGTCAGCGCC

CTGCAGTACAACTCCATGACCAGCTCGCAGACCTACATGA

ACGGCTCGCCCACCTACAGCATGTCCTACTCGCAGCAGGG

CACCCCCGGTATGGCGCTGGGCTCCATGGGCTCTGTGGTC

AAGTCCGAGGCCAGCTCCAGCCCCCCCGTGGTTACCTCTT

CCTCCCACTCCAGGGCGCCCTGCCAGGCCGGGGACCTCCG
```

-continued

```
GGACATGATCAGCATGTACCTCCCCGGCGCCGAGGTGCCG

GAGCCCGCTGCGCCCAGTAGACTGCACATGGCCCAGCACT

ACCAGAGCGGCCCGGTGCCCGGCACGGCCATTAACGGCAC

ACTGCCCCTGTCGCACATGGCATGCGGCTCCGGCGAGGGC

AGGGGAAGTCTTCTAACATGCGGGGACGTGGAGGAAAATC

CCGGCCCACTCGAGATGAGGCAGCCACCTGGCGAGTCTGA

CATGGCTGTCAGCGACGCTCTGCTCCCGTCCTTCTCCACG

TTCGCGTCCGGCCCGGCGGGAAGGGAGAAGACACTGCGTC

CAGCAGGTGCCCCGACTAACCGTTGGCGTGAGGAACTCTC

TCACATGAAGCGACTTCCCCCACTTCCCGGCCGCCCCTAC

GACCTGGCGGCGACGGTGGCCACAGACCTGGAGAGTGGCG

GAGCTGGTGCAGCTTGCAGCAGTAACAACCCGGCCCTCCT

AGCCCGGAGGGAGACCGAGGAGTTCAACGACCTCCTGGAC

CTAGACTTTATCCTTTCCAACTCGCTAACCCACCAGGAAT

CGGTGGCCGCCACCGTGACCACCTCGGCGTCAGCTTCATC

CTCGTCTTCCCCAGCGAGCAGCGGCCCTGCCAGCGCGCCC

TCCACCTGCAGCTTCAGCTATCCGATCCGGGCCGGGGGTG

ACCCGGGCGTGGCTGCCAGCAACACAGGTGGAGGGCTCCT

CTACAGCCGAGAATCTGCGCCACCTCCCACGGCCCCCTTC

AACCTGGCGGACATCAATGACGTGAGCCCCTCGGGCGGCT

TCGTGGCTGAGCTCCTGCGGCCGGAGTTGGACCCAGTATA

CATTCCGCCACAGCAGCCTCAGCCGCCAGGTGGCGGGCTG

ATGGGCAAGTTTGTGCTGAAGGCGTCTCTGACCACCCCTG

GCAGCGAGTACAGCAGCCCTTCGGTCATCAGTGTTAGCAA

AGGAAGCCCAGACGGCAGCCACCCCGTGGTAGTGGCGCCC

TACAGCGGTGGCCCGCCGCGCATGTGCCCCAAGATTAAGC

AAGAGGCGGTCCCGTCCTGCACGGTCAGCCGGTCCCTAGA

GGCCCATTTGAGCGCTGGACCCCAGCTCAGCAACGGCCAC

CGGCCCAACACACACGACTTCCCCCTGGGGCGGCAGCTCC

CCACCAGGACTACCCCTACACTGAGTCCCGAGGAACTGCT

GAACAGCAGGGACTGTCACCCTGGCCTGCCTCTTCCCCCA

GGATTCCATCCCCATCCGGGGCCCAACTACCCTCCTTTCC

TGCCAGACCAGATGCAGTCACAAGTCCCCTCTCTCCATTA

TCAAGAGCTCATGCCACCGGGTTCCTGCCTGCCAGAGGAG

CCCAAGCCAAAGAGGGGAAGAAGGTCGTGGCCCCGGAAAA

GAACAGCCACCCACACTTGTGACTATGCAGGCTGTGGCAA

AACCTATACCAAGAGTTCTCATCTCAAGGCACACCTGCGA

ACTCACACAGGCGAGAAACCTTACCACTGTGACTGGGACG

GCTGTGGGTGGAAATTCGCCCGCTCCGATGAACTGACCAG

GCACTACCGCAAACACACAGGGCACCGGCCCTTTCAGTGC

CAGAAGTGCGACAGGGCCTTTTCCAGGTCGGACCACCTTG
```

-continued

CCTTACACATGAAGAGGCACTAAATGACTAGTGCGCGCAG

CGGCCGACCATGGCCCAACTTGTTTATTGCAGCTTATAAT

GGTTACAAATAAAGCAATAGCATCACAAATTTCACAAATA

AAGCATTTTTTCACTGCATTCTAGTTGTGGTTTGTCCAA

ACTCATCAATGTATCTTATCATGTCTGGATCTCGGTACCG

GATCCAAATTCCCGATAAGGATCTTCCTAGAGCATGGCTA

CGTAGATAAGTAGCATGGCGGGTTAATCATTAACTACAAG

GAACCCCTAGTGATGGAGTTGGCCACTCCCTCTCTGCGCG

CTCGCTCGCTCACTGAGGCCGGGCGACCAAAGGTCGCCCG

ACGCCCGGGCTTTGCCCGGGCGGCCTCAGTGAGCGAGCGA

GCGCGCAGCCTTAATTAACCTAATTCACTGGCCGTCGTTT

TACAACGTCGTGACTGGGAAAACCCTGGCGTTACCCAACT

TAATCGCCTTGCAGCACATCCCCCTTTCGCCAGCTGGCGT

AATAGCGAAGAGGCCCGCACCGATCGCCCTTCCCAACAGT

TGCGCAGCCTGAATGGCGAATGGGACGCGCCCTGTAGCGG

CGCATTAAGCGCGGCGGGTGTGGTGGTTACGCGCAGCGTG

ACCGCTACACTTGCCAGCGCCCTAGCGCCCGCTCCTTTCG

CTTTCTTCCCTTCCTTTCTCGCCACGTTCGCCGGCTTTCC

CCGTCAAGCTCTAAATCGGGGGCTCCCTTTAGGGTTCCGA

TTTAGTGCTTTACGGCACCTCGACCCCAAAAAACTTGATT

AGGGTGATGGTTCACGTAGTGGGCCATCGCCCTGATAGAC

GGTTTTTCGCCCTTTGACGTTGGAGTCCACGTTCTTTAAT

AGTGGACTCTTGTTCCAAACTGGAACAACACTCAACCCTA

TCTCGGTCTATTCTTTTGATTTATAAGGGATTTTGCCGAT

TTCGGCCTATTGGTTAAAAAATGAGCTGATTTAACAAAAA

TTTAACGCGAATTTTAACAAAATATTAACGTTTATAATTT

CAGGTGGCATCTTTCGGGGAAATGTGCGCGGAACCCCTAT

TTGTTTATTTTTCTAAATACATTCAAATATGTATCCGCTC

ATGAGACAATAACCCTGATAAATGCTTCAATAATATTGAA

AAAGGAAGAGTATGAGTATTCAACATTTCCGTGTCGCCCT

TATTCCCTTTTTTGCGGCATTTTGCCTTCCTGTTTTTGCT

CACCCAGAAACGCTGGTGAAAGTAAAAGATGCTGAAGATC

AGTTGGGTGCACGAGTGGGTTACATCGAACTGGATCTCAA

TAGTGGTAAGATCCTTGAGAGTTTTCGCCCCGAAGAACGT

TTTCCAATGATGAGCACTTTTAAAGTTCTGCTATGTGGCG

CGGTATTATCCCGTATTGACGCCGGGCAAGAGCAACTCGG

TCGCCGCATACACTATTCTCAGAATGACTTGGTTGAGTAC

TCACCAGTCACAGAAAAGCATCTTACGGATGGCATGACAG

TAAGAGAA

-continued

Nucleic acid sequence of pAAV-UBC-rtTA4-
WPRE3-SV40pA vector (SEQ ID NO: 17):
TTATGCAGTGCTGCCATAACCATGAGTGATAACACTGCGG

CCAACTTACTTCTGACAACGATCGGAGGACCGAAGGAGCT

AACCGCTTTTTTGCACAACATGGGGGATCATGTAACTCGC

CTTGATCGTTGGGAACCGGAGCTGAATGAAGCCATACCAA

ACGACGAGCGTGACACCACGATGCCTGTAGTAATGGTAAC

AACGTTGCGCAAACTATTAACTGGCGAACTACTTACTCTA

GCTTCCCGGCAACAATTAATAGACTGGATGGAGGCGGATA

AAGTTGCAGGACCACTTCTGCGCTCGGCCCTTCCGGCTGG

CTGGTTTATTGCTGATAAATCTGGAGCCGGTGAGCGTGGG

TCTCGCGGTATCATTGCAGCACTGGGGCCAGATGGTAAGC

CCTCCCGTATCGTAGTTATCTACACGACGGGGAGTCAGGC

AACTATGGATGAACGAAATAGACAGATCGCTGAGATAGGT

GCCTCACTGATTAAGCATTGGTAACTGTCAGACCAAGTTT

ACTCATATATACTTTAGATTGATTTAAAACTTCATTTTTA

ATTTAAAAGGATCTAGGTGAAGATCCTTTTTGATAATCTC

ATGACCAAAATCCCTTAACGTGAGTTTTCGTTCCACTGAG

CGTCAGACCCCGTAGAAAAGATCAAAGGATCTTCTTGAGA

TCCTTTTTTTCTGCGCGTAATCTGCTGCTTGCAAACAAAA

AAACCACCGCTACCAGCGGTGGTTTGTTTGCCGGATCAAG

AGCTACCAACTCTTTTTCCGAAGGTAACTGGCTTCAGCAG

AGCGCAGATACCAAATACTGTCCTTCTAGTGTAGCCGTAG

TTAGGCCACCACTTCAAGAACTCTGTAGCACCGCCTACAT

ACCTCGCTCTGCTAATCCTGTTACCAGTGGCTGCTGCCAG

TGGCGATAAGTCGTGTCTTACCGGGTTGGACTCAAGACGA

TAGTTACCGGATAAGGCGCAGCGGTCGGGCTGAACGGGGG

GTTCGTGCACACAGCCCAGCTTGGAGCGAACGACCTACAC

CGAACTGAGATACCTACAGCGTGAGCTATGAGAAAGCGCC

ACGCTTCCCGAAGGGAGAAAGGCGGACAGGTATCCGGTAA

GCGGCAGGGTCGGAACAGGAGAGCGCACGAGGGAGCTTCC

AGGGGGAAACGCCTGGTATCTTTATAGTCCTGTCGGGTTT

CGCCACCTCTGACTTGAGCGTCGATTTTTGTGATGCTCGT

CAGGGGGGCGGAGCCTATGGAAAAACGCCAGCAACGCGGC

CTTTTTACGGTTCCTGGCCTTTTGCTGGCCTTTTGCTCAC

ATGTTCTTTCCTGCGTTATCCCCTGATTCTGTGGATAACC

GTATTACCGCCTTTGAGTGAGCTGATACCGCTCGCCGCAG

CCGAACGACCGAGCGCAGCGAGTCAGTGAGCGAGGAAGCG

GAAGAGCGCCCAATACGCAAACCGCCTCTCCCCGCGCGTT

GGCCGATTCATTAATGCAGCTGGCACGACAGGTTTCCCGA

CTGGAAAGCGGGCAGTGAGCGCAACGCAATTAATGTGAGT

-continued

TAGCTCACTCATTAGGCACCCCAGGCTTTACACTTTATGC

TTCCGGCTCGTATGTTGTGTGGAATTGTGAGCGGATAACA

ATTTCACACAGGAAACAGCTATGACCATGATTACGCCAGA

TTTAATTAAGGCCTTAATTAGGCTGCGCGCTCGCTCGCTC

ACTGAGGCCGCCCGGGCAAAGCCCGGGCGTCGGGCGACCT

TTGGTCGCCCGGCCTCAGTGAGCGAGCGAGCGCGCAGAGA

GGGAGTGGCCAACTCCATCACTAGGGGTTCCTTGTAGTTA

ATGATTAACCCGCCATGCTACTTATCTACGTAGCCATGCT

CTAGGAAGATCGGAATTCCTGATCTGGCCTCCGCGCCGGG

TTTTGGCGCCTCCCGCGGGCGCCCCCCTCCTCACGGCGAG

CGCTGCCACGTCAGACGAAGGGCGCAGCGAGCGTCCTGAT

CCTTCCGCCCGGACGCTCAGGACAGCGGCCCGCTGCTCAT

AAGACTCGGCCTTAGAACCCCAGTATCAGCAGAAGGACAT

TTTAGGACGGGACTTGGGTGACTCTAGGGCACTGGTTTTC

TTTCCAGAGAGCGGAACAGGCGAGGAAAAGTAGTCCCTTC

TCGGCGATTCTGCGGAGGGATCTCCGTGGGGCGGTGAACG

CCGATGATTATATAAGGACGCGCCGGGTGTGGCACAGCTA

GTTCCGTCGCAGCCGGGATTTGGGTCGCGGTTCTTGTTTG

TGGATCGCTGTGATCGTCACTTGGTGAGTAGCGGGCTGCT

GGGCTGGCCGGGGCTTTCGTGGCCGCCGGGCCGCTCGGTG

GGACGGAAGCGTGTGGAGAGACCGCCAAGGGCTGTAGTCT

GGGTCCGCGAGCAAGGTTGCCCTGAACTGGGGGTTGGGGG

GAGCGCAGCAAAATGGCGGCTGTTCCCGAGTCTTGAATGG

AAGACGCTTGTGAGGCGGGCTGTGAGGTCGTTGAAACAAG

GTGGGGGGCATGGTGGGCGGCAAGAACCCAAGGTCTTGAG

GCCTTCGCTAATGCGGGAAAGCTCTTATTCGGGTGAGATG

GGCTGGGGCACCATCTGGGGACCCTGACGTGAAGTTTGTC

ACTGACTGGAGAACTCGGTTTGTCGTCTGTTGCGGGGGCG

GCAGTTATGCGGTGCCGTTGGGCAGTGCACCCGTACCTTT

GGGAGCGCGCGCCTCGTCGTGTCGTGACGTCACCCGTTCT

GTTGGCTTATAATGCAGGGTGGGGCCACCTGCCGGTAGGT

GTGCGGTAGGCTTTTCTCCGTCGCAGGACGCAGGGTTCGG

GCCTAGGGTAGGCTCTCCTGAATCGACAGGCGCCGGACCT

CTGGTGAGGGGAGGGATAAGTGAGGCGTCAGTTTCTTTGG

TCGGTTTTATGTACCTATCTTCTTAAGTAGCTGAAGCTCC

GGTTTTGAACTATGCGCTCGGGGTTGGCGAGTGTGTTTTG

TGAAGTTTTTTAGGCACCTTTTGAAATGTAATCATTTGGG

TCAATATGTAATTTTCAGTGTTAGACTAGTAAATTGTCCG

CTAAATTCTGGCCGTTTTTGGCTTTTTTGTTAGACGAAGC

GGCCGCATTAAACGCCACCATGTCCCGCTTGGATAAGAGC

AAGGTAATAAATAGCGCACTCGAACTCCTCAACGGCGTGG

-continued

GCATCGAAGGTCTGACTACTCGAAAGCTCGCCCAGAAATT

GGGTGTGGAGCAACCTACATTGTATTGGCATGTCAAGAAC

AAAAGAGCCCTGCTGGACGCTCTTCCTATTGAAATGCTTG

ACAGGCATCACACTCATTCCTGCCCCCTTGAGGTCGAGAG

TTGGCAAGATTTTCTCCGAAACAATGCAAAGTCCTACCGC

TGCGCACTTTTGTCCCATAGGGATGGAGCAAAAGTGCACC

TGGGAACCAGGCCAACAGAGAAACAATACGAGACTCTCGA

GAACCAGTTGGCTTTCTTGTGCCAACAGGGGTTCTCACTT

GAAAATGCCCTTTACGCACTGTCAGCCGTTGGACATTTTA

CCCTGGGGTGCGTTCTTGAGGAGCAAGAACATCAGGTTGC

TAAGGAGGAGCGCGAGACTCCAACCACTGATTCTATGCCA

CCTTTGCTGAAACAGGCCATTGAACTTTTCGATAGACAGG

GTGCTGAACCTGCCTTTCTCTTCGGGTTGGAGCTGATTAT

TTGTGGTCTCGAAAAACAGCTGAAATGTGAAAGTGGTGGC

CCTACTGACGCCCTCGATGATTTCGACCTGGATATGCTGC

CAGCCGATGCACTTGATGATTTCGATTTGGATATGCTTCC

AGCCGACGCACTGGACGACTTCGATTTGGACATGCTTCCC

GGTTAAACTAGTCTAGCAATCAACCTCTGGATTACAAAAT

TTGTGAAAGATTGACTGGTATTCTTAACTATGTTGCTCCT

TTTACGCTATGTGGATACGCTGCTTTAATGCCTTTGTATC

ATGCTATTGCTTCCCGTATGGCTTTCATTTTCTCCTCCTT

GTATAAATCCTGGTTAGTTCTTGCCACGGCGGAACTCATC

GCCGCCTGCCTTGCCCGCTGCTGGACAGGGGCTCGGCTGT

TGGGCACTGACAATTCCGTGGTGTTTATTTGTGAAATTTG

TGATGCTATTGCTTTATTTGTAACCATTCTAGCTTTATTT

GTGAAATTTGTGATGCTATTGCTTTATTTGTAACCATTAT

AAGCTGCAATAAACAAGTTAACAACAACAATTGCATTCAT

TTTATGTTTCAGGTTCAGGGGGAGATGTGGGAGGTTTTTT

AAAGCGGGGGATCCAAATTCCCGATAAGGATCTTCCTAGA

GCATGGCTACGTAGATAAGTAGCATGGCGGGTTAATCATT

AACTACAAGGAACCCCTAGTGATGGAGTTGGCCACTCCCT

CTCTGCGCGCTCGCTCGCTCACTGAGGCCGGGCGACCAAA

GGTCGCCCGACGCCCGGGCTTTGCCCGGGCGGCCTCAGTG

AGCGAGCGAGCGCGCAGCCTTAATTAACCTAATTCACTGG

CCGTCGTTTTACAACGTCGTGACTGGGAAAACCCTGGCGT

TACCCAACTTAATCGCCTTGCAGCACATCCCCCTTTCGCC

AGCTGGCGTAATAGCGAAGAGGCCCGCACCGATCGCCCTT

CCCAACAGTTGCGCAGCCTGAATGGCGAATGGGACGCGCC

CTGTAGCGGCGCATTAAGCGCGGCGGGTGTGGTGGTTACG

CGCAGCGTGACCGCTACACTTGCCAGCGCCCTAGCGCCCG

-continued

CTCCTTTCGCTTTCTTCCCTTCCTTTCTCGCCACGTTCGC

CGGCTTTCCCCGTCAAGCTCTAAATCGGGGGCTCCCTTTA

GGGGTTCCGATTTAGTGCTTTACGGCACCTCGACCCCAAAA

AACTTGATTAGGGTGATGGTTCACGTAGTGGGCCATCGCC

CTGATAGACGGTTTTTCGCCCTTTGACGTTGGAGTCCACG

TTCTTTAATAGTGGACTCTTGTTCCAAACTGGAACAACAC

TCAACCCTATCTCGGTCTATTCTTTTGATTTATAAGGGAT

TTTGCCGATTTCGGCCTATTGGTTAAAAAATGAGCTGATT

TAACAAAAATTTAACGCGAATTTTAACAAAATATTAACGT

TTATAATTTCAGGTGGCATCTTTCGGGGAAATGTGCGCGG

AACCCCTATTTGTTTATTTTTCTAAATACATTCAAATATG

TATCCGCTCATGAGACAATAACCCTGATAAATGCTTCAAT

AATATTGAAAAAGGAAGAGTATGAGTATTCAACATTTCCG

TGTCGCCCTTATTCCCTTTTTTGCGGCATTTTGCCTTCCT

GTTTTTGCTCACCCAGAAACGCTGGTGAAAGTAAAAGATG

CTGAAGATCAGTTGGGTGCACGAGTGGGTTACATCGAACT

GGATCTCAATAGTGGTAAGATCCTTGAGAGTTTTCGCCCC

GAAGAACGTTTTCCAATGATGAGCACTTTTAAAGTTCTGC

TATGTGGCGCGGTATTATCCCGTATTGACGCCGGGCAAGA

GCAACTCGGTCGCCGCATACACTATTCTCAGAATGACTTG

GTTGAGTACTCACCAGTCACAGAAAAGCATCTTACGGATG

GCATGACAGTAAGAGAA

UBC promoter sequence (SEQ ID NO: 18):
GATCTGGCCTCCGCGCCGGGTTTTGGCGCCTCCCGCGGGC

GCCCCCCTCCTCACGGCGAGCGCTGCCACGTCAGACGAAG

GGCGCAGCGAGCGTCCTGATCCTTCCGCCCGGACGCTCAG

GACAGCGGCCCGCTGCTCATAAGACTCGGCCTTAGAACCC

CAGTATCAGCAGAAGGACATTTTAGGACGGGACTTGGGTG

ACTCTAGGGCACTGGTTTTCTTTCCAGAGAGCGGAACAGG

CGAGGAAAAGTAGTCCCTTCTCGGCGATTCTGCGGAGGGA

TCTCCGTGGGGCGGTGAACGCCGATGATTATATAAGGACG

CGCCGGGTGTGGCACAGCTAGTTCCGTCGCAGCCGGGATT

TGGGTCGCGGTTCTTGTTTGTGGATCGCTGTGATCGTCAC

TTGGTGAGTAGCGGGCTGCTGGGCTGGCCGGGGCTTTCGT

GGCCGCCGGGCCGCTCGGTGGGACGGAAGCGTGTGGAGAG

ACCGCCAAGGGCTGTAGTCTGGGTCCGCGAGCAAGGTTGC

CCTGAACTGGGGGTTGGGGGGAGCGCAGCAAAATGGCGGC

TGTTCCCGAGTCTTGAATGGAAGACGCTTGTGAGGCGGGC

TGTGAGGTCGTTGAAACAAGGTGGGGGGCATGGTGGGCGG

CAAGAACCCAAGGTCTTGAGGCCTTCGCTAATGCGGGAAA

GCTCTTATTCGGGTGAGATGGGCTGGGGCACCATCTGGGG

-continued

ACCCTGACGTGAAGTTTGTCACTGACTGGAGAACTCGGTT

TGTCGTCTGTTGCGGGGGCGGCAGTTATGCGGTGCCGTTG

GGCAGTGCACCCGTACCTTTGGGAGCGCGCGCCTCGTCGT

GTCGTGACGTCACCCGTTCTGTTGGCTTATAATGCAGGGT

GGGGCCACCTGCCGGTAGGTGTGCGGTAGGCTTTTCTCCG

TCGCAGGACGCAGGGTTCGGGCCTAGGGTAGGCTCTCCTG

AATCGACAGGCGCCGGACCTCTGGTGAGGGGAGGGATAAG

TGAGGCGTCAGTTTCTTTGGTCGGTTTTATGTACCTATCT

TCTTAAGTAGCTGAAGCTCCGGTTTTGAACTATGCGCTCG

GGGTTGGCGAGTGTGTTTTGTGAAGTTTTTTAGGCACCTT

TTGAAATGTAATCATTTGGGTCAATATGTAATTTTCAGTG

TTAGACTAGTAAATTGTCCGCTAAATTCTGGCCGTTTTTG

GCTTTTTTGTTAGAC

Tet-O sequence (SEQ ID NO: 19):
TCCCTATCAGTGATAGAGA

Nucleic acid sequence encoding minimal
CMV promoter (SEQ ID NO: 20):
GCTTTAGGCGTGTACGGTGGGCGCCTATAAAAGCAGAGCT

CGTTTAGTGAACCGTCAGATCGCCTGGA

Nucleic acid sequence encoding WPRE
(SEQ ID NO: 21):
AATCAACCTCTGGATTACAAAATTTGTGAAAGATTGACTG

GTATTCTTAACTATGTTGCTCCTTTTACGCTATGTGGATA

CGCTGCTTTAATGCCTTTGTATCATGCTATTGCTTCCCGT

ATGGCTTTCATTTTCTCCTCCTTGTATAAATCCTGGTTAG

TTCTTGCCACGGCGGAACTCATCGCCGCCTGCCTTGCCCG

CTGCTGGACAGGGGCTCGGCTGTTGGGCACTGACAATTCC

GTGGTGTT

Nucleic acid sequence encoding
inverted terminal
repeat sequence (SEQ ID NO: 22):
CCTTAATTAGGCTGCGCGCTCGCTCGCTCACTGAGGCCGC

CCGGGCAAAGCCCGGGCGTCGGGCGACCTTTGGTCGCCCG

GCCTCAGTGAGCGAGCGAGCGCGCAGAGAGGGAGTGGCCA

ACTCCATCACTAGGGGTTCCT

Nucleic acid sequence of a TRE2 promoter
(a non-limiting example of a TRE promoter)
(SEQ ID NO: 23):
AATTCGTACACGCCTACCTCGACCCATCAAGTGCCACCTG

ACGTCTCCCTATCAGTGATAGAGAAGTCGACACGTCTCGA

GCTCCCTATCAGTGATAGAGAAGGTACGTCTAGAACGTCT

CCCTATCAGTGATAGAGAAGTCGACACGTCTCGAGCTCCC

TATCAGTGATAGAGAAGGTACGTCTAGAACGTCTCCCTAT

CAGTGATAGAGAAGTCGACACGTCTCGAGCTCCCTATCAG

TGATAGAGAAGGTACGTCTAGAACGTCTCCCTATCAGTGA

TAGAGAAGTCGACACGTCTCGAGCTCCCTATCAGTGATAG

-continued

AGAAGGTACCCCCTATATAAGCAGAGCTCGTTTAGTGAAC

CGTCAGATCGCCTGGAGACGCCATCCACGCTGTTTTGAC

CTCCATAGAAGACACCGGGACCGATCCAGCCTGGATCGC

Nucleic acid sequence of P tight promoter
(a non-limiting example of a TRE promoter)
(SEQ ID NO: 24):
GAGTTTACTCCCTATCAGTGATAGAGAACGTATGTCGAGT

TTACTCCCTATCAGTGATAGAGAACGATGTCGAGTTTACT

CCCTATCAGTGATAGAGAACGTATGTCGAGTTTACTCCCT

ATCAGTGATAGAGAACGTATGTCGAGTTTACTCCCTATCA

GTGATAGAGAACGTATGTCGAGTTTATCCCTATCAGTGAT

AGAGAACGTATGTCGAGTTTACTCCCTATCAGTGATAGAG

AACGTATGTCGAGGTAGGCGTGTACGGTGGGAGGCCTATA

TAAGCAGAGCTCGTTTAGTGAACCGTCAGATCGCC

Nucleic acid sequence encoding TetR
(SEQ ID NO: 25):
ATGGCTAGATTAGATAAAAGTAAAGTGATTAACAGCGCAT

TAGAGCTGCTTAATGAGGTCGGAATCGAAGGTTTAACAAC

CCGTAAAACTCGCCCAGAAGCTAGGTGTAGAGCAGCCTACA

TTGTATTGGCATGTAAAAAATAAGCGGGCTTTGCTCGACG

CCTTAGCCATTGAGATGTTAGATAGGCACCATACTCACTT

TTGCCCTTTAGAAGGGGAAAGCTGGCAAGATTTTTTACGT

AATAACGCTAAAAGTTTTAGATGTGCTTTACTAAGTCATC

GCGATGGAGCAAAAGTACATTTAGGTACACGGCCTACAGA

AAAACAGTATGAAACTCTCGAAAATCAATTAGCCTTTTTA

TGCCAACAAGGTTTTTCACTAGAGAATGCATTATATGCA

CTCAGCGCTGTGGGGCATTTTACTTTAGGTTGCGTATTGG

AAGATCAAGAGCATCAAGTCGCTAAAGAAGAAAGGGAAAC

ACCTACTACTGATAGTATGCCGCCATTATTACGACAAGCT

ATCGAATTATTTGATCACCAAGGTGCAGAGCCAGCCTTCT

TATTCGGCCTTGAATTGATCATATGCGGATTAGAAAAACA

ACTTAAATGTGAAAGTGGG

Amino acid sequence encoding TetR
(SEQ ID NO: 26):
MARLDKSKVINSALELLNEVGIEGLTTRKLAQKLGVEQPT

LYWHVKNKRALLDALAIEMLDRHHTHFCPLEGESWQDFLR

NNAKSFRCALLSHRDGAKVHLGTRPTEKQYETLENQLAFL

CQQGFSLENALYALSAVGHFTLGCVLEDQEHQVAKEERET

PTTDSMPPLLRQAIELFDHQGAEPAFLFGLELIICGLEKQ

LKCESG

Nucleic acid sequence encoding
TetR-Krab (SEQ ID NO: 27)
ATGGCTAGATTAGATAAAAGTAAAGTGATTAACAGCGCAT

TAGAGCTGCTTAATGAGGTCGGAATCGAAGGTTTAACAAC

CCGTAAAACTCGCCCAGAAGCTAGGTGTAGAGCAGCCTACA

-continued

TTGTATTGGCATGTAAAAAATAAGCGGGCTTTGCTCGACG

CCTTAGCCATTGAGATGTTAGATAGGCACCATACTCACTT

TTGCCCTTTAGAAGGGGAAAGCTGGCAAGATTTTTTACGT

AATAACGCTAAAAGTTTTAGATGTGCTTTACTAAGTCATC

GCGATGGAGCAAAAGTACATTTAGGTACACGGCCTACAGA

AAAACAGTATGAAACTCTCGAAAATCAATTAGCCTTTTTA

TGCCAACAAGGTTTTTCACTAGAGAATGCATTATATGCAC

TCAGCGCTGTGGGGCATTTTACTTTAGGTTGCGTATTGGA

AGATCAAGAGCATCAAGTCGCTAAAGAAGAAAGGGAAACA

CCTACTACTGATAGTATGCCGCCATTATTACGACAAGCTA

TCGAATTATTTGATCACCAAGGTGCAGAGCCAGCCTTCTT

ATTCGGCCTTGAATTGATCATATGCGGATTAGAAAAACAA

CTTAAATGTGAAAGTGGGTCGCCAAAAAAGAAGAGAAAGG

TCGACGGCGGTGGTGCTTTGTCTCCTCAGCACTCTGCTGT

CACTCAAGGAAGTATCATCAAGAACAAGGAGGGCATGGAT

GCTAAGTCACTAACTGCCTGGTCCCGGACACTGGTGACCT

TCAAGGATGTATTTGTGGACTTCACCAGGGAGGAGTGGAA

GCTGCTGGACACTGCTCAGCAGATCGTGTACAGAAATGTG

ATGCTGGAGAACTATAAGAACCTGGTTTCCTTGGGTTATC

AGCTTACTAAGCCAGATGTGATCCTCCGGTTGGAGAAGGG

AGAAGAGCCCTGGCTGGTGGAGAGAGAAATTCACCAAGAG

ACCCATCCTGATTCAGAGACTGCATTTGAAATCAAATCAT

CAGTTTAA

Amino acid sequence encoding
TetR-KRAB (SEQ ID NO: 28):
MARLDKSKVINSALELLNEVGIEGLTTRKLAQKLGVEQPT

LYWHVKNKRALLDALAIEMLDRHHTHFCPLEGESWQDFLR

NNAKSFRCALLSHRDGAKVHLGTRPTEKQYETLENQLAFL

CQQGFSLENALYALSAVGHFTLGCVLEDQEHQVAKEERET

PTTDSMPPLLRQAIELFDHQGAEPAFLFGLELIICGLEKQ

LKCESGSPKKKRKVDGGGALSPQHSAVTQGSIIKNKEGMD

AKSLTAWSRTLVTFKDVFVDFTREEWKLLDTAQQIVYRNV

MLENYKNLVSLGYQLTKPDVILRLEKGEEPWLVEREIHQE

THPDSETAFEIKSSV

Desmin promoter (SEQ ID NO: 29):
ACCTTGCTTCCTAGCTGGGCCTTTCCTTCTCCTCTATAAA

TACCAGCTCTGGTATTTCGCCTTGGCAGCTGTTGCTGCTA

GGGAGACGGCTGGCTTGACATGCATCTCCTGACAAAACAC

AAACCCGTGGTGTGAGTGGGTGTGGGCGGTGTGAGTAGGG

GGATGAATCAGAGAGGGGGCGAGGGAGACAGGGGCGCAGG

AGTCAGGCAAAGGCGATGCGGGGGTGCGACTACACGCAGT

TGGAAACAGTCGTCAGAAGATTCTGGAAACTATCTTGCTG

-continued

GCTATAAACTTGAGGGAAGCAGAAGGCCAACATTCCTCCC

AAGGGAAACTGAGGCTCAGAGTTAAAACCCAGGTATCAGT

GATATGCATGTGCCCCGGCCAGGGTCACTCTCTGACTAAC

CGGTACCTACCCTACAGGCCTACCTAGAGACTCTTTTGAA

AGGATGGTAGAGACCTGTCCGGGCTTTGCCCACAGTCGTT

GGAAACCTCAGCATTTTCTAGGCAACTTGTGCGAATAAAA

CACTTCGGGGGTCCTTCTTGTTCATTCCAATAACCTAAAA

CCTCTCCTCGGAGAAAATAGGGGGCCTCAAACAAACGAAA

TTCTCTAGCCCGCTTTCCCCAGGATAAGGCAGGCATCCAA

ATGGAAAAAAGGGGCCGGCCGGGGGTCTCCTGTCAGCTC

CTTGCCCTGTGAAACCCAGCAGGCCTGCCTGTCTTCTGTC

CTCTTGGGGCTGTCCAGGGGCGCAGGCCTCTTGCGGGGGA

GCTGGCCTCCCCGCCCCCTCGCCTGTGGCCGCCCTTTTCC

TGGCAGGACAGAGGGATCCTGCAGCTGTCAGGGGAGGGGC

GCCGGGGGGTGATGTCAGGAGGGCTACAAATAGTGCAGAC

AGCTAAGGGGCTCCGTCACCCATCTTCACATCCACTCCAG

CCGGCTGCCCGCCCGCTGCCTCCTCTGTGCGTCCGCCCAG

CCAGCCTCGTCCACGCC

Desmin-rtTA4 vector (SEQ ID NO: 30):
TTATGCAGTGCTGCCATAACCATGAGTGATAACACTGCGG

CCAACTTACTTCTGACAACGATCGGAGGACCGAAGGAGCT

AACCGCTTTTTTGCACAACATGGGGGATCATGTAACTCGC

CTTGATCGTTGGGAACCGGAGCTGAATGAAGCCATACCAA

ACGACGAGCGTGACACCACGATGCCTGTAGTAATGGTAAC

AACGTTGCGCAAACTATTAACTGGCGAACTACTTACTCTA

GCTTCCCGGCAACAATTAATAGACTGGATGGAGGCGGATA

AAGTTGCAGGACCACTTCTGCGCTCGGCCCTTCCGGCTGG

CTGGTTTATTGCTGATAAATCTGGAGCCGGTGAGCGTGGG

TCTCGCGGTATCATTGCAGCACTGGGGCCAGATGGTAAGC

CCTCCCGTATCGTAGTTATCTACACGACGGGGAGTCAGGC

AACTATGGATGAACGAAATAGACAGATCGCTGAGATAGGT

GCCTCACTGATTAAGCATTGGTAACTGTCAGACCAAGTTT

ACTCATATATACTTTAGATTGATTTAAAACTTCATTTTTA

ATTTAAAAGGATCTAGGTGAAGATCCTTTTTGATAATCTC

ATGACCAAAATCCCTTAACGTGAGTTTTCGTTCCACTGAG

CGTCAGACCCCGTAGAAAAGATCAAAGGATCTTCTTGAGA

TCCTTTTTTTCTGCGCGTAATCTGCTGCTTGCAAACAAAA

AAACCACCGCTACCAGCGGTGGTTTGTTTGCCGGATCAAG

AGCTACCAACTCTTTTTCCGAAGGTAACTGGCTTCAGCAG

AGCGCAGATACCAAATACTGTCCTTCTAGTGTAGCCGTAG

TTAGGCCACCACTTCAAGAACTCTGTAGCACCGCCTACAT

ACCTCGCTCTGCTAATCCTGTTACCAGTGGCTGCTGCCAG

TGGCGATAAGTCGTGTCTTACCGGGTTGGACTCAAGACGA

TAGTTACCGGATAAGGCGCAGCGGTCGGGCTGAACGGGGG

GTTCGTGCACACAGCCCAGCTTGGAGCGAACGACCTACAC

CGAACTGAGATACCTACAGCGTGAGCTATGAGAAAGCGCC

ACGCTTCCCGAAGGGAGAAAGGCGGACAGGTATCCGGTAA

GCGGCAGGGTCGGAACAGGAGAGCGCACGAGGGAGCTTCC

AGGGGGAAACGCCTGGTATCTTTATAGTCCTGTCGGGTTT

CGCCACCTCTGACTTGAGCGTCGATTTTTGTGATGCTCGT

CAGGGGGGCGGAGCCTATGGAAAAACGCCAGCAACGCGGC

CTTTTTACGGTTCCTGGCCTTTTGCTGGCCTTTTGCTCAC

ATGTTCTTTCCTGCGTTATCCCCTGATTCTGTGGATAACC

GTATTACCGCCTTTGAGTGAGCTGATACCGCTCGCCGCAG

CCGAACGACCGAGCGCAGCGAGTCAGTGAGCGAGGAAGCG

GAAGAGCGCCCAATACGCAAACCGCCTCTCCCCGCGCGTT

GGCCGATTCATTAATGCAGCTGGCACGACAGGTTTCCCGA

CTGGAAAGCGGGCAGTGAGCGCAACGCAATTAATGTGAGT

TAGCTCACTCATTAGGCACCCCAGGCTTTACACTTTATGC

TTCCGGCTCGTATGTTGTGTGGAATTGTGAGCGGATAACA

ATTTCACACAGGAAACAGCTATGACCATGATTACGCCAGA

TTTAATTAAGGCCTTAATTAGGCTGCGCGCTCGCTCGCTC

ACTGAGGCCGCCCGGGCAAAGCCCGGGCGTCGGGCGACCT

TTGGTCGCCCGGCCTCAGTGAGCGAGCGAGCGCGCAGAGA

GGGAGTGGCCAACTCCATCACTAGGGGTTCCTTGTAGTTA

ATGATTAACCCGCCATGCTACTTATCTACGTAGCCATGCT

CTAGGAAGATCGGAATTCCTAGATCTACCTTGCTTCCTAG

CTGGGCCTTTCCTTCTCCTCTATAAATACCAGCTCTGGTA

TTTCGCCTTGGCAGCTGTTGCTGCTAGGGAGACGGCTGGC

TTGACATGCATCTCCTGACAAAACACAAACCCGTGGTGTG

AGTGGGTGTGGGCGGTGTGAGTAGGGGGATGAATCAGAGA

GGGGGCGAGGGAGACAGGGGCGCAGGAGTCAGGCAAAGGC

GATGCGGGGGTGCGACTACACGCAGTTGGAAACAGTCGTC

AGAAGATTCTGGAAACTATCTTGCTGGCTATAAACTTGAG

GGAAGCAGAAGGCCAACATTCCTCCCAAGGGAAACTGAGG

CTCAGAGTTAAAACCCAGGTATCAGTGATATGCATGTGCC

CCGGCCAGGGTCACTCTCTGACTAACCGGTACCTACCCTA

CAGGCCTACCTAGAGACTCTTTTGAAAGGATGGTAGAGAC

CTGTCCGGGCTTTGCCCACAGTCGTTGGAAACCTCAGCAT

TTTCTAGGCAACTTGTGCGAATAAAACACTTCGGGGGTCC

TTCTTGTTCATTCCAATAACCTAAAACCTCTCCTCGGAGA

AAATAGGGGGCCTCAAACAAACGAAATTCTCTAGCCCGCT

-continued

TTCCCCAGGATAAGGCAGGCATCCAAATGGAAAAAAAGGG

GCCGGCCGGGGGTCTCCTGTCAGCTCCTTGCCCTGTGAAA

CCCAGCAGGCCTGCCTGTCTTCTGTCCTCTTGGGGCTGTC

CAGGGGCGCAGGCCTCTTGCGGGGGAGCTGGCCTCCCCGC

CCCCTCGCCTGTGGCCGCCCTTTTCCTGGCAGGACAGAGG

GATCCTGCAGCTGTCAGGGGAGGGGCGCCGGGGGGTGATG

TCAGGAGGGCTACAAATAGTGCAGACAGCTAAGGGGCTCC

GTCACCCATCTTCACATCCACTCCAGCCGGCTGCCCGCCC

GCTGCCTCCTCTGTGCGTCCGCCCAGCCAGCCTCGTCCAC

GCCAAGCTTGCGGCCGCATTAAACGCCACCATGTCCCGCT

TGGATAAGAGCAAGGTAATAAATAGCGCACTCGAACTCCT

CAACGGCGTGGGCATCGAAGGTCTGACTACTCGAAAGCTC

GCCCAGAAATTGGGTGTGGAGCAACCTACATTGTATTGGC

ATGTCAAGAACAAAAGAGCCCTGCTGGACGCTCTTCCTAT

TGAAATGCTTGACAGGCATCACACTCATTCCTGCCCCCTT

GAGGTCGAGAGTTGGCAAGATTTTCTCCGAAACAATGCAA

AGTCCTACCGCTGCGCACTTTTGTCCCATAGGGATGGAGC

AAAAGTGCACCTGGGAACCAGGCCAACAGAGAAACAATAC

GAGACTCTCGAGAACCAGTTGGCTTTCTTGTGCCAACAGG

GGTTCTCACTTGAAAATGCCCTTTACGCACTGTCAGCCGT

TGGACATTTTACCCTGGGGTGCGTTCTTGAGGAGCAAGAA

CATCAGGTTGCTAAGGAGGAGCGCGAGACTCCAACCACTG

ATTCTATGCCACCTTTGCTGAAACAGGCCATTGAACTTTT

CGATAGACAGGGTGCTGAACCTGCCTTTCTCTTCGGGTTG

GAGCTGATTATTTGTGGTCTCGAAAAACAGCTGAAATGTG

AAAGTGGTGGCCCTACTGACGCCCTCGATGATTTCGACCT

GGATATGCTGCCAGCCGATGCACTTGATGATTTCGATTTG

GATATGCTTCCAGCCGACGCACTGGACGACTTCGATTTGG

ACATGCTTCCCGGTTAAACTAGTCTAGCAATCAACCTCTG

GATTACAAAATTTGTGAAAGATTGACTGGTATTCTTAACT

ATGTTGCTCCTTTTACGCTATGTGGATACGCTGCTTTAAT

GCCTTTGTATCATGCTATTGCTTCCCGTATGGCTTTCATT

TTCTCCTCCTTGTATAAATCCTGGTTAGTTCTTGCCACGG

CGGAACTCATCGCCGCCTGCCTTGCCCGCTGCTGGACAGG

GGCTCGGCTGTTGGGCACTGACAATTCCGTGGTGTTTATT

TGTGAAATTTGTGATGCTATTGCTTTATTTGTAACCATTC

TAGCTTTATTTGTGAAATTTGTGATGCTATTGCTTTATTT

GTAACCATTATAAGCTGCAATAAACAAGTTAACAACAACA

ATTGCATTCATTTTATGTTTCAGGTTCAGGGGGAGATGTG

GGAGGTTTTTTAAAGCGGGGGATCCAAATTCCCGATAAGG

-continued

ATCTTCCTAGAGCATGGCTACGTAGATAAGTAGCATGGCG

GGTTAATCATTAACTACAAGGAACCCCTAGTGATGGAGTT

GGCCACTCCCTCTCTGCGCGCTCGCTCGCTCACTGAGGCC

GGGCGACCAAAGGTCGCCCGACGCCCGGGCTTTGCCCGGG

CGGCCTCAGTGAGCGAGCGAGCGCGCAGCCTTAATTAACC

TAATTCACTGGCCGTCGTTTTACAACGTCGTGACTGGGAA

AACCCTGGCGTTACCCAACTTAATCGCCTTGCAGCACATC

CCCCTTTCGCCAGCTGGCGTAATAGCGAAGAGGCCCGCAC

CGATCGCCCTTCCCAACAGTTGCGCAGCCTGAATGGCGAA

TGGGACGCGCCCTGTAGCGGCGCATTAAGCGCGGCGGGTG

TGGTGGTTACGCGCAGCGTGACCGCTACACTTGCCAGCGC

CCTAGCGCCCGCTCCTTTCGCTTTCTTCCCTTCCTTTCTC

GCCACGTTCGCCGGCTTTCCCCGTCAAGCTCTAAATCGGG

GGCTCCCTTTAGGGTTCCGATTTAGTGCTTTACGGCACCT

CGACCCCAAAAAACTTGATTAGGGTGATGGTTCACGTAGT

GGGCCATCGCCCTGATAGACGGTTTTTCGCCCTTTGACGT

TGGAGTCCACGTTCTTTAATAGTGGACTCTTGTTCCAAAC

TGGAACAACACTCAACCCTATCTCGGTCTATTCTTTTGAT

TTATAAGGGATTTTGCCGATTTCGGCCTATTGGTTAAAAA

ATGAGCTGATTTAACAAAAATTTAACGCGAATTTTAACAA

AATATTAACGTTTATAATTTCAGGTGGCATCTTTCGGGGA

AATGTGCGCGGAACCCCTATTTGTTTATTTTTCTAAATAC

ATTCAAATATGTATCCGCTCATGAGACAATAACCCTGATA

AATGCTTCAATAATATTGAAAAAGGAAGAGTATGAGTATT

CAACATTTCCGTGTCGCCCTTATTCCCTTTTTTGCGGCAT

TTTGCCTTCCTGTTTTTGCTCACCCAGAAACGCTGGTGAA

AGTAAAAGATGCTGAAGATCAGTTGGGTGCACGAGTGGGT

TACATCGAACTGGATCTCAATAGTGGTAAGATCCTTGAGA

GTTTTCGCCCCGAAGAACGTTTTCCAATGATGAGCACTTT

TAAAGTTCTGCTATGTGGCGCGGTATTATCCCGTATTGAC

GCCGGGCAAGAGCAACTCGGTCGCCGCATACACTATTCTC

AGAATGACTTGGTTGAGTACTCACCAGTCACAGAAAAGCA

TCTTACGGATGGCATGACAGTAAGAGAA pAAV2 CMV rtTA(V16) (SEQ ID NO: 31):
AAATTGTAAACGTTAATATTTTGTTAAAATTCGCGTTAAA

TTTTTGTTAAATCAGCTCATTTTTTAACCAATAGGCCGAA

ATCGGCAAAATCCCTTATAAATCAAAAGAATAGCCCGAGA

TAGGGTTGAGTGTTGTTCCAGTTTGGAACAAGAGTCCACT

ATTAAAGAACGTGGACTCCAACGTCAAAGGGCGAAAAACC

GTCTATCAGGGCGATGGCCCACTACGTGAACCATCACCCA

AATCAAGTTTTTTGGGGTCGAGGTGCCGTAAAGCACTAAA

-continued

TCGGAACCCTAAAGGGAGCCCCGATTTAGAGCTTGACGG

GGAAAGCCGGCGAACGTGGCGAGAAAGGAAGGGAAGAAAG

CGAAAGGAGCGGGCGCTAGGGCGCTGGCAAGTGTAGCGG

TCACGCTGCGCGTAACCACCACACCCGCCGCGCTTAATGC

GCCGCTACAGGGCGCGTACTATGGTTGCTTTGACGTATGC

GGTGTGAAATACCGCACAGATGCGTAAGGAGAAAATACCG

CATCAGGCGCCCCTGCAGGCAGCTGCGCGCTCGCTCGCTC

ACTGAGGCCGCCCGGGCAAAGCCCGGGCGTCGGGCGACCT

TTGGTCGCCCGGCCTCAGTGAGCGAGCGAGCGCGCAGAGA

GGGAGTGGCCAACTCCATCACTAGGGGTTCCTGCGGCCGC

TCGGTCCGCACGATCTCAATTCGGCCATTACGGCCGGATC

CGGCTCGAGgagcttggcccattgcatacgttgtatccat atcataatatgtacatttatattggctcatgtccaacatt accgccatgttgacattgattattgactagttattaatag taatcaattacggggtcattagttcatagcccatatatgg agttccgcgttacataacttacggtaaatggcccgcctgg ctgaccgcccaacgaccccgcccattgacgtcaataatg acgtatgttcccatagtaacgccaatagggactttccatt gacgtcaatgggtggagtatttacgctaaactgcccactt ggcagtacatcaagtgtatcatatgccaagtacgccccct attgacgtcaatgacggtaaatggcccgcctggcattatg cccagtacatgaccttatgggactttcctacttggcagta catctacgtattagtcatcgctattaccatggtgatgcgg ttttggcagtacatcaatgggcgtggatagcggtttgact cacggggatttccaagtctccaccccattgacgtcaatgg gagtttgttttggcaccaaaatcaacgggactttccaaaa tgtcgtaacaactccgccccattgacgcaaatgggcggta ggcgtgtacggtgggaggtctatataagcagagctcgttt agtgaaccgtcagatcgcctggagacgccatccacgctgt tttgacctccatagaagacaccgggaccgatccagcctcc gcggccccgaattcaccATGTCTAGACTGGACAAGAGCAA

AATCATAAACAGCGCTCTGGAATTACTCAATGGAGTCGGT

ATCGAAGGCCTGACGACAAGGAAACTCGCTCAAAAGCTGG

GAGTTGAGCAGCCTACCCTGTACTGGCACGTGAAGAACAA

GCGGGCCCTGCTCGATGCCCTGCCAATCGAGATGCTGGAC

AGGCATCATACCCACAGCTGCCCCCTGGAAGGCGAGTCAT

GGCAAGACTTTCTGCGGAACAACGCCAAGTCATACCGCTG

TGCTCTCCTCTCACATCGCGACGGGGCTAAAGTGCATCTC

GGCACCCGCCCAACAGAGAAACAGTACGAAACCCTGGAAA

ATCAGCTCGCGTTCCTGTGTCAGCAAGGCTTCTCCCTGGA

GAACGCACTGTACGCTCTGTCCGCCGTGGGCCACTTTACA

-continued

CTGGGCTGCGTATTGGAGGAACAGGAGCATCAAGTAGCAA

AAGAGGAAAGAGAGACACCTACCACCGATTCTATGCCCCC

ACTTCTGAAGCAAGCAATTGAGCTGTTCGACCGGCAGGGA

GCCGAACCTGCCTTCCTTTTCGGCCTGGAACTAATCATAT

GTGGCCTGGAGAAACAGCTAAAGTGCGAAAGCGGCGGGCC

GACCGACGCCCTTGACGATTTTGACTTAGACATGCTCCCA

GCCGATGCCCTTGACGACTTTGACCTTGATATGCTGCCTG

CTGACGCTCTTGACGATTTTGACCTTGACATGCTCCCCGG

GTAActaagtaaggatcATCTTAATTAAATCGATAAGGAT

CTGGCCGCCTCGGCCTaatcaacctctggattacaaaatt tgtgaaagattgactggtattcttaactatgttgctcctt ttacgctatgtggatacgctgctttaatgcctttgtatca tgctattgcttcccgtatggctttcattttctcctccttg tataaatcctggttgctgtctctttatgaggagttgtggc ccgttgtcaggcaacgtggcgtggtgtgcactgtgtttgc tgacgcaacccccactggttggggcattgccaccacctgt cagctcctttccgggactttcgctttccccctccctattg ccacggcggaactcatcgccgcctgccttgcccgctgctg gacaggggctcggctgttgggcactgacaattccgtggtg ttgtcggggaaatcatcgtcctttccttggctgctcgcct gtgttgccacctggattctgcgcgggacgtccttctgcta cgtcccttcggccctcaatccagcggaccttccttcccgc ggcctgctgccggctctgcggcctcttccgcgtcttcgcc ttcgccctcagacgagtcggatctccctttgggccgcctc cccgcCAGACATGATAAGATACATTGATGAGTTTGGACAA

ACCACAACTAGAATGCAGTGAAAAAAATGCTTTATTTGTG

AAATTTGTGATGCTATTGCTTTATTTGTAACCATTATAAG

CTGCAATAAACAAGTTAACAACAACAATTGCATTCATTTT

ATGTTTCAGGTTCAGGGGGAGATGTGGGAGGTTTTTTAAA

GCAAGTAAAACCTCTACAAATGTGGTAACTAGCGCGTGCG

GCCGCAGGAACCCCTAGTGATGGAGTTGGCCACTCCCTCT

CTGCGCGCTCGCTCGCTCACTGAGGCCGGGCGACCAAAGG

TCGCCCGACGCCCGGGCTTTGCCCGGGCGGCCTCAGTGAG

CGAGCGAGCGCGCAGCTGCCTGCAGGACATGTGAGCAAAA

GGCCAGCAAAAGGCCAGGAACCGTAAAAAGGCCGCGTTGC

TGGCGTTTTTCCATAGGCTCCGCCCCCCTGACGAGCATCA

CAAAAATCGACGCTCAAGTCAGAGGTGGCGAAACCCGACA

GGACTATAAAGATACCAGGCGTTTCCCCCTGGAAGCTCCC

TCGTGCGCTCTCCTGTTCCGACCCTGCCGCTTACCGGATA

CCTGTCCGCCTTTCTCCCTTCGGGAAGCGTGGCGCTTTCT

-continued
CATAGCTCACGCTGTAGGTATCTCAGTTCGGTGTAGGTCG

TTCGCTCCAAGCTGGGCTGTGTGCACGAACCCCCCGTTCA

GCCCGACCGCTGCGCCTTATCCGGTAACTATCGTCTTGAG

TCCAACCCGGTAAGACACGACTTATCGCCACTGGCAGCAG

CCACTGGTAACAGGATTAGCAGAGCGAGGTATGTAGGCGG

TGCTACAGAGTTCTTGAAGTGGTGGCCTAACTACGGCTAC

ACTAGAAGGACAGTATTTGGTATCTGCGCTCTGCTGAAGC

CAGTTACCTTCGGAAAAAGAGTTGGTAGCTCTTGATCCGG

CAAACAAACCACCGCTGGTAGCGGTGGTTTTTTTGTTTGC

AAGCAGCAGATTACGCGCAGAAAAAAAGGATCTCAAGAAG

ATCCTTTGATCTTTTCTACGGGGTCTGACGCTCAGTGGAA

CGAAAACTCACGTTAAGGGATTTTGGTCATGAGATTATCA

AAAAGGATCTTCACCTAGATCCTTTTAAATTAAAAATGAA

GTTTTAAATCAATCTAAAGTATATATGAGTAAACTTGGTC

TGACAGTTACCAATGCTTAATCAGTGAGGCACCTATCTCA

GCGATCTGTCTATTTCGTTCATCCATAGTTGCCTGACTCC

CCGTCGTGTAGATAACTACGATACGGGAGGGCTTACCATC

TGGCCCCAGTGCTGCAATGATACCGCGAGACCCACGCTCA

CCGGCTCCAGATTTATCAGCAATAAACCAGCCAGCCGGAA

GGGCCGAGCGCAGAAGTGGTCCTGCAACTTTATCCGCCTC

CATCCAGTCTATTAATTGTTGCCGGGAAGCTAGAGTAAGT

AGTTCGCCAGTTAATAGTTTGCGCAACGTTGTTGCCATTG

CTACAGGCATCGTGGTGTCACGCTCGTCGTTTGGTATGGC

TTCATTCAGCTCCGGTTCCCAACGATCAAGGCGAGTTACA

TGATCCCCCATGTTGTGCAAAAAAGCGGTTAGCTCCTTCG

GTCCTCCGATCGTTGTCAGAAGTAAGTTGGCCGCAGTGTT

ATCACTCATGGTTATGGCAGCACTGCATAATTCTCTTACT

GTCATGCCATCCGTAAGATGCTTTTCTGTGACTGGTGAGT

ACTCAACCAAGTCATTCTGAGAATAGTGTATGCGGCGACC

GAGTTGCTCTTGCCCGGCGTCAATACGGGATAATACCGCG

CCACATAGCAGAACTTTAAAAGTGCTCATCATTGGAAAAC

GTTCTTCGGGGCGAAAACTCTCAAGGATCTTACCGCTGTT

GAGATCCAGTTCGATGTAACCCACTCGTGCACCCAACTGA

TCTTCAGCATCTTTTACTTTCACCAGCGTTTCTGGGTGAG

CAAAAACAGGAAGGCAAAATGCCGCAAAAAAGGGAATAAG

GGCGACACGGAAATGTTGAATACTCATACTCTTCCTTTTT

CAATATTATTGAAGCATTTATCAGGGTTATTGTCTCATGA

GCGGATACATATTTGAATGTATTTAGAAAAATAAACAAAT

AGGGGTTCCGCGCACATTTCCCCGAAAAGTGCCACCTGAC

GTCTAAGAAACCATTATTATCATGACATTAACCTATAAAA

ATAGGCGTATCACGAGGCCCTTTCGTCTCGCGCGTTTCGG

-continued
TGATGACGGTGAAAACCTCTGACACATGCAGCTCCCGGAG

ACGGTCACAGCTTGTCTGTAAGCGGATGCCGGGAGCAGAC

AAGCCCGTCAGGGCGCGTCAGCGGGTGTTGGCGGGTGTCG

GGGCTGGCTTAACTATGCGGCATCAGAGCAGATTGTACTG

AGAGTGCACCATA

CAG-tTA (SEQ ID NO: 32):
CCTGCAGGCAGCTGCGCGCTCGCTCGCTCACTGAGGCCGC

CCGGGCAAAGCCCGGGCGTCGGGCGACCTTTGGTCGCCCG

GCCTCAGTGAGCGAGCGAGCGCGCAGAGAGGGAGTGGCCA

ACTCCATCACTAGGGGTTCCTGCGGCCGCACGCGTGGAGC

TAGTTATTAATAGTAATCAATTACGGGGTCATTAGTTCAT

AGCCCATATATGGAGTTCCGCGTTACATAACTTACGGTAA

ATGGCCCGCCTGGCTGACCGCCCAACGACCCCCGCCCATT

GACGTCAATAATGACGTATGTTCCCATAGTAACGTCAATA

GGGACTTTCCATTGACGTCAATGGGTGGAGTATTTACGGT

AAACTGCCCACTTGGCAGTACATCAAGTGTATCATATGCC

AAGTACGCCCCCTATTGACGTCAATGACGGTAAATGGCCC

GCCTGGCATTATGCCCAGTACATGACCTTATGGGACTTTC

CTACTTGGCAGTACATCTACGTATTAGTCATCGCTATTAC

CATGGTGATGCGGTTTTGGCAGTACATCAATGGGCGTGGA

TAGCGGTTTGACTCACGGGGATTTCCAAGTCTCCACCCCA

TTGACGTCAATGGGAGTTTGTTTTGCACCAAAATCAACGG

GACTTTCCAAAATGTCGTAACAACTCCGCCCCATTGACGC

AAATGGGCGGTAGGCGTGTACGGTGGGAGGTCTATATAAG

CAGAGCTCGTTTAGTGAACCGTCAGATCGCCTGGAGACGC

CATCCACGCTGTTTTGACCTCCATAGAAGACACCGGGACC

GATCCAGCCTCCGCGGATTCGAATCCCGGCCGGGAACGGT

GCATTGGAACGCGGATTCCCCGTGCCAAGAGTGACGTAAG

TACCGCCTATAGAGTCTATAGGCCCACAAAAAATGCTTTC

TTCTTTTAATATACTTTTTTGTTTATCTTATTTCTAATAC

TTTCCCTAATCTCTTTCTTTCAGGGCAATAATGATACAAT

GTATCATGCCTCTTTGCACCATTCTAAAGAATAACAGTGA

TAATTTCTGGGTTAAGGCAATAGCAATATTTCTGCATATA

AATATTTCTGCATATAAATTGTAACTGATGTAAGAGGTTT

CATATTGCTAATAGCAGCTACAATCCAGCTACCATTCTGC

TTTTATTTTATGGTTGGGATAAGGCTGGATTATTCTGAGT

CCAAGCTAGGCCCTTTTGCTAATCATGTTCATACCTCTTA

TCTTCCTCCCACAGCTCCTGGGCAACGTGCTGGTCTGTGT

GCTGGCCCATCACTTTGGCAAAGAATTGGGATTCGAACAT

CGATTGAATTCATGTCTAGACTGGACAAGAGCAAAGTCAT

AAACTCTGCTCTGGAATTACTCAATGAAGTCGGTATCGAA

-continued

GGCCTGACGACAAGGAAACTCGCTCAAAAGCTGGGAGTTG

AGCAGCCTACCCTGTACTGGCACGTGAAGAACAAGCGGGC

CCTGCTCGATGCCCTGGCAATCGAGATGCTGGACAGGCAT

CATACCCACTTCTGCCCCCTGGAAGGCGAGTCATGGCAAG

ACTTTCTGCGGAACAACGCCAAGTCATTCCGCTGTGCTCT

CCTCTCACATCGCGACGGGGCTAAAGTGCATCTCGGCACC

CGCCCAACAGAGAAACAGTACGAAACCCTGGAAAATCAGC

TCGCGTTCCTGTGTCAGCAAGGCTTCTCCCTGGAGAACGC

ACTGTACGCTCTGTCCGCCGTGGGCCACTTTACACTGGGC

TGCGTATTGGAGGATCAGGAGCATCAAGTAGCAAAAGAGG

AAAGAGAGACACCTACCACCGATTCTATGCCCCCACTTCT

GAGACAAGCAATTGAGCTGTTCGACCATCAGGGAGCCGAA

CCTGCCTTCCTTTTCGGCCTGGAACTAATCATATGTGGCC

TGGAGAAACAGCTAAAGTGCGAAAGCGGCGGGCCGGCCGA

CGCCCTTGACGATTTTGACTTAGACATGCTCCCAGCCGAT

GCCCTTGACGACTTTGACCTTGATATGCTGCCTGCTGACG

CTCTTGACGATTTTGACCTTGACATGCTCCCCGGATGAGG

ATCCTCTAGAGTCGACCTGCAGAAGCTTGCCTCGAGCAGC

GCTGCTCGAGAGATCTACGGGTGGCATCCCTGTGACCCCT

CCCCAGTGCCTCTCCTGGCCCTGGAAGTTGCCACTCCAGT

GCCCACCAGCCTTGTCCTAATAAAATTAAGTTGCATCATT

TTGTCTGACTAGGTGTCCTTCTATAATATTATGGGGTGGA

GGGGGGTGGTATGGAGCAAGGGGCAAGTTGGGAAGACAAC

CTGTAGGGCCTGCGGGGTCTATTGGGAACCAAGCTGGAGT

GCAGTGGCACAATCTTGGCTCACTGCAATCTCCGCCTCCT

GGGTTCAAGCGATTCTCCTGCCTCAGCCTCCCGAGTTGTT

GGGATTCCAGGCATGCATGACCAGGCTCAGCTAATTTTTG

TTTTTTTGGTAGAGACGGGGTTTCACCATATTGGCCAGGC

TGGTCTCCAACTCCTAATCTCAGGTGATCTACCCACCTTG

GCCTCCCAAATTGCTGGGATTACAGGCGTGAACCACTGCT

CCCTTCCCTGTCCTTCTGATTTTGTAGGTAACCACGTGCG

GACCGAGCGGCCGCAGGAACCCCTAGTGATGGAGTTGGCC

ACTCCCTCTCTGCGCGCTCGCTCGCTCACTGAGGCCGGGC

GACCAAAGGTCGCCCGACGCCCGGGCTTTGCCCGGGCGGC

CTCAGTGAGCGAGCGAGCGCGCAGCTGCCTGCAGGGGCGC

CTGATGCGGTATTTTCTCCTTACGCATCTGTGCGGTATTT

CACACCGCATACGTCAAAGCAACCATAGTACGCGCCCTGT

AGCGGCGCATTAAGCGCGGCGGGTGTGGTGGTTACGCGCA

GCGTGACCGCTACACTTGCCAGCGCCCTAGCGCCCGCTCC

TTTCGCTTTCTTCCCTTCCTTTCTCGCCACGTTCGCCGGC

-continued

TTTCCCCGTCAAGCTCTAAATCGGGGGCTCCCTTTAGGGT

TCCGATTTAGTGCTTTACGGCACCTCGACCCCAAAAAACT

TGATTTGGGTGATGGTTCACGTAGTGGGCCATCGCCCTGA

TAGACGGTTTTTCGCCCTTTGACGTTGGAGTCCACGTTCT

TTAATAGTGGACTCTTGTTCCAAACTGGAACAACACTCAA

CCCTATCTCGGGCTATTCTTTTGATTTATAAGGGATTTTG

CCGATTTCGGCCTATTGGTTAAAAAATGAGCTGATTTAAC

AAAAATTTAACGCGAATTTTAACAAAATATTAACGTTTAC

AATTTTATGGTGCACTCTCAGTACAATCTGCTCTGATGCC

GCATAGTTAAGCCAGCCCCGACACCCGCCAACACCCGCTG

ACGCGCCCTGACGGGCTTGTCTGCTCCCGGCATCCGCTTA

CAGACAAGCTGTGACCGTCTCCGGGAGCTGCATGTGTCAG

AGGTTTTCACCGTCATCACCGAAACGCGCGAGACGAAAGG

GCCTCGTGATACGCCTATTTTTATAGGTTAATGTCATGAT

AATAATGGTTTCTTAGACGTCAGGTGGCACTTTTCGGGGA

AATGTGCGCGGAACCCCTATTTGTTTATTTTTCTAAATAC

ATTCAAATATGTATCCGCTCATGAGACAATAACCCTGATA

AATGCTTCAATAATATTGAAAAAGGAAGAGTATGAGTATT

CAACATTTCCGTGTCGCCCTTATTCCCTTTTTTGCGGCAT

TTTGCCTTCCTGTTTTTGCTCACCCAGAAACGCTGGTGAA

AGTAAAAGATGCTGAAGATCAGTTGGGTGCACGAGTGGGT

TACATCGAACTGGATCTCAACAGCGGTAAGATCCTTGAGA

GTTTTCGCCCCGAAGAACGTTTTCCAATGATGAGCACTTT

TAAAGTTCTGCTATGTGGCGCGGTATTATCCCGTATTGAC

GCCGGGCAAGAGCAACTCGGTCGCCGCATACACTATTCTC

AGAATGACTTGGTTGAGTACTCACCAGTCACAGAAAAGCA

TCTTACGGATGGCATGACAGTAAGAGAATTATGCAGTGCT

GCCATAACCATGAGTGATAACACTGCGGCCAACTTACTTC

TGACAACGATCGGAGGACCGAAGGAGCTAACCGCTTTTTT

GCACAACATGGGGGATCATGTAACTCGCCTTGATCGTTGG

GAACCGGAGCTGAATGAAGCCATACCAAACGACGAGCGTG

ACACCACGATGCCTGTAGCAATGGCAACAACGTTGCGCAA

ACTATTAACTGGCGAACTACTTACTCTAGCTTCCCGGCAA

CAATTAATAGACTGGATGGAGGCGGATAAAGTTGCAGGAC

CACTTCTGCGCTCGGCCCTTCCGGCTGGCTGGTTTATTGC

TGATAAATCTGGAGCCGGTGAGCGTGGGTCTCGCGGTATC

ATTGCAGCACTGGGGCCAGATGGTAAGCCCTCCCGTATCG

TAGTTATCTACACGACGGGGAGTCAGGCAACTATGGATGA

ACGAAATAGACAGATCGCTGAGATAGGTGCCTCACTGATT

AAGCATTGGTAACTGTCAGACCAAGTTTACTCATATATAC

TTTAGATTGATTTAAAACTTCATTTTTAATTTAAAAGGAT

-continued

```
CTAGGTGAAGATCCTTTTTGATAATCTCATGACCAAAATC

CCTTAACGTGAGTTTTCGTTCCACTGAGCGTCAGACCCCG

TAGAAAAGATCAAAGGATCTTCTTGAGATCCTTTTTTTCT

GCGCGTAATCTGCTGCTTGCAAACAAAAAAACCACCGCTA

CCAGCGGTGGTTTGTTTGCCGGATCAAGAGCTACCAACTC

TTTTTCCGAAGGTAACTGGCTTCAGCAGAGCGCAGATACC

AAATACTGTCCTTCTAGTGTAGCCGTAGTTAGGCCACCAC

TTCAAGAACTCTGTAGCACCGCCTACATACCTCGCTCTGC

TAATCCTGTTACCAGTGGCTGCTGCCAGTGGCGATAAGTC

GTGTCTTACCGGGTTGGACTCAAGACGATAGTTACCGGAT

AAGGCGCAGCGGTCGGGCTGAACGGGGGGTTCGTGCACAC

AGCCCAGCTTGGAGCGAACGACCTACACCGAACTGAGATA

CCTACAGCGTGAGCTATGAGAAAGCGCCACGCTTCCCGAA

GGGAGAAAGGCGGACAGGTATCCGGTAAGCGGCAGGGTCG

GAACAGGAGAGCGCACGAGGGAGCTTCCAGGGGGAAACGC

CTGGTATCTTTATAGTCCTGTCGGGTTTCGCCACCTCTGA

CTTGAGCGTCGATTTTTGTGATGCTCGTCAGGGGGGCGGA

GCCTATGGAAAAACGCCAGCAACGCGGCCTTTTTACGGTT

CCTGGCCTTTTGCTGGCCTTTTGCTCACATGT
``` pAAV-Tet-O-OSK-SV40LpA
(or pAAV-TRE2-OSK-SV40LpA)
(SEQ ID NO: 33):
```
ttatgcagtgctgccataaccatgagtgataacactgcgg ccaacttacttctgacaacgatcggaggaccgaaggagct aaccgcttttttgcacaacatgggggatcatgtaactcgc cttgatcgttgggaaccggagctgaatgaagccataccaa acgacgagcgtgacaccacgatgcctgtagtaatggtaac aacgttgcgcaaactattaactggcgaactacttactcta gcttcccggcaacaattaatagactggatggaggcggata aagttgcaggaccacttctgcgctcggcccttccggctgg ctggtttattgctgataaatctggagccggtgagcgtggg tctcgcggtatcattgcagcactggggccagatggtaagc cctcccgtatcgtagttatctacacgacggggagtcaggc aactatggatgaacgaaatagacagatcgctgagatagg gcctcactgattaagcattggtaactgtcagaccaagttt actcatatatactttagattgatttaaaacttcattttta atttaaaaggatctaggtgaagatcattttgataatctca tgaccaaaatcccttaacgtgagttttcgttccactgagc gtcagaccccgtagaaaagatcaaaggatcttcttgagat cctttttttctgcgcgtaatctgctgcttgcaaacaaaaa aaccaccgctaccagcggtggtttgtttgccggatcaaga gctaccaactctttttccgaaggtaactggcttcagcaga
```

-continued

```
gcgcagataccaaatactgtccttctagtgtagccgtagt taggccaccacttcaagaactctgtagcaccgcctacata cctcgctctgctaatcctgttaccagtggctgctgccagt ggcgataagtcgtgtcttaccgggttggactcaagacgat agttaccggataaggcgcagcggtcgggctgaacgggggg ttcgtgcacacagcccagcttggagcgaacgacctacacc gaactgagatacctacagcgtgagctatgagaaagcgcca cgcttcccgaagggagaaaggcggacaggtatccggtaag cggcagggtcggaacaggagagcgcacgagggagcttcca ggggggaaacgcctggtatctttatagtcctgtcgggtttc gccacctctgacttgagcgtcgattttttgtgatgctcgtc agggggcggagcctatggaaaaacgccagcaacgcggcc tttttacggttcctggccttttgctggcctttttgctcaca tgttctttcctgcgttatcccctgattctgtggataaccg tattaccgcctttgagtgagctgataccgctcgccgcagc cgaacgaccgagcgcagcgagtcagtgagcgaggaagcgg aagagcgcccaatacgcaaaccgcctctccccgcgcgttg gccgattcattaatgcagctggcacgacaggtttcccgac tggaaagcgggcagtgagcgcaacgcaattaatgtgagtt agctcactcattaggcaccccaggctttacactttatgct tccggctcgtatgttgtgtggaattgtgagcggataacaa tttcacacaggaaacagctatgaccatgattacgccagat ttaattaaggccttaattaggctgcgcgctcgctcgctca ctgaggccgcccgggcaaagcccgggcgtcgggcgacctt tggtcgcccggcctcagtgagcgagcgagcgcgcagagag ggagtggccaactccatcactaggggttccttgtagttaa tgattaacccgccatgctacttatctacgtagccatgctc taggaagatcggaattcgtacacgcctacctcgacccatc aagtgccacctgacgtctccctatcagtgatagagaagtc gacacgtctcgagctccctatcagtgatagagaaggtacg tctagaacgtctccctatcagtgatagagaagtcgacacg tctcgagctccctatcagtgatagagaaggtacgtctaga acgtctccctatcagtgatagagaagtcgacacgtctcga gctccctatcagtgatagagaaggtacgtctagaacgtct ccctatcagtgatagagaagtcgacacgtctcgagctccc tatcagtgatagagaaggtaccccctatataagcagagct cgtttagtgaaccgtcagatcgcctggagacgccatccac gctgttttgacctccatagaagacaccgggaccgatccag cctggatcgcggccgcgccaccatggctggacacctggct tcagacttcgccttctcaccccaccaggtggggggtgatg
```

-continued

```
ggtcagcagggctggagccgggctgggtggatcctcgaac ctggctaagcttccaagggcctccaggtgggcctggaatc ggaccaggctcagaggtattggggatctccccatgtccgc ccgcatacgagttctgcgggagggatggcatactgtggacc tcaggttggactgggcctagtcccccaagttggcgtggag actttgcagcctgagggccaggcaggagcacgagtggaaa gcaactcagagggaacctcctctgagccctgtgccgaccg ccccaatgccgtgaagttggagaaggtggaaccaactccc gaggagtcccaggacatgaaagccctgcagaaggagctag aacagtttgccaagctgctgaagcagaagaggatcacctt ggggtacacccaggccgacgtggggctcacccctgggcgtt ctctttggaaaggtgttcagccagaccaccatctgtcgct tcgaggccttgcagctcagccttaagaacatgtgtaagct gcggcccctgctggagaagtgggtggaggaagccgacaac aatgagaaccttcaggagatatgcaaatcggagaccctgg tgcaggcccggaagagaaagcgaactagcattgagaaccg tgtgaggtggagtctggagaccatgtttctgaagtgcccg aagccctccctacagcagatcactcacatcgccaatcagc ttgggctagagaaggatgtggttcgagtatggttctgtaa ccggcgccagaagggcaaaagatcaagtattgagtattcc caacgagaagagtatgaggctacagggacacctttcccag gggggggctgtatcctttcctctgcccccaggtccccactt tggcaccccaggctatggaagcccccacttcaccacactc tactcagtcccttttcctgagggcgaggcctttccctctg ttcccgtcactgctctgggctctcccatgcattcaaacgc tagcggcagcggcgccacgaacttctctctgttaaagcaa gcaggagatgttgaagaaaaccccgggcctgcatgcatgt ataacatgatggagacggagctgaagccgccgggccgca gcaagcttcggggggcggcggcggaggaggcaacgccacg gcggcggcgaccggcggcaaccagaagaacagcccggacc gcgtcaagaggcccatgaacgccttcatggtatggtcccg ggggcagcggcgtaagatggcccaggagaaccccaagatg cacaactcggagatcagcaagcgcctgggcgcggagtgga aactttgtccgagaccgagaagcggccgttcatcgacga ggccaagcggctgcgcgctctgcacatgaaggagcacccg gattataaataccggccgcggcggaaaaccaagacgctca tgaagaaggataagtacacgcttcccggaggcttgctggc ccccggcgggaacagcatggcgagcggggttggggtgggc gccggcctgggtgcgggcgtgaaccagcgcatggacagct acgcgcacatgaacggctggagcaacggcagctacagcat gatgcaggagcagctgggctacccgcagcacccgggcctc
```

-continued

```
gcctgccagaggagcccaagccaaagaggggaagaaggtc gtggccccggaaaagaacagccacccacacttgtgactat gcaggctgtggcaaaacctataccaagagttctcatctca aggcacacctgcgaactcacacaggcgagaaaccttacca ctgtgactgggacggctgtgggtggaaattcgccgctcc gatgaactgaccaggcactaccgcaaacacacagggcacc ggccctttcagtgccagaagtgcgacagggccttttccag gtcggaccaccttgccttacacatgaagaggcactaaatg actagtctagcaatcaacctctggattacaaaatttgtga aagattgactggtattcttaactatgttgctccttttacg ctatgtggatacgctgctttaatgcctttgtatcatgcta ttgcttcccgtatggctttcattttctcctccttgtataa atcctggttagttcttgccacggcggaactcatcgccgcc tgccttgcccgctgctggacaggggctcggctgttgggca ctgacaattccgtggtgtttatttgtgaaatttgtgatgc tattgctttatttgtaaccattctagctttatttgtgaaa tttgtgatgctattgctttatttgtaaccattataagctg caataaacaagttaacaacaacaattgcattcattttatg tttcaggttcagggggagatgtgggaggtttttttaaagcg ggggatccaaattcccgataaggatcttcctagagcatgg ctacgtagataagtagcatggcgggttaatcattaactac aaggaacccctagtgatggagttggccactccctctctgc gcgctcgctcgctcactgaggccgggcgaccaaaggtcgc ccgacgcccgggctttgcccgggcggcctcagtgagcgag cgagcgcgcagccttaattaacctaattcactggccgtcg ttttacaacgtcgtgactgggaaaaccctggcgttaccca acttaatcgccttgcagcacatccccctttcgccagctgg cgtaatagcgaagaggcccgcaccgatcgcccttcccaac agttgcgcagcctgaatggcgaatgggacgcgccctgtag cggcgcattaagcgcggcgggtgtggtggttacgcgcagc gtgaccgctacacttgccagcgccctagcgcccgctcctt tcgctttcttcccttcctttctcgccacgttcgccggctt tccccgtcaagctctaaatcggggggctccctttagggttc cgatttagtgctttacggcacctcgaccccaaaaaacttg attagggtgatggttcacgtagtgggccatcgccctgata gacggtttttcgccctttgacgttggagtccacgttcttt aatagtggactcttgttccaaactggaacaacactcaacc ctatctcggtctattcttttgatttataagggattttgcc gatttcggcctattggttaaaaaatgagctgatttaacaa aaatttaacgcgaatttttaacaaaatattaacgtttataa tttcaggtggcatctttcggggaaatgtgcgcggaacccc
```

-continued

```
tatttgtttattttctaaatacattcaaatatgtatccg ctcatgagacaataaccctgataaatgcttcaataatatt gaaaaaggaagagtatgagtattcaacatttccgtgtcgc ccttattcccttttttgcggcattttgccttcctgttttt gctcacccagaaacgctggtgaaagtaaaagatgctgaag atcagttgggtgcacgagtgggttacatcgaactggatct caatagtggtaagatccttgagagttttcgccccgaagaa cgttttccaatgatgagcacttttaaagttctgctatgtg gcgcggtattatcccgtattgacgccgggcaagagcaact cggtcgccgcatacactattctcagaatgacttggttgag tactcaccagtcacagaaaagcatcttacggatggcatga cagtaagagaa
```

VP64, 4 repeats of VP16 (SEQ ID NO: 34)
(Non-limiting example of a
transactivation domain):

```
GAGGCCAGCGGTTCCGGACGGGCTGACGCATTGGACGATT

TTGATCTGGATATGCTGGGAAGTGACGCCCTCGATGATTT

TGACCTTGACATGCTTGGTTCGGATGCCCTTGATGACTTT

GACCTCGACATGCTCGGCAGTGACGCCCTTGATGATTTCG

ACCTGGACATGCTGATTAACTCTAGA
```

P65 (SEQ ID NO: 35) (Non-limiting example
of a transactivation domain):

```
AGCCAGTACCTGCCCGACACCGACGACCGGCACCGGATCG

AGGAAAAGCGGAAGCGGACCTACGAGACATTCAAGAGCAT

CATGAAGAAGTCCCCCTTCAGCGGCCCCACCGACCCTAGA

CCTCCACCTAGAAGAATCGCCGTGCCCAGCAGATCCAGCG

CCAGCGTGCCAAAACCTGCCCCCCAGCCTTACCCCTTCAC

CAGCAGCCTGAGCACCATCAACTACGACGAGTTCCCTACC

ATGGTGTTCCCCAGCGGCCAGATCTCTCAGGCCTCTGCTC

TGGCTCCAGCCCCTCCTCAGGTGCTGCCTCAGGCTCCTGC

TCCTGCACCAGCTCCAGCCATGGTGTCTGCACTGGCTCAG

GCACCAGCACCCGTGCCTGTGCTGGCTCCTGGACCTCCA

CAGGCTGTGGCTCCACCAGCCCCTAAACCTACACAGGCCG

GCGAGGGCACACTGTCTGAAGCTCTGCTGCAGCTGCAGTT

CGACGACGAGGATCTGGGAGCCCTGCTGGGAAACAGCACC

GATCCTGCCGTGTTCACCGACCTGGCCAGCGTGGACAACA

GCGAGTTCCAGCAGCTGCTGAACCAGGGCATCCCTGTGGC

CCCTCACACCACCGAGCCCATGCTGATGGAATACCCCGAG

GCCATCACCCGGCTCGTGACAGGCGCTCAGAGGCCTCCTG

ATCCAGCTCCTGCCCCTCTGGGAGCACCAGGCCTGCCTAA

TGGACTGCTGTCTGGCGACGAGGACTTCAGCTCTATCGC

CGATATGGATTTCTCAGCCTTGCTG
```

-continued

RTA (SEQ ID NO: 36) (Non-limiting example
of a transactivation domain):
CGGGATTCCAGGGAAGGGATGTTTTTGCCGAAGCCTGAGG

CCGGCTCCGCTATTAGTGACGTGTTTGAGGGCCGCGAGGT

GTGCCAGCCAAAACGAATCCGGCCATTTCATCCTCCAGGA

AGTCCATGGGCCAACCGCCCACTCCCCGCCAGCCTCGCAC

CAACACCAACCGGTCCAGTACATGAGCCAGTCGGGTCACT

GACCCCGGCACCAGTCCCTCAGCCACTGGATCCAGCGCCC

GCAGTGACTCCCGAGGCCAGTCACCTGTTGGAGGATCCCG

ATGAAGAGACGAGCCAGGCTGTCAAAGCCCTTCGGGAGAT

GGCCGATACTGTGATTCCCCAGAAGGAAGAGGCTGCAATC

TGTGGCCAAATGGACCTTTCCCATCCGCCCCCAAGGGGC

CATCTGGATGAGCTGACAACCACACTTGAGTCCATGACCG

AGGATCTGAACCTGGACTCACCCCTGACCCCGGAATTGAA

CGAGATTCTGGATACCTTCCTGAACGACGAGTGCCTCTTG

CATGCCATGCATATCAGCACAGGACTGTCCATCTTCGACA

CATCTCTGTTT

MPH MS2-P65-HSF1 (SEQ ID NO: 37)
(Non-limiting example of a
transactivationdomain):
GCTTCAAACTTTACTCAGTTCGTGCTCGTGGACAATGGTG

GGACAGGGGATGTGACAGTGGCTCCTTCTAATTTCGCTAA

TGGGGTGGCAGAGTGGATCAGCTCCAACTCACGGAGCCAG

GCCTACAAGGTGACATGCAGCGTCAGGCAGTCTAGTGCCC

AGAAGAGAAAGTATACCATCAAGGTGGAGGTCCCCAAAGT

GGCTACCCAGACAGTGGGCGGAGTCGAACTGCCTGTCGCC

GCTTGGAGGTCCTACCTGAACATGGAGCTCACTATCCCAA

TTTTCGCTACCAATTCTGACTGTGAACTCATCGTGAAGGC

AATGCAGGGGCTCCTCAAAGACGGTAATCCTATCCCTTCC

GCCATCGCCGCTAACTCAGGTATCTACAGCGCTGGAGGA

GGTGGAAGCGGAGGAGGAGGAAGCGGAGGAGGAGGTAGCG

GACCTAAGAAAAAGAGGAAGGTGGCGGCCGCTGGATCCCC

TTCAGGGCAGATCAGCAACCAGGCCCTGGCTCTGGCCCCT

AGCTCCGCTCCAGTGCTGGCCCAGACTATGGTGCCCTCTA

GTGCTATGGTGCCTCTGGCCCAGCCACCTGCTCCAGCCCC

TGTGCTGACCCCAGGACCACCCCAGTCACTGAGCGCTCCA

GTGCCCAAGTCTACACAGGCCGGCGAGGGGACTCTGAGTG

AAGCTCTGCTGCACCTGCAGTTCGACGCTGATGAGGACCT

GGGAGCTCTGCTGGGGAACAGCACCGATCCCGGAGTGTT

CACAGATCTGGCCTCCGTGGACAACTCTGAGTTTCAGCAG

CTGCTGAATCAGGGCGTGTCCATGTCTCATAGTACAGCCG

AACCAATGCTGATGGAGTACCCCGAAGCCATTACCCGGCT

GGTGACCGGCAGCCAGCGGCCCCCCGACCCCGCTCCAACT

-continued

CCCCTGGGAACCAGCGGCCTGCCTAATGGGCTGTCCGGAG

ATGAAGACTTCTCAAGCATCGCTGATATGGACTTTAGTGC

CCTGCTGTCACAGATTTCCTCTAGTGGGCAGGGAGGAGGT

GGAAGCGGCTTCAGCGTGGACACCAGTGCCCTGCTGGACC

TGTTCAGCCCCTCGGTGACCGTGCCCGACATGAGCCTGC

CTGACCTTGACAGCAGCCTGGCCAGTATCCAAGAGCTCCT

GTCTCCCCAGGAGCCCCCCAGGCCTCCCGAGGCAGAGAAC

AGCAGCCCGGATTCAGGGAAGCAGCTGGTGCACTACACAG

CGCAGCCGCTGTTCCTGCTGGACCCCGGCTCCGTGGACAC

CGGGAGCAACGACCTGCCGGTGCTGTTTGAGCTGGGAGAG

GGCTCCTACTTCTCCGAAGGGGACGGCTTCGCCGAGGACC

CCACCATCTCCCTGCTGACAGGCTCGGAGCCTCCCAAAGC

CAAGGACCCCACTGTCTCC

Equivalents and Scope

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the disclosure, or aspects described herein, is/are referred to as comprising particular elements and/or features, certain embodiments described herein or aspects described herein consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments described herein, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment described herein can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. An engineered nucleic acid comprising a promoter operably linked to a first nucleic acid comprising a sequence that is at least 80% identical to the sequence of SEQ ID NO: 12, wherein the first nucleic acid sequence encodes a mutant reverse tetracycline transactivator (rtTA) comprising an amino acid sequence at least 70% identical to the sequence of SEQ ID NO: 11, which comprises the following mutations relative to rtTA3 (SEQ ID NO: 11):

(a) a G72V mutation;

(b) a G12S or G12T mutation;

(c) an F67S or F67T mutation; and (d) an R171K or R171H mutation.

2. The engineered nucleic acid of claim 1, wherein the promoter is a constitutive promoter selected from the group consisting of CP1, CMV, EF1a, SV40, PGK1, Ubc, human beta actin, CAG, Ac5, polyhedrin, TEF1, GDS, CaMV 35S, Ubi, H1, and U6 promoters.

3. The engineered nucleic acid of claim 1, wherein the promoter is a tissue-specific promoter.

4. The engineered nucleic acid of claim 1 further comprising a second nucleic acid sequence that encodes a tetracycline repressor.

5. The engineered nucleic acid of claim 4, wherein the promoter that is operably linked to the first nucleic acid is also operably linked to the second nucleic acid.

6. The engineered nucleic acid of claim 4 further comprising a separator sequence encoding an internal ribosome entry site (IRES) or a 2A peptide between the first and the second nucleic acid.

7. The engineered nucleic acid of claim 4, wherein the tetracycline repressor is tetRKRAB.

8. The engineered nucleic acid of claim 1, wherein the engineered nucleic acid is a viral vector, wherein the viral vector is an adeno-associated virus (AAV), lentiviral, retroviral, adenoviral, or herpes viral vector.

9. The engineered nucleic acid of claim 8, wherein the viral vector comprises inverted terminal repeats (ITRs) flanking one or more nucleic acids.

10. The engineered nucleic acid of claim 1 further comprising a WPRE3 sequence.

11. The engineered nucleic acid of claim 1, wherein the engineered nucleic acid comprises a sequence that is at least 70% identical to the sequence of SEQ ID NO: 17 or SEQ ID NO: 30.

12. The engineered nucleic acid of claim 1, wherein the engineered nucleic acid further comprises a first transgene sequence operably linked to an inducible promoter that comprises a tetracycline-responsive element (TRE).

13. The engineered nucleic acid of claim 12, wherein the TRE promoter is a TRE3G promoter.

14. The engineered nucleic acid of claim 12, wherein the TRE comprises at least one Tet-O sequence set forth as SEQ ID NO: 19.

15. A recombinant virus comprising the engineered nucleic acid of claim 1.

16. A pharmaceutical composition comprising the recombinant virus of claim 15.

17. A pharmaceutical composition comprising the engineered nucleic acid of claim 1 and a pharmaceutically acceptable excipient.

18. An in vitro or ex vivo cell comprising the engineered nucleic acid of claim 1.

19. The engineered nucleic acid of claim 1, wherein the mutant rtTA comprises the following mutations:

(a) G72V;

(b) G12S;

(c) F67S; and (d) R171K.

20. The engineered nucleic acid of claim 1, wherein the mutant rtTA comprises a sequence that is at least 70% identical to the sequence of SEQ ID NO: 13.

21. The engineered nucleic acid of claim 1, wherein the mutant rtTA comprises SEQ ID NO: 13.

22. The engineered nucleic acid of claim 1, wherein the first nucleic acid comprises the sequence that is set forth in SEQ ID NO: 12.

23. The engineered nucleic acid of claim 1, wherein the engineered nucleic acid comprises a sequence that is at least 80% identical to the sequence of SEQ ID NO: 17 or SEQ ID NO: 30.

24. The engineered nucleic acid of claim 1, wherein the engineered nucleic acid comprises the sequence that is set forth in SEQ ID NO: 17 or SEQ ID NO: 30.

25. The engineered nucleic acid of claim 1, wherein the mutant rtTA comprises a sequence that is at least 80% identical to the sequence of SEQ ID NO: 13.

26. The engineered nucleic acid of claim 1, wherein the first nucleic acid comprises a sequence that is at least 90% identical to the sequence of SEQ ID NO: 12.

27. A method of promoting gene expression comprising administering to a cell, tissue, or subject in need thereof:

(a) a first engineered nucleic acid of claim 12; and (b) a tetracycline, thereby promoting expression of the first transgene.

\* \* \* \* \*

SEQUENCE LISTING

```
<160> NUMBER OF SEQ ID NOS: 38

<210> SEQ ID NO 1
<211> LENGTH: 1056
<212> TYPE: DNA
<213> ORGANISM: Mus musculus

<400> SEQUENCE: 1
atggctggac acctggcttc agacttcgcc ttctcacccc caccaggtgg gggtgatggg      60
tcagcagggc tggagccggg ctgggtggat cctcgaacct ggctaagctt ccaagggcct     120
ccaggtgggc ctggaatcgg accaggctca gaggtattgg ggatctcccc atgtccgccc     180
gcatacgagt tctgcggagg gatggcatac tgtgtgacctc aggttggact gggcctagtc     240
ccccaagttg gcgtggagac tttgcagcct gagggccagg caggagcacg agtggaaagc     300
aactcagagg gaacctcctc tgagccctgt gccgaccgcc ccaatgccgt gaagttggag     360
aaggtggaac caactcccga ggagtcccag gacatgaaag ccctgcagaa ggagctagaa     420
cagtttgcca agctgctgaa gcagaagagg atcaccttgg ggtacaccca ggccgacgtg     480
gggctcaccc tgggcgttct ctttggaaag gtgttcagcc agaccaccat ctgtcgcttc     540
gaggccttgc agctcagcct taagaacatg tgtaagctgc ggcccctgct ggagaagtgg     600
gtggaggaag ccgacaacaa tgagaacctt caggagatat gcaaatcgga gaccctggtg     660
caggcccgga agagaaagcg aactagcatt gagaaccgtg tgaggtggag tctggagacc     720
atgtttctga agtgcccgaa gccctcccta cagcagatca ctcacatcgc caatcagctt     780
gggctagaga aggatgtggt tcgagtatgg ttctgtaacc ggcgccagaa gggcaaaaga     840
tcaagtattg agtattccca acgagaagag tatgaggcta cagggacacc tttcccaggg     900
ggggctgtat cctttcctct gccccaggt ccccactttg gcaccccagg ctatggaagc     960
ccccacttca ccacactcta ctcagtccct tttcctgagg gcgaggcctt tccctctgtt    1020
cccgtcactg ctctgggctc tcccatgcat tcaaac                             1056

<210> SEQ ID NO 2
<211> LENGTH: 352
<212> TYPE: PRT
<213> ORGANISM: Mus musculus

<400> SEQUENCE: 2

Met Ala Gly His Leu Ala Ser Asp Phe Ala Phe Ser Pro Pro Pro Gly
1               5                   10                  15

Gly Gly Asp Gly Ser Ala Gly Leu Glu Pro Gly Trp Val Asp Pro Arg
            20                  25                  30

Thr Trp Leu Ser Phe Gln Gly Pro Pro Gly Gly Pro Gly Ile Gly Pro
        35                  40                  45

Gly Ser Glu Val Leu Gly Ile Ser Pro Cys Pro Pro Ala Tyr Glu Phe
    50                  55                  60
```

-continued

```
Cys Gly Gly Met Ala Tyr Cys Gly Pro Gln Val Gly Leu Gly Leu Val
65                  70                  75                  80

Pro Gln Val Gly Val Glu Thr Leu Gln Pro Glu Gly Gln Ala Gly Ala
                85                  90                  95

Arg Val Glu Ser Asn Ser Glu Gly Thr Ser Ser Glu Pro Cys Ala Asp
            100                 105                 110

Arg Pro Asn Ala Val Lys Leu Glu Lys Val Glu Pro Thr Pro Glu Glu
            115                 120                 125

Ser Gln Asp Met Lys Ala Leu Gln Lys Glu Leu Glu Gln Phe Ala Lys
        130                 135                 140

Leu Leu Lys Gln Lys Arg Ile Thr Leu Gly Tyr Thr Gln Ala Asp Val
145                 150                 155                 160

Gly Leu Thr Leu Gly Val Leu Phe Gly Lys Val Phe Ser Gln Thr Thr
                165                 170                 175

Ile Cys Arg Phe Glu Ala Leu Gln Leu Ser Leu Lys Asn Met Cys Lys
                180                 185                 190

Leu Arg Pro Leu Leu Glu Lys Trp Val Glu Glu Ala Asp Asn Asn Glu
            195                 200                 205

Asn Leu Gln Glu Ile Cys Lys Ser Glu Thr Leu Val Gln Ala Arg Lys
        210                 215                 220

Arg Lys Arg Thr Ser Ile Glu Asn Arg Val Arg Trp Ser Leu Glu Thr
225                 230                 235                 240

Met Phe Leu Lys Cys Pro Lys Pro Ser Leu Gln Gln Ile Thr His Ile
                245                 250                 255

Ala Asn Gln Leu Gly Leu Glu Lys Asp Val Val Arg Val Trp Phe Cys
            260                 265                 270

Asn Arg Arg Gln Lys Gly Lys Arg Ser Ser Ile Glu Tyr Ser Gln Arg
            275                 280                 285

Glu Glu Tyr Glu Ala Thr Gly Thr Pro Phe Pro Gly Gly Ala Val Ser
        290                 295                 300

Phe Pro Leu Pro Pro Gly Pro His Phe Gly Thr Pro Gly Tyr Gly Ser
305                 310                 315                 320

Pro His Phe Thr Thr Leu Tyr Ser Val Pro Phe Pro Glu Gly Glu Ala
                325                 330                 335

Phe Pro Ser Val Pro Val Thr Ala Leu Gly Ser Pro Met His Ser Asn
            340                 345                 350
```

```
<210> SEQ ID NO 3
<211> LENGTH: 957
<212> TYPE: DNA
<213> ORGANISM: Mus musculus

<400> SEQUENCE: 3
atgtataaca tgatggagac ggagctgaag ccgccgggcc cgcagcaagc ttcgggggggc       60 ggcggcggag gaggcaacgc cacggcggcg gcgaccggcg gcaaccagaa gaacagcccg      120
gaccgcgtca agaggcccat gaacgccttc atggtatggt cccggggggca gcggcgtaag      180 atggcccagg agaaccccaa gatgcacaac tcggagatca gcaagcgcct gggcgcggag      240
tggaaacttt tgtccgagac cgagaagcgg ccgttcatcg acgaggccaa gcggctgcgc      300
gctctgcaca tgaaggagca cccggattat aaataccggc cgcggcggaa aaccaagacg      360
ctcatgaaga aggataagta cacgcttccc ggaggcttgc tggcccccgg cgggaacagc      420
atggcgagcg gggttggggt gggcgccggc ctgggtgcgg gcgtgaacca gcgcatggac      480
```

-continued

```
agctacgcgc acatgaacgg ctggagcaac ggcagctaca gcatgatgca ggagcagctg     540
ggctacccgc agcacccggg cctcaacgct cacggcgcgg cacagatgca accgatgcac     600
cgctacgacg tcagcgccct gcagtacaac tccatgacca gctcgcagac ctacatgaac     660
ggctcgccca cctacagcat gtcctactcg cagcagggca cccccggtat ggcgctgggc     720
tccatgggct ctgtggtcaa gtccgaggcc agctccagcc ccccgtggt tacctcttcc      780 tcccactcca gggcgccctg ccaggccggg gacctccggg acatgatcag catgtacctc     840
cccggcgccg aggtgccgga gcccgctgcg cccagtagac tgcacatggc ccagcactac     900
cagagcggcc cggtgcccgg cacggccatt aacggcacac tgcccctgtc gcacatg       957
```

<210> SEQ ID NO 4
<211> LENGTH: 319
<212> TYPE: PRT
<213> ORGANISM: Mus musculus

<400> SEQUENCE: 4

```
Met Tyr Asn Met Met Glu Thr Glu Leu Lys Pro Pro Gly Pro Gln Gln
1               5                   10                  15

Ala Ser Gly Gly Gly Gly Gly Gly Asn Ala Thr Ala Ala Ala Thr
            20                  25                  30

Gly Gly Asn Gln Lys Asn Ser Pro Asp Arg Val Lys Arg Pro Met Asn
        35                  40                  45

Ala Phe Met Val Trp Ser Arg Gly Gln Arg Arg Lys Met Ala Gln Glu
    50                  55                  60

Asn Pro Lys Met His Asn Ser Glu Ile Ser Lys Arg Leu Gly Ala Glu
65                  70                  75                  80

Trp Lys Leu Leu Ser Glu Thr Glu Lys Arg Pro Phe Ile Asp Glu Ala
                85                  90                  95

Lys Arg Leu Arg Ala Leu His Met Lys Glu His Pro Asp Tyr Lys Tyr
            100                 105                 110

Arg Pro Arg Arg Lys Thr Lys Thr Leu Met Lys Lys Asp Lys Tyr Thr
        115                 120                 125

Leu Pro Gly Gly Leu Leu Ala Pro Gly Gly Asn Ser Met Ala Ser Gly
    130                 135                 140

Val Gly Val Gly Ala Gly Leu Gly Ala Gly Val Asn Gln Arg Met Asp
145                 150                 155                 160

Ser Tyr Ala His Met Asn Gly Trp Ser Asn Gly Ser Tyr Ser Met Met
                165                 170                 175

Gln Glu Gln Leu Gly Tyr Pro Gln His Pro Gly Leu Asn Ala His Gly
            180                 185                 190

Ala Ala Gln Met Gln Pro Met His Arg Tyr Asp Val Ser Ala Leu Gln
        195                 200                 205

Tyr Asn Ser Met Thr Ser Ser Gln Thr Tyr Met Asn Gly Ser Pro Thr
    210                 215                 220

Tyr Ser Met Ser Tyr Ser Gln Gln Gly Thr Pro Gly Met Ala Leu Gly
225                 230                 235                 240

Ser Met Gly Ser Val Val Lys Ser Glu Ala Ser Ser Ser Pro Pro Val
                245                 250                 255

Val Thr Ser Ser Ser His Ser Arg Ala Pro Cys Gln Ala Gly Asp Leu
            260                 265                 270

Arg Asp Met Ile Ser Met Tyr Leu Pro Gly Ala Glu Val Pro Glu Pro
        275                 280                 285

Ala Ala Pro Ser Arg Leu His Met Ala Gln His Tyr Gln Ser Gly Pro
```

-continued

```
        290              295              300

Val Pro Gly Thr Ala Ile Asn Gly Thr Leu Pro Leu Ser His Met
305              310              315
```

```
<210> SEQ ID NO 5
<211> LENGTH: 1446
<212> TYPE: DNA
<213> ORGANISM: Mus musculus

<400> SEQUENCE: 5
atgaggcagc cacctggcga gtctgacatg gctgtcagcg acgctctgct cccgtccttc       60
tccacgttcg cgtccggccc ggcgggaagg gagaagacac tgcgtccagc aggtgccccg      120
actaaccgtt ggcgtgagga actctctcac atgaagcgac ttcccccact tcccggccgc      180
ccctacgacc tggcggcgac ggtggccaca gacctggaga gtggcggagc tggtgcagct      240
tgcagcagta acaacccggc cctcctagcc cggagggaga ccgaggagtt caacgacctc      300
ctggacctag actttatcct ttccaactcg ctaacccacc aggaatcggt ggccgccacc      360
gtgaccacct cggcgtcagc ttcatcctcg tcttccccag cgagcagcgg ccctgccagc      420
gcgccctcca cctgcagctt cagctatccg atccgggccg ggggtgaccc gggcgtggct      480
gccagcaaca caggtggagg gctcctctac agccgagaat ctgcgccacc tcccacggcc      540
cccttcaacc tggcggacat caatgacgtg agccctcgg gcggcttcgt ggctgagctc      600
ctgcggccgg agttggaccc agtatacatt ccgccacagc agcctcagcc gccaggtggc      660
gggctgatgg gcaagtttgt gctgaaggcg tctctgacca cccctggcag cgagtacagc      720
agcccttcgg tcatcagtgt tagcaaagga agcccagacg gcagccaccc cgtggtagtg      780
gcgccctaca gcggtggccc gccgcgcatg tgccccaaga ttaagcaaga ggcggtcccg      840
tcctgcacgg tcagccggtc cctagaggcc catttgagcg ctggacccca gctcagcaac      900
ggccaccggc ccaacacaca cgacttcccc ctggggcggc agctccccac caggactacc      960
cctacactga gtcccgagga actgctgaac agcagggact gtcaccctgg cctgcctctt     1020
cccccaggat ccatccccca tccgggggccc aactaccctc ctttcctgcc agaccagatg     1080
cagtcacaag tccctctctc ccattatcaa gagctcatgc caccgggttc ctgcctgcca     1140
gaggagccca gccaaagag gggaagaagg tcgtggcccc ggaaaagaac agccacccac     1200
acttgtgact atgcaggctg tggcaaaacc tataccaaga gttctcatct caaggcacac     1260
ctgcgaactc acacaggcga gaaaccttac cactgtgact gggacggctg tgggtggaaa     1320
ttcgcccgct ccgatgaact gaccaggcac taccgcaaac acacagggca ccggccccttt     1380 cagtgccaga gtgcgacag ggcctttcc aggtcggacc accttgcctt acacatgaag     1440
aggcac                                                              1446
```

```
<210> SEQ ID NO 6
<211> LENGTH: 482
<212> TYPE: PRT
<213> ORGANISM: Mus musculus

<400> SEQUENCE: 6

Met Arg Gln Pro Pro Gly Glu Ser Asp Met Ala Val Ser Asp Ala Leu
1               5                   10                  15

Leu Pro Ser Phe Ser Thr Phe Ala Ser Gly Pro Ala Gly Arg Glu Lys
            20                  25                  30

Thr Leu Arg Pro Ala Gly Ala Pro Thr Asn Arg Trp Arg Glu Glu Leu
        35                  40                  45
```

-continued

```
Ser His Met Lys Arg Leu Pro Pro Leu Pro Gly Arg Pro Tyr Asp Leu
    50                  55                  60

Ala Ala Thr Val Ala Thr Asp Leu Glu Ser Gly Gly Ala Gly Ala Ala
65                  70                  75                  80

Cys Ser Ser Asn Asn Pro Ala Leu Leu Ala Arg Arg Glu Thr Glu Glu
                85                  90                  95

Phe Asn Asp Leu Leu Asp Leu Asp Phe Ile Leu Ser Asn Ser Leu Thr
                100                 105                 110

His Gln Glu Ser Val Ala Ala Thr Val Thr Thr Ser Ala Ser Ala Ser
            115                 120                 125

Ser Ser Ser Ser Pro Ala Ser Ser Gly Pro Ala Ser Ala Pro Ser Thr
        130                 135                 140

Cys Ser Phe Ser Tyr Pro Ile Arg Ala Gly Gly Asp Pro Gly Val Ala
145                 150                 155                 160

Ala Ser Asn Thr Gly Gly Gly Leu Leu Tyr Ser Arg Glu Ser Ala Pro
                165                 170                 175

Pro Pro Thr Ala Pro Phe Asn Leu Ala Asp Ile Asn Asp Val Ser Pro
                180                 185                 190

Ser Gly Gly Phe Val Ala Glu Leu Leu Arg Pro Glu Leu Asp Pro Val
            195                 200                 205

Tyr Ile Pro Pro Gln Gln Pro Gln Pro Gly Gly Gly Leu Met Gly
    210                 215                 220

Lys Phe Val Leu Lys Ala Ser Leu Thr Thr Pro Gly Ser Glu Tyr Ser
225                 230                 235                 240

Ser Pro Ser Val Ile Ser Val Ser Lys Gly Ser Pro Asp Gly Ser His
                245                 250                 255

Pro Val Val Val Ala Pro Tyr Ser Gly Gly Pro Pro Arg Met Cys Pro
                260                 265                 270

Lys Ile Lys Gln Glu Ala Val Pro Ser Cys Thr Val Ser Arg Ser Leu
            275                 280                 285

Glu Ala His Leu Ser Ala Gly Pro Gln Leu Ser Asn Gly His Arg Pro
    290                 295                 300

Asn Thr His Asp Phe Pro Leu Gly Arg Gln Leu Pro Thr Arg Thr Thr
305                 310                 315                 320

Pro Thr Leu Ser Pro Glu Glu Leu Leu Asn Ser Arg Asp Cys His Pro
                325                 330                 335

Gly Leu Pro Leu Pro Pro Gly Phe His Pro His Pro Gly Pro Asn Tyr
            340                 345                 350

Pro Pro Phe Leu Pro Asp Gln Met Gln Ser Gln Val Pro Ser Leu His
        355                 360                 365

Tyr Gln Glu Leu Met Pro Pro Gly Ser Cys Leu Pro Glu Glu Pro Lys
    370                 375                 380

Pro Lys Arg Gly Arg Arg Ser Trp Pro Arg Lys Arg Thr Ala Thr His
385                 390                 395                 400

Thr Cys Asp Tyr Ala Gly Cys Gly Lys Thr Tyr Thr Lys Ser Ser His
                405                 410                 415

Leu Lys Ala His Leu Arg Thr His Thr Gly Glu Lys Pro Tyr His Cys
            420                 425                 430

Asp Trp Asp Gly Cys Gly Trp Lys Phe Ala Arg Ser Asp Glu Leu Thr
        435                 440                 445

Arg His Tyr Arg Lys His Thr Gly His Arg Pro Phe Gln Cys Gln Lys
    450                 455                 460
```

```
Cys Asp Arg Ala Phe Ser Arg Ser Asp His Leu Ala Leu His Met Lys
465                 470                 475                 480

Arg His

<210> SEQ ID NO 7
<211> LENGTH: 376
<212> TYPE: DNA
<213> ORGANISM: Artificial Sequence
<220> FEATURE:
<223> OTHER INFORMATION: Synthetic Polynucleotide

<400> SEQUENCE: 7
tttactccct atcagtgata gagaacgtat gaagagttta ctccctatca gtgatagaga      60
acgtatgcag actttactcc ctatcagtga tagagaacgt ataaggagtt tactccctat     120
cagtgataga gaacgtatga ccagtttact ccctatcagt gatagagaac gtatctacag     180
tttactccct atcagtgata gagaacgtat atccagttta ctccctatca gtgatagaga     240
acgtataagc tttaggcgtg tacggtgggc gcctataaaa gcagagctcg tttagtgaac     300
cgtcagatcg cctggagcaa ttccacaaca cttttgtctt ataccaactt ccgtaccac     360 ttcctaccct cgtaaa                                                     376

<210> SEQ ID NO 8
<211> LENGTH: 169
<212> TYPE: DNA
<213> ORGANISM: Artificial Sequence
<220> FEATURE:
<223> OTHER INFORMATION: Synthetic Polynucleotide

<400> SEQUENCE: 8
tgcgcgcagc ggccgaccat ggcccaactt gtttattgca gcttataatg gttacaaata      60
aagcaatagc atcacaaatt tcacaaataa agcatttttt tcactgcatt ctagttgtgg     120
tttgtccaaa ctcatcaatg tatcttatca tgtctggatc tcggtaccg                 169

<210> SEQ ID NO 9
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 9

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 10
<211> LENGTH: 708
<212> TYPE: DNA
<213> ORGANISM: Artificial Sequence
<220> FEATURE:
<223> OTHER INFORMATION: Synthetic Polynucleotide

<400> SEQUENCE: 10
atgtctaggc tggacaagag caaagtcata aacggagctc tggaattact caatggtgtc      60
ggtatcgaag gcctgacgac aaggaaactc gctcaaaagc tgggagttga gcagcctacc     120
ctgtactggc acgtgaagaa caagcgggcc ctgctcgatg ccctgccaat cgagatgctg     180
gacaggcatc atacccactt ctgcccctg gaaggcgagt catggcaaga ctttctgcgg     240
```

-continued

```
aacaacgcca agtcataccg ctgtgctctc ctctcacatc gcgacgggc taaagtgcat      300 ctcggcaccc gcccaacaga gaaacagtac gaaaccctgg aaaatcagct cgcgttcctg      360
tgtcagcaag gcttctccct ggagaacgca ctgtacgctc tgtccgccgt gggccacttt      420
acactgggct gcgtattgga ggaacaggag catcaagtag caaaagagga aagagagaca      480
cctaccaccg attctatgcc cccacttctg agacaagcaa ttgagctgtt cgaccggcag      540
ggagccgaac ctgccttcct tttcggcctg gaactaatca tatgtggcct ggagaaacag      600
ctaaagtgcg aaagcggcgg gccgaccgac gcccttgacg attttgactt agacatgctc      660
ccagccgatg cccttgacga ttttgacctt gacatgctcc ccgggtaa              708
```

<210> SEQ ID NO 11
<211> LENGTH: 235
<212> TYPE: PRT
<213> ORGANISM: Artificial Sequence
<220> FEATURE:
<223> OTHER INFORMATION: Synthetic Polypeptide

<400> SEQUENCE: 11

```
Met Ser Arg Leu Asp Lys Ser Lys Val Ile Asn Gly Ala Leu Glu Leu
1               5                   10                  15

Leu Asn Gly Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Pro Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Tyr Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Glu Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp Arg Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Gly Pro
            195                 200                 205

Thr Asp Ala Leu Asp Asp Phe Asp Leu Asp Met Leu Pro Ala Asp Ala
    210                 215                 220

Leu Asp Asp Phe Asp Leu Asp Met Leu Pro Gly
225                 230                 235
```

<210> SEQ ID NO 12
<211> LENGTH: 747
<212> TYPE: DNA
<213> ORGANISM: Artificial Sequence
<220> FEATURE:
<223> OTHER INFORMATION: Synthetic Polynucleotide -continued

```
<400> SEQUENCE: 12
atgtcccgct tggataagag caaggtaata aatagcgcac tcgaactcct caacggcgtg      60
ggcatcgaag gtctgactac tcgaaagctc gcccagaaat tgggtgtgga gcaacctaca     120
ttgtattggc atgtcaagaa caaaagagcc ctgctggacg ctcttcctat tgaaatgctt     180
gacaggcatc acactcattc ctgccccctt gaggtcgaga gttggcaaga ttttctccga     240
aacaatgcaa agtcctaccg ctgcgcactt ttgtcccata gggatggagc aaaagtgcac     300
ctgggaacca ggccaacaga aaacaatac gagactctcg agaaccagtt ggctttcttg     360
tgccaacagg ggttctcact tgaaaatgcc ctttacgcac tgtcagccgt tggacatttt     420
accctggggt gcgttcttga ggagcaagaa catcaggttg ctaaggagga gcgcgagact     480
ccaaccactg attctatgcc acctttgctg aaacaggcca ttgaacttt cgatagacag     540 ggtgctgaac ctgcctttct cttcgggttg gagctgatta tttgtggtct cgaaaaacag     600
ctgaaatgtg aaagtggtgg ccctactgac gccctcgatg atttcgacct ggatatgctg     660
ccagccgatg cacttgatga tttcgatttg gatatgcttc cagccgacgc actggacgac     720
ttcgatttgg acatgcttcc cggttaa                                         747

<210> SEQ ID NO 13
<211> LENGTH: 248
<212> TYPE: PRT
<213> ORGANISM: Artificial Sequence
<220> FEATURE:
<223> OTHER INFORMATION: Synthetic Polypeptide

<400> SEQUENCE: 13

Met Ser Arg Leu Asp Lys Ser Lys Val Ile Asn Ser Ala Leu Glu Leu
1               5                   10                  15

Leu Asn Gly Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Pro Ile Glu Met Leu Asp Arg His His
    50                  55                  60

Thr His Ser Cys Pro Leu Glu Val Glu Ser Trp Gln Asp Phe Leu Arg
65                  70                  75                  80

Asn Asn Ala Lys Ser Tyr Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Glu Gln Glu His Gln Val Ala Lys Glu Glu Arg Glu Thr
145                 150                 155                 160

Pro Thr Thr Asp Ser Met Pro Pro Leu Leu Lys Gln Ala Ile Glu Leu
                165                 170                 175

Phe Asp Arg Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Gly Pro
        195                 200                 205

Thr Asp Ala Leu Asp Asp Phe Asp Leu Asp Met Leu Pro Ala Asp Ala
    210                 215                 220
```

Leu Asp Asp Phe Asp Leu Asp Met Leu Pro Ala Asp Ala Leu Asp Asp
225                 230                 235                 240

Phe Asp Leu Asp Met Leu Pro Gly
                245

<210> SEQ ID NO 14
<211> LENGTH: 1050
<212> TYPE: DNA
<213> ORGANISM: Artificial Sequence
<220> FEATURE:
<223> OTHER INFORMATION: Synthetic Polynucleotide

<400> SEQUENCE: 14
atgcctttgt atcatgctat tgcttcccgt atggctttca ttttctcctc cttgtataaa      60
tcctggttgc tgtctcttta tgaggagttg tggcccgttg tcaggcaacg tggcgtggtg     120
tgcactgtgt ttgctgacgc aaccccact ggttggggca ttgccaccac ctgtcagctc     180
ctttccggga ctttcgcttt ccccctccct attgccacgg cggaactcat cgccgcctgc     240
cttgcccgct gctggacagg ggctcggctg ttgggcactg acaattccgt ggtgttgtcg     300
gggaaatcat cgtcctttcc ttggctgctc gcctgtgttg ccacctggat tctgcgcggg     360
acgtccttct gctacgtccc ttcggccctc aatccagcgg accttccttc ccgcggcctg     420
ctgccggctc tgcggcctct tccgcgtctt cgccttcgcc ctcagacgag tcggatctcc     480
ctttgggccg cctccccgca tcgataccgt cgacctcgag acctagaaaa acatggagca     540
atcacaagta gcaatacagc agctaccaat gctgattgtg cctggctaga agcacaagag     600
gaggaggagg tgggtttttcc agtcacacct caggtacctt taagaccaat gacttacaag     660
gcagctgtag atcttagcca ctttttaaaa gaaaagggg gactggaagg gctaattcac     720
tcccaacgaa gacaagatat ccttgatctg tggatctacc acacacaagg ctacttccct     780
gattggcaga actacacacc agggccaggg atcagatatc cactgacctt tggatggtgc     840
tacaagctag taccagttga gcaagagaag gtagaagaag ccaatgaagg agagaacacc     900
cgcttgttac accctgtgag cctgcatggg atggatgacc cggagagaga agtattagag     960
tggaggtttg acagccgcct agcatttcat cacatggccc gagagctgca tccggactgt    1020
actgggtctc tctggttaga ccagatctga                                     1050

<210> SEQ ID NO 15
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 15

Met Pro Leu Tyr His Ala Ile Ala Ser Arg Met Ala Phe Ile Phe Ser
1               5                   10                  15

Ser Leu Tyr Lys Ser Trp Leu Leu Ser Leu Tyr Glu Glu Leu Trp Pro
                20                  25                  30

Val Val Arg Gln Arg Gly Val Val Cys Thr Val Phe Ala Asp Ala Thr
            35                  40                  45

Pro Thr Gly Trp Gly Ile Ala Thr Thr Cys Gln Leu Leu Ser Gly Thr
        50                  55                  60

Phe Ala Phe Pro Leu Pro Ile Ala Thr Ala Glu Leu Ile Ala Ala Cys
65                  70                  75                  80

Leu Ala Arg Cys Trp Thr Gly Ala Arg Leu Leu Gly Thr Asp Asn Ser

-continued

```
                85                    90                    95

Val Val Leu Ser Gly Lys Ser Ser Ser Phe Pro Trp Leu Leu Ala Cys
            100                   105                   110

Val Ala Thr Trp Ile Leu Arg Gly Thr Ser Phe Cys Tyr Val Pro Ser
            115                   120                   125

Ala Leu Asn Pro Ala Asp Leu Pro Ser Arg Gly Leu Leu Pro Ala Leu
            130                   135                   140

Arg Pro Leu Pro Arg Leu Arg Leu Arg Pro Gln Thr Ser Arg Ile Ser
145                   150                   155                   160

Leu Trp Ala Ala Ser Pro His Arg Tyr Arg Arg Pro Arg Asp Leu Glu
                165                   170                   175

Lys His Gly Ala Ile Thr Ser Ser Asn Thr Ala Ala Thr Asn Ala Asp
            180                   185                   190

Cys Ala Trp Leu Glu Ala Gln Glu Glu Glu Val Gly Phe Pro Val
            195                   200                   205

Thr Pro Gln Val Pro Leu Arg Pro Met Thr Tyr Lys Ala Ala Val Asp
    210                   215                   220

Leu Ser His Phe Leu Lys Glu Lys Gly Gly Leu Glu Gly Leu Ile His
225                   230                   235                   240

Ser Gln Arg Arg Gln Asp Ile Leu Asp Leu Trp Ile Tyr His Thr Gln
                245                   250                   255

Gly Tyr Phe Pro Asp Trp Gln Asn Tyr Thr Pro Gly Pro Gly Ile Arg
            260                   265                   270

Tyr Pro Leu Thr Phe Gly Trp Cys Tyr Lys Leu Val Pro Val Glu Gln
            275                   280                   285

Glu Lys Val Glu Glu Ala Asn Glu Gly Glu Asn Thr Arg Leu Leu His
    290                   295                   300

Pro Val Ser Leu His Gly Met Asp Asp Pro Glu Arg Glu Val Leu Glu
305                   310                   315                   320

Trp Arg Phe Asp Ser Arg Leu Ala Phe His His Met Ala Arg Glu Leu
                325                   330                   335

His Pro Asp Cys Thr Gly Ser Leu Trp Leu Asp Gln Ile
            340                   345
```

```
<210> SEQ ID NO 16
<211> LENGTH: 7408
<212> TYPE: DNA
<213> ORGANISM: Artificial Sequence
<220> FEATURE:
<223> OTHER INFORMATION: Synthetic Polynucleotide

<400> SEQUENCE: 16
ttatgcagtg ctgccataac catgagtgat aacactgcgg ccaacttact tctgacaacg      60
atcggaggac cgaaggagct aaccgctttt ttgcacaaca tggggggatca tgtaactcgc     120 cttgatcgtt gggaaccgga gctgaatgaa gccataccaa acgacgagcg tgacaccacg     180
atgcctgtag taatggtaac aacgttgcgc aaactattaa ctggcgaact acttactcta     240
gcttcccggc aacaattaat agactggatg gaggcggata agttgcagg accacttctg      300 cgctcggccc ttccggctgg ctggtttatt gctgataaat ctggagccgg tgagcgtggg     360
tctcgcggta tcattgcagc actggggcca gatggtaagc cctcccgtat cgtagttatc     420
tacacgacgg ggagtcaggc aactatggat gaacgaaata gacagatcgc tgagataggt     480
gcctcactga ttaagcattg gtaactgtca gaccaagttt actcatatat actttagatt     540
gatttaaaac ttcattttta atttaaaagg atctaggtga agatcctttt tgataatctc     600
```

-continued

```
atgaccaaaa tcccttaacg tgagttttcg ttccactgag cgtcagaccc cgtagaaaag      660
atcaaaggat cttcttgaga tccttttttt ctgcgcgtaa tctgctgctt gcaaacaaaa      720
aaaccaccgc taccagcggt ggtttgtttg ccggatcaag agctaccaac tcttttttccg     780 aaggtaactg gcttcagcag agcgcagata ccaaatactg tccttctagt gtagccgtag      840
ttaggccacc acttcaagaa ctctgtagca ccgcctacat acctcgctct gctaatcctg      900
ttaccagtgg ctgctgccag tggcgataag tcgtgtctta ccgggttgga ctcaagacga      960
tagttaccgg ataaggcgca gcggtcgggc tgaacggggg gttcgtgcac acagcccagc     1020
ttggagcgaa cgacctacac cgaactgaga tacctacagc gtgagctatg agaaagcgcc     1080
acgcttcccg aagggagaaa ggcggacagg tatccggtaa gcggcagggt cggaacagga     1140
gagcgcacga gggagcttcc aggggggaaac gcctggtatc tttatagtcc tgtcgggttt     1200
cgccacctct gacttgagcg tcgatttttg tgatgctcgt caggggggcg gagcctatgg     1260
aaaaacgcca gcaacgcggc cttttttacgg ttcctggcct tttgctggcc ttttgctcac     1320
atgttctttc ctgcgttatc ccctgattct gtggataacc gtattaccgc ctttgagtga     1380
gctgataccg ctcgccgcag ccgaacgacc gagcgcagcg agtcagtgag cgaggaagcg     1440
gaagagcgcc caatacgcaa accgcctctc cccgcgcgtt ggccgattca ttaatgcagc     1500
tggcacgaca ggtttcccga ctggaaagcg ggcagtgagc gcaacgcaat taatgtgagt     1560
tagctcactc attaggcacc ccaggcttta cactttatgc ttccggctcg tatgttgtgt     1620
ggaattgtga gcggataaca atttcacaca ggaaacagct atgaccatga ttacgccaga     1680
tttaattaag gccttaatta ggctgcgcgc tcgctcgctc actgaggccg cccgggcaaa     1740
gcccgggcgt cgggcgacct ttggtcgccc ggcctcagtg agcgagcgag cgcgcagaga     1800
gggagtggcc aactccatca ctaggggttc cttgtagtta atgattaacc cgccatgcta     1860
cttatctacg tagccatgct ctaggaagat cggaattctt tactccctat cagtgataga     1920
gaacgtatga agagtttact ccctatcagt gatagagaac gtatgcagac tttactccct     1980
atcagtgata gagaacgtat aaggagttta ctccctatca gtgatagaga acgtatgacc     2040
agtttactcc ctatcagtga tagagaacgt atctacagtt tactccctat cagtgataga     2100
gaacgtatat ccagtttact ccctatcagt gatagagaac gtataagctt taggcgtgta     2160
cggtgggcgc ctataaaagc agagctcgtt tagtgaaccg tcagatcgcc tggagcaatt     2220
ccacaacact tttgtcttat accaactttc cgtaccactt cctaccctcg taaagcggcc     2280
gcgccaccat ggctggacac ctggcttcag acttcgcctt ctcaccccca ccaggtgggg     2340
gtgatgggtc agcagggctg agccgggct gggtggatcc tcgaacctgg ctaagcttcc      2400
aagggcctcc aggtgggcct ggaatcggac caggctcaga ggtattgggg atctccccat     2460
gtccgcccgc atacgagttc tgcggaggga tggcatactg tggacctcag gttggactgg     2520
gcctagtccc ccaagttggc gtggagactt gcagcctga gggccaggca ggagcacgag      2580
tggaaagcaa ctcagaggga acctcctctg agccctgtgc cgaccgcccc aatgccgtga     2640
agttggagaa ggtggaacca actcccgagg agtcccagga catgaaagcc ctgcagaagg     2700
agctagaaca gtttgccaag ctgctgaagc agaagaggat cacctggggg tacacccagg     2760
ccgacgtggg gctcaccctg ggcgttctct ttggaaaggt gttcagccag accaccatct     2820
gtcgcttcga ggccttgcag ctcagcctta agaacatgtg taagctgcgg ccctgctgg      2880 agaagtgggt ggaggaagcc gacaacaatg agaaccttca ggagatatgc aaatcggaga     2940
```

-continued

```
ccctggtgca ggcccggaag agaaagcgaa ctagcattga gaaccgtgtg aggtggagtc   3000
tggagaccat gtttctgaag tgcccgaagc cctccctaca gcagatcact cacatcgcca   3060
atcagcttgg gctagagaag gatgtggttc gagtatggtt ctgtaaccgg cgccagaagg   3120
gcaaaagatc aagtattgag tattcccaac gagaagagta tgaggctaca gggacacctt   3180
tcccaggggg ggctgtatcc tttcctctgc ccccaggtcc ccactttggc accccaggct   3240
atggaagccc ccacttcacc acactctact cagtcccttt tcctgagggc gaggcctttc   3300
cctctgttcc cgtcactgct ctgggctctc ccatgcattc aaacgctagc ggcagcggcg   3360
ccacgaactt ctctctgtta aagcaagcag gagatgttga agaaaacccc gggcctgcat   3420
gcatgtataa catgatggag acggagctga agccgccggg cccgcagcaa gcttcggggg   3480
gcggcggcgg aggaggcaac gccacggcgg cggcgaccgg cggcaaccag aagaacagcc   3540
cggaccgcgt caagaggccc atgaacgcct tcatggtatg gtcccggggg cagcggcgta   3600
agatggccca ggagaacccc aagatgcaca actcggagat cagcaagcgc ctgggcgcgg   3660
agtggaaact tttgtccgag accgagaagc ggccgttcat cgacgaggcc aagcggctgc   3720
gcgctctgca catgaaggag cacccggatt ataaataccg gccgcggcgg aaaaccaaga   3780
cgctcatgaa gaaggataag tacacgcttc ccggaggctt gctggccccc ggcgggaaca   3840
gcatggcgag cggggttggg gtgggcgccg gcctgggtgc gggcgtgaac cagcgcatgg   3900
acagctacgc gcacatgaac ggctggagca acggcagcta cagcatgatg caggagcagc   3960
tgggctaccc gcagcacccg ggcctcaacg ctcacggcgc ggcacagatg caaccgatgc   4020
accgctacga cgtcagcgcc ctgcagtaca actccatgac cagctcgcag acctacatga   4080
acggctcgcc cacctacagc atgtcctact cgcagcaggg cacccccggt atggcgctgg   4140
gctccatggg ctctgtggtc aagtccgagg ccagctccag cccccccgtg gttacctctt   4200
cctcccactc cagggcgccc tgccaggccg gggacctccg ggacatgatc agcatgtacc   4260
tccccggcgc cgaggtgccg gagccgctg cgcccagtag actgcacatg gcccagcact   4320
accagagcgg cccggtgccc ggcacggcca ttaacggcac actgcccctg tcgcacatgg   4380
catgcggctc cggcgagggc agggggaagtc ttctaacatg cggggacgtg gaggaaaatc   4440
ccggcccact cgagatgagg cagccacctg gcgagtctga catggctgtc agcgacgctc   4500
tgctcccgtc cttctccacg ttcgcgtccg gcccggcggg aagggagaag acactgcgtc   4560
cagcaggtgc cccgactaac cgttggcgtg aggaactctc tcacatgaag cgacttcccc   4620
cacttcccgg ccgcccctac gacctggcgg cgacggtggc cacagacctg gagagtggcg   4680
gagctggtgc agcttgcagc agtaacaacc cggccctcct agcccggagg gagaccgagg   4740
agttcaacga cctcctggac ctagacttta tcctttccaa ctcgctaacc caccaggaat   4800
cggtggccgc caccgtgacc acctcggcgt cagcttcatc ctcgtcttcc ccagcgagca   4860
gcggccctgc cagcgcgccc tccacctgca gcttcagcta tccgatccgg gccggggggtg   4920 acccgggcgt ggctgccagc aacacaggtg gagggctcct ctacagccga gaatctgcgc   4980
cacctcccac ggcccccttc aacctggcgg acatcaatga cgtgagcccc tcgggcggct   5040
tcgtggctga gctcctgcgg ccggagttgg acccagtata cattccgcca cagcagcctc   5100
agccgccagg tggcgggctg atgggcaagt ttgtgctgaa ggcgtctctg accaccccctg   5160 gcagcgagta cagcagccct tcggtcatca gtgttagcaa aggaagccca gacggcagcc   5220
accccgtggt agtggcgccc tacagcggtg ccccgccgcg catgtgcccc aagattaagc   5280
aagaggcggt cccgtcctgc acggtcagcc ggtccctaga ggcccatttg agcgctggac   5340
```

```
cccagctcag caacggccac cggcccaaca cacacgactt ccccctgggg cggcagctcc    5400
ccaccaggac tacccctaca ctgagtcccg aggaactgct gaacagcagg gactgtcacc    5460
ctggcctgcc tcttccccca ggattccatc cccatccggg gcccaactac cctcctttcc    5520
tgccagacca gatgcagtca caagtcccct ctctccatta tcaagagctc atgccaccgg    5580
gttcctgcct gccagaggag cccaagccaa agaggggaag aaggtcgtgg ccccggaaaa    5640
gaacagccac ccacacttgt gactatgcag gctgtggcaa aacctatacc aagagttctc    5700
atctcaaggc acacctgcga actcacacag gcgagaaacc ttaccactgt gactgggacg    5760
gctgtgggtg gaaattcgcc cgctccgatg aactgaccag gcactaccgc aaacacacag    5820
ggcaccggcc ctttcagtgc cagaagtgcg acagggcctt ttccaggtcg gaccaccttg    5880
ccttacacat gaagaggcac taaatgacta gtgcgcgcag cggccgacca tggcccaact    5940
tgtttattgc agcttataat ggttacaaat aaagcaatag catcacaaat ttcacaaata    6000
aagcattttt ttcactgcat tctagttgtg gtttgtccaa actcatcaat gtatcttatc    6060
atgtctggat ctcggtaccg gatccaaatt cccgataagg atcttcctag agcatggcta    6120
cgtagataag tagcatggcg ggttaatcat taactacaag gaacccctag tgatggagtt    6180
ggccactccc tctctgcgcg ctcgctcgct cactgaggcc gggcgaccaa aggtcgcccg    6240
acgcccgggc tttgcccggg cggcctcagt gagcgagcga gcgcgcagcc ttaattaacc    6300
taattcactg gccgtcgttt tacaacgtcg tgactgggaa aaccctggcg ttacccaact    6360
taatcgcctt gcagcacatc cccctttcgc cagctggcgt aatagcgaag aggcccgcac    6420
cgatcgccct tcccaacagt tgcgcagcct gaatggcgaa tgggacgcgc cctgtagcgg    6480
cgcattaagc gcggcgggtg tggtggttac gcgcagcgtg accgctacac ttgccagcgc    6540
cctagcgccc gctcctttcg ctttcttccc ttcctttctc gccacgttcg ccggctttcc    6600
ccgtcaagct ctaaatcggg ggctcccttt agggttccga tttagtgctt tacggcacct    6660
cgaccccaaa aaacttgatt agggtgatgg ttcacgtagt gggccatcgc cctgatagac    6720
ggtttttcgc cctttgacgt tggagtccac gttctttaat agtggactct tgttccaaac    6780
tggaacaaca ctcaaccta tctcggtcta ttctttgat ttataaggga ttttgccgat    6840
ttcggcctat tggttaaaaa atgagctgat ttaacaaaaa tttaacgcga attttaacaa    6900
aatattaacg tttataattt caggtggcat ctttcgggga aatgtgcgcg gaacccctat    6960
ttgtttattt ttctaaatac attcaaatat gtatccgctc atgagacaat aaccctgata    7020
aatgcttcaa taatattgaa aaaggaagag tatgagtatt caacatttcc gtgtcgccct    7080
tattcccttt tttgcggcat tttgccttcc tgtttttgct cacccagaaa cgctggtgaa    7140
agtaaaagat gctgaagatc agttgggtgc acgagtgggt tacatcgaac tggatctcaa    7200
tagtggtaag atccttgaga gttttcgccc cgaagaacgt tttccaatga tgagcacttt    7260
taaagttctg ctatgtggcg cggtattatc ccgtattgac gccgggcaag agcaactcgg    7320
tcgccgcata cactattctc agaatgactt ggttgagtac tcaccagtca cagaaaagca    7380
tcttacggat ggcatgacag taagagaa                                         7408
```

<210> SEQ ID NO 17
<211> LENGTH: 5657
<212> TYPE: DNA
<213> ORGANISM: Artificial Sequence
<220> FEATURE:
<223> OTHER INFORMATION: Synthetic Polynucleotide -continued

```
<400> SEQUENCE: 17
ttatgcagtg ctgccataac catgagtgat aacactgcgg ccaacttact tctgacaacg      60
atcggaggac cgaaggagct aaccgctttt ttgcacaaca tgggggatca tgtaactcgc     120
cttgatcgtt gggaaccgga gctgaatgaa gccataccaa acgacgagcg tgacaccacg     180
atgcctgtag taatggtaac aacgttgcgc aaactattaa ctggcgaact acttactcta     240 gcttccggc aacaattaat agactggatg gaggcggata agttgcagg accacttctg        300 cgctcggccc ttccggctgg ctggtttatt gctgataaat ctggagccgg tgagcgtggg     360
tctcgcggta tcattgcagc actggggcca gatggtaagc cctcccgtat cgtagttatc     420
tacacgacgg ggagtcaggc aactatggat gaacgaaata gacagatcgc tgagataggt     480
gcctcactga ttaagcattg gtaactgtca gaccaagttt actcatatat actttagatt     540
gatttaaaac ttcatttta atttaaaagg atctaggtga agatcctttt tgataatctc      600
atgaccaaaa tcccttaacg tgagttttcg ttccactgag cgtcagaccc cgtagaaaag     660
atcaaaggat cttcttgaga tcctttttttt ctgcgcgtaa tctgctgctt gcaaacaaaa     720
aaaccaccgc taccagcggt ggtttgtttg ccggatcaag agctaccaac tcttttttccg     780 aaggtaactg gcttcagcag agcgcagata ccaaatactg tccttctagt gtagccgtag     840
ttaggccacc acttcaagaa ctctgtagca ccgcctacat acctcgctct gctaatcctg     900
ttaccagtgg ctgctgccag tggcgataag tcgtgtctta ccgggttgga ctcaagacga     960
tagttaccgg ataaggcgca gcggtcgggc tgaacggggg gttcgtgcac acagcccagc    1020
ttggagcgaa cgacctacac cgaactgaga tacctacagc gtgagctatg agaaagcgcc    1080
acgcttcccg aagggagaaa ggcggacagg tatccggtaa gcggcagggt cggaacagga    1140
gagcgcacga gggagcttcc aggggggaaac gcctggtatc tttatagtcc tgtcgggttt    1200
cgccacctct gacttgagcg tcgatttttg tgatgctcgt caggggggcg gagcctatgg    1260
aaaaacgcca gcaacgcggc cttttttacgg ttcctggcct tttgctggcc ttttgctcac    1320
atgttctttc ctgcgttatc ccctgattct gtggataacc gtattaccgc ctttgagtga    1380
gctgataccg ctcgccgcag ccgaacgacc gagcgcagcg agtcagtgag cgaggaagcg    1440
gaagagcgcc caatacgcaa accgcctctc cccgcgcgtt ggccgattca ttaatgcagc    1500
tggcacgaca ggtttcccga ctggaaagcg ggcagtgagc gcaacgcaat taatgtgagt    1560
tagctcactc attaggcacc ccaggcttta cactttatgc ttccggctcg tatgttgtgt    1620
ggaattgtga gcggataaca atttcacaca ggaaacagct atgaccatga ttacgccaga    1680
tttaattaag gccttaatta ggctgcgcgc tcgctcgctc actgaggccg cccgggcaaa    1740
gcccgggcgt cgggcgacct ttggtcgccc ggcctcagtg agcgagcgag cgcgcagaga    1800
gggagtggcc aactccatca ctaggggttc cttgtagtta atgattaacc cgccatgcta    1860
cttatctacg tagccatgct ctaggaagat cggaattcct gatctggcct ccgcgccggg    1920
ttttggcgcc tcccgcgggc gcccccctcc tcacggcgag cgctgccacg tcagacgaag    1980
ggcgcagcga gcgtcctgat ccttccgccc ggacgctcag gacagcggcc cgctgctcat    2040
aagactcggc cttagaaccc cagtatcagc agaaggacat tttaggacgg gacttgggtg    2100
actctagggc actggttttc tttccagaga gcggaacagg cgaggaaaag tagtcccttc    2160
tcggcgattc tgcggaggga tctccgtggg gcggtgaacg ccgatgatta tataaggacg    2220
cgccgggtgt ggcacagcta gttccgtcgc agccgggatt tgggtcgcgg ttcttgtttg    2280
tggatcgctg tgatcgtcac ttggtgagta gcgggctgct gggctggccg gggctttcgt    2340
```

-continued

```
ggccgccggg ccgctcggtg ggacggaagc gtgtggagag accgccaagg gctgtagtct    2400
gggtccgcga gcaaggttgc cctgaactgg gggttggggg gagcgcagca aaatggcggc    2460
tgttcccgag tcttgaatgg aagacgcttg tgaggcgggc tgtgaggtcg ttgaaacaag    2520 gtgggggggca tggtgggcgg caagaaccca aggtcttgag gccttcgcta atgcgggaaa    2580
gctcttattc gggtgagatg ggctggggca ccatctgggg accctgacgt gaagtttgtc    2640
actgactgga gaactcggtt tgtcgtctgt tgcgggggcg gcagttatgc ggtgccgttg    2700
ggcagtgcac ccgtaccttt gggagcgcgc gcctcgtcgt gtcgtgacgt cacccgttct    2760
gttggcttat aatgcagggt ggggccacct gccggtaggt gtgcggtagg cttttctccg    2820
tcgcaggacg cagggttcgg gcctagggta ggctctcctg aatcgacagg cgccggacct    2880
ctggtgaggg gagggataag tgaggcgtca gtttctttgg tcggttttat gtacctatct    2940
tcttaagtag ctgaagctcc ggttttgaac tatgcgctcg gggttggcga gtgtgttttg    3000
tgaagttttt taggcacctt ttgaaatgta atcatttggg tcaatatgta attttcagtg    3060
ttagactagt aaattgtccg ctaaattctg gccgtttttg gctttttttgt tagacgaagc    3120 ggccgcatta aacgccacca tgtcccgctt ggataagagc aaggtaataa atagcgcact    3180
cgaactcctc aacggcgtgg gcatcgaagg tctgactact cgaaagctcg cccagaaatt    3240
gggtgtggag caacctacat tgtattggca tgtcaagaac aaaagagccc tgctggacgc    3300
tcttcctatt gaaatgcttg acaggcatca cactcattcc tgcccccttg aggtcgagag    3360
ttggcaagat tttctccgaa acaatgcaaa gtcctaccgc tgcgcacttt tgtcccatag    3420
ggatggagca aaagtgcacc tgggaaccag gccaacagag aaacaatacg agactctcga    3480
gaaccagttg gctttcttgt gccaacaggg gttctcactt gaaaatgccc tttacgcact    3540
gtcagccgtt ggacatttta ccctgggggtg cgttcttgag gagcaagaac atcaggttgc    3600
taaggaggag cgcgagactc caaccactga ttctatgcca cctttgctga aacaggccat    3660
tgaacttttc gatagacagg gtgctgaacc tgcctttctc ttcgggttgg agctgattat    3720
ttgtggtctc gaaaaacagc tgaaatgtga aagtggtggc cctactacg ccctcgatga    3780 tttcgacctg gatatgctgc cagccgatgc acttgatgat ttcgatttgg atatgcttcc    3840
agccgacgca ctggacgact tcgatttgga catgcttccc ggttaaacta gtctagcaat    3900
caacctctgg attacaaaat ttgtgaaaga ttgactggta ttcttaacta tgttgctcct    3960
tttacgctat gtggatacgc tgctttaatg cctttgtatc atgctattgc ttcccgtatg    4020
gctttcattt tctcctcctt gtataaatcc tggttagttc ttgccacggc ggaactcatc    4080
gccgcctgcc ttgcccgctg ctggacaggg gctcggctgt tgggcactga caattccgtg    4140
gtgtttattt gtgaaatttg tgatgctatt gctttatttg taaccattct agctttattt    4200
gtgaaatttg tgatgctatt gctttatttg taaccattat aagctgcaat aaacaagtta    4260
acaacaacaa ttgcattcat tttatgtttc aggttcaggg ggagatgtgg gaggtttttt    4320
aaagcggggg atccaaattc ccgataagga tcttcctaga gcatggctac gtagataagt    4380
agcatggcgg gttaatcatt aactacaagg aaccccctagt gatggagttg gccactccct    4440
ctctgcgcgc tcgctcgctc actgaggccg ggcgaccaaa ggtcgcccga cgcccgggct    4500
ttgcccgggc ggcctcagtg agcgagcgag cgcgcagcct taattaacct aattcactgg    4560
ccgtcgtttt acaacgtcgt gactgggaaa accctggcgt tacccaactt aatcgccttg    4620
cagcacatcc cccttttcgcc agctggcgta atagcgaaga ggcccgcacc gatcgccctt    4680
```

-continued

```
cccaacagtt gcgcagcctg aatggcgaat gggacgcgcc ctgtagcggc gcattaagcg   4740
cggcgggtgt ggtggttacg cgcagcgtga ccgctacact tgccagcgcc ctagcgcccg   4800
ctcctttcgc tttcttccct tcctttctcg ccacgttcgc cggctttccc cgtcaagctc   4860
taaatcgggg gctcccttta gggttccgat ttagtgcttt acggcacctc gaccccaaaa   4920
aacttgatta gggtgatggt tcacgtagtg ggccatcgcc ctgatagacg gttttttcgcc  4980 ctttgacgtt ggagtccacg ttctttaata gtggactctt gttccaaact ggaacaacac   5040
tcaaccctat ctcggtctat tcttttgatt tataagggat tttgccgatt tcggcctatt   5100
ggttaaaaaa tgagctgatt taacaaaaat ttaacgcgaa ttttaacaaa atattaacgt   5160
ttataatttc aggtggcatc tttcggggaa atgtgcgcgg aacccctatt tgtttatttt   5220
tctaaataca ttcaaatatg tatccgctca tgagacaata accctgataa atgcttcaat   5280
aatattgaaa aaggaagagt atgagtattc aacatttccg tgtcgccctt attccctttt   5340
ttgcggcatt ttgccttcct gtttttgctc acccagaaac gctggtgaaa gtaaaagatg   5400
ctgaagatca gttgggtgca cgagtgggtt acatcgaact ggatctcaat agtggtaaga   5460
tccttgagag ttttcgcccc gaagaacgtt ttccaatgat gagcactttt aaagttctgc   5520
tatgtggcgc ggtattatcc cgtattgacg ccgggcaaga gcaactcggt cgccgcatac   5580
actattctca gaatgacttg gttgagtact caccagtcac agaaaagcat cttacggatg   5640
gcatgacagt aagagaa                                                  5657

<210> SEQ ID NO 18
<211> LENGTH: 1215
<212> TYPE: DNA
<213> ORGANISM: Artificial Sequence
<220> FEATURE:
<223> OTHER INFORMATION: Synthetic Polynucleotide

<400> SEQUENCE: 18
gatctggcct ccgcgccggg ttttggcgcc tcccgcgggc gcccccctcc tcacggcgag     60
cgctgccacg tcagacgaag ggcgcagcga gcgtcctgat ccttccgccc ggacgctcag    120
gacagcggcc cgctgctcat aagactcggc cttagaaccc cagtatcagc agaaggacat    180
tttaggacgg gacttgggtg actctagggc actggttttc tttccagaga gcggaacagg    240
cgaggaaaag tagtcccttc tcggcgattc tgcggaggga tctccgtggg gcggtgaacg    300
ccgatgatta tataaggacg cgccgggtgt ggcacagcta gttccgtcgc agccgggatt    360
tgggtcgcgg ttcttgtttg tggatcgctg tgatcgtcac ttggtgagta gcgggctgct    420
gggctggccg gggctttcgt ggccgccggg ccgctcggtg ggacggaagc gtgtggagag    480
accgccaagg gctgtagtct gggtccgcga gcaaggttgc cctgaactgg gggttggggg    540
gagcgcagca aaatggcggc tgttcccgag tcttgaatgg aagacgcttg tgaggcgggc    600
tgtgaggtcg ttgaaacaag gtggggggca tggtgggcgg caagaaccca aggtcttgag    660
gccttcgcta atgcgggaaa gctcttattc gggtgagatg gctggggca ccatctgggg    720 accctgacgt gaagtttgtc actgactgga gaactcggtt tgtcgtctgt tgcggggggcg   780 gcagttatgc ggtgccgttg ggcagtgcac ccgtaccttt gggagcgcgc gcctcgtcgt    840
gtcgtgacgt cacccgttct gttggcttat aatgcagggt ggggccacct gccggtaggt    900
gtgcggtagg ctttttctcc gtcgcaggacg caggttcgg gcctagggta ggctctcctg    960
aatcgacagc gcgccggacct ctggtgaggg gaggggataag tgaggcgtca gtttctttgg  1020
tcggttttat gtacctatct tcttaagtag ctgaagctcc ggttttgaac tatgcgctcg   1080
```

-continued

```
gggttggcga gtgtgttttg tgaagttttt taggcacctt ttgaaatgta atcatttggg      1140
tcaatatgta attttcagtg ttagactagt aaattgtccg ctaaattctg gccgtttttg      1200
gcttttttgt tagac                                                       1215

<210> SEQ ID NO 19
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 19
tccctatcag tgatagaga                                                     19

<210> SEQ ID NO 20
<211> LENGTH: 68
<212> TYPE: DNA
<213> ORGANISM: Artificial Sequence
<220> FEATURE:
<223> OTHER INFORMATION: Synthetic Polynucleotide

<400> SEQUENCE: 20
gctttaggcg tgtacggtgg gcgcctataa aagcagagct cgtttagtga accgtcagat       60
cgcctgga                                                                 68

<210> SEQ ID NO 21
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 21
aatcaacctc tggattacaa aatttgtgaa agattgactg gtattcttaa ctatgttgct        60
ccttttacgc tatgtggata cgctgcttta atgcctttgt atcatgctat tgcttcccgt       120
atggctttca ttttctcctc cttgtataaa tcctggttag ttcttgccac ggcggaactc       180
atcgccgcct gccttgcccg ctgctggaca ggggctcggc tgttgggcac tgacaattcc       240
gtggtgtt                                                                248

<210> SEQ ID NO 22
<211> LENGTH: 141
<212> TYPE: DNA
<213> ORGANISM: Artificial Sequence
<220> FEATURE:
<223> OTHER INFORMATION: Synthetic Polynucleotide

<400> SEQUENCE: 22
ccttaattag gctgcgcgct cgctcgctca ctgaggccgc ccgggcaaag cccgggcgtc        60
gggcgacctt tggtcgcccg gcctcagtga gcgagcgagc gcgcagagag ggagtggcca       120
actccatcac tagggggttcc t                                                141

<210> SEQ ID NO 23
<211> LENGTH: 438
<212> TYPE: DNA
<213> ORGANISM: Artificial Sequence
<220> FEATURE:
<223> OTHER INFORMATION: Synthetic Polynucleotide

<400> SEQUENCE: 23
```

-continued

```
aattcgtaca cgcctacctc gacccatcaa gtgccacctg acgtctccct atcagtgata      60
gagaagtcga cacgtctcga gctccctatc agtgatagag aaggtacgtc tagaacgtct     120
ccctatcagt gatagagaag tcgacacgtc tcgagctccc tatcagtgat agagaaggta     180
cgtctagaac gtctccctat cagtgataga gaagtcgaca cgtctcgagc tccctatcag     240
tgatagagaa ggtacgtcta gaacgtctcc ctatcagtga tagagaagtc gacacgtctc     300
gagctcccta tcagtgatag agaaggtacc cctatataa gcagagctcg tttagtgaac     360
cgtcagatcg cctggagacg ccatccacgc tgttttgacc tccatagaag acaccgggac     420
cgatccagcc tggatcgc                                                    438

<210> SEQ ID NO 24
<211> LENGTH: 315
<212> TYPE: DNA
<213> ORGANISM: Artificial Sequence
<220> FEATURE:
<223> OTHER INFORMATION: Synthetic Polynucleotide

<400> SEQUENCE: 24
gagtttactc cctatcagtg atagagaacg tatgtcgagt ttactcccta tcagtgatag      60
agaacgatgt cgagtttact ccctatcagt gatagagaac gtatgtcgag tttactccct     120
atcagtgata gagaacgtat gtcgagttta ctccctatca gtgatagaga acgtatgtcg     180
agtttatccc tatcagtgat agagaacgta tgtcgagttt actccctatc agtgatagag     240
aacgtatgtc gaggtaggcg tgtacggtgg gaggcctata taagcagagc tcgtttagtg     300
aaccgtcaga tcgcc                                                      315

<210> SEQ ID NO 25
<211> LENGTH: 618
<212> TYPE: DNA
<213> ORGANISM: Artificial Sequence
<220> FEATURE:
<223> OTHER INFORMATION: Synthetic Polynucleotide

<400> SEQUENCE: 25
atggctagat tagataaaag taaagtgatt aacagcgcat tagagctgct taatgaggtc      60
ggaatcgaag gtttaacaac ccgtaaactc gcccagaagc taggtgtaga gcagcctaca     120
ttgtattggc atgtaaaaaa taagcgggct ttgctcgacg ccttagccat tgagatgtta     180
gataggcacc atactcactt ttgccctta gaaggggaaa gctggcaaga ttttttacgt     240
aataacgcta aaagttttag atgtgcttta ctaagtcatc gcgatggagc aaaagtacat     300
ttaggtacac ggcctacaga aaaacagtat gaaactctcg aaaatcaatt agcctttta     360 tgccaacaag gttttcact agagaatgca ttatatgcac tcagcgctgt ggggcatttt     420
actttaggtt gcgtattgga agatcaagag catcaagtcg ctaaagaaga aagggaaaca     480
cctactactg atagtatgcc gccattatta cgacaagcta tcgaattatt tgatcaccaa     540
ggtgcagagc cagccttctt attcggcctt gaattgatca tatgcggatt agaaaaacaa     600
cttaaatgtg aaagtggg                                                    618

<210> SEQ ID NO 26
<211> LENGTH: 206
<212> TYPE: PRT
<213> ORGANISM: Artificial Sequence
<220> FEATURE:
<223> OTHER INFORMATION: Synthetic Polypeptide

<400> SEQUENCE: 26
```

```
Met Ala Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
            165                 170                 175

Phe Asp His Gln Gly Ala Glu Pro Ala Phe Leu Phe Gly Leu Glu Leu
        180                 185                 190

Ile Ile Cys Gly Leu Glu Lys Gln Leu Lys Cys Glu Ser Gly
        195                 200                 205
```

```
<210> SEQ ID NO 27
<211> LENGTH: 1008
<212> TYPE: DNA
<213> ORGANISM: Artificial Sequence
<220> FEATURE:
<223> OTHER INFORMATION: Synthetic Polynucleotide

<400> SEQUENCE: 27
atggctagat tagataaaag taaagtgatt aacagcgcat tagagctgct taatgaggtc      60
ggaatcgaag gtttaacaac ccgtaaactc gcccagaagc taggtgtaga gcagcctaca     120
ttgtattggc atgtaaaaaa taagcgggct ttgctcgacg ccttagccat tgagatgtta     180
gataggcacc atactcactt ttgccctta gaaggggaaa gctggcaaga ttttttacgt      240
aataacgcta aaagttttag atgtgcttta ctaagtcatc gcgatggagc aaaagtacat     300
ttaggtacac ggcctacaga aaaacagtat gaaactctcg aaaatcaatt agccttttta     360
tgccaacaag gttttttcact agagaatgca ttatatgcac tcagcgctgt ggggcatttt    420
actttaggtt gcgtattgga agatcaagag catcaagtcg ctaaagaaga aagggaaaca     480
cctactactg atagtatgcc gccattatta cgacaagcta tcgaattatt tgatcaccaa     540
ggtgcagagc cagccttctt attcggcctt gaattgatca tatgcggatt agaaaaacaa     600
cttaaatgtg aaagtgggtc gccaaaaaag aagagaaagg tcgacggcgg tggtgctttg     660
tctcctcagc actctgctgt cactcaagga agtatcatca gaacaagga gggcatggat      720 gctaagtcac taactgcctg gtcccggaca ctggtgacct tcaaggatgt atttgtggac     780
ttcaccaggg aggagtggaa gctgctggac actgctcagc gatcgtgta cagaaatgtg      840 atgctggaga actataagaa cctggtttcc ttgggttatc agcttactaa gccagatgtg     900
```
atcctccggt tggagaaggg agaagagccc tggctggtgg agagagaaat tcaccaagag        960
acccatcctg attcagagac tgcatttgaa atcaaatcat cagtttaa                    1008

<210> SEQ ID NO 28
<211> LENGTH: 335
<212> TYPE: PRT
<213> ORGANISM: Artificial Sequence
<220> FEATURE:
<223> OTHER INFORMATION: Synthetic Polypeptide

<400> SEQUENCE: 28

Met Ala Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
            85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
            165                 170                 175

Phe Asp His Gln Gly Ala Glu Pro Ala Phe Leu Phe Gly Leu Glu Leu
        180                 185                 190

Ile Ile Cys Gly Leu Glu Lys Gln Leu Lys Cys Glu Ser Gly Ser Pro
        195                 200                 205

Lys Lys Lys Arg Lys Val Asp Gly Gly Gly Ala Leu Ser Pro Gln His
    210                 215                 220

Ser Ala Val Thr Gln Gly Ser Ile Ile Lys Asn Lys Glu Gly Met Asp
225                 230                 235                 240

Ala Lys Ser Leu Thr Ala Trp Ser Arg Thr Leu Val Thr Phe Lys Asp
            245                 250                 255

Val Phe Val Asp Phe Thr Arg Glu Glu Trp Lys Leu Leu Asp Thr Ala
            260                 265                 270

Gln Gln Ile Val Tyr Arg Asn Val Met Leu Glu Asn Tyr Lys Asn Leu
        275                 280                 285

Val Ser Leu Gly Tyr Gln Leu Thr Lys Pro Asp Val Ile Leu Arg Leu
    290                 295                 300

Glu Lys Gly Glu Glu Pro Trp Leu Val Glu Arg Glu Ile His Gln Glu
305                 310                 315                 320

Thr His Pro Asp Ser Glu Thr Ala Phe Glu Ile Lys Ser Ser Val
                325                 330                 335

```
<210> SEQ ID NO 29
<211> LENGTH: 977
<212> TYPE: DNA
<213> ORGANISM: Artificial Sequence
<220> FEATURE:
<223> OTHER INFORMATION: Synthetic Polynucleotide

<400> SEQUENCE: 29
accttgcttc ctagctgggc ctttccttct cctctataaa taccagctct ggtatttcgc      60
cttggcagct gttgctgcta gggagacggc tggcttgaca tgcatctcct gacaaaacac     120
aaacccgtgg tgtgagtggg tgtgggcggt gtgagtaggg ggatgaatca gagagggggc     180
gagggagaca ggggcgcagg agtcaggcaa aggcgatgcg ggggtgcgac tacacgcagt     240
tggaaacagt cgtcagaaga ttctggaaac tatcttgctg gctataaact tgagggaagc     300
agaaggccaa cattcctccc aagggaaact gaggctcaga gttaaaaccc aggtatcagt     360
gatatgcatg tgccccggcc agggtcactc tctgactaac cggtacctac cctacaggcc     420
tacctagaga ctcttttgaa aggatggtag agacctgtcc gggctttgcc cacagtcgtt     480
ggaaacctca gcattttcta ggcaacttgt gcgaataaaa cacttcgggg gtccttcttg     540
ttcattccaa taacctaaaa cctctcctcg gagaaaatag ggggcctcaa acaaacgaaa     600
ttctctagcc cgctttcccc aggataaggc aggcatccaa atggaaaaaa aggggccggc     660
cgggggtctc ctgtcagctc cttgccctgt gaaacccagc aggcctgcct gtcttctgtc     720
ctcttggggc tgtccagggg cgcaggcctc ttgcgggga gctggcctcc ccgcccctc      780 gcctgtggcc gcccttttcc tggcaggaca gagggatcct gcagctgtca ggggaggggc     840
gccggggggt gatgtcagga gggctacaaa tagtgcagac agctaagggg ctccgtcacc     900
catcttcaca tccactccag ccggctgccc gcccgctgcc tcctctgtgc gtccgcccag     960
ccagcctcgt ccacgcc                                                    977

<210> SEQ ID NO 30
<211> LENGTH: 5428
<212> TYPE: DNA
<213> ORGANISM: Artificial Sequence
<220> FEATURE:
<223> OTHER INFORMATION: Synthetic Polynucleotide

<400> SEQUENCE: 30
ttatgcagtg ctgccataac catgagtgat aacactgcgg ccaacttact tctgacaacg      60
atcggaggac cgaaggagct aaccgctttt ttgcacaaca tggggggatca tgtaactcgc     120 cttgatcgtt gggaaccgga gctgaatgaa gccataccaa acgacgagcg tgacaccacg     180
atgcctgtag taatggtaac aacgttgcgc aaactattaa ctggcgaact acttactcta     240
gcttcccggc aacaattaat agactggatg gaggcggata agttgcagg accacttctg      300 cgctcggccc ttccggctgg ctggtttatt gctgataaat ctggagccgg tgagcgtggg     360
tctcgcggta tcattgcagc actggggcca gatggtaagc cctcccgtat cgtagttatc     420
tacacgacgg ggagtcaggc aactatggat gaacgaaata gacagatcgc tgagataggt     480
gcctcactga ttaagcattg gtaactgtca gaccaagttt actcatatat actttagatt     540
gatttaaaac ttcattttta atttaaaagg atctaggtga agatccttt tgataatctc     600 atgaccaaaa tcccttaacg tgagttttcg ttccactgag cgtcagaccc cgtagaaaag     660
atcaaaggat cttcttgaga tcctttttt ctgcgcgtaa tctgctgctt gcaaacaaaa     720
aaaccaccgc taccagcggt ggtttgtttg ccggatcaag agctaccaac tcttttttccg     780
```

-continued

```
aaggtaactg gcttcagcag agcgcagata ccaaatactg tccttctagt gtagccgtag     840
ttaggccacc acttcaagaa ctctgtagca ccgcctacat acctcgctct gctaatcctg     900
ttaccagtgg ctgctgccag tggcgataag tcgtgtctta ccgggttgga ctcaagacga     960
tagttaccgg ataaggcgca gcggtcgggc tgaacggggg gttcgtgcac acagcccagc    1020
ttggagcgaa cgacctacac cgaactgaga tacctacagc gtgagctatg agaaagcgcc    1080
acgcttcccg aagggagaaa ggcggacagg tatccggtaa gcggcaggt cggaacagga    1140 gagcgcacga gggagcttcc aggggggaaac gcctggtatc tttatagtcc tgtcgggttt    1200
cgccacctct gacttgagcg tcgattttttg tgatgctcgt caggggggcg gagcctatgg    1260
aaaaacgcca gcaacgcggc cttttttacgg ttcctggcct tttgctggcc ttttgctcac    1320
atgttcttcc ctgcgttatc ccctgattct gtggataacc gtattaccgc ctttgagtga    1380
gctgataccg ctcgccgcag ccgaacgacc gagcgcagcg agtcagtgag cgaggaagcg    1440
gaagagcgcc caatacgcaa accgcctctc cccgcgcgtt ggccgattca ttaatgcagc    1500
tggcacgaca ggtttcccga ctggaaagcg ggcagtgagc gcaacgcaat taatgtgagt    1560
tagctcactc attaggcacc ccaggcttta cactttatgc ttccggctcg tatgttgtgt    1620
ggaattgtga gcggataaca atttcacaca ggaaacagct atgaccatga ttacgccaga    1680
tttaattaag gccttaatta ggctgcgcgc tcgctcgctc actgaggccg cccgggcaaa    1740
gcccgggcgt cgggcgacct ttggtcgccc ggcctcagtg agcgagcgag cgcgcagaga    1800
gggagtggcc aactccatca ctaggggttc cttgtagtta atgattaacc cgccatgcta    1860
cttatctacg tagccatgct ctaggaagat cggaattcct agatctacct tgcttcctag    1920
ctgggccttt ccttctcctc tataaatacc agctctggta tttcgccttg gcagctgttg    1980
ctgctaggga gacggctggc ttgacatgca tctcctgaca aaacacaaac ccgtggtgtg    2040
agtgggtgtg ggcggtgtga gtaggggat gaatcagaga ggggcgagg gagacagggg    2100 cgcaggagtc aggcaaaggc gatgcggggg tgcgactaca cgcagttgga aacagtcgtc    2160
agaagattct ggaaactatc ttgctggcta taaacttgag ggaagcagaa ggccaacatt    2220
cctcccaagg gaaactgagg ctcagagtta aaacccaggt atcagtgata tgcatgtgcc    2280
ccggccaggg tcactctctg actaaccggt acctacccta caggcctacc tagagactct    2340
tttgaaagga tggtagagac ctgtccgggc tttgcccaca gtcgttggaa acctcagcat    2400
tttctaggca acttgtgcga ataaaacact tcgggggtcc ttcttgttca ttccaataac    2460
ctaaaacctc tcctcggaga aaatagggggg cctcaaacaa acgaaattct ctagcccgct    2520
ttccccagga taaggcaggc atccaaatgg aaaaaaaggg gccggccggg ggtctcctgt    2580
cagctccttg ccctgtgaaa cccagcaggc ctgcctgtct tctgtcctct tggggctgtc    2640
caggggcgca ggcctcttgc gggggagctg gcctccccgc cccctcgcct gtggccgccc    2700
ttttcctggc aggacagagg gatcctgcag ctgtcagggg aggggcgccg ggggtgatg    2760 tcaggagggc tacaaatagt gcagacagct aaggggctcc gtcacccatc ttcacatcca    2820
ctccagccgg ctgcccgccc gctgcctcct ctgtgcgtcc gcccagccag cctcgtccac    2880
gccaagcttg cggccgcatt aaacgccacc atgtcccgct tggataagag caaggtaata    2940
aatagcgcac tcgaactcct caacggcgtg ggcatcgaag gtctgactac tcgaaagctc    3000
gcccagaaat tgggtgtgga gcaacctaca ttgtattggc atgtcaagaa caaaagagcc    3060
ctgctggacg ctcttcctat tgaaatgctt gacaggcatc acactcattc ctgccccctt    3120
gaggtcgaga gttggcaaga tttttctccga aacaatgcaa agtcctaccg ctgcgcactt    3180
```

```
ttgtcccata gggatggagc aaaagtgcac ctgggaacca ggccaacaga gaaacaatac   3240
gagactctcg agaaccagtt ggctttcttg tgccaacagg ggttctcact tgaaaatgcc   3300
ctttacgcac tgtcagccgt tggacatttt accctggggt gcgttcttga ggagcaagaa   3360
catcaggttg ctaaggagga gcgcgagact ccaaccactg attctatgcc acctttgctg   3420
aaacaggcca ttgaactttt cgatagacag ggtgctgaac ctgcctttct cttcgggttg   3480
gagctgatta tttgtggtct cgaaaaacag ctgaaatgtg aaagtggtgg ccctactgac   3540
gccctcgatg atttcgacct ggatatgctg ccagccgatg cacttgatga tttcgatttg   3600
gatatgcttc cagccgacgc actggacgac ttcgatttgg acatgcttcc cggttaaact   3660
agtctagcaa tcaacctctg gattacaaaa tttgtgaaag attgactggt attcttaact   3720
atgttgctcc ttttacgcta tgtggatacg ctgctttaat gcctttgtat catgctattg   3780
cttcccgtat ggctttcatt ttctcctcct tgtataaatc ctggttagtt cttgccacgg   3840
cggaactcat cgccgcctgc cttgcccgct gctggacagg ggctcggctg ttgggcactg   3900
acaattccgt ggtgtttatt tgtgaaattt gtgatgctat tgctttattt gtaaccattc   3960
tagctttatt tgtgaaattt gtgatgctat tgctttattt gtaaccatta taagctgcaa   4020
taaacaagtt aacaacaaca attgcattca ttttatgttt caggttcagg gggagatgtg   4080
ggaggttttt aaagcggggg gatccaaatt cccgataagg atcttcctag agcatggcta   4140
cgtagataag tagcatggcg ggttaatcat taactacaag gaacccctag tgatggagtt   4200
ggccactccc tctctgcgcg ctcgctcgct cactgaggcc gggcgaccaa aggtcgcccg   4260
acgcccgggc tttgcccggg cggcctcagt gagcgagcga gcgcgcagcc ttaattaacc   4320
taattcactg gccgtcgttt tacaacgtcg tgactgggaa aaccctggcg ttacccaact   4380
taatcgcctt gcagcacatc cccctttcgc cagctggcgt aatagcgaag aggcccgcac   4440
cgatcgccct tcccaacagt tgcgcagcct gaatggcgaa tgggacgcgc cctgtagcgg   4500
cgcattaagc gcggcgggtg tggtggttac gcgcagcgtg accgctacac ttgccagcgc   4560
cctagcgccc gctcctttcg ctttcttccc ttcctttctc gccacgttcg ccggctttcc   4620
ccgtcaagct ctaaatcggg ggctcccttt agggttccga tttagtgctt tacggcacct   4680
cgaccccaaa aaacttgatt agggtgatgg ttcacgtagt gggccatcgc cctgatagac   4740 ggttttttcgc cctttgacgt tggagtccac gttctttaat agtggactct tgttccaaac   4800
tggaacaaca ctcaacccta tctcggtcta ttcttttgat ttataaggga ttttgccgat   4860
ttcggcctat tggttaaaaa atgagctgat ttaacaaaaa tttaacgcga attttaacaa   4920
aatattaacg tttataattt caggtggcat ctttcgggga aatgtgcgcg gaacccctat   4980
ttgtttattt ttctaaatac attcaaatat gtatccgctc atgagacaat aaccctgata   5040
aatgcttcaa taatattgaa aaaggaagag tatgagtatt caacatttcc gtgtcgccct   5100
tattcccttt tttgcggcat tttgccttcc tgttttttgct cacccagaaa cgctggtgaa   5160
agtaaaagat gctgaagatc agttgggtgc acgagtgggt tacatcgaac tggatctcaa   5220
tagtggtaag atccttgaga gttttcgccc cgaagaacgt tttccaatga tgagcacttt   5280
taaagttctg ctatgtggcg cggtattatc ccgtattgac gccgggcaag agcaactcgg   5340
tcgccgcata cactattctc agaatgactt ggttgagtac tcaccagtca cagaaaagca   5400
tcttacggat ggcatgacag taagagaa                                       5428
```

<210> SEQ ID NO 31

<211> LENGTH: 5332
<212> TYPE: DNA
<213> ORGANISM: Artificial Sequence
<220> FEATURE:
<223> OTHER INFORMATION: Synthetic Polynucleotide

<400> SEQUENCE: 31

```
aaattgtaaa cgttaatatt ttgttaaaat tcgcgttaaa tttttgttaa atcagctcat        60
tttttaacca ataggccgaa atcggcaaaa tcccttataa atcaaaagaa tagcccgaga       120
tagggttgag tgttgttcca gtttggaaca agagtccact attaaagaac gtggactcca       180
acgtcaaagg gcgaaaaacc gtctatcagg gcgatggccc actacgtgaa ccatcaccca       240
aatcaagttt tttggggtcg aggtgccgta aagcactaaa tcggaaccct aaagggagcc       300
cccgatttag agcttgacgg ggaaagccgg cgaacgtggc gagaaaggaa gggaagaaag       360
cgaaaggagc gggcgctagg gcgctggcaa gtgtagcggt cacgctgcgc gtaaccacca       420
cacccgccgc gcttaatgcg ccgctacagg gcgcgtacta tggttgcttt gacgtatgcg       480
gtgtgaaata ccgcacagat gcgtaaggag aaaataccgc atcaggcgcc cctgcaggca       540
gctgcgcgct cgctcgctca ctgaggccgc ccgggcaaag cccgggcgtc gggcgacctt       600
tggtcgcccg gcctcagtga gcgagcgagc gcgcagagag ggagtggcca actccatcac       660 tagggggttcc tgcggccgct cggtccgcac gatctcaatt cggccattac ggccggatcc       720
ggctcgagga gcttggccca ttgcatacgt tgtatccata tcataatatg tacatttata       780
ttggctcatg tccaacatta ccgccatgtt gacattgatt attgactagt tattaatagt       840
aatcaattac ggggtcatta gttcatagcc catatatgga gttccgcgtt acataactta       900
cggtaaatgg cccgcctggc tgaccgccca acgacccccg cccattgacg tcaataatga       960
cgtatgttcc catagtaacg ccaataggga ctttccattg acgtcaatgg gtggagtatt      1020
tacgctaaac tgcccacttg gcagtacatc aagtgtatca tatgccaagt acgccccta      1080 ttgacgtcaa tgacggtaaa tggcccgcct ggcattatgc ccagtacatg accttatggg      1140
actttcctac ttggcagtac atctacgtat tagtcatcgc tattaccatg gtgatgcggt      1200
tttggcagta catcaatggg cgtggatagc ggtttgactc acggggattt ccaagtctcc      1260
accccattga cgtcaatggg agtttgtttt ggcaccaaaa tcaacgggac tttccaaaat      1320
gtcgtaacaa ctccgcccca ttgacgcaaa tgggcggtag cgtgtacgg tgggaggtct      1380 atataagcag agctcgttta gtgaaccgtc agatcgcctg gagacgccat ccacgctgtt      1440
ttgacctcca tagaagacac cgggaccgat ccagcctccg cggccccgaa ttcaccatgt      1500
ctagactgga caagagcaaa atcataaaca gcgctctgga attactcaat ggagtcggta      1560
tcgaaggcct gacgacaagg aaactcgctc aaaagctggg agttgagcag cctaccctgt      1620
actggcacgt gaagaacaag cgggccctgc tcgatgccct gccaatcgag atgctggaca      1680
ggcatcatac ccacagctgc cccctggaag gcgagtcatg gcaagacttt ctgcggaaca      1740
acgccaagtc ataccgctgt gctctcctct cacatcgcga cggggctaaa gtgcatctcg      1800
gcacccgccc aacagagaaa cagtacgaaa ccctggaaaa tcagctcgcg ttcctgtgtc      1860
agcaaggctt ctccctggag aacgcactgt acgctctgtc cgccgtgggc cactttacac      1920
tgggctgcgt attggaggaa caggagcatc aagtagcaaa agaggaaaga gagacaccta      1980
ccaccgattc tatgcccca cttctgaagc aagcaattga gctgttcgac cggcagggag      2040
ccgaacctgc cttccttttt ggcctggaac taatcatatg tggcctggag aaacagctaa      2100
agtgcgaaag cggcgggccg accgacgccc ttgacgattt tgacttagac atgctcccag      2160
```

```
ccgatgccct tgacgacttt gaccttgata tgctgcctgc tgacgctctt gacgattttg   2220
accttgacat gctccccggg taactaagta aggatcatct taattaaatc gataaggatc   2280
tggccgcctc ggcctaatca acctctggat tacaaaattt gtgaaagatt gactggtatt   2340
cttaactatg ttgctccttt tacgctatgt ggatacgctg ctttaatgcc tttgtatcat   2400
gctattgctt cccgtatggc tttcattttc tcctccttgt ataaatcctg gttgctgtct   2460
ctttatgagg agttgtggcc cgttgtcagg caacgtggcg tggtgtgcac tgtgtttgct   2520
gacgcaaccc ccactggttg gggcattgcc accacctgtc agctcctttc cgggactttc   2580
gctttccccc tccctattgc cacggcggaa ctcatcgccg cctgccttgc ccgctgctgg   2640
acaggggctc ggctgttggg cactgacaat tccgtggtgt tgtcggggaa atcatcgtcc   2700
tttccttggc tgctcgcctg tgttgccacc tggattctgc gcgggacgtc cttctgctac   2760
gtcccttcgg ccctcaatcc agcggacctt ccttcccgcg gcctgctgcc ggctctgcgg   2820
cctcttccgc gtcttcgcct tcgccctcag acgagtcgga tctccctttg ggccgcctcc   2880
ccgccagaca tgataagata cattgatgag tttggacaaa ccacaactag aatgcagtga   2940
aaaaaatgct ttatttgtga aatttgtgat gctattgctt tatttgtaac cattataagc   3000
tgcaataaac aagttaacaa caacaattgc attcatttta tgtttcaggt tcaggggggag   3060 atgtgggagg tttttaaag caagtaaaac ctctacaaat gtggtaacta gcgcgtgcgg   3120
ccgcaggaac ccctagtgat ggagttggcc actccctctc tgcgcgctcg ctcgctcact   3180
gaggccgggc gaccaaaggt cgcccgacgc ccgggctttg cccgggcggc ctcagtgagc   3240
gagcgagcgc gcagctgcct gcaggacatg tgagcaaaag gccagcaaaa ggccaggaac   3300
cgtaaaaagg ccgcgttgct ggcgtttttc cataggctcc gcccccctga cgagcatcac   3360
aaaaatcgac gctcaagtca gaggtggcga aacccgacag gactataaag ataccaggcg   3420 tttcccctg gaagctccct cgtgcgctct cctgttccga ccctgccgct taccggatac   3480
ctgtccgcct ttctcccttc gggaagcgtg gcgctttctc atagctcacg ctgtaggtat   3540
ctcagttcgg tgtaggtcgt tcgctccaag ctgggctgtg tgcacgaacc ccccgttcag   3600
cccgaccgct gcgccttatc cggtaactat cgtcttgagt ccaacccggt aagacacgac   3660
ttatcgccac tggcagcagc cactggtaac aggattagca gagcgaggta tgtaggcggt   3720
gctacagagt tcttgaagtg gtggcctaac tacggctaca ctagaaggac agtatttggt   3780
atctgcgctc tgctgaagcc agttaccttc ggaaaaagag ttggtagctc ttgatccggc   3840
aaacaaacca ccgctggtag cggtggtttt tttgtttgca agcagcagat tacgcgcaga   3900
aaaaaaggat ctcaagaaga tcctttgatc ttttctacgg ggtctgacgc tcagtggaac   3960
gaaaactcac gttaagggat tttggtcatg agattatcaa aaaggatctt cacctagatc   4020 ctttttaaatt aaaaatgaag ttttaaatca atctaaagta tatatgagta aacttggtct   4080
gacagttacc aatgcttaat cagtgaggca cctatctcag cgatctgtct atttcgttca   4140
tccatagttg cctgactccc cgtcgtgtag ataactacga tacgggaggg cttaccatct   4200
ggccccagtg ctgcaatgat accgcgagac ccacgctcac cggctccaga tttatcagca   4260
ataaaccagc cagccggaag ggccgagcgc agaagtggtc ctgcaacttt atccgcctcc   4320
atccagtcta ttaattgttg ccgggaagct agagtaagta gttcgccagt taatagtttg   4380
cgcaacgttg ttgccattgc tacaggcatc gtggtgtcac gctcgtcgtt ggtatggct   4440 tcattcagct ccggttccca acgatcaagg cgagttacat gatcccccat gttgtgcaaa   4500
```

-continued

```
aaagcggtta gctccttcgg tcctccgatc gttgtcagaa gtaagttggc cgcagtgtta      4560
tcactcatgg ttatggcagc actgcataat tctcttactg tcatgccatc cgtaagatgc      4620
ttttctgtga ctggtgagta ctcaaccaag tcattctgag aatagtgtat gcggcgaccg      4680
agttgctctt gcccggcgtc aatacgggat aataccgcgc cacatagcag aactttaaaa      4740
gtgctcatca ttggaaaacg ttcttcgggg cgaaaactct caaggatctt accgctgttg      4800
agatccagtt cgatgtaacc cactcgtgca cccaactgat cttcagcatc ttttactttc      4860
accagcgttt ctgggtgagc aaaaacagga aggcaaaatg ccgcaaaaaa gggaataagg      4920
gcgacacgga aatgttgaat actcatactc ttcctttttc aatattattg aagcatttat      4980
cagggttatt gtctcatgag cggatacata tttgaatgta tttagaaaaa taaacaaata      5040 gggggttccgc gcacatttcc ccgaaaagtg ccacctgacg tctaagaaac cattattatc      5100
atgacattaa cctataaaaa taggcgtatc acgaggccct ttcgtctcgc gcgtttcggt      5160
gatgacggtg aaaacctctg acacatgcag ctcccggaga cggtcacagc ttgtctgtaa      5220
gcggatgccg ggagcagaca gcccgtcag ggcgcgtcag cgggtgttgg cgggtgtcgg      5280
ggctggctta actatgcggc atcagagcag attgtactga gagtgcacca ta              5332
```

<210> SEQ ID NO 32
<211> LENGTH: 5392
<212> TYPE: DNA
<213> ORGANISM: Artificial Sequence
<220> FEATURE:
<223> OTHER INFORMATION: Synthetic Polynucleotide

<400> SEQUENCE: 32

```
cctgcaggca gctgcgcgct cgctcgctca ctgaggccgc ccgggcaaag cccgggcgtc        60
gggcgacctt tggtcgcccg gcctcagtga gcgagcgagc gcgcagagag ggagtggcca       120
actccatcac taggggttcc tgcggccgca cgcgtggagc tagttattaa tagtaatcaa       180
ttacggggtc attagttcat agcccatata tggagttccg cgttacataa cttacggtaa       240
atggcccgcc tggctgaccg cccaacgacc cccgcccatt gacgtcaata atgacgtatg       300
ttcccatagt aacgtcaata gggactttcc attgacgtca atgggtggag tatttacggt       360
aaactgccca cttggcagta catcaagtgt atcatatgcc aagtacgccc cctattgacg       420
tcaatgacgg taaatggccc gcctggcatt atgcccagta catgacctta tgggactttc       480
ctacttggca gtacatctac gtattagtca tcgctattac catggtgatg cggttttggc       540
agtacatcaa tgggcgtgga tagcggtttg actcacgggg atttccaagt ctccacccca       600
ttgacgtcaa tgggagtttg ttttgcacca aaatcaacgg gactttccaa aatgtcgtaa       660
caactccgcc ccattgacgc aaatgggcgg taggcgtgta cggtgggagg tctatataag       720
cagagctcgt ttagtgaacc gtcagatcgc ctggagacgc catccacgct gttttgacct       780
ccatagaaga caccgggacc gatccagcct ccgcggattc gaatcccggc cgggaacggt       840
gcattggaac gcggattccc cgtgccaaga gtgacgtaag taccgcctat agagtctata       900
ggcccacaaa aaatgctttc ttcttttaat atactttttt gtttatctta tttctaatac       960
tttccctaat ctctttcttt cagggcaata atgatacaat gtatcatgcc tctttgcacc      1020
attctaaaga ataacagtga taatttctgg gttaaggcaa tagcaatatt ctgcatata       1080 aatatttctg catataaatt gtaactgatg taagaggttt catattgcta atagcagcta      1140
caatccagct accattctgc ttttatttta tggttgggat aaggctggat tattctgagt      1200
ccaagctagg cccttttgct aatcatgttc atacctctta tcttcctccc acagctcctg      1260
```

```
ggcaacgtgc tggtctgtgt gctggcccat cactttggca aagaattggg attcgaacat      1320
cgattgaatt catgtctaga ctggacaaga gcaaagtcat aaactctgct ctggaattac      1380
tcaatgaagt cggtatcgaa ggcctgacga caaggaaact cgctcaaaag ctgggagttg      1440
agcagcctac cctgtactgg cacgtgaaga acaagcgggc cctgctcgat gccctggcaa      1500
tcgagatgct ggacaggcat catacccact tctgccccct ggaaggcgag tcatggcaag      1560 acttctgcg gaacaacgcc aagtcattcc gctgtgctct cctctcacat cgcgacgggg       1620
ctaaagtgca tctcggcacc cgcccaacag agaaacagta cgaaaccctg gaaaatcagc      1680
tcgcgttcct gtgtcagcaa ggcttctccc tggagaacgc actgtacgct ctgtccgccg      1740
tgggccactt tacactgggc tgcgtattgg aggatcagga gcatcaagta gcaaaagagg      1800
aaagagagac acctaccacc gattctatgc ccccacttct gagacaagca attgagctgt      1860
tcgaccatca gggagccgaa cctgccttcc ttttcggcct ggaactaatc atatgtggcc      1920
tggagaaaca gctaaagtgc gaaagcggcg ggccggccga cgcccttgac gattttgact      1980
tagacatgct cccagccgat gcccttgacg actttgacct tgatatgctg cctgctgacg      2040
ctcttgacga tttttgacctt gacatgctcc ccggatgagg atcctctaga gtcgacctgc     2100
agaagcttgc ctcgagcagc gctgctcgag agatctacgg gtggcatccc tgtgacccct      2160
ccccagtgcc tctcctggcc ctggaagttg ccactccagt gcccaccagc cttgtcctaa      2220
taaaattaag ttgcatcatt ttgtctgact aggtgtcctt ctataatatt atggggtgga      2280
ggggggtggt atggagcaag gggcaagttg ggaagacaac ctgtagggcc tgcggggtct      2340
attgggaacc aagctggagt gcagtggcac aatcttggct cactgcaatc tccgcctcct      2400
gggttcaagc gattctcctg cctcagcctc ccgagttgtt gggattccag gcatgcatga      2460
ccaggctcag ctaatttttg tttttttggt agagacgggg tttcaccata ttggccaggc      2520
tggtctccaa ctcctaatct caggtgatct acccaccttg gcctcccaaa ttgctgggat      2580
tacaggcgtg aaccactgct cccttccctg tccttctgat tttgtaggta accacgtgcg      2640
gaccgagcgg ccgcaggaac ccctagtgat ggagttggcc actccctctc tgcgcgctcg      2700
ctcgctcact gaggccgggc gaccaaaggt cgcccgacgc ccgggctttg cccgggcggc      2760
ctcagtgagc gagcgagcgc gcagctgcct gcaggggcgc ctgatgcggt attttctcct      2820
tacgcatctg tgcggtattt cacaccgcat acgtcaaagc aaccatagta cgcgccctgt      2880
agcggcgcat taagcgcggc gggtgtggtg gttacgcgca gcgtgaccgc tacacttgcc      2940
agcgccctag cgcccgctcc tttcgctttc ttcccttcct ttctcgccac gttcgccggc      3000
tttccccgtc aagctctaaa tcgggggctc cctttagggt tccgatttag tgctttacgg      3060
cacctcgacc ccaaaaaact tgatttgggt gatggttcac gtagtgggcc atcgccctga      3120
tagacggttt ttcgcccttt gacgttggag tccacgttct ttaatagtgg actcttgttc      3180
caaactggaa caacactcaa ccctatctcg ggctattctt ttgatttata agggattttg      3240
ccgatttcgg cctattggtt aaaaaatgag ctgatttaac aaaaatttaa cgcgaatttt      3300
aacaaaatat taacgtttac aattttatgg tgcactctca gtacaatctg ctctgatgcc      3360
gcatagttaa gccagccccg acacccgcca acacccgctg acgcgccctg acgggcttgt      3420
ctgctcccgg catccgctta cagacaagct gtgaccgtct ccgggagctg catgtgtcag      3480
aggttttcac cgtcatcacc gaaacgcgcg agacgaaagg gcctcgtgat acgcctattt      3540
ttataggtta atgtcatgat aataatggtt tcttagacgt caggtggcac ttttcgggga     3600
```

```
aatgtgcgcg gaaccccctat ttgtttattt ttctaaatac attcaaatat gtatccgctc    3660
atgagacaat aaccctgata aatgcttcaa taatattgaa aaaggaagag tatgagtatt    3720
caacatttcc gtgtcgccct tattcccttt tttgcggcat tttgccttcc tgttttttgct   3780 cacccagaaa cgctggtgaa agtaaaagat gctgaagatc agttgggtgc acagagtgggt   3840 tacatcgaac tggatctcaa cagcggtaag atccttgaga gttttcgccc cgaagaacgt    3900
tttccaatga tgagcacttt taaagttctg ctatgtggcg cggtattatc ccgtattgac    3960
gccgggcaag agcaactcgg tcgccgcata cactattctc agaatgactt ggttgagtac    4020
tcaccagtca cagaaaagca tcttacggat ggcatgacag taagagaatt atgcagtgct    4080
gccataacca tgagtgataa cactgcggcc aacttacttc tgacaacgat cggaggaccg    4140
aaggagctaa ccgcttttttt gcacaacatg ggggatcatg taactcgcct tgatcgttgg   4200
gaaccggagc tgaatgaagc cataccaaac gacgagcgtg acaccacgat gcctgtagca    4260
atggcaacaa cgttgcgcaa actattaact ggcgaactac ttactctagc ttcccggcaa    4320
caattaatag actggatgga ggcggataaa gttgcaggac cacttctgcg ctcggccctt    4380
ccggctggct ggtttattgc tgataaatct ggagccggtg agcgtgggtc tcgcggtatc    4440
attgcagcac tggggccaga tggtaagccc tcccgtatcg tagttatcta cacgacgggg    4500
agtcaggcaa ctatggatga acgaaataga cagatcgctg agataggtgc ctcactgatt    4560
aagcattggt aactgtcaga ccaagtttac tcatatatac tttagattga tttaaaactt    4620
catttttaat ttaaaaggat ctaggtgaag atccttttttg ataatctcat gaccaaaatc    4680
ccttaacgtg agttttcgtt ccactgagcg tcagaccccg tagaaaagat caaaggatct    4740
tcttgagatc cttttttttct gcgcgtaatc tgctgcttgc aaacaaaaaa accaccgcta    4800
ccagcggtgg tttgtttgcc ggatcaagag ctaccaactc tttttccgaa ggtaactggc    4860
ttcagcagag cgcagatacc aaatactgtc cttctagtgt agccgtagtt aggccaccac    4920
ttcaagaact ctgtagcacc gcctacatac ctcgctctgc taatcctgtt accagtggct    4980
gctgccagtg gcgataagtc gtgtcttacc gggttggact caagacgata gttaccggat    5040
aaggcgcagc ggtcgggctg aacggggggt tcgtgcacac agcccagctt ggagcgaacg    5100
acctacaccg aactgagata cctacagcgt gagctatgag aaagcgccac gcttcccgaa    5160
gggagaaagg cggacaggta tccggtaagc ggcagggtcg aacaggaga gcgcacgagg     5220 gagcttccag ggggaaacgc ctggtatctt tatagtcctg tcgggtttcg ccacctctga    5280
cttgagcgtc gatttttgtg atgctcgtca gggggggcgga gcctatggaa aaacgccagc   5340
aacgcggcct ttttacggtt cctggccttt tgctggcctt ttgctcacat gt             5392
```

```
<210> SEQ ID NO 33
<211> LENGTH: 7732
<212> TYPE: DNA
<213> ORGANISM: Artificial Sequence
<220> FEATURE:
<223> OTHER INFORMATION: Synthetic Polynucleotide

<400> SEQUENCE: 33
```

```
ttatgcagtg ctgccataac catgagtgat aacactgcgg ccaacttact tctgacaacg     60
atcggaggac cgaaggagct aaccgcttttt ttgcacaaca tgggggatca tgtaactcgc    120
cttgatcgtt gggaaccgga gctgaatgaa gccataccaa acgacgagcg tgacaccacg    180
atgcctgtag taatggtaac aacgttgcgc aaactattaa ctggcgaact acttactcta    240
gcttcccggc aacaattaat agactggatg gaggcggata aagttgcagg accacttctg    300
```

-continued

```
cgctcggccc ttccggctgg ctggtttatt gctgataaat ctggagccgg tgagcgtggg      360
tctcgcggta tcattgcagc actggggcca gatggtaagc cctcccgtat cgtagttatc      420
tacacgacgg ggagtcaggc aactatggat gaacgaaata gacagatcgc tgagataggt      480
gcctcactga ttaagcattg gtaactgtca gaccaagttt actcatatat actttagatt      540
gatttaaaac ttcattttta atttaaaagg atctaggtga agatcctttt tgataatctc      600
atgaccaaaa tcccttaacg tgagttttcg ttccactgag cgtcagaccc cgtagaaaag      660
atcaaaggat cttcttgaga tccttttttt ctgcgcgtaa tctgctgctt gcaaacaaaa      720
aaaccaccgc taccagcggt ggtttgtttg ccggatcaag agctaccaac tctttttccg      780
aaggtaactg gcttcagcag agcgcagata ccaaatactg tccttctagt gtagccgtag      840
ttaggccacc acttcaagaa ctctgtagca ccgcctacat acctcgctct gctaatcctg      900
ttaccagtgg ctgctgccag tggcgataag tcgtgtctta ccgggttgga ctcaagacga      960
tagttaccgg ataaggcgca gcggtcgggc tgaacggggg gttcgtgcac acagcccagc     1020
ttggagcgaa cgacctacac cgaactgaga tacctacagc gtgagctatg agaaagcgcc     1080
acgcttcccg aagggagaaa ggcggacagg tatccggtaa gcggcagggt cggaacagga     1140
gagcgcacga gggagcttcc aggggggaaac gcctggtatc tttatagtcc tgtcgggttt     1200
cgccacctct gacttgagcg tcgattttt g tgatgctcgt cagggggggcg gagcctatgg     1260 aaaaacgcca gcaacgcggc cttttt acgg ttcctggcct tttgctggcc ttttgctcac     1320
atgttctttc ctgcgttatc ccctgattct gtggataacc gtattaccgc ctttgagtga     1380
gctgataccg ctcgccgcag ccgaacgacc gagcgcagcg agtcagtgag cgaggaagcg     1440
gaagagcgcc caatacgcaa accgcctctc cccgcgcgtt ggccgattca ttaatgcagc     1500
tggcacgaca ggtttcccga ctggaaagcg ggcagtgagc gcaacgcaat taatgtgagt     1560
tagctcactc attaggcacc ccaggcttta cactttatgc ttccggctcg tatgttgtgt     1620
ggaattgtga gcggataaca atttcacaca ggaaacagct atgaccatga ttacgccaga     1680
tttaattaag gccttaatta ggctgcgcgc tcgctcgctc actgaggccg cccgggcaaa     1740 gccc gggcgt cgggcgacct ttggtcgccc ggcctcagtg agcgagcgag cgcgcagaga     1800
gggagtggcc aactccatca ctaggggttc cttgtagtta atgattaacc cgccatgcta     1860
cttatctacg tagccatgct ctaggaagat cggaattcgt acacgcctac ctcgacccat     1920
caagtgccac ctgacgtctc cctatcagtg atagagaagt cgacacgtct cgagctccct     1980
atcagtgata gagaaggtac gtctagaacg tctccctatc agtgatagag aagtcgacac     2040
gtctcgagct ccctatcagt gatagagaag gtacgtctag aacgtctccc tatcagtgat     2100
agagaagtcg acacgtctcg agctccctat cagtgataga gaaggtacgt ctagaacgtc     2160
tccctatcag tgatagagaa gtcgacacgt ctcgagctcc ctatcagtga tagagaaggt     2220
accccctata taagcagagc tcgtttagtg aaccgtcaga tcgcctggag acgccatcca     2280
cgctgttttg acctccatag aagacaccgg gaccgatcca gcctggatcg cggccgcgcc     2340
accatggctg gacacctggc ttcagacttc gccttctcac ccccaccagg tgggggtgat     2400
gggtcagcag ggctggagcc gggctgggtg gatcctcgaa cctggctaag cttccaaggg     2460
cctccaggtg ggcctggaat cggaccaggc tcagaggtat tggggatctc cccatgtccg     2520
cccgcatacg agttctgcgg agggatggca tactgtggac ctcaggttgg actgggccta     2580
gtcccccaag ttggcgtgga gactttgcag cctgagggcc aggcaggagc acgagtggaa     2640
```

-continued

```
agcaactcag agggaacctc ctctgagccc tgtgccgacc gccccaatgc cgtgaagttg   2700
gagaaggtgg aaccaactcc cgaggagtcc caggacatga aagccctgca gaaggagcta   2760
gaacagtttg ccaagctgct gaagcagaag aggatcacct tggggtacac ccaggccgac   2820
gtggggctca ccctgggcgt tctctttgga aaggtgttca gccagaccac catctgtcgc   2880
ttcgaggcct tgcagctcag ccttaagaac atgtgtaagc tgcggcccct gctggagaag   2940
tgggtggagg aagccgacaa caatgagaac cttcaggaga tatgcaaatc ggagaccctg   3000
gtgcaggccc ggaagagaaa cgcgaactagc attgagaacc gtgtgaggtg gagtctggag   3060
accatgtttc tgaagtgccc gaagccctcc ctacagcaga tcactcacat cgccaatcag   3120
cttgggctag agaaggatgt ggttcgagta tggttctgta accggcgcca gaagggcaaa   3180
agatcaagta ttgagtattc ccaacgagaa gagtatgagg ctacagggac acctttccca   3240 ggggggggctg tatcctttcc tctgcccccca ggtccccact ttggcacccc aggctatgga   3300
agcccccact tcaccacact ctactcagtc cctttttcctg agggcgaggc ctttccctct   3360
gttcccgtca ctgctctggg ctctcccatg cattcaaacg ctagcggcag cggcgccacg   3420
aacttctctc tgttaaagca agcaggagat gttgaagaaa accccgggcc tgcatgcatg   3480
tataacatga tggagacgga gctgaagccg ccgggccccgc agcaagcttc ggggggcggc   3540
ggcggaggag gcaacgccac ggcggcggcg accggcggca accagaagaa cagcccggac   3600
cgcgtcaaga ggcccatgaa cgccttcatg gtatggtccc gggggcagcg gcgtaagatg   3660
gcccaggaga accccaagat gcacaactcg gagatcagca agcgcctggg cgcggagtgg   3720
aaacttttgt ccgagaccga gaagcggccg ttcatcgacg aggccaagcg gctgcgcgct   3780
ctgcacatga aggagcaccc ggattataaa taccggccgc ggcggaaaac caagacgctc   3840
atgaagaagg ataagtacac gcttcccgga ggcttgctgg cccccggcgg gaacagcatg   3900
gcgagcgggg ttggggtggg cgccggcctg ggtgcgggcg tgaaccagcg catggacagc   3960
tacgcgcaca tgaacggctg gagcaacggc agctacagca tgatgcagga gcagctgggc   4020 taccccgcagc acccgggcct caacgctcac ggcgcggcac agatgcaacc gatgcaccgc   4080
tacgacgtca gcgccctgca gtacaactcc atgaccagct cgcagaccta catgaacggc   4140
tcgcccacct acagcatgtc ctactcgcag cagggcaccc ccggtatggc gctgggctcc   4200
atgggctctg tggtcaagtc cgaggccagc tccagccccc ccgtggttac ctcttcctcc   4260
cactccaggg cgccctgcca ggccggggac ctccgggaca tgatcagcat gtacctcccc   4320
ggcgccgagg tgccggagcc cgctgcgccc agtagactgc acatggccca gcactaccag   4380
agcggcccgg tgcccggcac ggccattaac ggcacactgc ccctgtcgca catggcatgc   4440
ggctccggcg agggcagggg aagtcttcta acatgcgggg acgtggagga aaatcccggc   4500
ccactcgaga tgaggcagcc acctggcgag tctgacatgg ctgtcagcga cgctctgctc   4560
ccgtccttct ccacgttcgc gtccggcccg cgggaagggg agaagacact gcgtccagca   4620
ggtgccccga ctaaccgttg gcgtgaggaa ctctctcaca tgaagcgact tccccccactt   4680 cccggccgcc cctacgacct ggcggcgacg gtggccacag acctggagag tggcggagct   4740
ggtgcagctt gcagcagtaa caacccggcc ctcctagccc ggaggggagac cgaggagttc   4800 aacgacctcc tggacctaga ctttatcctt tccaactcgc taacccacca ggaatcggtg   4860
gccgccaccg tgaccacctc ggcgtcagct tcatcctcgt cttcccccagc gagcagcggc   4920 cctgccagcg cgccctccac ctgcagcttc agctatccga tccgggccgg gggtgacccg   4980
ggcgtggctg ccagcaacac aggtggaggg ctcctctaca gccgagaatc tgcgccacct   5040
```

-continued

```
cccacggccc ccttcaacct ggcggacatc aatgacgtga gcccctcggg cggcttcgtg    5100
gctgagctcc tgcggccgga gttggaccca gtatacattc cgccacagca gcctcagccg    5160
ccaggtggcg ggctgatggg caagtttgtg ctgaaggcgt ctctgaccac ccctggcagc    5220
gagtacagca gcccttcggt catcagtgtt agcaaaggaa gcccagacgg cagccacccc    5280
gtggtagtgg cgccctacag cggtggcccg ccgcgcatgt gccccaagat taagcaagag    5340
gcggtcccgt cctgcacggt cagccggtcc ctagaggccc atttgagcgc tggaccccag    5400
ctcagcaacg gccaccggcc caacacacac gacttccccc tggggcggca gctccccacc    5460
aggactaccc ctacactgag tcccgaggaa ctgctgaaca gcagggactg tcaccctggc    5520
ctgcctcttc ccccaggatt ccatccccat ccggggccca actaccctcc tttcctgcca    5580
gaccagatgc agtcacaagt cccctctctc cattatcaag agctcatgcc accgggttcc    5640
tgcctgccag aggagcccaa gccaaagagg ggaagaaggt cgtggccccg gaaaagaaca    5700
gccacccaca cttgtgacta tgcaggctgt ggcaaaacct ataccaagag ttctcatctc    5760
aaggcacacc tgcgaactca cacaggcgag aaaccttacc actgtgactg ggacggctgt    5820
gggtggaaat tcgcccgctc cgatgaactg accaggcact accgcaaaca cacagggcac    5880
cggccctttc agtgccagaa gtgcgacagg gccttttcca ggtcggacca ccttgcctta    5940
cacatgaaga ggcactaaat gactagtcta gcaatcaacc tctggattac aaaatttgtg    6000
aaagattgac tggtattctt aactatgttg ctccttttac gctatgtgga tacgctgctt    6060
taatgccttt gtatcatgct attgcttccc gtatggcttt cattttctcc tccttgtata    6120
aatcctggtt agttcttgcc acggcggaac tcatcgccgc ctgccttgcc cgctgctgga    6180
caggggctcg gctgttgggc actgacaatt ccgtggtgtt tatttgtgaa atttgtgatg    6240
ctattgcttt atttgtaacc attctagctt tatttgtgaa atttgtgatg ctattgcttt    6300
atttgtaacc attataagct gcaataaaca agttaacaac aacaattgca ttcattttat    6360
gtttcaggtt cagggggaga tgtgggaggt tttttaaagc gggggatcca aattcccgat    6420
aaggatcttc ctagagcatg gctacgtaga taagtagcat ggcgggttaa tcattaacta    6480
caaggaaccc ctagtgatgg agttggccac tccctctctg cgcgctcgct cgctcactga    6540
ggccgggcga ccaaaggtcg cccgacgccc gggctttgcc cgggcggcct cagtgagcga    6600
gcgagcgcgc agccttaatt aacctaattc actggccgtc gttttacaac gtcgtgactg    6660
ggaaaaccct ggcgttaccc aacttaatcg ccttgcagca catccccctt cgccagctg     6720 gcgtaatagc gaagaggccc gcaccgatcg cccttcccaa cagttgcgca gcctgaatgg    6780
cgaatgggac gcgccctgta gcggcgcatt aagcgcggcg ggtgtggtgg ttacgcgcag    6840
cgtgaccgct acacttgcca gcgccctagc gcccgctcct ttcgctttct cccttccctt    6900
tctcgccacg ttcgccggct ttccccgtca gctctaaat cggggggctcc ctttagggtt    6960 ccgatttagt gctttacggc acctcgaccc caaaaaactt gattagggtg atggttcacg    7020
tagtgggcca tcgccctgat agacggtttt tcgccctttg acgttggagt ccacgttctt    7080
taatagtgga ctcttgttcc aaactggaac aacactcaac cctatctcgg tctattcttt    7140
tgatttataa gggattttgc cgatttcggc ctattggtta aaaaatgagc tgatttaaca    7200
aaaatttaac gcgaatttta acaaaatatt aacgtttata atttcaggtg gcatctttcg    7260
gggaaatgtg cgcggaaccc ctatttgttt attttttctaa atacattcaa atatgtatcc    7320
gctcatgaga caataaccct gataaatgct tcaataatat tgaaaaagga agagtatgag    7380
```

-continued

```
tattcaacat ttccgtgtcg cccttattcc cttttttgcg gcattttgcc ttcctgtttt      7440
tgctcaccca gaaacgctgg tgaaagtaaa agatgctgaa gatcagttgg gtgcacgagt      7500
gggttacatc gaactggatc tcaatagtgg taagatcctt gagagttttc gccccgaaga      7560
acgtttccca atgatgagca cttttaaagt tctgctatgt ggcgcggtat tatcccgtat      7620
tgacgccggg caagagcaac tcggtcgccg catacactat tctcagaatg acttggttga      7680
gtactcacca gtcacagaaa agcatcttac ggatggcatg acagtaagag aa              7732
```

```
<210> SEQ ID NO 34
<211> LENGTH: 186
<212> TYPE: DNA
<213> ORGANISM: Artificial Sequence
<220> FEATURE:
<223> OTHER INFORMATION: Synthetic Polynucleotide

<400> SEQUENCE: 34
gaggccagcg gttccggacg ggctgacgca ttggacgatt ttgatctgga tatgctggga      60
agtgacgccc tcgatgattt tgaccttgac atgcttggtt cggatgccct tgatgacttt     120
gacctcgaca tgctcggcag tgacgccctt gatgatttcg acctggacat gctgattaac     180
tctaga                                                                 186
```

```
<210> SEQ ID NO 35
<211> LENGTH: 783
<212> TYPE: DNA
<213> ORGANISM: Artificial Sequence
<220> FEATURE:
<223> OTHER INFORMATION: Synthetic Polynucleotide

<400> SEQUENCE: 35
agccagtacc tgcccgacac cgacgaccgg caccggatcg aggaaaagcg gaagcggacc      60
tacgagacat tcaagagcat catgaagaag tccccccttca gcggccccac cgaccctaga    120
cctccaccta gaagaatcgc cgtgcccagc agatccagcg ccagcgtgcc aaaacctgcc     180
ccccagcctt accccttcac cagcagcctg agcaccatca actacgacga gttccctacc     240
atggtgttcc ccagcggcca gatctctcag gcctctgctc tggctccagc ccctcctcag     300
gtgctgcctc aggctcctgc tcctgcacca gctccagcca tggtgtctgc actggctcag     360
gcaccagcac ccgtgcctgt gctggctcct ggacctccac aggctgtggc tccaccagcc     420
cctaaaccta cacaggccgg cgagggcaca ctgtctgaag ctctgctgca gctgcagttc     480
gacgacgagg atctgggagc cctgctggga aacagcaccg atcctgccgt gttcaccgac     540
ctggccagcg tggacaacag cgagttccag cagctgctga accagggcat ccctgtggcc     600
cctcacacca ccgagcccat gctgatggaa taccccgagg ccatcacccg gctcgtgaca     660
ggcgctcaga ggcctcctga tccagctcct gcccctctgg gagcaccagg cctgcctaat     720
ggactgctgt ctggcgacga ggacttcagc tctatcgccg atatggattt ctcagccttg     780
ctg                                                                    783
```

```
<210> SEQ ID NO 36
<211> LENGTH: 570
<212> TYPE: DNA
<213> ORGANISM: Artificial Sequence
<220> FEATURE:
<223> OTHER INFORMATION: Synthetic Polynucleotide

<400> SEQUENCE: 36
cgggattcca gggaagggat gtttttgccg aagcctgagg ccggctccgc tattagtgac      60
```

-continued

```
gtgtttgagg ccgcgaggt gtgccagcca aaacgaatcc ggccatttca tcctccagga      120
agtccatggg ccaaccgccc actccccgcc agcctcgcac caacaccaac cggtccagta      180
catgagccag tcgggtcact gaccccggca ccagtccctc agccactgga tccagcgccc      240
gcagtgactc ccgaggccag tcacctgttg gaggatcccg atgaagagac gagccaggct      300
gtcaaagccc ttcgggagat ggccgatact gtgattcccc agaaggaaga ggctgcaatc      360
tgtggccaaa tggaccttc ccatccgccc ccaaggggcc atctggatga gctgacaacc      420
acacttgagt ccatgaccga ggatctgaac ctggactcac ccctgacccc ggaattgaac      480
gagattctgg ataccttcct gaacgacgag tgcctcttgc atgccatgca tatcagcaca      540
ggactgtcca tcttcgacac atctctgttt                                      570
```

<210> SEQ ID NO 37
<211> LENGTH: 1416
<212> TYPE: DNA
<213> ORGANISM: Artificial Sequence
<220> FEATURE:
<223> OTHER INFORMATION: Synthetic Polynucleotide

<400> SEQUENCE: 37

```
gcttcaaact ttactcagtt cgtgctcgtg dacaatggtg ggacagggga tgtgacagtg       60
gctccttcta atttcgctaa tggggtggca gagtggatca gctccaactc acggagccag      120
gcctacaagg tgacatgcag cgtcaggcag tctagtgccc agaagagaaa gtataccatc      180
aaggtggagg tccccaaagt ggctacccag acagtgggcg gagtcgaact gcctgtcgcc      240
gcttggaggt cctacctgaa catggagctc actatcccaa ttttcgctac caattctgac      300
tgtgaactca tcgtgaaggc aatgcagggg ctcctcaaag acggtaatcc tatcccttcc      360
gccatcgccg ctaactcagg tatctacagc gctggaggag gtggaagcgg aggaggagga      420
agcggaggag gaggtagcgg acctaagaaa aagaggaagg tggcggccgc tggatcccct      480
tcagggcaga tcagcaacca ggccctggct ctggcccta gctccgctcc agtgctggcc      540
cagactatgg tgccctctag tgctatggtg cctctggccc agccacctgc tccagcccct      600
gtgctgaccc caggaccacc ccagtcactg agcgctccag tgcccaagtc tacacaggcc      660
ggcgagggga ctctgagtga agctctgctg cacctgcagt tcgacgctga tgaggacctg      720
ggagctctgc tggggaacag caccgatccc ggagtgttca cagatctggc ctccgtggac      780
aactctgagt ttcagcagct gctgaatcag ggcgtgtcca tgtctcatag tacagccgaa      840
ccaatgctga tggagtaccc cgaagccatt acccggctgg tgaccggcag ccagcggccc      900
cccgaccccg ctccaactcc cctgggaacc agcggcctgc ctaatgggct gtccggagat      960
gaagacttct caagcatcgc tgatatggac tttagtgccc tgctgtcaca gatttcctct     1020
agtgggcagg gaggagtgg aagcggcttc agcgtggaca ccagtgccct gctggacctg     1080 ttcagccct cggtgaccgt gcccgacatg agcctgcctg accttgacag cagcctggcc     1140
agtatccaag agctcctgtc tccccaggag ccccccaggc ctcccgaggc agagaacagc     1200
agcccggatt cagggaagca gctggtgcac tacacagcgc agccgctgtt cctgctggac     1260
cccggctccg tggacaccgg gagcaacgac ctgccggtgc tgtttgagct gggagagggc     1320
tcctacttct ccgaagggga cggcttcgcc gaggacccca ccatctccct gctgacaggc     1380
tcggagcctc ccaaagccaa ggaccccact gtctcc                               1416
```

<210> SEQ ID NO 38

-continued

<211> LENGTH: 5657
<212> TYPE: DNA
<213> ORGANISM: Artificial Sequence
<220> FEATURE:
<223> OTHER INFORMATION: Synthetic Polynucleotide

<400> SEQUENCE: 38

```
ttctcttact gtcatgccat ccgtaagatg cttttctgtg actggtgagt actcaaccaa         60
gtcattctga gaatagtgta tgcggcgacc gagttgctct tgcccggcgt caatacggga        120
taataccgcg ccacatagca gaactttaaa agtgctcatc attggaaaac gttcttcggg        180
gcgaaaactc tcaaggatct taccactatt gagatccagt tcgatgtaac ccactcgtgc        240
acccaactga tcttcagcat cttttacttt caccagcgtt tctgggtgag caaaaacagg        300
aaggcaaaat gccgcaaaaa agggaataag ggcgacacgg aaatgttgaa tactcatact        360
cttccttttt caatattatt gaagcattta tcagggttat tgtctcatga gcggatacat        420
atttgaatgt atttagaaaa ataaacaaat aggggttccg cgcacatttc cccgaaagat        480
gccacctgaa attataaacg ttaatatttt gttaaaattc gcgttaaatt tttgttaaat        540
cagctcattt tttaaccaat aggccgaaat cggcaaaatc ccttataaat caaaagaata        600
gaccgagata gggttgagtg ttgttccagt ttggaacaag agtccactat taaagaacgt        660
ggactccaac gtcaaagggc gaaaaaccgt ctatcagggc gatggcccac tacgtgaacc        720
atcaccctaa tcaagttttt tggggtcgag gtgccgtaaa gcactaaatc ggaaccctaa        780
agggagcccc cgatttagag cttgacgggg aaagccggcg aacgtggcga gaaaggaagg        840
gaagaaagcg aaaggagcgg cgctagggc gctggcaagt gtagcggtca cgctgcgcgt         900
aaccaccaca cccgccgcgc ttaatgcgcc gctacagggc gcgtcccatt cgccattcag        960
gctgcgcaac tgttgggaag ggcgatcggt gcgggcctct tcgctattac gccagctggc       1020
gaaaggggga tgtgctgcaa ggcgattaag ttgggtaacg ccagggtttt cccagtcacg       1080
acgttgtaaa acgacggcca gtgaattagg ttaattaagg ctgcgcgctc gctcgctcac       1140
tgaggccgcc cgggcaaagc ccgggcgtcg ggcgaccttt ggtcgcccgg cctcagtgag       1200
cgagcgagcg cgcagagagg gagtggccaa ctccatcact aggggttcct tgtagttaat       1260
gattaacccg ccatgctact tatctacgta gccatgctct aggaagatcc ttatcgggaa       1320
tttggatccc ccgctttaaa aaacctccca catctccccc tgaacctgaa acataaaatg       1380
aatgcaattg ttgttgttaa cttgtttatt gcagcttata atggttacaa ataaagcaat       1440
agcatcacaa atttcacaaa taaagctaga atggttacaa ataaagcaat agcatcacaa       1500
atttcacaaa taaacaccac ggaattgtca gtgcccaaca gccgagcccc tgtccagcag       1560
cgggcaaggc aggcggcgat gagttccgcc gtggcaagaa ctaaccagga tttatacaag       1620
gaggagaaaa tgaaagccat acgggaagca atagcatgat acaaaggcat taaagcagcg       1680
tatccacata gcgtaaaagg agcaacatag ttaagaatac cagtcaatct ttcacaaatt       1740
ttgtaatcca gaggttgatt gctagactag tttaaccggg aagcatgtcc aaatcgaagt       1800
cgtccagtgc gtcggctgga agcatatcca aatcgaaatc atcaagtgca tcggctggca       1860
gcatatccag gtcgaaatca tcgagggcgt cagtagggcc accactttca catttcagct       1920 gttttttcgag accacaaata atcagctcca acccgaagag aaaggcaggt tcagcaccct       1980
gtctatcgaa aagttcaatg gcctgtttca gcaaaggtgg catagaatca gtggttggag       2040
tctcgcgctc ctccttagca acctgatgtt cttgctcctc aagaacgcac cccagggtaa       2100
aatgtccaac ggctgacagt gcgtaaaggg cattttcaag tgagaacccc tgttggcaca       2160
```

-continued

```
agaaagccaa ctggttctcg agagtctcgt attgtttctc tgttggcctg gttcccaggt    2220
gcacttttgc tccatcccta tgggacaaaa gtgcgcagcg gtaggacttt gcattgtttc    2280
ggagaaaatc ttgccaactc tcgacctcaa gggggcagga atgagtgtga tgcctgtcaa    2340
gcatttcaat aggaagagcg tccagcaggg ctcttttgtt cttgacatgc caatacaatg    2400
taggttgctc cacacccaat ttctgggcga gctttcgagt agtcagacct tcgatgccca    2460
cgccgttgag gagttcgagt gcgctattta ttaccttgct cttatccaag cgggacatgg    2520
tggcgtttaa tgcggccgct tcgtctaaca aaaaagccaa aaacggccag aatttagcgg    2580
acaatttact agtctaacac tgaaaattac atattgaccc aaatgattac atttcaaaag    2640
gtgcctaaaa aacttcacaa aacacactcg ccaaccccga gcgcatagtt caaaaccgga    2700
gcttcagcta cttaagaaga taggtacata aaaccgacca aagaaactga cgcctcactt    2760
atccctcccc tcaccagagg tccggcgcct gtcgattcag gagagcctac cctaggcccg    2820
aaccctgcgt cctgcgacgg agaaaagcct accgcacacc taccggcagg tggccccacc    2880
ctgcattata agccaacaga acgggtgacg tcacgacacg acgaggcgcg cgctcccaaa    2940
ggtacgggtg cactgcccaa cggcaccgca taactgccgc ccccgcaaca gacgacaaac    3000
cgagttctcc agtcagtgac aaacttcacg tcagggtccc cagatggtgc cccagcccat    3060
ctcacccgaa taagagcttt cccgcattag cgaaggcctc aagaccttgg gttcttgccg    3120
cccaccatgc cccccacctt gtttcaacga cctcacagcc cgcctcacaa gcgtcttcca    3180
ttcaagactc gggaacagcc gccattttgc tgcgctcccc ccaaccccca gttcagggca    3240
accttgctcg cggacccaga ctacagccct tggcggtctc tccacacgct tccgtcccac    3300
cgagcggccc ggcggccacg aaagccccgg ccagcccagc agcccgctac tcaccaagtg    3360
acgatcacag cgatccacaa acaagaaccg cgacccaaat cccggctgcg acggaactag    3420
ctgtgccaca cccggcgcgt ccttatataa tcatcggcgt tcaccgcccc acggagatcc    3480
ctccgcagaa tcgccgagaa gggactactt ttcctcgcct gttccgctct ctggaaagaa    3540
aaccagtgcc ctagagtcac ccaagtcccg tcctaaaatg tccttctgct gatactgggg    3600
ttctaaggcc gagtcttatg agcagcgggc cgctgtcctg agcgtccggg cggaaggatc    3660
aggacgctcg ctgcgcccctt cgtctgacgt ggcagcgctc gccgtgagga gggggggcgcc    3720 cgcgggaggc gccaaaaccc ggcgcggagg ccagatcagg aattccgatc ttcctagagc    3780
atggctacgt agataagtag catggcgggt taatcattaa ctacaaggaa cccctagtga    3840
tggagttggc cactccctct ctgcgcgctc gctcgctcac tgaggccggg cgaccaaagg    3900
tcgcccgacg cccgggcttt gcccgggcgg cctcagtgag cgagcgagcg cgcagcctaa    3960
ttaaggcctt aattaaatct ggcgtaatca tggtcatagc tgtttcctgt gtgaaattgt    4020
tatccgctca caattccaca caacatacga gccggaagca taaagtgtaa agcctggggt    4080
gcctaatgag tgagctaact cacattaatt gcgttgcgct cactgcccgc tttccagtcg    4140
ggaaacctgt cgtgccagct gcattaatga atcggccaac gcgcggggag aggcggtttg    4200
cgtattgggc gctcttccgc ttcctcgctc actgactcgc tgcgctcggt cgttcggctg    4260
cggcgagcgg tatcagctca ctcaaaggcg gtaatacggt tatccacaga atcagggggat    4320 aacgcaggaa agaacatgtg agcaaaaggc cagcaaaagg ccaggaaccg taaaaaggcc    4380
gcgttgctgg cgtttttcca taggctccgc ccccctgacg agcatcacaa aaatcgacgc    4440
tcaagtcaga ggtggcgaaa cccgacagga ctataaagat accaggcgtt tccccctgga    4500
```

-continued

```
agctccctcg tgcgctctcc tgttccgacc ctgccgctta ccggatacct gtccgccttt   4560
ctcccttcgg gaagcgtggc gctttctcat agctcacgct gtaggtatct cagttcggtg   4620
taggtcgttc gctccaagct gggctgtgtg cacgaacccc ccgttcagcc cgaccgctgc   4680
gccttatccg gtaactatcg tcttgagtcc aacccggtaa gacacgactt atcgccactg   4740
gcagcagcca ctggtaacag gattagcaga gcgaggtatg taggcggtgc tacagagttc   4800
ttgaagtggt ggcctaacta cggctacact agaaggacag tatttggtat ctgcgctctg   4860
ctgaagccag ttaccttcgg aaaaagagtt ggtagctctt gatccggcaa acaaaccacc   4920
gctggtagcg gtggtttttt tgtttgcaag cagcagatta cgcgcagaaa aaaggatct    4980 caagaagatc ctttgatctt ttctacgggg tctgacgctc agtggaacga aaactcacgt   5040
taagggattt tggtcatgag attatcaaaa aggatcttca cctagatcct tttaaattaa   5100
aaatgaagtt ttaaatcaat ctaaagtata tatgagtaaa cttggtctga cagttaccaa   5160
tgcttaatca gtgaggcacc tatctcagcg atctgtctat ttcgttcatc catagttgcc   5220
tgactccccg tcgtgtagat aactacgata cgggagggct taccatctgg ccccagtgct   5280
gcaatgatac cgcgagaccc acgctcaccg gctccagatt tatcagcaat aaaccagcca   5340
gccggaaggg ccgagcgcag aagtggtcct gcaactttat ccgcctccat ccagtctatt   5400
aattgttgcc gggaagctag agtaagtagt tcgccagtta atagtttgcg caacgttgtt   5460
accattacta caggcatcgt ggtgtcacgc tcgtcgtttg gtatggcttc attcagctcc   5520
ggttcccaac gatcaaggcg agttacatga tcccccatgt tgtgcaaaaa agcggttagc   5580
tccttcggtc ctccgatcgt tgtcagaagt aagttggccg cagtgttatc actcatggtt   5640
atggcagcac tgcataa                                                  5657
```